US010226238B2

(12) United States Patent
Pannell et al.

(10) Patent No.: US 10,226,238 B2
(45) Date of Patent: Mar. 12, 2019

(54) NON-INVASIVE METHODS OF DETECTING TARGET MOLECULES

(75) Inventors: Lewis Pannell, Mobile, AL (US); Jana Rocker, Mobile, AL (US); Carlo Contreras, Mobile, AL (US); Jack Di Palma, Mobile, AL (US)

(73) Assignee: Creatics LLC, Rockland, MA (US)

( * ) Notice: Subject to any disclaimer, the term of this patent is extended or adjusted under 35 U.S.C. 154(b) by 163 days.

(21) Appl. No.: 14/344,399

(22) PCT Filed: Sep. 12, 2011

(86) PCT No.: PCT/US2011/051269
§ 371 (c)(1),
(2), (4) Date: Mar. 12, 2014

(87) PCT Pub. No.: WO2013/039477
PCT Pub. Date: Mar. 21, 2013

(65) Prior Publication Data
US 2014/0343451 A1 Nov. 20, 2014

(51) Int. Cl.
A61B 10/00 (2006.01)
G01N 33/68 (2006.01)
A61B 1/31 (2006.01)
A61B 5/00 (2006.01)

(52) U.S. Cl.
CPC ............ A61B 10/0045 (2013.01); A61B 1/31 (2013.01); A61B 5/425 (2013.01); A61B 10/0038 (2013.01); G01N 33/68 (2013.01); G01N 33/6803 (2013.01); A61B 2010/0061 (2013.01)

(58) Field of Classification Search
CPC ............ A61B 10/0045; A61B 10/0038; A61B 2010/0061; A61B 1/31
See application file for complete search history.

(56) References Cited

U.S. PATENT DOCUMENTS

| 5,331,973 A | 7/1994 | Fiedler et al. |
| 6,057,166 A | 5/2000 | Childs et al. |
| 6,447,763 B1 * | 9/2002 | Gordon .............. A61B 10/0038 424/78.01 |

(Continued)

FOREIGN PATENT DOCUMENTS

| EP | 1298205 A1 | 4/2003 |
| JP | 2004-010604 A | 1/2004 |

(Continued)

OTHER PUBLICATIONS

Kildare, Beverly. 16s rRNA-based assays for quantitative detection of universal, human-, cow-, and dog-specific fecal Bacteroidales: A Bayesian appoach, 2007, Water Research, 41, 3701-3715.*

(Continued)

Primary Examiner — Daniel L Cerioni
Assistant Examiner — Yasmeen S Warsi
(74) Attorney, Agent, or Firm — McCarter & English, LLP; Maria Laccotripe Zacharakis; Maneesh Gulati

(57) ABSTRACT

Embodiments of the present invention relate to non-invasive methods and compositions for collecting detecting, measuring, and identifying target molecules. In some embodiments, methods and compositions relate to target molecules in gastrointestinal lavage fluid or feces.

30 Claims, 3 Drawing Sheets
Specification includes a Sequence Listing.

(56) References Cited

U.S. PATENT DOCUMENTS

| | | | |
|---|---|---|---|
| 7,368,233 B2* | 5/2008 | Shuber | C07K 14/47 |
| | | | 435/6.11 |
| 2002/0119472 A1 | 8/2002 | Lapidus et al. | |
| 2007/0298008 A1* | 12/2007 | Dennett | A61K 31/765 |
| | | | 424/78.31 |
| 2008/0299555 A1 | 12/2008 | Nitta et al. | |
| 2009/0004058 A1* | 1/2009 | Liang | A61B 10/0096 |
| | | | 422/68.1 |
| 2009/0258090 A1 | 10/2009 | Cleveland | |
| 2009/0311707 A1* | 12/2009 | Xia | G01N 33/5091 |
| | | | 435/6.16 |
| 2010/0068702 A1* | 3/2010 | Watanabe | C12Q 1/6806 |
| | | | 435/6.1 |
| 2010/0121046 A1* | 5/2010 | Ahlquist | A61B 10/0038 |
| | | | 536/25.41 |
| 2010/0248250 A1 | 9/2010 | Tanigami et al. | |
| 2010/0279382 A1 | 11/2010 | Aebersold et al. | |
| 2010/0304397 A1 | 12/2010 | Burns et al. | |
| 2011/0183328 A1 | 7/2011 | Taylor et al. | |
| 2013/0247232 A1* | 9/2013 | Wang | A61K 47/48284 |
| | | | 800/13 |
| 2016/0033511 A1 | 2/2016 | Pannell et al. | |

FOREIGN PATENT DOCUMENTS

| | | |
|---|---|---|
| WO | WO-2000029852 | 5/2000 |
| WO | WO-03/014298 A2 | 2/2003 |
| WO | WO-2004/055519 A2 | 7/2004 |
| WO | WO-2005053512 A2 | 6/2005 |
| WO | WO-2007132844 A1 | 11/2007 |
| WO | WO-2009102788 A2 | 8/2009 |
| WO | WO-2010062663 A1 | 6/2010 |
| WO | WO-2010/127782 A1 | 11/2010 |
| WO | WO-2011/027311 A2 | 3/2011 |
| WO | WO-2011057078 A2 | 5/2011 |
| WO | WO-2011/151252 A2 | 12/2011 |
| WO | WO-2012/092529 A2 | 7/2012 |
| WO | WO-2013/039477 A1 | 3/2013 |

OTHER PUBLICATIONS

Midwinter, M., Watson, A., Wadehra, V., & Charnley, R. (2001). Laparoscopic peritoneal lavage cytology and immunocytology in pancreatic and periampullary carcinoma. HPB: The Official Journal of the International Hepato Pancreato Biliary Association, 3(3), 207-211. http://doi.org/10.1080/136518201753242226.*

Kuramitsu, Yasuhiro, and Kazuyuki Nakamura. "Proteomic analysis of cancer tissues: shedding light on carcinogenesis and possible biomarkers." Proteomics 6.20 (2006): 5650-5661.*

European Search Report issued for EP14729753.5, dated Oct. 31, 2016.

International Preliminary Report on Patentability and Written Opinion issued in PCT/US2014/026857 dated Dec. 16, 2014.

Wuerker Rb et al: "Characteristics of cancer cells in gastrointestinal lavage specimens'" Acta Cytologia, vol. 37, No. 3, 1993, p. 379-384, Xp00818964.

U.S. Appl. No. 14/773,969, filed Sep. 9, 2015, US 2016-0033511.

Aebersold R, et al., Mass spectrometry in proteomics. Chem Rev. Feb. 2001;101(2):269-95.

Aebersold R, et al., Mass spectrometry-based proteomics. Nature. Mar. 13, 2003;422(6928):198-207.

Aebersold R, et al., Proteomics—advances, applications and the challenges that remain. Trends Biotechnol. Dec. 2002;20(12 Suppl):S1-2.

Aebersold R. A mass spectrometric journey into protein and proteome research. J Am Soc Mass Spectrom. Jul. 2003;14(7):685-95.

Aebersold R. Quantitative proteome analysis: methods and applications. J Infect Dis. Jun. 15, 2003;187 Suppl 2:S315-20.

Akakura N, et al., Constitutive expression of hypoxia-inducible factor-1alpha renders pancreatic cancer cells resistant to apoptosis induced by hypoxia and nutrient deprivation. Cancer Res. Sep. 1, 2001;61(17):6548-54.

Bao JJ. Capillary electrophoretic immunoassays. J Chromatogr B Biomed Sci Appl. Oct. 10, 1997;699(1-2):463-80.

Bark CJ. Mitochondrial creatine kinase. A poor prognostic sign. JAMA. May 23-30, 1980;243(20):2058-60.

Belinsky GS, et al., Expression of secretory phospholipase A2 in colon tumor cells potentiates tumor growth. Mol Carcinog. Feb. 2007;46(2):106-16.

Bresalier RS, et al., A circulating ligand for galectin-3 is a haptoglobin-related glycoprotein elevated in individuals with colon cancer. Gastroenterology. Sep. 2004;127(3):741-8.

Brydon WG, et al., Haemoglobin in gut lavage fluid as a measure of gastrointestinal blood loss. Lancet. Dec. 5, 1992;340(8832):1381-2.

Cavard C, et al., Overexpression of regenerating islet-derived 1 alpha and 3 alpha genes in human primary liver tumors with beta-catenin mutations. Oncogene. Jan. 26, 2006;25(4):599-608.

Chelius D, et al., Quantitative profiling of proteins in complex mixtures using liquid chromatography and mass spectrometry. J Proteome Res. Jul.-Aug. 2002;1(4):317-23.

Chen R, et al., Comparison of pancreas juice proteins from cancer versus pancreatitis using quantitative proteomic analysis. Pancreas. Jan. 2007;34(1):70-9.

Chen R, et al., Elevated level of anterior gradient-2 in pancreatic juice from patients with pre-malignant pancreatic neoplasia. Mol Cancer. Jun. 15, 2010;9:149.

Chen R, et al., Quantitative proteomic profiling of pancreatic cancer juice. Proteomics. Jul. 2006;6(13):3871-9.

Chen X, et al., Quantitative organellar proteomics analysis of rough endoplasmic reticulum from normal and acute pancreatitis rat pancreas. J Proteome Res. Feb. 5, 2010;9(2):885-96.

Cho CS, et al., A novel prognostic nomogram is more accurate than conventional staging systems for predicting survival after resection of hepatocellular carcinoma. J Am Coll Surg. Feb. 2008;206(2):281-91.

Choudari CP, et al., Gut lavage fluid protein concentrations: objective measures of disease activity in inflammatory bowel disease. Gastroenterology. Apr. 1993;104(4):1064-71.

Cui L., et al., Screening and Verification of Differentially Expressed Proteins from Pancreatic Cancer Tissue. Chinese Journal of Chemistry, 2010, 28(6):884-890.

Database Protein [Online] May 3, 2014, "pancreatic triacylglycerol lipase precursor [*Homo sapiens*]", retrieved from NCBI Database accession No. NP_000927, abstract.

Database UniProtKB [Online] Apr. 1, 1990, "LIPP HUMAN", Database accession No. P16233, abstract.

Davis GR, et al., Development of a lavage solution associated with minimal water and electrolyte absorption or secretion. Gastroenterology. May 1980;78(5 Pt 1):991-5.

DeSouza L, et al., Search for cancer markers from endometrial tissues using differentially labeled tags iTRAQ and cICAT with multidimensional liquid chromatography and tandem mass spectrometry. J Proteome Res. Mar.-Apr. 2005;4(2):377-86.

DiPalma JA, et al., Comparison of colon cleansing methods in preparation for colonoscopy. Gastroenterology. May 1984;86(5 Pt 1):856-60.

Egea L, et al., Role of secreted glyceraldehyde-3-phosphate dehydrogenase in the infection mechanism of enterohemorrhagic and enteropathogenic *Escherichia coli*: interaction of the extracellular enzyme with human plasminogen and fibrinogen. Int J Biochem Cell Biol. 2007;39(6):1190-203.

Evgenikos N, et al., Immunoglobulin G and albumin levels in whole gut lavage fluid provide an objective measure of pouch ileitis. Br J Surg. Jun. 2000;87(6):808-13.

Fentz AK, et al., Detection of colorectal adenoma and cancer based on transthyretin and C3a-desArg serum levels. Proteomics Clin Appl. Jun. 2007;1(6):536-44.

Ferguson A, et al., Use of whole gut perfusion to investigate gastrointestinal blood loss in patients with iron deficiency anaemia. Gut. Jan. 1996;38(1):120-4.

Flory MR, et al., Advances in quantitative proteomics using stable isotope tags. Trends Biotechnol. Dec. 2002;20(12 Suppl):S23-9.

(56) References Cited

OTHER PUBLICATIONS

Friess H, et al., Microarray-based identification of differentially expressed growth- and metastasis-associated genes in pancreatic cancer. Cell Mol Life Sci. Jun. 2003;60(6):1180-99.
Gao J, et al., Identification of pancreatic juice proteins as biomarkers of pancreatic cancer. Oncol Rep. Jun. 2010;23(6):1683-92.
Gazi MH, et al., Downregulation of IgG Fc binding protein (Fc gammaBP) in prostate cancer. Cancer Biol Ther. Jan. 2008;7(1):70-5.
Gerstel D, et al., CEACAM1 creates a pro-angiogenic tumor microenvironment that supports tumor vessel maturation. Oncogene. Oct. 13, 2011;30(41):4275-88.
Gold DV, et al., Localization of pancreatic cancer with radiolabeled monoclonal antibody PAM4. Crit Rev Oncol Hematol. Jul.-Aug. 2001;39(1-2):147-54.
Goodlett DR, et al., Protein identification with a single accurate mass of a cysteine-containing peptide and constrained database searching. Anal Chem. Mar. 15, 2000;72(6):1112-8.
Grisendi S, et al., Nucleophosmin and cancer. Nat Rev Cancer. Jul. 2006;6(7):493-505.
Grønborg M, et al., Comprehensive proteomic analysis of human pancreatic juice. J Proteome Res. Sep.-Oct. 2004;3(5):1042-55.
Gu N, et al., Sucrase-isomaltase gene expression is inhibited by mutant hepatocyte nuclear factor (HNF)-1 alpha and mutant HNF-1 beta in Caco-2 cells. J Nutr Sci Vitaminol (Tokyo). Apr. 2006;52(2):105-12.
Gómez-Lázaro M, et al., Proteomic analysis of zymogen granules. Expert Rev Proteomics. Oct. 2010;7(5):735-47.
Handy LM, et al., Investigation of neutrophils in the gut lumen by assay of granulocyte elastase in whole-gut lavage fluid. Scand J Gastroenterol. Jul. 1996;31(7):700-5.
Harding et al., "Humoral immune response induced to filamin B in patients with metastatic hormone-refractory prostate cancer (HRPC) treated with a GM-CSF-transduced allogeneic prostate cancer vaccine (GVAX(R))," Proceeding s of the Annual Meeting of the American Association for Cancer Research, vol. 47th, (2006), p. 680.
Harlow et al., Antibodies, A Laboratory Manual, Cold Spring Harbor Laboratory, New York, 1988.
Haug U, et al., Mutant-enriched PCR and allele-specific hybridization reaction to detect K-ras mutations in stool DNA: high prevalence in a large sample of older adults. Clin Chem. Apr. 2007;53(4):787-90.
Hockla A, et al., Mesotrypsin promotes malignant growth of breast cancer cells through shedding of CD109. Breast Cancer Res Treat. Nov. 2010;124(1):27-38.
Huang KC, et al., Selenium binding protein 1 in ovarian cancer. Int J Cancer. May 15, 2006;118(10):2433-40.
International Preliminary Report on Patentability and Written Opinion issued on PCT/US2011/051269, dated Mar. 20, 2014.
Invitation to pay additional fees, issued for PCT/US2014/026857, dated Sep. 24, 2014.
Jiang HB, et al., Pancreatic stellate cells promote proliferation and invasiveness of human pancreatic cancer cells via galectin-3. World J Gastroenterol. Apr. 7, 2008;14(13):2023-8.
Kang JU, et al., AMY2A: a possible tumor-suppressor gene of 1p21.1 loss in gastric carcinoma. Int J Oncol. Jun. 2010;36(6):1429-35.
Kim GE, et al., Aberrant expression of MUC5AC and MUC6 gastric mucins and sialyl Tn antigen in intraepithelial neoplasms of the pancreas. Gastroenterology. Oct. 2002;123(4):1052-60.
Kim YS, et al., Galectin-3 binding protein promotes cell motility in colon cancer by stimulating the shedding of protein tyrosine phosphatase kappa by proprotein convertase 5. Biochem Biophys Res Commun. Jan. 7, 2011;404(1):96-102.
Kinter M, Protein Sequencing and Identification Using Tandem Mass Spectrometry, John Wiley & Sons, New York, Oct. 2000, 320 pages.
Kipps TJ, et al., Autoantibody-associated kappa light chain variable region gene expressed in chronic lymphocytic leukemia with little or no somatic mutation. Implications for etiology and immunotherapy. J Exp Med. Mar. 1, 1988;167(3):840-52.
Kobayashi D, et al., Olfactomedin 4 promotes S-phase transition in proliferation of pancreatic cancer cells. Cancer Sci. Mar. 2007;98(3):334-40.
Kos J, et al., Cysteine proteinase inhibitors stefin A, stefin B, and cystatin C in sera from patients with colorectal cancer: relation to prognosis. Clin Cancer Res. Feb. 2000;6(2):505-11.
Koshida S, et al., Specific overexpression of OLFM4(GW112/HGC-1) mRNA in colon, breast and lung cancer tissues detected using quantitative analysis. Cancer Sci. Mar. 2007;98(3):315-20.
Koyama I, et al., alpha-Amylase expressed in human liver is encoded by the AMY-2B gene identified in tumorous tissues. Clin Chim Acta. Jul. 5, 2001;309(1):73-83.
Krasnov GS, et al., [Colorectal cancer 2D-proteomics: identification of altered protein expression]. Mol Biol (Mosk). Mar.-Apr. 2009;43(2):348-56. Russian.
Kuopio T, et al., Cysteine proteinase inhibitor cystatin A in breast cancer. Cancer Res. Feb. 1, 1998;58(3):432-6.
Kuramitsu Y, et al., Proteomic analysis of cancer tissues: shedding light on carcinogenesis and possible biomarkers. Proteomics. Oct. 2006;6(20):5650-61.
Liang X, et al., Quantification of membrane and membrane-bound proteins in normal and malignant breast cancer cells isolated from the same patient with primary breast carcinoma. J Proteome Res. Oct. 2006;5(10):2632-41.
Lin HH, et al., Lipocalin-2-induced cytokine production enhances endometrial carcinoma cell survival and migration. Int J Biol Sci. Jan. 18, 2011;7(1):74-86.
Lottaz D, et al., Nonpolarized secretion of human meprin alpha in colorectal cancer generates an increased proteolytic potential in the stroma. Cancer Res. Mar. 1, 1999;59(5):1127-33.
Mahadevan NR, et al., ER stress drives Lipocalin 2 upregulation in prostate cancer cells in an NF-?B-dependent manner. BMC Cancer. Jun. 7, 2011;11:229.
Maher DM, et al., Mucin 13: structure, function, and potential roles in cancer pathogenesis. Mol Cancer Res. May 2011;9(5):531-7.
Mann BF, et al., Glycomic and proteomic profiling of pancreatic cyst fluids identifies hyperfucosylated lactosamines on the N-linked glycans of overexpressed glycoproteins. Mol Cell Proteomics. Jul. 2012;11(7): pp. M111.015792-1-M111.015792-11.
Matsugi S, et al., Serum carboxypeptidase A activity as a biomarker for early-stage pancreatic carcinoma. Clin Chim Acta. Mar. 2007;378(1-2):147-53.
Miao Q, et al., Chymotrypsin B cached in rat liver lysosomes and involved in apoptotic regulation through a mitochondrial pathway. J Biol Chem. Mar. 28, 2008;283(13):8218-28.
Millar EK, et al., Prediction of local recurrence, distant metastases, and death after breast-conserving therapy in early-stage invasive breast cancer using a five-biomarker panel. J Clin Oncol. Oct. 1, 2009;27(28):4701-8.
Mohammad HS, et al., Annexin A2 expression and phosphorylation are up-regulated in hepatocellular carcinoma. Int J Oncol. Dec. 2008;33(6):1157-63.
Normandin K, et al., Protease inhibitor SERPINA1 expression in epithelial ovarian cancer. Clin Exp Metastasis. 2010;27(1):55-69.
O'Mahony S, et al., Appraisal of gut lavage in the study of intestinal humoral immunity. Gut. Dec. 1990;31(12):1341-4.
Paik S, et al., A multigene assay to predict recurrence of tamoxifen-treated, node-negative breast cancer. N Engl J Med. Dec. 30, 2004;351(27):2817-26.
Park HU, et al., Aberrant expression of MUC3 and MUC4 membrane-associated mucins and sialyl Le(x) antigen in pancreatic intraepithelial neoplasia. Pancreas. Apr. 2003;26(3):e48-54.
Parra JR, et al., Tissue inhibitor of metalloproteinase-1 is increased in the saphenofemoral junction of patients with varices in the leg. J Vasc Surg. Oct. 1998;28(4):669-75.
Patterson SD, et al., Proteomics: the first decade and beyond. Nat Genet. Mar. 2003;33 Suppl:311-23.
Paulo JA, et al., Identification of pancreas-specific proteins in endoscopically (endoscopic pancreatic function test) collected pancreatic fluid with liquid chromatography—tandem mass spectrometry. Pancreas. Aug. 2010;39(6):889-96.

(56) References Cited

OTHER PUBLICATIONS

Perkins DN, et al., Probability-based protein identification by searching sequence databases using mass spectrometry data. Electrophoresis. Dec. 1999;20(18):3551-67.
Pham TM, et al., Relationship between serum levels of superoxide dismutase activity and subsequent risk of cancer mortality: Findings from a nested case-control study within the Japan Collaborative Cohort Study. Asian Pac J Cancer Prey. Dec. 2009;10 Suppl:69-73.
Rongen HA, et al., Liposomes and immunoassays. J Immunol Methods. May 26, 1997;204(2):105-33.
Rosty C, et al., Identification of hepatocarcinoma-intestine-pancreas/pancreatitis-associated protein I as a biomarker for pancreatic ductal adenocarcinoma by protein biochip technology. Cancer Res. Mar. 15, 2002;62(6):1868-75.
Sasaki K, et al., Peptidomics-based approach reveals the secretion of the 29-residue COOH-terminal fragment of the putative tumor suppressor protein DMBT1 from pancreatic adenocarcinoma cell lines. Cancer Res. Sep. 1, 2002;62(17):4894-8.
Sato N, et al., Gene expression profiling identifies genes associated with invasive intraductal papillary mucinous neoplasms of the pancreas. Am J Pathol. Mar. 2004;164(3):903-14.
Schmalzing D, et al., Capillary electrophoresis based immunoassays: a critical review. Electrophoresis. Nov. 1997;18(12-13):2184-93.
Self CH, et al., Advances in immunoassay technology. Curr Opin Biotechnol. Feb. 1996;7(1):60-5.
Shimada S, et al., Pancreatic elastase IIIA and its variants are expressed in pancreatic carcinoma cells. Int J Mol Med. Nov. 2002;10(5):599-603.
Shin YK, et al., Upregulation of glycolytic enzymes in proteins secreted from human colon cancer cells with 5-fluorouracil resistance. Electrophoresis. Jun. 2009;30(12):2182-92.
Silvers AL, et al., Decreased selenium-binding protein 1 in esophageal adenocarcinoma results from posttranscriptional and epigenetic regulation and affects chemosensitivity. Clin Cancer Res. Apr. 1, 2010;16(7):2009-21.
Stanley AJ, et al., Transjugular intrahepatic portosystemic shunt as a treatment for protein-losing enteropathy caused by portal hypertension. Gastroenterology. Dec. 1996;111(6):1679-82.
Sved P, et al., Oncogenic action of secreted phospholipase A2 in prostate cancer. Cancer Res. Oct. 1, 2004;64(19):6934-40.
Tamesa MS, et al., Detection of autoantibodies against cyclophilin A and triosephosphate isomerase in sera from breast cancer patients by proteomic analysis. Electrophoresis. Jun. 2009;30(12):2168-81.
Tang K, et al., Charge competition and the linear dynamic range of detection in electrospray ionization mass spectrometry. J Am Soc Mass Spectrom. Oct. 2004;15(10):1416-23.
Tao WA, et al., Advances in quantitative proteomics via stable isotope tagging and mass spectrometry. Curr Opin Biotechnol. Feb. 2003;14(1):110-8.
Terris B, et al., Characterization of gene expression profiles in intraductal papillary-mucinous tumors of the pancreas. Am J Pathol. May 2002;160(5):1745-54.
Tobi M, et al., Prospective markers for early diagnosis and prognosis of sporadic pancreatic ductal adenocarcinoma. Dig Dis Sci. Mar. 2013;58(3):744-50.
Tomita N, et al., A novel type of human alpha-amylase produced in lung carcinoid tumor. Gene. Mar. 15, 1989;76(1):11-8.
van Gisbergen KP, et al., Dendritic cells recognize tumor-specific glycosylation of carcinoembryonic antigen on colorectal cancer cells through dendritic cell-specific intercellular adhesion molecule-3-grabbing nonintegrin. Cancer Res. Jul. 1, 2005;65(13):5935-44.
Vilen ST, et al., Intracellular co-localization of trypsin-2 and matrix metalloprotease-9: possible proteolytic cascade of trypsin-2, MMP-9 and enterokinase in carcinoma. Exp Cell Res. Feb. 15, 2008;314(4):914-26.
Wang H, et al., Effect of chymotrypsin C and related proteins on pancreatic cancer cell migration. Acta Biochim Biophys Sin (Shanghai). May 2011;43(5):362-71.
Wang Y, et al., Alpha 1 antichymotrypsin is aberrantly expressed during melanoma progression and predicts poor survival for patients with metastatic melanoma. Pigment Cell Melanoma Res. Aug. 2010;23(4):575-8.
Wiener MC, et al., Differential mass spectrometry: a label-free LC-MS method for finding significant differences in complex peptide and protein mixtures. Anal Chem. Oct. 15, 2004;76(20):6085-96.
Wolf M, et al., Cathepsin D specifically cleaves the chemokines macrophage inflammatory protein-1 alpha, macrophage inflammatory protein-1 beta, and SLC that are expressed in human breast cancer. Am J Pathol. Apr. 2003;162(4):1183-90.
Xiao J, et al., Profiling pancreatic cancer-secreted proteome using 15N amino acids and serum-free media Pancreas. Jan. 2010;39(1):e17-23.
Yamamoto H, et al., Intestinal-type alkaline phosphatase produced by human hepatoblastoma cell line HUH-6 clone 5. Cancer Res. Jan. 1984;44(1):339-44.
Yamamura H, Effectiveness of discriminant analysis of serum CA 19-9 and elastase 1 in diagnosis of pancreatic carcinoma. Pancreas. 1989;4(4):401-5.
Yamashiro Y, et al., Ectopic coexpression of keratin 8 and 18 promotes invasion of transformed keratinocytes and is induced in patients with cutaneous squamous cell carcinoma. Biochem Biophys Res Commun. Aug. 27, 2010;399(3):365-72.
Yang XR, et al., Cytokeratin 10 and cytokeratin 19: predictive markers for poor prognosis in hepatocellular carcinoma patients after curative resection. Clin Cancer Res. Jun. 15, 2008;14(12):3850-9.
Yates JR 3rd, et al., Automated protein identification using microcolumn liquid chromatography-tandem mass spectrometry. Methods Mol Biol. 1999;112:553-69.
Yates JR 3rd. Mass spectrometry and the age of the proteome. J Mass Spectrom. Jan. 1998;33(1):1-19.
Zhang J, et al., Reduced selenium-binding protein 1 is associated with poor survival rate in gastric carcinoma. Med Oncol. Jun. 2011;28(2):481-7.
Zhang P, et al., The expression of selenium-binding protein 1 is decreased in uterine leiomyoma. Diagn Pathol. Dec. 9, 2010;5:80.
Zheng H, et al., MUC6 down-regulation correlates with gastric carcinoma progression and a poor prognosis: an immunohistochemical study with tissue microarrays. J Cancer Res Clin Oncol. Dec. 2006;132(12):817-23.
Zhou H, et al., Is heterozygous alpha-1-antitrypsin deficiency type PIZ a risk factor for primary liver carcinoma? Cancer. Jun. 15, 2000;88(12):2668-76.
Zhou L, et al., Comparative proteomic analysis of human pancreatic juice: methodological study. Proteomics. Apr. 2007;7(8):1345-55.
Zhu W, et al., Mass spectrometry-based label-free quantitative proteomics. J Biomed Biotechnol. 2010;2010:840518. pp. 1-6.
Liu et al., "Fecal markers, intestinal inflammation and inflammatory enteritis," Clinical Journal of digestive disease, vol. 15, No. 6, pp. 275-277 (2003).
Imamura et al. "Usefulness of cytologic examination using pancreatic duct lavage fluid for diagnosis of pancreatic ductal carcinoma—A novel examination developed for pancreatic ductal carcinoma," Clinical Research, vol. 62, No. 2, pp. 55-59 (2003).
Imamura et al., "Effectiveness of cytodiagnosis with pancreatic duct lavage fluid for pancreatic ductal carcinoma: new sampling technique," Dig Endosc, vol. 18, No. 4, pp. 303-307 (2006).
Office Action Cited in Corresponding Chinese Patent Application 2011800743066 dated Feb. 15, 2015.
Siegel, R. L.; Miller, K. D.; Jemal, A. Cancer Statistics, 2017. CA: A Cancer Journal for Clinicians 2017, 67 (1), 7-30.
Del Chiaro, M.; Segersvard, R.; Lohr, M.; Verbeke, C. Early Detection and Prevention of Pancreatic Cancer: Is It Really Possible Today? World J Gastroenterol 2014, 20 (34), 12118-12131.
Nolen, B. M. et al. Prediagnostic Serum Biomarkers as Early Detection Tools for Pancreatic Cancer in a Large Prospective Cohort Study. PLoS ONE 9, (2014).

(56) References Cited

OTHER PUBLICATIONS

Potter, An evaluation of whole gut lavage fluid for the detection of colorectal cancer using molecular techniques. Submitted for the Degree of Doctor of Medicine (MD), The University of Edinburgh. 168 pages. (1999).

Liu et al., Fecal markers, intestinal inflammation and inflammatory enteritis. Clinical Journal of Digestive Disease. 2003;15(6)175-277.

Nakamura et al., Analysis of K-ras codon 12 point mutations using duodenal lavage fluid for diagnosis of pancreatic carcinoma. Pancreas. Mar. 1999;18(2):133-40.

Evgenikos et al., Luminal neutrophil migration in ileoanal pouches studied by whole gut lavage, European journal of gastroenterology & hepatology, 2000, vol. 12, No. 5, p. 553-558.

Kayazawa et al., Lactoferrin in Whole Gut Lavage Fluid as a Marker for Disease Activity in Inflammatory Bowel Disease: Comparison With Other Neutrophil- Derived Proteins, The American Journal of Gastroenterology 2002 vol. 97, No. 2, 2002, p. 360-369.

Troncone et al., Increased Concentrations of Eosinophilic Cationic Protein in Whole-Gut Lavage Fluid From Children With Inflammatory Bowel Disease, Journal of pediatric gastroenterology and nutrition, 1999, vol. 28, No. 2, p. 164-168.

\* cited by examiner

NON-INVASIVE METHODS OF DETECTING TARGET MOLECULES

CROSS-REFERENCE TO RELATED PATENT APPLICATIONS

This application is a 35 U.S.C. § 371 national stage filing of International Application No. PCT/US2011/051269, filed Sep. 12, 2011, the entire contents of which are hereby incorporated herein by reference.

FIELD OF THE INVENTION

Embodiments of the present invention relate to non-invasive methods and compositions for collecting, detecting, measuring, and identifying target molecules. In some embodiments, methods and compositions relate to target molecules in gastrointestinal lavage fluid (GLF) or feces.

REFERENCE TO SEQUENCE LISTING

The present application is being filed along with a Sequence Listing in electronic format. The Sequence Listing is provided as a file entitled USA_007WO.TXT, created Sep. 7, 2011, which is approximately 231 KB in size. The information in the electronic format of the Sequence Listing is incorporated herein by reference in its entirety.

BACKGROUND

Disorders associated with the gastrointestinal (GI) and hepatobiliary tracts and the organs/tissues associated with the GI tract include cancers such as gastric cancer, esophageal cancer, liver cancer, and pancreatic cancer. Pancreatic cancer (e.g., pancreatic adenocarcinoma), in particular, is a malignant growth of the pancreas that mainly occurs in the cells of the pancreatic ducts. This disease is the ninth most common form of cancer, yet it is the fourth and fifth leading cause of cancer deaths in men and women, respectively. Cancer of the pancreas is almost always fatal, with a five-year survival rate that is less than 3%.

The most common symptoms of pancreatic cancer include jaundice, abdominal pain, and weight loss, which, together with other presenting factors, are often nonspecific in nature. Thus, diagnosing pancreatic cancer at an early stage of tumor growth is often difficult and requires extensive diagnostic work-up, often times incidentally discovered during exploratory surgery. Endoscopic ultrasonography is an example non-surgical technique available for diagnosis of pancreatic cancer. However, reliable detection of small tumors, as well as differentiation of pancreatic cancer from focal pancreatitis, is difficult. The vast majority of patients with pancreatic cancer are presently diagnosed at a late stage when the tumor has already extended beyond the pancreas to invade surrounding organs and/or has metastasized extensively. Gold et al., Crit. Rev. Oncology/Hematology, 39:147-54 (2001), incorporated herein by reference in its entirety. Late detection of the disease is common with the majority of patients being diagnosed with advanced disease that often results in death; only a minority of patients are detected with early stage disease.

Invasive techniques to diagnose disorders and diseases related to the GI tract are inconvenient and expose a subject to significant risk. Accordingly, there is a need for non-invasive methods and compositions for the detection and identification of target molecules from the GI tract or associated organs/tissues. In some embodiments, the target molecules may be evaluated to determine whether they are useful as biomarkers associated with a particular characteristic, such as disease, predisposition to disease, positive response to a treatment regimen, or no response or negative response to a treatment regimen. In addition, biomarkers from the GI tract or associated organs/tissues may be used to determine whether an individual has any of the particular characteristics listed above.

SUMMARY

Embodiments of the present invention relate to non-invasive methods and compositions for collecting, detecting, measuring, and identifying target molecules. In some embodiments, methods and compositions relate to target molecules in gastrointestinal lavage fluid (GLF) or feces.

Some embodiments include a method for assessing the physiological state of a subject comprising: obtaining a gastrointestinal lavage fluid from the subject; and detecting a target molecule which originated from outside the gastrointestinal system in the gastrointestinal lavage fluid.

Some embodiments include a method for assessing the physiological state of a subject comprising: obtaining a fecal sample from the subject; and detecting a target molecule which originated from outside the gastrointestinal system in the fecal sample.

In some embodiments, the gastrointestinal lavage fluid is obtained from the subject by partially purging the subject's gastrointestinal system.

In some embodiments, the gastrointestinal lavage fluid comprises fecal matter. In some embodiments, the fecal sample comprises a gastrointestinal lavage fluid.

In some embodiments, the target molecule comprises a polypeptide, antibody, bile acid, metabolite, or glycan. In some embodiments, the target molecule comprises a biomarker. In some embodiments, the biomarker is associated with a disease, a positive response to treatment, a partial response to treatment, a negative response to treatment, or no response to treatment. In some embodiments, the target molecule is associated with presence of a cancer or predisposition to a cancer. In some embodiments, the cancer is pancreatic cancer, colorectal cancer, liver cancer, or gastric cancer. In some embodiments, the target molecule originated from an accessory digestive gland. In some embodiments, the accessory digestive gland is salivary glands, pancreas, gallbladder, or liver.

Some embodiments include administering a lavage fluid to the subject. In some embodiments, lavage fluid is administered orally. In some embodiments, the lavage fluid comprises an ingredient selected from the group consisting of polyethylene glycol, magnesium sulfate, sodium sulfate, potassium sulfate, magnesium citrate, ascorbic acid, sodium picosulfate, and bisacodyl. In some embodiments, the lavage fluid is selected from the group consisting of GOLYTELY, HALFLYTELY, NULYTELY, SUPREP, FLEET'S PHOSPHO-SODA, magnesium citrate, and their generic equivalents.

Some embodiments include performing a colonoscopy on the subject.

In some embodiments, the subject is mammalian. In some embodiments, the subject is human.

Some embodiments include a method for identifying a biomarker comprising: obtaining a test gastrointestinal lavage fluid from a plurality of test subjects having a condition or physiological state of interest and a control gastrointestinal lavage fluid from a plurality of control subjects who do not have said condition or physiological state; determining the level of at least 5 target molecules in the test gastrointestinal lavage fluid and the control gastrointestinal lavage fluid, and identifying a target molecule which is present at significantly different levels in the test gastrointestinal lavage fluid relative to the levels in the control gastrointestinal lavage fluid, thereby identifying a biomarker.

In some embodiments, the gastrointestinal lavage fluid comprises fecal matter.

In some embodiments, the target molecules are selected form the group consisting of polypeptides, bile acids, antibodies, metabolites, glycans, and a combination thereof.

Some embodiments include determining the level of at least 10 target molecules in the test gastrointestinal lavage fluid and the control gastrointestinal lavage fluid. Some embodiments include determining the level of at least 20 target molecules in the test gastrointestinal lavage fluid and the control gastrointestinal lavage fluid. Some embodiments include determining the level of at least 30 target molecules in the test gastrointestinal lavage fluid and the control gastrointestinal lavage fluid. Some embodiments include determining the level of at least 50 target molecules in the test gastrointestinal lavage fluid and the control gastrointestinal lavage fluid. Some embodiments include determining the level of at least 100 target molecules in the test gastrointestinal lavage fluid and the control gastrointestinal lavage fluid.

In some embodiments, the biomarker is associated with a disease, a positive response to treatment, a partial response to treatment, a negative response to treatment or no response to treatment.

In some embodiments, the biomarker is associated with the presence of a cancer or predisposition to a cancer. In some embodiments, the cancer is pancreatic cancer, liver cancer, or gastric cancer.

In some embodiments, at least one target molecule originated from an accessory digestive gland. In some embodiments, the accessory digestive gland is salivary glands, pancreas, gallbladder, or liver.

Some embodiments include administering a lavage fluid to the test subjects and the control subjects. In some embodiments, the lavage fluid is administered orally. In some embodiments, the lavage fluid comprises an ingredient selected from the group consisting of polyethylene glycol, magnesium sulfate, sodium sulfate, potassium sulfate, magnesium citrate, ascorbic acid, sodium picosulfate, and bisacodyl. In some embodiments, the lavage fluid is selected from the group consisting of GOLYTELY, HALFLYTELY, NULYTELY, SUPREP, and FLEET'S PHOSPHO-SODA, magnesium citrate, and their generic equivalents.

Some embodiments include performing a colonoscopy on the test subjects and control subjects.

In some embodiments, the test subjects and control subjects are mammalian. In some embodiments, the test subjects and control subjects are human.

Some embodiments include a method for identifying a biomarker comprising: obtaining a test fecal sample from a plurality of test subjects having a condition of interest and a control fecal sample from a plurality of control subjects and; determining the level of at least 5 target molecules in the test fecal sample and the control fecal sample, identifying a target molecule which is present at significantly different levels in the test fecal sample relative to the levels in the control fecal sample, thereby identifying a biomarker.

In some embodiments, the fecal sample comprises a gastrointestinal lavage fluid.

In some embodiments, the target molecules are selected from the group consisting of polypeptides, bile acids, antibodies, metabolites, glycans, and a combination thereof.

Some embodiments include determining the level of at least 10 target molecules in the test fecal sample and the control fecal sample. Some embodiments include determining the level of at least 20 target molecules in the fecal sample and the control fecal sample. Some embodiments include determining the level of at least 30 target molecules in the fecal sample and the control fecal sample. Some embodiments include determining the level of at least 50 target molecules in the fecal sample and the control fecal sample. Some embodiments include determining the level of at least 100 target molecules in the fecal sample and the control fecal sample.

In some embodiments, the biomarker is associated with a disease, a positive response to treatment, or a negative response to treatment.

In some embodiments, the biomarker is associated with the presence of a cancer or predisposition to a cancer. In some embodiments, the cancer is pancreatic cancer, colorectal cancer, liver cancer, or gastric cancer.

In some embodiments, at least one target molecule originated from an accessory digestive gland. In some embodiments, the accessory digestive gland is salivary glands, pancreas, gallbladder, or liver.

In some embodiments, the test subjects and control subjects are mammalian. In some embodiments, the test subjects and control subjects are human.

Some embodiments include a kit for detecting a target molecule in a gastrointestinal lavage fluid comprising: a lavage fluid for oral administration to a subject; a vessel for collecting the gastrointestinal lavage fluid from the subject; and an agent for detecting a target molecule which originated from outside the gastrointestinal system.

Some embodiments include a kit for detecting a target molecule in a fecal sample comprising: a lavage fluid for oral administration to a subject; a vessel for collecting the fecal sample from the subject; and an agent for detecting a target molecule which originated from outside the gastrointestinal system.

Some embodiments include a protease inhibitor.

In some embodiments, the target molecule comprises a polypeptide, antibody, bile acid, metabolite, or glycan. In some embodiments, the target molecule comprises a biomarker. In some embodiments, the biomarker is associated with a disease, a positive response to treatment, or a negative response to treatment.

In some embodiments, the target molecule is associated with presence of a cancer or predisposition to a cancer. In some embodiments, the cancer is pancreatic cancer, liver cancer, colorectal cancer, or gastric cancer.

In some embodiments, the target molecule originated from an accessory digestive gland. In some embodiments, the accessory digestive gland is salivary glands, pancreas, gallbladder, or liver.

In some embodiments, the lavage fluid comprises an ingredient selected from the group consisting of polyethylene glycol, magnesium sulfate, sodium sulfate, potassium sulfate, magnesium citrate, ascorbic acid, sodium picosulfate, and bisacodyl. In some embodiments, the lavage fluid is selected from the group consisting of GOLYTELY, HALFLYTELY, NULYTELY, SUPREP, FLEET'S PHOSPHO-SODA, magnesium citrate, and their generic equivalents.

DETAILED DESCRIPTION

Figure 1:
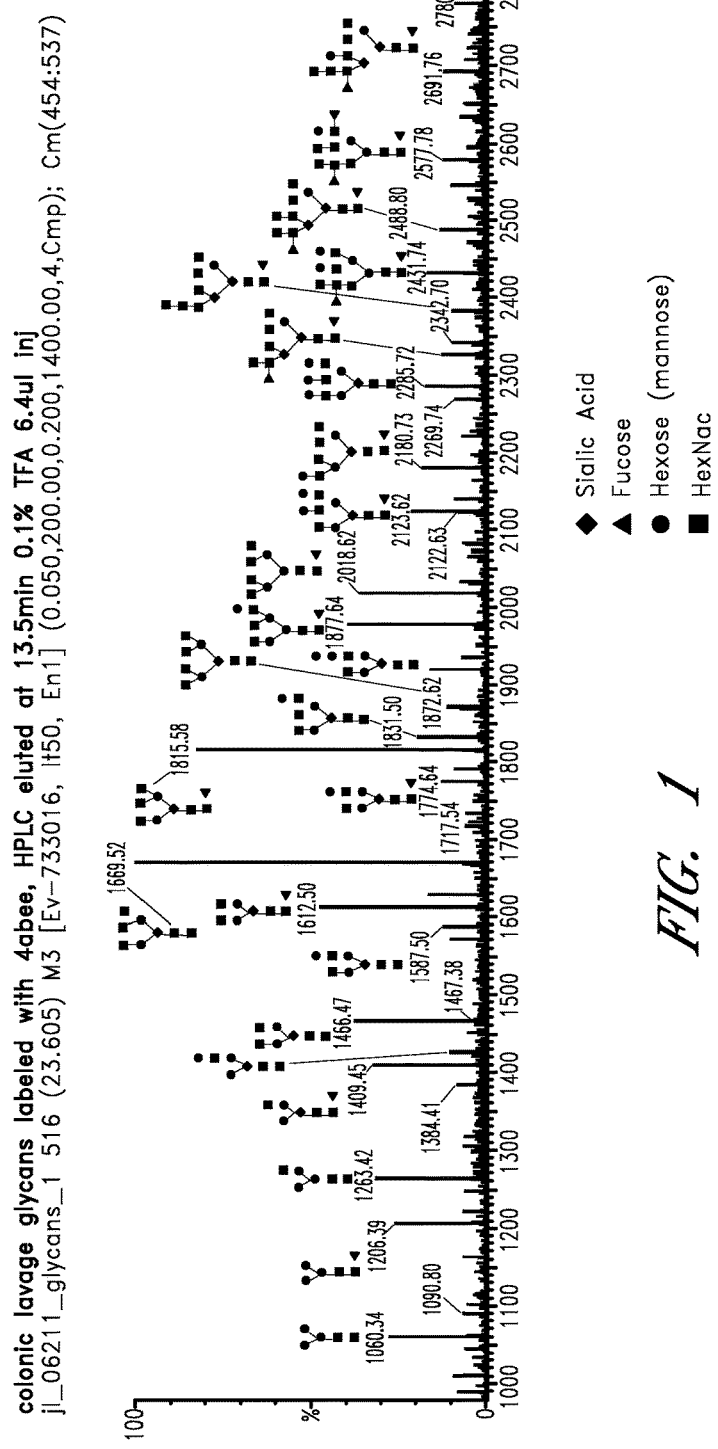
FIG. 1 depicts a graph of the relative abundance of various glycoprotein derived glycan structures present in a fraction of a gastrointestinal lavage fluid. Derivatized glycans were eluted from a C18 reverse phase column on a Q-TOF MS at about 20-25% acetonitrile in 0.2% formic acid. The mass spectrometer was scanned in MS-only mode from m/z 150-2000 every second to acquire the derivatized glycan profile data.

Embodiments of the present invention relate to non-invasive methods and compositions for collecting, detecting, measuring, and identifying target molecules. In some embodiments, methods and compositions relate to target molecules in gastrointestinal lavage fluid (GLF) or feces.

Gastrointestinal lavage is widely used as a lower gastrointestinal (GI) tract preparation for colonoscopy or colorectal surgery (see e.g., DiPalma J A. et al., (1984) Gastroenterology 86:856-60), incorporated herein by reference in its entirety). Particular pathophysiologies of intestinal diseases have been investigated by measuring proteins in GLF (Evgenikos N, et al. (2000) Br J Surg 87:808-13; Brydon W G, Ferguson A. (1992) Lancet 340: 1381-2; Choudari C P, et al. (1993) Gastroenterology 104: 1064-71; Ferguson A, et al. (1996) Gut 38:120-4; Handy L M, et al. (1996) Scand J Gastroenterol 31:700-5; and Stanley A J, et al. (1996) Gastroenterology 111:1679-82), each incorporated herein by reference in its entirety).

Measurements of fecal proteins can be useful for investigating various pathophysiologies such as protein-losing enteropathy and mucosal inflammation. However, while feces may be used in some embodiments described herein, GLF is preferred over feces as a sample for detecting and identifying biomarkers because GLF contains smaller amounts of substances that interfere with assays, and destruction of protein by digestive enzymes and bacterial proteases is less in GLF than a fecal sample because of its quick transit through the GI tract. In addition, it is possible to estimate the rate of protein release from the mucosa, because the rate of fluid passage along the gut can be estimated.

In some embodiments, a GLF can be produced by orally administering a lavage fluid to a subject that causes a large volume of fluid to pass through the intestinal tract, the lavage fluid can contain a mixture of salts and other materials such as polyethylene glycol and bisacodyl. The lavage fluid causes an influx of liquid into the colon that causes a flushing out of solids. Lavage fluids are commonly used to cause clearing of the GI tract as is commonly used in preparation for a colonoscopy and other methods used to examine the GI tract. These liquids that are flushed out or remain in the largely cleared GI tract are useful to evaluate a variety of diseases due to the continuity of the mouth to the anus along the GI tract. Consequently, any and all organs, including the GI tract, which deposit fluids into the GI tract are candidates for the methods and compositions provided herein.

GI Tract and Associated Organs/Tissues

Some of the methods and compositions provided herein relate to the GI tract and organs/tissues associated with the GI tract including accessory digestive glands. As is well known in the art, the GI tract includes the upper GI tract and lower GI tract. The upper GI tract includes the oral or buccal cavity, esophagus, stomach and duodenum. The lower GI tract includes the jejunum, ileum and the large intestine and the anus. The large intestine includes the appendix, cecum, colon, and rectum.

Organs and tissues associated with the GI tract include structures outside the GI tract. Examples of such structures include accessory digestive organs such as salivary glands, e.g., parotid salivary glands, submandibular salivary glands, and sublingual salivary glands, pancreas, e.g., exocrine pancreas, gallbladder, bile duct, and liver. More examples of structures associated with the GI tract and outside the GI tract include the pancreatic duct, biliary tree, and bile duct.

Gastrointestinal Lavage Fluid (GLF)

Generally, a lavage fluid can be orally administered to a subject, the oral lavage fluid passes through the GI tract of the subject, and the resulting GLF is collected from the subject. As used herein, the term "subject" can include an animal, such as a mammal, such as a human. As noted above, GLF provides a cleaner sampling of the GI tract than the examination of feces/stool samples. GLFs appear to mitigate variability related to food intake, type and digestive status.

Some embodiments described herein include analysis of a GLF for detecting a target molecule or for screening, triage, disease detection, diagnosis, prognosis, response to treatment, selection of treatment and personalized medicine for diseases and pathological conditions of the gastrointestinal tract or associated organs/tissues. Some embodiments include analysis of a GLF sample for eliminating particular diseases and pathological conditions from the possible diseases or conditions from which a subject may be suffering. Some embodiments include analysis of a GLF for indicating the need for further testing for diagnosis. More embodiments include the analysis of GLF to establish a new disease diagnosis, further classifying a previous diagnosis, determining the sensitivity to potential treatment regimens, and/or evaluating the response to previous or ongoing treatment regimens.

Methods for Obtaining a GLF

Some embodiments of the methods and compositions provided herein include obtaining a GLF from a subject. Methods of obtaining a GLF are well known in the art. For example, during medical and or diagnostic procedures such as sigmoidoscopy, colonoscopy, radiographic examination, preparation for patients undergoing bowel surgery, it is important that the bowels and colon be thoroughly purged and cleaned. In particular, it is essential that as much fecal matter as possible be removed from the colon to permit adequate visualization of the intestinal mucosa. This is important prior to, for example, diagnostic procedures such as flexible sigmoidoscopy or colonoscopy, diagnostic examinations widely performed to screen patients for diseases of the colon. In addition, it is important that the intestines be cleansed thoroughly in order to obtain satisfactory radiographs of the colon. The same condition also applies when the colon is preoperatively prepared for surgery, where removal of fecal waste materials is critically important for patient safety. To prepare the colon for endoscopic exam, current cleaning procedures include orthograde colonic lavage. Orthograde lavage can include orally administering a lavage composition to a subject comprising 4 L of a polyethylene glycol/electrolyte solution (U.S. Patent Application Publication No. 20070298008, incorporated by reference in its entirety). Some embodiments include antegrade lavage and retrograde lavage.

Generally, oral lavage compositions include solutions of electrolytes, such as sodium, potassium and magnesium salts of sulfate, bicarbonate, chloride, phosphate or citrate. Some such compositions may also include polyethylene glycol, which can act as a non-absorbable osmotic agent. Generic compositions include polyethylene glycol with an electrolyte solution, optionally also including bisacodyl, or ascorbic acid, and compositions including sulfate salts such as sodium sulfate, magnesium sulfate, or potassium sulfate. In some embodiments, an oral lavage fluid can include magnesium citrate. In some embodiments, an oral lavage fluid can include sodium picosulfate. One example composition of an oral lavage solution comprising polyethylene glycol with an electrolyte solution is GOLYTELY (Braintree Labs. Inc.). GOLYTELY is formulated according to the following: polyethylene glycol 59 g, sodium sulfate 5.68 g, sodium bicarbonate 1.69 g, sodium chloride 1.46 g, potassium chloride 0.745 g and water to make up one liter (Davis et al. (1980) Gastroenterology 78:991-995, incorporated by reference in its entirety). Ingestion of GOLYTELY produces a voluminous, liquid stool with minimal changes in the subject's water and electrolyte balance. Another example of an oral lavage composition comprising polyethylene glycol with an electrolyte solution is NULYTELY (Braintree Labs. Inc.). An example oral lavage composition comprising polyethylene glycol with an electrolyte solution and bisacodyl is HALFLYTELY (Braintree Labs. Inc.). An example oral lavage composition comprising sulfate salts, such as sodium sulfate, magnesium sulfate, or potassium sulfate is SUPREP (Braintree Labs. Inc.). An example composition of an oral lavage solution comprising polyethylene glycol with an electrolyte solution and ascorbic acid is MOVIPREP (Salix Pharmaceuticals, Inc.).

Polyethylene glycol is effective as an oral lavage composition when large amounts of polyethylene glycol are administered in large volumes of a dilute salt solution. Usually about 250-400 g polyethylene glycol are administered to the subject in about 4 L of an electrolyte solution in water. Oral administration of polyethylene glycol can be used to produce a bowel movement over a period of time, e.g., overnight. The dose required will vary, but from about 10-100 g of polyethylene glycol in 8 oz. of water can be effective. A dose of from about 68-85 g of polyethylene glycol can be effective to produce an overnight bowel movement, without profuse diarrhea. A volume of a solution of polyethylene glycol in an isotonic fluid can be an effective amount of an osmotic laxative. Volumes from about 0.5 L to about 4 L can be effective. Preferably the effective volume is between about 1.5 L and about 2.5 L. Oral administration of 2 L of isotonic solution is effective.

More examples of oral lavage compositions include hypertonic solutions of non-phosphate salts with an osmotic laxative agent such as polyethylene glycol (U.S. Pat. App. No. 20090258090, incorporated by reference in its entirety). Mixtures of sulfate salts that omit phosphates, for example, effective amounts of one or more of the following sulfate salts $Na_2SO_4$, $MgSO_4$, and $K_2SO_4$ can be effective (e.g., SUPREP). Some embodiments include about 0.1 g to about 20.0 g $Na_2SO_4$, and from about 1.0 g to 10.0 g $Na_2SO_4$ may be useful. Dosage amounts of $MgSO_4$ from about 0.01 g to about 40.0 g can be effective. Doses of from about 0.1 g to about 20.0 g $Na_2SO_4$ may also be advantageously used, as well as dosages of 1.0 to 10.0 g. Dosage amounts of $K_2SO_4$ from about 0.01 g to about 20.0 g can be effective to produce purgation, and doses of from about 0.1 g to about 10.0 g and from about 0.5 g to about 5.0 g $K_2SO_4$ may also be useful. Addition of an osmotic laxative agent, such as polyethylene glycol (PEG) may improve the effectiveness of the above salt mixtures. Doses of PEG from about 1.0 g to about 100 g PEG are effective. Doses from about 10.0 g to about 50 g of PEG are also effective, as is a dose of about 34 g. For ease of administration, the above mixture of salts can be dissolved in a convenient volume of water. A volume of less than one liter of water can be well tolerated by most subjects. The mixture can be dissolved in any small volume of water, and volumes of between 100 and 500 ml are useful. The effective dose may be divided and administered to the patient in two or more administrations over an appropriate time period. Generally, administration of two doses of equal portions of the effective dose, separated by 6 to 24 hours produces satisfactory purgation. Some embodiments include cessation of normal oral intake during a defined period before and during administration of an oral lavage composition.

Some lavage compositions include a laxative, such as bisacodyl. In some embodiments, a laxative can be co-administered to a subject with a lavage composition. As will be understood, such co-administration can include, for example, administration of a laxative up to several hours before administration of a lavage composition to a subject, administration of a laxative with the administration of a lavage composition to a subject, or administration of a laxative up to several hours after administration of a lavage composition to a subject. Examples of laxatives and their effective doses include Aloe, 250-1000 mg.; Bisacodyl, about 5-80 mg.; Casanthranol, 30-360 mg.; Cascara aromatic fluid extract, 2-24 ml.; Cascara sagrada bark, 300-4000 mg.; Cascada sagrada extract, 300-2000 mg.; Cascara sagrada fluid extract, 0.5-5.0 ml.; Castor oil, 15-240 ml.; Danthron, 75-300 mg.; Dehydrocholic Acid, 250-2000 mg; Phenolphthalein, 30-1000 mg.; Sennosides A and B, 12-200 mg.; and Picosulfate, 1-100 mg.

More examples of lavage compositions include aqueous solutions of concentrated phosphate salts. The aqueous phosphate salt concentrate produces an osmotic effect on the intra-luminal contents of the GI tract, evacuation of the bowel occurs with a large influx of water and electrolytes into the colon from the body. One exemplary composition comprises 480 g/L monobasic sodium phosphate and 180 g/L dibasic sodium phosphate in stabilized buffered aqueous solution (FLEET'S PHOSPHO-SODA, C. S. Fleet Co., Inc.). Subjects are typically required to take 2-3 oz doses of this composition, separated by a three to 12 hour interval for a total of 6 ounces (180 ml).

GLF may be collected from a subject before, during, or after a medical or diagnostic procedure. In some embodiments, a subject may collect GLF, for example, using a receptacle such as a toilet insert which captures the fluid. Enzyme inhibitors and denaturants may be used to preserve the quality of the GLF. In some embodiments, the pH of the sample may be adjusted to help stabilize the samples. In some embodiments, GLF samples may be further treated to remove some or all solids and/or bacteria, such as by centrifugation. In some embodiments, the GI tract may not be fully purged by administration of an oral lavage composition. For example, a portion of a complete dose of an oral lavage composition required to fully purge the GI tract of a subject can be administered to the subject. In some embodiments, a GLF can comprise fecal matter. In more embodiments, fecal matter can comprise a GLF.

Target Molecules

Some embodiments described herein relate to methods of detecting target molecules in samples obtained from the GI tract or compositions useful for such detection. As used herein, "target molecule" includes any molecule that can be detected or measured or identified in a sample from the GI tract. Such samples include a GLF from a subject, and a fecal sample from a subject. Examples of target molecules include molecules such as peptides, polypeptides, proteins, mutant proteins, proteins generated from alternative splicing, modified proteins, such as post-translationally modified proteins e.g., glycosylated proteins, phosphorylated proteins, antibodies (e.g., autoantibodies, IgG, IgA, and IgM), antibody fragments, sugars, e.g., monosaccharides, disaccharides, oligosaccharides, and glycans, lipids, small molecules, e.g. metabolites, pharmaceutical compositions, metabolized pharmaceutical compositions, and pro-drugs. More examples of target molecules include bile salts and bile acids, e.g., cholic acid. More examples include chenodeoxycholic acid, glycocholic acid, taurocholic acid, deoxycholic acid, and lithocholic acid. Target molecules can originate in the GI tract and outside the GI tract, e.g., from organs and/or tissues associated with the GI tract, such as accessory digestive glands. In some embodiments, cells including their fragments and their other biproducts, e.g., red blood cells, white blood cells, and endothelial cells, organisms, e.g., bacteria, protozoans, and viruses and viral particles can be detected in a GLF or fecal samples. In some embodiments, the target molecules may be any of the proteins or portions thereof listed in any of Tables 1-10 herein or a portion thereof. In some embodiments, the portion of the proteins listed in any of Tables 1-10 can comprise at least 10, at least 15, at least 20, at least 25, at least 50, or more than 50 consecutive amino acids of any the proteins listed in Tables 1-10. In some embodiments, the target molecules may comprise, consist essentially of, or consist of a polypeptide of one of SEQ ID NO.s: 01-804. A polypeptide consisting essentially of one of SEQ ID NO.s: 01-804 may include additional amino acids or substituents beyond those in SEQ ID NO.s: 01-804 where such additional amino acids or substituents do not prevent the polypeptide from being detectable.

Target molecules also include biomarkers. As used herein, the term "biomarker" includes any target molecule present in a GLF or fecal sample that is associated with a disease, predisposition to disease, positive response to a particular treatment regimen, no response to a particular treatment regimen, or negative response to a particular treatment regimen. In some embodiments, a biomarker can be identified, measured and/or correlated with a diagnosis or prognosis of a disease.

In some embodiments, a target molecule is a component of a fluid of the subject selected from the group consisting of blood, saliva, gastric juice, hepatic secretion, bile, duodenal juice, and pancreatic juice. In some embodiments, a target molecule is expressed in the upper gastrointestinal tract of the subject, or the lower gastrointestinal tract of the subject. In some embodiments, a target molecule is expressed at a location in the subject selected from the group consisting of buccal cavity, esophagus, stomach, biliary tree, gallbladder, duodenum, jejunum, ileum, appendix, cecum, colon, rectum, and anal canal.

In some embodiments, a target molecule does not include a protein or other compound found in a GLF, for example, lactoferrin, eosinophil-derived neurotoxin, eosinophil cationic protein, bilirubin (Bil), alkaline phosphatase (ALP), aspartate aminotransferase, hemoglobin, or eosinophil peroxidase. In some embodiments, a target molecule does not include a protein found in feces, for example, heptaglobulin, hemopexin, α-2-macroglobulin, cadherin-17, calprotectin, carcinoembryogenic antigen, metalloproteinase-1 (TIMP-1), S100A12, K-ras, or p53. In some embodiments, a target molecule does not include a protein found in pancreatic juice, for example, anterior gradient-2 (AGR2), insulin-like growth factor binding protein-2, CEACAM6, MUC1, CA19-9, serine proteinase-2 (PRSS2) preproprotein, pancreatic lipase-related protein-1 (PLRP1), chymotrypsinogen B (CTRB), elastase 3B (ELA3B), tumor rejection antigen (pg96), azurocidin, hepatocarcinoma-intestine-pancreas/pancreatitis-associated-protein I (HIP/PAP-I), matrix metalloproteinase-9 (MMP-9), oncogene DJ1 (DJ-1), or alpha-1B-glycoprotein precursor (A1BG).

Methods for Characterizing Target Molecules

Some embodiments of the methods and compositions provided herein include characterizing a target molecule in a GLF or fecal sample. Characterizing a target molecule can include, for example, identifying a target molecule, detecting a target molecule, and/or quantifying a target molecule. Methods to identify, detect and quantify target molecule are well known in the art.

Some embodiments include identifying, determining the presence or absence of a target molecule, and/or quantifying a target molecule, wherein the target molecule comprises a peptide, polypeptide, and/or protein. Such target molecules may be characterized by a variety of methods such as immunoassays, including radioimmunoas says, enzyme-linked immunoassays and two-antibody sandwich assays as described herein. A variety of immunoassay formats, including competitive and non-competitive immunoassay formats, antigen capture assays and two-antibody sandwich assays also are useful (Self and Cook, (1996) Curr. Opin. Biotechnol. 7:60-65, incorporated by reference in its entirety). Some embodiments include one or more antigen capture assays. In an antigen capture assay, antibody is bound to a solid phase, and sample is added such that antigen, e.g., a target molecule in GLF or a fecal sample, is bound by the antibody. After unbound proteins are removed by washing, the amount of bound antigen can be quantitated, if desired, using, for example, a radioassay (Harlow and Lane, (1988) Antibodies A Laboratory Manual Cold Spring Harbor Laboratory: New York, incorporated by reference in its entirety). Immunoassays can be performed under conditions of antibody excess, or as antigen competitions, to quantitate the amount of antigen and, thus, determine a level of a target molecule in GLF or a fecal sample.

Enzyme-linked immunosorbent assays (ELISAs) can be useful in certain embodiments provided herein. An enzyme such as horseradish peroxidase (HRP), alkaline phosphatase (AP), β-galactosidase or urease can be linked, for example, to an anti-HMGB1 antibody or to a secondary antibody for use in a method of the invention. A horseradish-peroxidase detection system can be used, for example, with the chromogenic substrate tetramethylbenzidine (TMB), which yields a soluble product in the presence of hydrogen peroxide that is detectable at 450 nm. Other convenient enzyme-linked systems include, for example, the alkaline phosphatase detection system, which can be used with the chromogenic substrate p-nitrophenyl phosphate to yield a soluble product readily detectable at 405 nm. Similarly, a β-galactosidase detection system can be used with the chromogenic substrate o-nitrophenyl-β-D-galactopyranoside (ONPG) to yield a soluble product detectable at 410 nm, or a urease detection system can be used with a substrate such as urea-bromocresol purple (Sigma Immunochemicals). Useful enzyme-linked primary and secondary antibodies can be obtained from a number of commercial sources such as Jackson Immuno-Research (West Grove, Pa.) as described further herein.

In certain embodiments, a target molecule in GLF or a fecal sample can be detected and/or measured using chemiluminescent detection. For example in certain embodiments, specific antibodies to a particular target molecule are used to capture the target molecule present in the biological sample, e.g., GLF or a fecal sample and an antibody specific for the target molecule-specific antibodies and labeled with an chemiluminescent label is used to detect the target molecule present in the sample. Any chemiluminescent label and detection system can be used in the present methods. Chemiluminescent secondary antibodies can be obtained commercially from various sources such as Amersham. Methods of detecting chemiluminescent secondary antibodies are known in the art.

Fluorescent detection also can be useful for detecting a target molecule in certain methods provided herein. Useful fluorochromes include, DAPI, fluorescein, Hoechst 33258, R-phycocyanin, B-phycoerythrin, R-phycoerythrin, rhodamine, Texas red and lissamine. Fluorescein or rhodamine labeled antibodies, or fluorescein- or rhodamine-labeled secondary antibodies can be useful in the invention.

Radioimmunoassays (RIAs) also can be useful in certain methods provided herein. Such assays are well known in the art. Radioimmunoassays can be performed, for example, with $^{125}$I-labeled primary or secondary antibody (Harlow and Lane, supra, 1988).

A signal from a detectable reagent can be analyzed, for example, using a spectrophotometer to detect color from a chromogenic substrate; a radiation counter to detect radiation, such as a gamma counter for detection of $^{125}$I; or a fluorometer to detect fluorescence in the presence of light of a certain wavelength. Where an enzyme-linked assay is used, quantitative analysis of the amount of a target molecule can be performed using a spectrophotometer such as an EMAX Microplate Reader (Molecular Devices; Menlo Park, Calif.) in accordance with the manufacturer's instructions. The assays of the invention can be automated or performed robotically, if desired, and that the signal from multiple samples can be detected simultaneously.

In some embodiments, capillary electrophoresis based immunoassays (CEIA), which can be automated if desired, may be used to detect and/or measure the target molecule. Immunoassays also can be used in conjunction with laser-induced fluorescence as described, for example, in Schmalzing and Nashabeh, Electrophoresis 18:2184-93 (1997), and Bao, J. Chromatogr. B. Biomed. Sci. 699:463-80 (1997), each incorporated by reference in its entirety. Liposome immunoassays, such as flow-injection liposome immunoassays and liposome immunosensors, also can be used to detect target molecules or to determine a level of a target molecule according to certain methods provided herein (Rongen et al., (1997) J. Immunol. Methods 204:105-133, incorporated by reference in its entirety).

Sandwich enzyme immunoassays also can be useful in certain embodiments. In a two-antibody sandwich assay, a first antibody is bound to a solid support, and the antigen is allowed to bind to the first antibody. The amount of a target molecule is quantitated by measuring the amount of a second antibody that binds to it.

Quantitative Western blotting also can be used to detect a target molecule or to determine a level of target molecule in a method provided herein. Western blots can be quantitated by well known methods such as scanning densitometry. As an example, protein samples are electrophoresed on 10% SDS-PAGE Laemmli gels. Primary murine monoclonal antibodies, for example, against a target molecule are reacted with the blot, and antibody binding confirmed to be linear using a preliminary slot blot experiment. Goat anti-mouse horseradish peroxidase-coupled antibodies (BioRad) are used as the secondary antibody, and signal detection performed using chemiluminescence, for example, with the Renaissance chemiluminescence kit (New England Nuclear; Boston, Mass.) according to the manufacturer's instructions. Autoradiographs of the blots are analyzed using a scanning densitometer (Molecular Dynamics; Sunnyvale, Calif.) and normalized to a positive control. Values are reported, for example, as a ratio between the actual value to the positive control (densitometric index). Such methods are well known in the art as described, for example, in Parra et al., J. Vasc. Surg. 28:669-675 (1998), incorporated herein by reference in its entirety.

As described herein, immunoassays including, for example, enzyme-linked immunosorbent assays, radioimmunoassays and quantitative western analysis, can be useful in some embodiments for detecting a target molecule or determining a level of a target molecule. Such assays typically rely on one or more antibodies. As would be understood by the skilled artisan, methods described herein can be used to readily distinguish proteins with alternative forms of post-translation modifications, e.g., phosphorylated proteins, and glycosylated proteins.

Target molecules, such as protein target molecules, can be characterized by a variety of methods. Proteins, polypeptides and peptides can be isolated by a variety of methods well known in the art, such as protein precipitation, chromatography (e.g., reverse phase chromatography, size exclusion chromatography, ion exchange chromatography, liquid chromatography), affinity capture, and differential extractions.

Isolated proteins can under go enzymatic digestion or chemical cleavage to yield polypeptide fragments and peptides. Such fragments can be identified and quantified. A particularly useful method for analysis of polypeptide/peptide fragments and other target molecules is mass spectrometry (U.S. Pat. App. No. 20100279382, incorporated by reference in its entirety). A number of mass spectrometry-based quantitative proteomics methods have been developed that identify the proteins contained in each sample and determine the relative abundance of each identified protein across samples (Flory et al., Trends Biotechnol. 20:S23-29 (2002); Aebersold, J. Am. Soc. Mass Spectrom. 14:685-695 (2003); Aebersold, J. Infect. Dis. 187 Suppl 2:S315-320 (2003); Patterson and Aebersold, Nat. Genet. 33 Suppl, 311-323 (2003); Aebersold and Mann, Nature 422:198-207 (2003); Aebersold, R. and Cravatt, Trends Biotechnol. 20:S1-2 (2002); Aebersold and Goodlett, Chem. Rev. 101, 269-295 (2001); Tao and Aebersold, Curr. Opin. Biotechnol. 14:110-118 (2003), each incorporated by reference in its entirety). Generally, the proteins in each sample are labeled to acquire an isotopic signature that identifies their sample of origin and provides the basis for accurate mass spectrometric quantification. Samples with different isotopic signatures are then combined and analyzed, typically by multidimensional chromatography tandem mass spectrometry. The resulting collision induced dissociation (CID) spectra are then assigned to peptide sequences and the relative abundance of each detected protein in each sample is calculated based on the relative signal intensities for the differentially isotopically labeled peptides of identical sequence.

More techniques for identifying and quantifying target molecules label-free quantitative proteomics methods. Such methods include: (i) sample preparation including protein extraction, reduction, alkylation, and digestion; (ii) sample separation by liquid chromatography (LC or LC/LC) and analysis by MS/MS; (iii) data analysis including peptide/protein identification, quantification, and statistical analysis. Each sample can be separately prepared, then subjected to individual LC-MS/MS or LC/LC-MS/MS runs (Zhu W. et al., J. of Biomedicine and Biotech. (2010) Article ID 840518, 6 pages, incorporated by reference in its entirety). An example technique includes LC-MS in which the mass of a peptide coupled with its corresponding chromatographic elution time as peptide properties that uniquely define a peptide sequence, a method termed the accurate mass and time (AMT) tag approach. Using LC coupled with Fourier transform ion cyclotron resonance (LC-FTICR) MS to obtain the chromatographic and high mass accuracy information, peptide sequences can be identified by matching the AMT tags to previously acquired LC-MS/MS sequence information stored in a database. By taking advantage of the observed linear correlation between peak area of measured peptides and their abundance, these peptides can be relatively quantified by the signal intensity ratio of their corresponding peaks compared between MS runs (Tang, K., et al., (2004) J. Am. Soc. Mass Spectrom. 15:1416-1423; and Chelius, D. and Bondarenko, P. V. (2002) J. Proteome Res. 1: 317-323, incorporated by reference in their entireties). Statistics tools such as the Student's t-test can be used to analyse data from multiple LC-MS runs for each sample (Wiener, M. C., et al., (2004) Anal. Chem. 76:6085-6096, incorporated by reference in its entirety). At each point of acquisition time and m/z, the amplitudes of signal intensities from multiple LC-MS runs can be compared between two samples to detect peptides with statistically significant differences in abundance between samples.

As will be understood, a variety of mass spectrometry systems can be employed in the methods for identifying and/or quantifying a polypeptide/peptide fragments. Mass analyzers with high mass accuracy, high sensitivity and high resolution include, ion trap, triple quadrupole, and time-of-flight, quadrupole time-of-flight mass spectrometeres and Fourier transform ion cyclotron mass analyzers (FT-ICR-MS). Mass spectrometers are typically equipped with matrix-assisted laser desorption (MALDI) or electrospray ionization (ESI) ion sources, although other methods of peptide ionization can also be used. In ion trap MS, analytes are ionized by ESI or MALDI and then put into an ion trap. Trapped ions can then be separately analyzed by MS upon selective release from the ion trap. Fragments can also be generated in the ion trap and analyzed. Sample molecules such as released polypeptide/peptide fragments can be analyzed, for example, by single stage mass spectrometry with a MALDI-TOF or ESI-TOF system. Methods of mass spectrometry analysis are well known to those skilled in the art (see, e.g., Yates, J. (1998) Mass Spect. 33:1-19; Kinter and Sherman, (2000) Protein Sequencing and Identification Using Tandem Mass. Spectrometry, John Wiley & Sons, New York; and Aebersold and Goodlett, (2001) Chem. Rev. 101:269-295, each incorporated by reference in its entirety).

For high resolution polypeptide fragment separation, liquid chromatography ESI-MS/MS or automated LC-MS/MS, which utilizes capillary reverse phase chromatography as the separation method, can be used (Yates et al., Methods Mol. Biol. 112:553-569 (1999), incorporated by reference in its entirety). Data dependent collision-induced dissociation (CID) with dynamic exclusion can also be used as the mass spectrometric method (Goodlett, et al., Anal. Chem. 72:1112-1118 (2000), incorporated by reference in its entirety).

Once a peptide is analyzed by MS/MS, the resulting CID spectrum can be compared to databases for the determination of the identity of the isolated peptide. Methods for protein identification using single peptides have been described previously (Aebersold and Goodlett, Chem. Rev. 101:269-295 (2001); Yates, J. Mass Spec. 33:1-19 (1998), David N. et al., Electrophoresis, 20 3551-67 (1999), each incorporated by reference in its entirety). In particular, it is possible that one or a few peptide fragments can be used to identify a parent polypeptide from which the fragments were derived if the peptides provide a unique signature for the parent polypeptide. Moreover, identification of a single peptide, alone or in combination with knowledge of a site of glycosylation, can be used to identify a parent glycopolypeptide from which the glycopeptide fragments were derived. As will be understood, methods that include MS can be used to characterize proteins, fragments thereof, as well as other types of target molecules described herein.

Some embodiments can include enriching proteins and/or protein fractions of a GLF. Example methods can include protein precipitation, chromatography, such as reverse phase chromatography, size exclusion chromatography, ion exchange chromatography, liquid chromatography, as well as affinity capture, differential extraction methods and centrifugation. Proteins and/or protein fractions can be further examined using intact protein methods such as top-down proteomics or gel chromatography such as SDS-PAGE.

Some embodiments include identifying, determining the presence or absence of a target molecule, and/or quantifying a target molecule, wherein the target molecule comprises a glycosylated protein and/or glycan. Glycosylated proteins and glycans can be analyzed by various methods well known in the art. Changes in glycosylation can be indicative of a disease or disease state. Thus, particular target molecules can include particular glycosylated proteins and/or glycans. As will be understood, a glycan may be a component of a glycoprotein, proteoglycan or other glycan containing compounds.

Some embodiments include identifying, determining the presence or absence of a target molecule, and/or quantifying a target molecule, wherein the target molecule comprises a metabolite. Metabolites may be analyzed in a GLF or fecal sample using a variety of methods. For example, a GLF or fecal sample can be analyzed for metabolites using methods such as chromatography. Some components of the metabolome include bile acids and other small organic compounds. Metabolites can include peptides that are present in a GLF or fecal sample.

Methods for Identifying Biomarkers

In some embodiments, the target molecules detected in GLF or a fecal sample can be evaluated to determine whether they are biomarkers associated with a particular condition, such as a disease, or physiological state. Such biomarkers can be indicative for a particular disease, predisposition to disease, prognosis, positive response to a particular treatment regimen, or negative response to a particular treatment regimen. In some embodiments, the presence or absence, or level of a biomarker can be associated with a particular condition, such as a disease, or physiological state. In some embodiments, the presence or absence, or level of a biomarker can be statistically correlated to the particular condition, such as a disease, or physiological state. In some embodiments, a physiological state can include a disease. In some embodiments, a biomarker can be correlated to a particular condition, such as disease, or physiological state by comparing the level of expression of a biomarker in a subject having a condition, such as a disease, or physiological state with the level of expression of the biomarker in a subject not having a condition or physiological state.

In some embodiments, the differential expression of a biomarker in a subject having a condition compared to the expression of a biomarker in a subject not having a condition is indicative of a condition or physiological state. As used herein, "differential expression" refers to a difference in the level of expression of a biomarker in a subject having a condition, such as a disease, or physiological state and a subject not having the condition, such as a disease, or physiological state. For example, the term "differential expression" can refer to the presence or absence of a biomarker in a subject having a condition, such as a disease, or physiological state compared with a subject not having a condition or physiological state. In some embodiments, differential expression can refer to a difference in the level of expression of a biomarker in a subject having a condition, such as disease, or physiological state compared with the level of expression of a biomarker in a subject not having the condition, such as a disease, or physiological state.

Differences in the level of a biomarker can be determined by measuring the amount or level of expression of a biomarker using methods provided herein. In some embodiments, differential expression can be determined as the ratio of the levels of one or more biomarker products between reference subjects/populations having or not having a condition or physiological state, wherein the ratio is statistically significant. Differential expression between populations can be determined to be statistically significant as a function of p-value. When using p-value to determine statistical significance, a biomarker, the p-value is preferably less than 0.2. In another embodiment, the biomarker is identified as being differentially expressed when the p-value is less than 0.15, 0.1, 0.05, 0.01, 0.005, 0.0001 etc. When determining differential expression on the basis of the ratio, a biomarker product is differentially expressed if the ratio of the level of expression in a first sample as compared with a second sample is greater than or less than 1.0. For example, a ratio of greater than 1.0 for example includes a ratio of greater than 1.1, 1.2, 1.5, 1.7, 2, 3, 4, 10, 20 and the like. A ratio of less than 1.0, for example, includes a ratio of less than 0.9, 0.8, 0.6, 0.4, 0.2, 0.1, 0.05 and the like. In another embodiment, a biomarker can be differentially expressed if the ratio of the mean of the level of expression of a first population as compared with the mean level of expression of the second population is greater than or less than 1.0. For example, a ratio of greater than 1.0 includes a ratio of greater than 1.1, 1.2, 1.5, 1.7, 2, 3, 4, 10, 20 and the like and a ratio less than 1.0, for example includes a ration of less than 0.9, 0.8, 0.6, 0.4, 0.2, 0.1, 0.05 and the like. In another embodiment a biomarker is differentially expressed if the ratio of its level of expression in a first sample as compared with the mean of the second population is greater than or less than 1.0 and includes for example, a ratio of greater than 1.1, 1.2, 1.5, 1.7, 2, 3, 4, 10, 20, or a ratio less than 1, for example 0.9, 0.8, 0.6, 0.4, 0.2, 0.1, 0.05.

In some embodiments, a biomarker can be identified by measuring the level of at least 1 target molecule in a test GLF or test fecal sample from at least one test subject having a condition or physiological state and a control GLF or control fecal sample from at least 1 control subject not having the condition or physiological state; comparing the level of the at least 1 target molecule in the test GLF or test fecal sample with the level of the at least 1 target molecule in the control GLF or control fecal sample, wherein a significant difference in the level of the at least 1 target identifies a biomarker. Some embodiments include measuring and comparing a plurality of target molecules in a test GLF or test fecal sample from plurality of test subjects having a condition or physiological state and a control GLF or control fecal sample from plurality of control subjects not having a condition or physiological state. In some embodiments, at least 5, 10, 15, 20, 25, 30, 35, 40, 45, 50, 55, 60, 65, 70, 75, 80, 85, 90, 95, or 100 target molecules can be measured and compared. In some embodiments, a GLF or fecal sample can be obtained from at least 5, 10, 15, 20, 25, 30, 35, 40, 45, 50, 55, 60, 65, 70, 75, 80, 85, 90, 95, or 100 test subjects. In some embodiments, a GLF or fecal sample can be obtained from at least 5, 10, 15, 20, 25, 30, 35, 40, 45, 50, 55, 60, 65, 70, 75, 80, 85, 90, 95, or 100 control subjects. In some embodiments, a significant difference in the level of a target molecule in a test GLF or a test fecal sample compared to a control GLF or a control fecal sample can be a statistically significant.

Kits

Some embodiments of the methods and compositions provided herein relate to kits for detecting a target molecule in a GLF or fecal sample, determining the presence or absence of a target molecule in a GLF or fecal sample, quantifying a target molecule in a GLF or fecal sample, or identifying a target molecule in a GLF or fecal sample. Some such kits can include a lavage composition for oral administration to a subject. In some embodiments, the lavage fluid can include an ingredient such as polyethylene glycol, magnesium sulfate, sodium sulfate, potassium sulfate, magnesium citrate, and bisacodyl. In some embodiments, the lavage fluid can include polyethylene glycol with an electrolyte solution, optionally also including bisacodyl, or ascorbic acid (e.g., GOLYTELY, HALFLYTELY, NULYTELY, MOVIPREP). In some embodiments, the lavage fluid can include phosphate salts (e.g. FLEET'S PHOSPHO-SODA). In some embodiments, the lavage fluid can include sulfate salts such as sodium sulfate, magnesium sulfate, or potassium sulfate (e.g., SUPREP). In some embodiments, the lavage fluid can include magnesium citrate. In some embodiments, the lavage fluid can include sodium picosulfate.

In some embodiments, a kit can also include a vessel for collecting a GLF and/or fecal sample from a subject. A vessel for collecting a GLF can include an insert for a toilet which captures the GLF or fecal sample and the like. In some embodiments, the vessel can include a material to stabilize and/or preserve a target molecule, such as one or more isolated protease inhibitors. In some embodiments, the vessel can include an agent for detecting a target molecule, determining the presence or absence of a target molecule, quantifying a target molecule or identifying a target molecule.

Diseases

Some embodiments of the methods and compositions provided herein relate to the diagnosis, prognosis for a particular disease. Some embodiments include diseases and disorders related to the GI tract and organs associated therewith. Example diseases include cancers of the GI tract and organs associated therewith, e.g., gastric cancer, liver cancer, pancreatic cancer. More examples of diseases include pancreatitis, pancreatic adenocarcinoma, gastrointestinal neuroendocrine tumors, gastric adenocarcinoma, colon adenocarcinoma, hepatocellular carcinoma, cholangiocarcinoma, gallbladder adenoccarcinoma, ulcerative colitis, and Crohn's disease. Some diseases relate to an inflammatory bowel disease (IBD). As used herein, the term "inflammatory bowel disease" can refer to a broad class of diseases characterized by inflammation of at least part of the gastrointestinal tract. IBD symptoms may include inflammation of the intestine and resulting in abdominal cramping and persistent diarrhea. Inflammatory bowel diseases include ulcerative colitis (UC), Crohn's disease (CD), indeterminate colitis, chronic colitis, discontinuous or patchy disease, ileal inflammation, extracolonic inflammation, granulomatous inflammation in response to ruptured crypts, aphthous ulcers, transmural inflammation, microscopic colitis, diverticulitis and diversion colitis. More examples of diseases include celiac sprue, malabsorption disorders, and other conditions of digestive tract, liver, pancreas, and biliary tree.

Some embodiments of the methods and compositions provided herein relate to determining the selection of a treatment (often referred to as personalized medicine), a subject's positive response to treatment, negative response to treatment, or lack of response to treatment. Some such embodiments include determining a patient's partial response to a treatment regimen. For example, the presence of a biomarker, absence of a biomarker, or level of a biomarker can be determined in a GLF or fecal sample from a subject at a first time point. At a second time point after treatment has begun and/or treatment has been completed, the presence of the biomarker, absence of the biomarker, or level of the biomarker can be determined in a GLF or fecal sample from the subject. The difference in the presence of the biomarker, absence of the biomarker, or level of the biomarker in the GLF or fecal sample at the second time point compared with the presence of the biomarker, absence of the biomarker, or level of the biomarker in the GLF or fecal sample from the first time point can be indicative of the subject's positive response to treatment, negative response to treatment, partial response to treatment, or lack of response to treatment. Alternatively, subjects can be given a treatment regimen and categorized as having a positive response, negative response, partial response, or no response. The presence, absence, or level of a target molecule in each group of subjects can be determined and those target molecules having a statistically significant association with each category of response can be identified. Some embodiments also include determining a future treatment regimen to be provided to a subject in view of determining the subject's positive response, negative response, partial response, or no response to a former or current treatment regimen. Accordingly, a former or current treatment regimen can be modified based on determinations made by the methods provided herein.

More embodiments include methods for determining a subject's physiological status by evaluating a plurality of biomarkers. Some such methods include determining the presence, absence and/or levels of a plurality of biomarkers. The presence, absence and/or levels of a plurality of biomarkers can be correlated to the likelihood of the subject's physiological status, such as the subject's likelihood of developing a disease, and/or a subject's likely response to a treatment regimen to treat a particular disease. In some such methods, a subject's "clinical risk score" can be determined by correlating the presence, absence and/or levels of a plurality of biomarkers to determine the likelihood that a subject has a disease or will develop a disease (see, e.g., Soonmyung P. et al., (2004) New Eng. J. of Medicine 351:2817-2826; and Cho C. S. et al., (2008) J. Am. Coll. Surg. 206:281-291, incorporated by reference herein in their entireties).

While the present invention has been described in some detail for purposes of clarity and understanding, one skilled in the art will appreciate that various changes in form and detail can be made without departing from the true scope of the invention.

EXAMPLES

Example 1—Proteomic Analysis of Sulfate-Based GLF

In this analysis, the ability of a sulfate-based GLF to support proteomic analysis was assessed. To identify target molecules in a GLF obtaining using a sulfate-based lavage composition, SUPREP was administered to three human subjects, and proteins in the resultant GLF were analyzed by mass spectroscopy. In this example, the GLF was collected from subjects as part of a colonoscopy procedure.

Upon collection, a complete protease inhibitor tablet (ROCHE) was added and samples were spun at 1000 rpm for 30 minutes at 4° C. Supernatants were spun again at 14,000×g for 30 min to pellet bacteria and debris. 1.8 ml of supernatant was precipitated with 6 volumes of acetone followed by extraction with an equal volume of chloroform followed by separation on a C-2 reverse phase SPE column (Sep-Pak, Waters). The column was washed with 3 column volumes each of 0.1% trifluoroacetic acid (TFA), 10%, 20%, and 30% acetonitrile (ACN) in 0.1% TFA, and eluted with 3 column volumes of 60% ACN in 0.1% TFA. Samples were dried by centrifugal lyophilization, resuspended in 100 µl of 50 mM ammonium bicarbonate/10 mM tris(2-carboxyethyl) phosphine and digested with 2 µl of 10 mM sequencing-grade trypsin (Promega, Madison, Wis.).

Data were acquired on an LTQ-Orbitrap mass spectrometer using input from an LC system. The A solvent contained 3% of B and 0.2% formic acid in water. The B solvent contained 3% of A and 0.2% formic acid in acetonitrile. Solvents were HPLC grade from Fisher. For a 120 min run, the starting solvent was 5% B and remains for 7 min. The gradient was changed to 10% by 13 min, 40% by 83 min, 90% by 103 min, then reduced from 90% to 5% at 111 min. It was then re-equilibrated for the next injection. Three injections were performed for each sample for repeatability determination.

The MS was scanned (Orbitrap) over the mass range from 400 m/z to 2000 m/z every second while the LTQ (Trap) acquired up to 5 MSMS (peptide sequence) spectra in parallel. Data were acquired using the standard Thermo Xcalibur software. MS data (Orbitrap) was stable to 2-3 ppm and a background ion was used for mass drift assessment. MSMS data (LTQ) was measured to approximately 0.6 Da but the parent mass was acquired from the low ppm Orbitrap data. Peptides were eluted from a C18 LC column using triplicate injections to ensure reliability and repeatability of the data. A search file was created from the triplicate injections from each lavage preparation (patient sample) and converted into a MGF (Mascot Generic Format) file using a combination of Xcalibur and Mascot software packages.

Database searching was done using the Mascot search engine (Matrix Science, UK) against the RefSeq database (http://www.ncbi.nlm.nih.gov/RefSeq/) with taxonomy specified as human (*homo sapiens*), a mass accuracy of 10 ppm for the parent ion (MS) and 0.6 Da for the fragment ions (MS/MS), and "no enzyme" selected. Searching without enzyme specificity was performed due to the presence of digestive enzymes in the sample that may modify or truncate peptides being examined. The RefSeq database was supplemented by the addition of antibody sequences that are included in the SwissProt protein database, as these antibody sequences are not part of the standard RefSeq listing.

Higher Mascot scores indicate better proteins hits and can be correlated to relative protein levels. A score threshold of ">40" was indicative of a p-value significance of <0.05 as determined by the Mascot scoring system based on the search of this database with no enzyme specificity; a score of 40 is consistent with a p<0.01. Standard Mascot scoring was used whereby only the highest score was added for each peptide detected, even if it was sampled during MS/MS multiple times. For all data included, scores were all >40 in at least one sample per protein line. For additional confidence, the numbers of significant peptides were also reported and a minimum criterion of at least 2 peptides was selected. Very few had less than 3 peptides. All significant peptides counted represented different sequences (individual peptides) from their respective proteins. The score and numbers of significant peptides are reported in the format x/y where x is the score and y the number of significant peptides. If a protein was not detected in a particular sample it is listed as "ND". Proteins are reported as protein name and the "gi" number defined by the protein database of the NCBI has been provided. The sequences contained in each of the "gi" numbers in the NCBI database listed throughout the present application are incorporated herein by reference. Where a protein is named in its preprotein or other non-mature form, the mature form of the protein is equally implied including such changes as removal of signal sequences and the addition of post-translational modifications. In all cases, the protein has been named by its gene derived sequence to provide consistency.

Table 1 lists examples of the most abundant proteins identified in GLF from three separate patients defined as patients 3, 4 and 6, presented in the format described above. As can be seen from Table 1, many proteins can be identified from GLF and a large number of these may be associated with the pancreas. Other proteins include DMBT1 (gi #148539840) which may be associated with colon cancer and other cancers. Antibodies and putative glycosylated proteins were also identified.

TABLE 1

| NCBI gi # | Protein | Mascot score/number of significant peptides | | |
|---|---|---|---|---|
| | | Sample 3 | Sample 4 | Sample 6 |
| 10835000 | pancreatic lipase precursor | 2224/24 | 1238/13 | 2926/34 |
| 4506147 | protease serine 2 preproprotein | 665/7 | 46/0 | 1189/11 |
| 4506145 | protease serine 1 preproprotein | 239/2 | 64/0 | 1002/11 |
| 29725633 | regenerating islet-derived 1 alpha precursor | 231/2 | 132/1 | 802/6 |
| 6679625 | elastase 3B pancreatic preproprotein | 852/12 | 1144/11 | 772/8 |
| 236460050 | elastase 3A pancreatic preproprotein | 1291/17 | 1306/14 | 769/7 |
| 118498350 | chymotrypsin B2 | 945/10 | 244/2 | 724/6 |
| 15559207 | elastase 2A preproprotein | 752/10 | 952/8 | 593/6 |
| 54607080 | pancreatic carboxypeptidase B1 preproprotein | 702/9 | 84/1 | 499/4 |
| 50363217 | serine proteinase inhibitor clade A member 1 | 655/9 | 406/3 | 490/2 |
| 10280622 | amylase pancreatic alpha-2B precursor | ND | ND | 388/2 |
| 4505847 | phospholipase A2 group IB | 258/3 | 639/8 | 384/5 |
| 4502085 | pancreatic amylase alpha 2A precursor | 95/1 | 193/3 | 365/2 |
| 4502997 | carboxypeptidase A1 precursor | 454/4 | 88/1 | 349/5 |
| 62526043 | chymotrypsin C preproprotein | 696/9 | 440/3 | 343/4 |
| 148539840 | deleted in malignant brain tumors 1 isoform a precursor (DMBT1) | 88/1 | 101/1 | 280/3 |
| 31377806 | polymeric immunoglobulin receptor precursor | 566/7 | ND | 279/3 |
| 41152086 | serine (or cysteine) proteinase inhibitor clade B (ovalbumin) member 6 | ND | 269/3 | 276/2 |
| 148539842 | deleted in malignant brain tumors 1 isoform b precursor | ND | ND | 275/3 |
| 4507149 | superoxide dismutase 1 soluble | ND | 87/1 | 253/3 |
| 113584 | RecName: Full = Ig alpha-1 chain C region | 940/10 | 53/1 | 204/2 |
| 125145 | RecName: Full = Ig kappa chain C region | 659/9 | 106/1 | 180/1 |
| 98986445 | carcinoembryonic antigen-related cell adhesion molecule 5 preproprotein | ND | 219/3 | 135/0 |
| 218512088 | RecName: Full = Ig alpha-2 chain C region | 886/9 | ND | ND |
| 119395750 | keratin 1 | ND | 499/7 | ND |
| 55956899 | keratin 9 | ND | 395/3 | ND |

In another experiment, SUPREP was administered to a subject according to the manufacturer's guidelines and the resultant GLF was self-collected by the subject into a collection container placed in the toilet immediately prior to colonoscopy. The proteome of the GLF was analyzed by MS as described above. The results showing the Mascot scores for the most abundant species present are summarized in Table 2. The results indicated some urinary contamination. A similar proteomic profile was observed for a sample collected subsequently during colonoscopy. Table 2 shows that many different proteins were identified in GLF collected by a subject. Identified proteins included DMBT1, pancreatic proteins and antibodies, consistent with data in Table 1.

TABLE 2

| NCBI gi # | Protein | Mascot score/number of significant peptides Sample 25 |
|---|---|---|
| 148539842 | deleted in malignant brain tumors 1 isoform b precursor | 1184/13 |
| 119395750 | keratin 1 | 742/9 |
| 10835000 | pancreatic lipase precursor | 538/8 |
| 113584 | RecName: Full = Ig alpha-1 chain C region | 506/6 |
| 31377806 | polymeric immunoglobulin receptor precursor | 474/5 |
| 98986445 | carcinoembryonic antigen-related cell adhesion molecule 5 preproprotein | 424/5 |
| 125817 | RecName: Full = Ig kappa chain V-III region HAH; Flags: Precursor | 382/5 |

TABLE 2-continued

| NCBI gi # | Protein | Mascot score/number of significant peptides Sample 25 |
|---|---|---|
| 125797 | RecName: Full = Ig kappa chain V-III region SIE | 341/5 |
| 54607080 | pancreatic carboxypeptidase B1 preproprotein | 340/5 |
| 236460050 | elastase 3A pancreatic preproprotein | 328/4 |
| 125145 | RecName: Full = Ig kappa chain C region | 327/5 |
| 4502027 | albumin preproprotein | 319/3 |
| 33456 | immunoglobulin M chain | 239/3 |
| 118498350 | chymotrypsin B2 | 238/3 |
| 125811 | RecName: Full = Ig kappa chain V-III region VG; Flags: Precursor | 237/3 |
| 123843 | RecName: Full = Ig heavy chain V-III region VH26; Flags: Precursor | 219/3 |
| 157266300 | membrane alanine aminopeptidase precursor | 213/3 |
| 563454 | Ig heavy chain (VH4) V region (VDJ) | 206/3 |
| 125788 | RecName: Full = Ig kappa chain V-II region TEW | 202/3 |
| 4506147 | protease serine 2 preproprotein | 177/3 |
| 125809 | RecName: Full = Ig kappa chain V-III region CLL; AltName: Full = Rheumatoid factor; Flags: Precursor | 149/3 |

The foregoing analyses demonstrate that a large number of target molecules can be detected in samples obtained using a sulfate-based GLF.

Example 2—Proteomic Analysis of Polyethylene Glycol Based GLF

In this analysis, the ability of a polyethylene glycol based GLF to support proteomic analysis was assessed. To identify target molecules in a GLF obtaining using a polyethylene-based lavage composition, a polyethylene glycol-based lavage composition was administered to two human subjects, and proteins in the resultant GLF were analyzed by mass spectrometry as described in Example 1. Removal of the polyethylene glycol was largely achieved by chloroform extraction of the lavage fluid. Many different proteins were identified in the GLFs from these subjects administered a polyethylene glycol-based lavage composition. Examples of the most abundant identified proteins identified, which are consistent with those observed in previous tables, are presented in Table 3.

TABLE 3

| | | Mascot score/number of significant peptides | |
|---|---|---|---|
| NCBI gi# | Protein | Sample 1 | Sample 5 |
| 98986445 | carcinoembryonic antigen-related cell adhesion molecule 5 preproprotein | 767/10 | 127/1 |
| 4502085 | pancreatic amylase alpha 2A precursor | 619/8 | ND |
| 1684927 | immunoglobulin light chain | 586/6 | 152/1 |
| 50363217 | serine proteinase inhibitor clade A member 1 | 550/4 | 268/2 |
| 40254482 | salivary amylase alpha 1A precursor | 548/6 | ND |
| 298351713 | RecName: Full = Ig lambda-1 chain C regions | 501/6 | 139/1 |
| 4507725 | transthyretin precursor | 477/5 | ND |
| 236460050 | elastase 3A pancreatic preproprotein | 432/5 | 84/0 |
| 4502997 | carboxypeptidase A1 precursor | 412/5 | 106/1 |
| 113584 | RecName: Full = Ig alpha-1 chain C region | 404/4 | 214/3 |
| 4885165 | cystatin A | 352/4 | 66/1 |
| 40255013 | carcinoembryonic antigen-related cell adhesion molecule 6 (non-specific cross reacting antigen) | 349/3 | ND |
| 4506147 | protease serine 2 preproprotein | 326/5 | 434/6 |
| 125145 | RecName: Full = Ig kappa chain C region | 291/4 | 265/5 |
| 218512088 | RecName: Full = Ig alpha-2 chain C region | 272/3 | ND |
| 121039 | RecName: Full = Ig gamma-1 chain C region | 265/3 | ND |
| 54607080 | pancreatic carboxypeptidase B1 preproprotein | 263/2 | ND |

In another experiment, a PEG-based lavage composition was administered to a subject and the subject self-collected the resultant GLF into a collection container placed in the toilet immediately prior to colonoscopy. The proteome of the GLF was analyzed by MS as described herein. Many different proteins were identified in the self collected GLF sample. Examples of the most abundant identified proteins, and the corresponding Mascot scores and numbers of significant peptides for each protein are listed in Table 4. The more extensive protein list showed evidence of urinary contamination. A similar proteomic profile was observed for a sample collected subsequently during colonoscopy.

TABLE 4

| NCBI gi # | Protein | Mascot score/number of significant peptides Sample 26 |
|---|---|---|
| 50363217 | serine proteinase inhibitor clade A member 1 | 406/3 |
| 4885165 | cystatin A | 294/3 |
| 4502027 | albumin preproprotein | 287/3 |
| 55956899 | keratin 9 | 287/4 |
| 4506147 | protease serine 2 preproprotein | 227/3 |
| 4502085 | pancreatic amylase alpha 2A precursor | 217/3 |

The proteomes of GLFs resultant from the administration of sulfate-based lavage compositions and either collected during as part of a colonoscopy procedure or self-collected by a subject were compared. The Mascot scores and number of significant peptides for the most abundant proteins are summarized in Table 5. While there was a close correlation between the two proteomes observed, different isoforms were identified for at least two proteins. The selection of different isoforms may be a result of the collection of the sequence data during MS/MS and the search engine. There were fewer proteins detected in the self collected sample which was more dilute than that collected during the colonoscopy.

TABLE 5

| | | Mascot score/number of significant peptides | |
|---|---|---|---|
| NCBI gi # | Protein | Colonoscopy collected sample | Subject collected sample |
| 148539842 | deleted in malignant brain tumors 1 isoform b precursor | See isoform a | 1184/13 |
| 148539840 | deleted in malignant brain tumors 1 isoform a precursor | 417/4 | See isoform b |
| 119395750 | keratin 1 | 159/2 | 742/9 |
| 10835000 | pancreatic lipase precursor | 3719/37 | 538/8 |
| 113584 | RecName: Full = Ig alpha-1 chain C region | 958/9 | 506/6 |
| 31377806 | polymeric immunoglobulin receptor precursor | 469/4 | 474/5 |
| 98986445 | carcinoembryonic antigen-related cell adhesion molecule 5 preproprotein | 74/1 | 424/5 |
| 125817 | RecName: Full = Ig kappa chain V-III region HAH; Flags: Precursor | ND | 382/5 |
| 125797 | RecName: Full = Ig kappa chain V-III region SIE | ND | 341/5 |
| 54607080 | pancreatic carboxypeptidase B1 preproprotein | 1389/17 | 340/5 |
| 236460050 | elastase 3A pancreatic preproprotein | 2268/27 | 328/4 |
| 125145 | RecName: Full = Ig kappa chain C region | 734/7 | 327/5 |
| 118498350 | chymotrypsin B2 | See chymotrypsin B1 | 238/3 |
| 118498341 | chymotrypsin B1 | 881/7 | See chymotrypsin B2 |
| 62526043 | chymotrypsin C preprotein | 1002/10 | ND |
| 125811 | RecName: Full = Ig kappa chain V-III region VG; Flags: Precursor | ND | 237/3 |
| 1684927 | immunoglobulin light chain | 371/4 | 221/2 |
| 123843 | RecName: Full = Ig heavy chain V-III region VH26; Flags: Precursor | 181/2 | 219/3 |
| 157266300 | membrane alanine aminopeptidase precursor | 544/5 | 213/3 |

TABLE 5-continued

| | | Mascot score/number of significant peptides | |
|---|---|---|---|
| NCBI gi # | Protein | Colonoscopy collected sample | Subject collected sample |
| 125788 | RecName: Full = Ig kappa chain V-II region TEW | ND | 202/3 |
| 4502085 | pancreatic amylase alpha 2A precursor | 4258/49 | ND |
| 10280622 | amylase pancreatic alpha-2B precursor | 3916/45 | ND |
| 6679625 | elastase 3B pancreatic preproprotein | 1955/22 | ND |
| 4506147 | protease serine 2 preproprotein | 1442/14 | ND |
| 4502997 | carboxypeptidase A1 precursor | 1168/14 | ND |
| 15559207 | elastase 2A preproprotein | 959/5 | ND |
| 217416390 | carboxypeptidase A2 (pancreatic) precursor | 811/10 | ND |
| 29725633 | regenerating islet-derived 1 alpha precursor | 714/8 | ND |
| 218512088 | RecName: Full = Ig alpha-2 chain C region | 663/6 | ND |
| 7669492 | glyceraldehyde-3-phosphate dehydrogenase | 593/5 | ND |
| 4506145 | protease serine 1 preproprotein | 551/6 | ND |
| 157266300 | membrane alanine aminopeptidase precursor | 544/5 | ND |
| 298351713 | RecName: Full = Ig lambda-1 chain C regions | 322/4 | ND |
| 119220569 | zymogen granule membrane glycoprotein 2 isoform 1 | 304/3 | ND |
| 51593090 | mucin 13 epithelial transmembrane | 293/3 | ND |
| 125807 | RecName: Full = Ig kappa chain V-III region GOL; AltName: Full = Rheumatoid factor | 288/3 | ND |
| 10334859 | creatine kinase mitochondrial 1B precursor | 265/3 | ND |

The foregoing analyses demonstrate that a large number of target molecules can be detected in samples obtained using a polyethylene glycol based GLF.

Example 3—Proteomic Analysis of Magnesium Citrate Based GLF

In this analysis, the ability of a magnesium citrate based GLF to support proteomic analysis was assessed. To identify target molecules in a GLF from a human subject administered a magnesium citrate-based lavage composition, a magnesium citrate-based lavage composition was administered to a subject; the GLF was collected from subject as part of a colonoscopy procedure. The proteome of the GLF was analyzed by mass spectroscopy as described in Example 1. Many different proteins were identified in the GLF. Examples of the most abundant identified proteins are listed in Table 6. Many of the identified proteins were detected with different colonoscopy preparations suggesting that the proteome is not dependent on the bowel preparation used.

TABLE 6

| NCBI gi # | Protein | Mascot score/number of significant peptides Sample 27 |
|---|---|---|
| 4502085 | pancreatic amylase alpha 2A precursor | 2977/31 |
| 10280622 | amylase pancreatic alpha-2B precursor | 2891/30 |
| 40254482 | salivary amylase alpha 1A precursor | 2472/26 |
| 50363217 | serine proteinase inhibitor clade A member 1 | 1316/12 |
| 236460050 | elastase 3A pancreatic preproprotein | 1299/13 |
| 15559207 | elastase 2A preproprotein | 1109/11 |
| 6679625 | elastase 3B pancreatic preproprotein | 987/10 |
| 29725633 | regenerating islet-derived 1 alpha precursor | 577/6 |
| 4507725 | transthyretin precursor | 570/7 |
| 4506147 | protease serine 2 preproprotein | 521/6 |
| 58331211 | elastase 2B preproprotein | 498/4 |
| 157266292 | intestinal alkaline phosphatase precursor | 491/7 |
| 113584 | RecName: Full = Ig alpha-1 chain C region | 338/3 |
| 125145 | RecName: Full = Ig kappa chain C region | 337/4 |
| 98986445 | carcinoembryonic antigen-related cell adhesion molecule 5 preproprotein | 329/3 |

TABLE 6-continued

| NCBI gi # | Protein | Mascot score/number of significant peptides Sample 27 |
|---|---|---|
| 218512088 | RecName: Full = Ig alpha-2 chain C region | 293/3 |
| 41152086 | serine (or cysteine) proteinase inhibitor clade B (ovalbumin) member 6 | 293/4 |
| 4506145 | protease serine 1 preproprotein | 267/3 |
| 4502997 | carboxypeptidase A1 precursor | 146/3 |

The foregoing analysis demonstrates that a large number of target molecules can be detected in samples obtained using a magnesium citrate based GLF.

Example 4—Detection of IgA-1 and IgA-2 Antibodies in Samples Obtained Using a GLF in Combination with SSL-7 Enrichment In this analysis, the ability of a samples obtained using a GLF in combination with SSL-7 enrichment to detect IgA-1 and IgA-2 antibodies was assessed. To identify target molecules in a GLF with affinity to *Staphylococcus aureus* superantigen-like protein 7 (SSL-7), a sulfate-based lavage composition (SUPREP) was administered to human subjects, and proteins were enriched in each GLF using SSL-7 affinity beads. The GLF was collected from subjects as part of a colonoscopy procedure.

SSL-7 affinity beads were used to isolate IgA-1 and IgA-2 specifically. 20 μl of SSL-7 agarose (Invitrogen, San Diego, Calif.) was added to 1 ml of sample and incubated overnight on a roller at 4° C. Tubes were spun at 1,000×g for 2 minutes to pellet beads and supernatant discarded. Beads were washed 4× with 1× phosphate buffered saline and eluted with 20 μl of 100 mM glycine, pH 2.7 in a shaker for 1 hr at 600 rpm and 37° C. Eluted antibodies were diluted with 60 μl of 100 mM ammonium bicarbonate/10 mM tris(2-carboxyethyl)phosphine and digested with 2 μl of sequencing grade trypsin (Promega, Madison, Wis.). Mass spectrometry and database searches were performed as described above. The most abundant identified proteins present in GLF with affinity to SSL-7 and their corresponding Mascot scores are summarized in Table 7. As has been observed in prior examples, antibodies were present in the GLF and enrichment and analysis of these is possible using the affinity reagents, thus allowing the specific analysis of this subproteome in the GLF. The most abundant antibodies were IgAs. IgAs are consistently reported to be present in the intestinal tract.

TABLE 7

| NCBI gi # | Protein | Mascot score/number of significant peptides | |
|---|---|---|---|
| | | Sample 12 | Sample 13 |
| 113584 | RecName: Full = Ig alpha-1 chain C region | 3084/29 | 2477/24 |
| 31377806 | polymeric immunoglobulin receptor precursor | 3065/36 | 898/13 |
| 218512088 | RecName: Full = Ig alpha-2 chain C region | 2736/24 | 2225/18 |
| 125145 | RecName: Full = Ig kappa chain C region | 477/4 | 542/6 |
| 21489959 | immunoglobulin J chain | 403/4 | 308/2 |
| 298351715 | RecName: Full = Ig lambda-3 chain C regions | 352/3 | ND |

TABLE 7-continued

| NCBI gi # | Protein | Mascot score/number of significant peptides | |
|---|---|---|---|
| | | Sample 12 | Sample 13 |
| 298351713 | RecName: Full = Ig lambda-1 chain C regions | 317/3 | 581/6 |
| 1684927 | immunoglobulin light chain | ND | 636/6 |

The foregoing analysis demonstrates that IgA antibodies can be detected in samples obtained using a GLF in combination with SSL-7 enrichment.

Example 5—Detection of IgA and IgM in Samples Obtained Using a GLF in Combination with ProteinL Enrichment In this analysis, the ability of samples obtained using a GLF in combination with Protein L enrichment to detect IgA and IgM antibodies was assessed. To identify target molecules in a GLF with affinity to Protein L, a sulfate-based lavage composition (SUPREP) was administered to human subjects, and proteins were enriched in each GLF using Protein L affinity beads. The GLF was collected from subjects as part of a colonoscopy procedure.

Protein L affinity beads were used to isolate antibodies containing kappa light chains. 20 μl of Protein L agarose (Santa Cruz Biotechnology, Santa Cruz, Calif.) was added to 1 ml of sample and incubated overnight on a roller at 4 C. Tubes were spun at 1,000×g for 2 minutes to pellet beads and supernatant discarded. Beads were washed 4 times with 1× phosphate buffered saline and eluted with 20 μl of 100 mM glycine, pH 2.7 in a shaker for 1 hr at 600 rpm and 37° C. Eluted antibodies were diluted with 60 μl of 100 mM Ammonium bicarbonate/10 mM tris(2-carboxyethyl)phosphine and digested with 2 μl of sequencing grade trypsin (Promega, Madison, Wis.). The most abundant identified proteins present in GLF with affinity to Protein L and their corresponding Mascot scores and numbers of significant peptides are summarized in Table 8. As expected, IgA and associated chains from antibodies were again detected. As the Protein L is not totally specific for IgA antibodies, an IgM antibody (gi#193806374) was also detected.

TABLE 8

| NCBI gi # | Protein | Mascot score/number of significant peptides Sample 9 |
|---|---|---|
| 113584 | RecName: Full = Ig alpha-1 chain C region | 1183/14 |
| 31377806 | polymeric immunoglobulin receptor precursor | 1149/14 |
| 218512088 | RecName: Full = Ig alpha-2 chain C region | 985/11 |
| 125145 | RecName: Full = Ig kappa chain C region | 654/8 |
| 193806374 | RecName: Full = Ig mu chain C region | 407/5 |
| 187950123 | immunoglobulin heavy chain variable region | 289/3 |
| 21489959 | immunoglobulin J chain | 249/2 |

The foregoing analysis demonstrates that IgA and IgM antibodies can be detected in samples obtained using a GLF in combination with ProteinL enrichment.

Example 6—Detection of Proteins of Bacterial Origin in Samples Obtained Using a GLF In this analysis, the ability of a GLF to facilitate detection of proteins of bacterial origin was assessed. To identify target molecules associated with bacteria in a GLF, a sulfate-based lavage composition (SUPREP) was administered to two human subjects; the resultant GLF was collected from the subjects as part of a colonoscopy procedure. Super Optimal Broth (SOB) media was inoculated with 100 µl from each GLF and incubated overnight at 37° C. and 220 rpm shaking. Pellets were lysed in a bead-beater in 8M urea and lysates were diluted to 2 M urea in 50 mM ammonium bicarbonate/10 mM tris(2-carboxyethyl)phosphine and digested with sequencing grade trypsin (Promega, Madison, Wis.). Data were acquired on the Orbitrap MS system using 120 mins runs as described earlier. A MGF search file was created and searched with the Mascot search engine (Matrix Science, UK) against the RefSeq database (http://www.ncbi.nlm.nih.gov/RefSeq/) with the taxonomy specified as Eubacteria with a mass accuracy of 10 ppm for the parent ion (MS) and 0.6 Da for the fragment ions (MS/MS). The most abundant identified proteins present in GLF associated with bacteria and their corresponding Mascot scores and numbers of significant peptides are summarized in Table 9. In the sample shown, the bacterium that was cultured was *Escherichia coli*. Other samples show different bacteria showing that the lavage fluid still retains some of the gut bacteria.

TABLE 9

| NCBI gi # | Protein | Mascot score/number of significant peptides Bacterial isolate |
|---|---|---|
| 15834378 | chaperonin GroEL [*Escherichia coli*] | 1294/3 |

TABLE 9-continued

| NCBI gi # | Protein | Mascot score/number of significant peptides Bacterial isolate |
|---|---|---|
| 15803852 | elongation factor Tu [*Escherichia coli*] | 1244/7 |
| 157159481 | Molecular chaperone DnaK [*Escherichia coli*] | 683/3 |
| 123444102 | elongation factor Tu [*Yersinia enterocolitica* subsp. *enterocolitica* 8081] | 518/3 |

The foregoing analysis demonstrates that proteins of bacterial origin can be detected in samples obtained using a GLF.

Example 7—Proteomic Analysis of Combined Samples from Several Subjects

In order to further facilitate the identification of a large number of target proteins detectable in samples obtained using a GLF, the search files generated from the data acquired individually from 12 subjects were concatenated into a single search file and searched using the previously specified parameters for the Orbitrap data. Many proteins were analyzed in various GLF samples and proteins selected that (predominantly) had at least 3 unique significant peptides detected with thresholds of p<0.05 (Mascot score approximately 41). Only 3 listed proteins (gi's 5031863, 6466801 and 115430223) had less than 3 significant peptides but these had Mascot scores of approximately 400, well above the 95% confidence level for protein identification. Proteins identified in this combined analysis are listed in Table 10 along with reported origins of particular proteins and reported associated cancers. Table 10 also lists SEQ ID NO.s for identified peptides that had Mascot scores of 40 or greater for each unique identified protein. Many identified proteins have been reported to be present in pancreatic juice. References listed in Table 10 are provided in this application.

TABLE 10

| NCBI gi# | Detected protein | Mascot score/ number of significant peptides | SEQ ID NO.s of peptides with Mascot scores >40 | Origin of detected protein | Presence in pancreatic juice | Associated cancer | References |
|---|---|---|---|---|---|---|---|
| 10835000 | pancreatic lipase precursor | 6919/75 | 1-77 | pancreas | Yes | pancreatic | Friess (2003) |
| 4502085 | pancreatic amylase alpha 2A precursor | 5766/60 | 78-137 | pancreas | Yes | gastric | Kang (2010) |

TABLE 10-continued

| NCBI gi# | Detected protein | Mascot score/ number of significant peptides | SEQ ID NO.s of peptides with Mascot scores >40 | Origin of detected protein | Presence in pancreatic juice | Associated cancer | References |
|---|---|---|---|---|---|---|---|
| 10280622 | amylase, pancreatic, alpha-2B precursor | 5332/55 | 78-83, 85-100, 102, 103, 105-108, 110-130, 133, 136-141 | pancreas | Yes | liver | Koyama (2001) |
| 40254482 | salivary amylase alpha 1A precursor | 4712/50 | 78-83, 86-90, 93-99, 102, 105-107, 110-116, 118-126, 128, 129, 131, 133-135, 139, 140, 142, 143 | pancreas/ salivary gland | Yes | lung | Tomita (1989) |
| 236460050 | elastase 3A, pancreatic preproprotein | 4267/49 | 144-193 | pancreas | Yes | lung | Shimada (2002) |
| 6679625 | elastase 3B, pancreatic preproprotein | 4123/44 | 145-147, 151-153, 155, 157, 161-163, 165, 166, 168, 170, 172-176, 178, 179, 181, 183, 185, 186, 188, 191, 194-211 | pancreas | Yes | pancreatic | Gao (2010) |
| 4506147 | protease, serine, 2 preproprotein | 3427/33 | 212-247 | pancreas | Yes | pancreatic | Gao (2010) |
| 118498350 | chymotrypsin B2 | 2621/27 | 248-274 | pancreas | Yes | pancreatic | Miao (2008) |
| 118498341 | chymotrypsin B1 | 2527/26 | 248-256, 258-274 | pancreas | Yes | general | Miao (2008) |
| 50363217 | serine proteinase inhibitor, clade A, member 1 | 2443/27 | 275-304 | pancreas/liver | Yes | general | Normandin (2010), Sato (2004), Zhou (2000) |
| 15559207 | elastase 2A preproprotein | 2351/25 | 305-331 | pancreas | Yes | pancreatic | Akakura (2001) Yamamura (1989) |
| 54607080 | pancreatic carboxypeptidase B1 preproprotein | 2143/24 | 332-355 | pancreas | Yes | liver | Matsugi (2007) |
| 4506145 | protease, serine, 1 preproprotein | 2135/21 | 215, 217, 219, 221, 222, 225, 228, 229, 231, 232, 236, 238-240, 242, 245, 356-361 | pancreas | Yes | pancreatic | |
| 148539844 | deleted in malignant brain tumors 1 isoform c precursor | 2129/23 | 362-385 | epithelial, pancreas | Yes | pancreatic, brain, lung, colon, gastric | Sasaki (2002), Kuramitsu (2006) |
| 113584 | RecName: Ful = Ig alpha-1 chain C region | 2065/19 | 386-405 | antibody-heavy chain IgA | Yes | | |
| 4502997 | carboxypeptidase A1 precursor | 2026/25 | 334, 406-429 | pancreas | Yes | pancreatic | Matsugi (2007) |
| 29725633 | regenerating islet-derived 1 alpha precursor | 1799/17 | 430-444 | pancreas | Yes | liver | Cavard (2006) |
| 31377806 | polymeric immunoglobulin receptor precursor | 1783/19 | 445-465 | epithelial | Yes | endometrial | DeSouza (2005) |
| 218512088 | RecName: Full = Ig alpha-2 chain C region | 1779/16 | 386-388, 390-392, 397, 399-404, 466-469 | antibody-heavy chain | Yes | | |
| 157266300 | membrane alanine aminopeptidase precursor | 1581/16 | 470-486 | small intestine | Yes | breast | Liang (2006) |
| 119395750 | keratin 1 | 1491/15 | 487-501 | epithelial | | | |
| 62526043 | chymotrypsin C preproprotein | 1407/16 | 502-517 | pancreas | Yes | liver | Wang (2011) |
| 98986445 | carcinoembryonic antigen-related cell adhesion molecule 5 preproprotein | 1140/11 | 518-528 | epithelial | Yes | pancreatic, colon | Sato (2004), Van Gisbergen (2005) |

TABLE 10-continued

| NCBI gi# | Detected protein | Mascot score/ number of significant peptides | SEQ ID NO.s of peptides with Mascot scores >40 | Origin of detected protein | Presence in pancreatic juice | Associated cancer | References |
|---|---|---|---|---|---|---|---|
| 217416390 | carboxypeptidase A2 (pancreatic) precursor | 1129/11 | 529-539 | pancreas | Yes | pancreatic | Matsugi (2007) |
| 4505847 | phospholipase A2 group IB | 1124/13 | 540-552 | pancreas | Yes | colon, prostate | Belinsky (2007), Sved (2004) |
| 125145 | RecName: Full = Ig kappa chain C region | 1121/14 | 553-566 | antibody-light chain | Yes | | |
| 7669492 | glyceraldehyde-3-phosphate dehydrogenase | 1106/11 | 567-578 | epithelial/bacterial | | colon | Egea (2007), Shin (2009) |
| 58331211 | elastase 2B preproprotein | 1083/11 | 305, 307-310, 312-314, 318, 324, 328, 331 | pancreas | | | |
| 105990514 | filamin B, beta (actin binding protein 278) | 1041/7 | 579-586 | multiple cell types | | prostate | Harding (2006) |
| 4507725 | transthyretin precursor | 952/11 | 587-597 | Liver/serum protein | Yes | colon | Fentz (2007) |
| 55956899 | keratin 9 | 945/9 | 598-607 | epithelial | | | |
| 170296790 | mesotrypsin isoform 1 preproprotein | 907/8 | 214, 215, 218, 219, 221, 224, 226, 233, 608 | pancreas | | breast | Hockla (2010) |
| 10835248 | regenerating islet-derived 1 beta precursor | 903/9 | 430, 431, 433-437, 441 | pancreas | Yes | pancreatic | Cui (2010) |
| 41152086 | serine (or cysteine) proteinase inhibitor, clade B (ovalbumin), member 6 | 902/9 | 609-617 | keritinocytes, muscle, lung, liver, pancreas | Yes | colon | Krasnov (2009) |
| 1684927 | immunoglobulin light chain | 889/8 | 618-625 | | | | |
| 4505605 | pancreatitis-associated protein precursor | 848/9 | 626-634 | pancreas | Yes | pancreatic | Rosty (2002) |
| 13489087 | serine (or cysteine) proteinase inhibitor, clade B (ovalbumin), member 1 | 842/8 | 635-642 | keritinocytes, muscle, lung, liver, pancreas | Yes | pancreatic | Sato (2004) |
| 226529917 | triosephosphate isomerase 1 isoform 2 | 760/7 | 643-649 | multiple cell types | Yes | breast | Tamesa (2009) |
| 298351713 | RecName: Full = Ig lambda-1 chain C regions | 760/8 | 618-623, 625, 650 | antibody-light chain | | | |
| 47132620 | keratin 2 | 713/7 | 487, 495, 651-655 | epithelial | | | |
| 5080756 | Human Fc gamma BP [AA 1-2843] | 706/4 | 656-659 | | | | |
| 195972866 | keratin 10 | 676/5 | 660-664 | epithelial | | Liver, pancreatic | Yang (2008), Xiao (2010) |
| 4502027 | albumin preproprotein | 642/4 | 665-668 | | | | |
| 40255013 | carcinoembryonic antigen-related cell adhesion molecule 6 (non-specific cross reacting antigen) | 614/5 | 522, 524, 669-671 | epithelial | Yes | colon | Van Gisbergen (2005) |
| 125819 | RecName: Full = Ig kappa chain V-III region HIC; Flags: Precursor | 611/6 | 672-677 | antibody-light chain | | leukemia | Kipps (1988) |
| 154146262 | Fc fragment of IgG binding protein | 607/4 | 656-659 | | | prostate | Gazi (2008) |
| 157266292 | intestinal alkaline phosphatase precursor | 605/7 | 678-684 | small intestine | | liver | Yamamoto (1984) |
| 50845388 | annexin A2 isoform 1 | 604/5 | 685-689 | multiple cell types | | liver | Mohammad (2008) |

TABLE 10-continued

| NCBI gi# | Detected protein | Mascot score/ number of significant peptides | SEQ ID NO.s of peptides with Mascot scores >40 | Origin of detected protein | Presence in pancreatic juice | Associated cancer | References |
|---|---|---|---|---|---|---|---|
| 50659080 | serpin peptidase inhibitor, clade A, member 3 precursor | 599/4 | 690-693 | liver | | melanoma | Wang (2010) |
| 51593090 | mucin 13, epithelial transmembrane | 575/5 | 694-698 | colon | | GI cancer | Maher (2011) |
| 119220569 | zymogen granule membrane glycoprotein 2 isoform 1 | 567/4 | 699-702 | pancreas | Yes | | |
| 125817 | RecName: Full = Ig kappa chain V-III region HAH; Flags: Precursor | 554/6 | 672-677 | antibody-light chain | | leukemia | Kipps (1988) |
| 151301154 | mucin 6, gastric | 544/3 | 703-705 | | | | |
| 10334859 | creatine kinase, mitochondrial 1B precursor | 533/5 | 706-711 | mitochondria | | tissue damage | Bark (1980) |
| 223099 | Ig Aalpha 1 Bur | 520/4 | 388, 391, 467-469 | | | | |
| 4504919 | keratin 8 | 506/6 | 712-717 | epithelial | | skin | Yamashiro (2010) |
| 119703753 | keratin 6B | 504/4 | 488, 653, 654, 718 | epithelial | | breast | Millar (2009) |
| 121039 | RecName: Full = Ig gamma-1 chain C region | 501/4 | 719-722 | antibody-heavy chain | | | |
| 4507149 | superoxide dismutase 1, soluble | 98/5 | 723-727 | epithelial/mitochondria | Yes | multiple | Pham (2009) |
| 223942069 | enterokinase precursor | 497/3 | 728-731 | small intestine | | multiple | Vilen (2008) |
| 153070262 | meprin A alpha | 497/4 | 732-735 | small intestine | | colon | Lottaz (1999) |
| 157364974 | sucrase-isomaltase | 480/3 | 736-738 | small intestine | | colon | Gu (2006) |
| 125797 | RecName: Full = Ig kappa chain V-III region SIE | 478/5 | 672-676, 739 | antibody-light chain | | | |
| 38455402 | lipocalin 2 | 463/4 | 740-743 | Epithelial, many cell types | Yes | pancreatic, breast, endometrial, prostate | Sato (2004), Lin(2011), Mahadevin (2011) |
| 167857790 | orosomucoid 1 precursor | 446/6 | 744-750 | serum/acute phase protein | | | |
| 5031839 | keratin 6A | 441/3 | 653, 654, 718 | epithelial | | breast | Millar (2009) |
| 32313593 | olfactomedin 4 precursor | 437/4 | 751-754 | small intestine, colon, pancreas | | pancreatic, colon | Kobayashi (2007), Koshida (2007) |
| 125803 | RecName: Full = Ig kappa chain V-II region WOL | 432/5 | 672-676 | antibody-light chain | | | |
| 10835063 | nucleophosmin 1 isoform 1 | 414/5 | 755-759 | multiple cell types | | liver, others | Kuramitsu (2006), Grisendi (2006) |
| 75707587 | immunoglobulin light chain variable region | 414/4 | 673, 674, 676, 760 | antibody-light chain | | | |
| 5031863 | galectin 3 binding protein | 414/2 | 761, 762 | multiple cell types | Yes | colon | Bresalier (2004), Kim (2011) |
| 187960098 | medium-chain acyl-CoA dehydrogenase isoform b precursor | 407/3 | 763-765 | mitochondrial/bacterial | | | |
| 4503143 | cathepsin D preproprotein | 407/4 | 766-769 | multiple cell types | | breast | Wolf (2003) |
| 106507261 | pancreatic lipase related protein 2 | 393/2 | 1, 5, 770 | pancreas | Yes | | |
| 223718246 | plastin 1 | 393/3 | 771-774 | small intestine, colon, kidney | | pancreatic | Terris (2002) |
| 4885165 | cystatin A | 384/4 | 775-778 | macrophages | | colon | Kupio (1998), Kos (2000) |

TABLE 10-continued

| NCBI gi# | Detected protein | Mascot score/ number of significant peptides | SEQ ID NO.s of peptides with Mascot scores >40 | Origin of detected protein | Presence in pancreatic juice | Associated cancer | References |
|---|---|---|---|---|---|---|---|
| 6466801 | intestinal mucin 3 | 379/1 | 779 | epithelial | | pancreatic | Park (2003) |
| 115430223 | alectin 3 | 377/2 | 780, 781 | multiple cell types | | pancreatic | Jiang (2008) |
| 19923195 | carcinoembryonic antigen-related cell adhesion molecule 1 isoform 1 precursor | 375/4 | 518, 670, 782, 783 | epithelial | Yes | multiple | Gerstel (2011) |
| 19923748 | dihydrolipoamide S-succinyltransferase (E2 component of 2-oxo-glutarate complex) | 362/3 | 784-786 | mitochondria | | | |
| 193806374 | RecName: Full = Ig mu chain C region | 361/4 | 787-790 | antibody-heavy chain | | | |
| 16306550 | selenium binding protein 1 | 361/3 | 791-793 | | | ovarian, uterine, gastric, esophageal | Huang (2006), Zhang (2010), Zhang (2011), Silvers (2010) |
| 33456 | immunoglobulin M chain | 353/4 | 794-797 | antibody-heavy chain | | | |
| 125811 | RecName: Full = Ig kappa chain V-III region VG; Flags: Precursor | 319/3 | 760, 798, 799 | antibody-light chain | | | |
| 123843 | RecName: Full = Ig heavy chain V-III region VH26; Flags: Precursor | 219/3 | 796, 800, 801 | antibody-heavy chain | | | |
| 563454 | Ig heavy chain (VH4) V region (VDJ) | 206/3 | 802-804 | antibody-heavy chain | | | |

The foregoing analysis demonstrates that a large number of proteins can be detected in samples obtained using a GLF.

Example 8—Proteomic Analysis of Fecal Samples

In this analysis, the ability of fecal samples to support proteomic analysis was assessed. To identify target molecules in a fecal sample, no lavage composition was administered to a human subject. A fecal sample was collected from the subject during normal defecation using a collection container placed in the toilet. A small amount of the fecal (stool) sample was homogenized in 0.1% TFA and then centrifuged at 13000×g. The protein was precipitated with 6 volumes of acetone, resuspended in 0.1% TFA, extracted with an equal volume of chloroform, and then processed in a SPE column as described in Example 1. The most abundant identified proteins and their corresponding Mascot scores and number of significant peptides are summarized in Table 11. Proteins, largely with likely pancreatic origin, were detected in the sample indicating that, after discovery in GLF, stool is a source for the detection of these biomarker proteins. However, the sample did also contain a number of other non-human materials that make the analysis much more limiting, especially for discovery of biomarkers.

TABLE 11

| NCBI gi # | Protein | Mascot score/number of significant peptides Sample Fecal 1 |
|---|---|---|
| 119395750 | keratin 1 | 549/7 |
| 15559207 | elastase 2A preprotein | 546/5 |
| 236460050 | elastase 3A pancreatic preproprotein | 532/4 |
| 55956899 | keratin 9 | 444/5 |
| 125145 | RecName: Full = Ig kappa chain C region | 396/5 |
| 4506147 | protease serine 2 preproprotein | 344/4 |
| 4506145 | protease serine 1 preproprotein | 320/5 |
| 118498350 | chymotrypsin B2 | 298/3 |
| 6679625 | elastase 3B pancreatic preproprotein | 286/3 |

The foregoing analysis demonstrates that a large number of target molecules can be detected in fecal samples.

Example 9—Detection of Glycans in Samples Obtained Using a GLF

In this analysis, the ability of glycans to be detected in samples obtained in samples using a GLF was assessed. To identify and analyze target molecules, including glycans, in a GLF, GLF was collected from a human subject. 1.8 mL GLF was added to 12 mL ice cold acetone and incubated for one hour to pellet the protein. The sample was centrifuged at 12,000×g for 15 minutes and the acetone removed. After washing with ice cold acetone, the pellet was resuspended in 0.1% TFA and passed through a 5 mL, syringe style, SepPak C2 column. Proteins were eluted with 60% acetonitrile/40%

0.1% TFA. After removal of the solvent under vacuum, the protein fraction was redissolved in 100 µL 50 mM ammonium bicarbonate and deglycosylated with 2 µL PNGaseF overnight at 37° C. in a shaker. After quenching with 1 mL 0.1% TFA, the glycans were collected as the flow through fraction from a 1 mL, syringe style, SepPak C18 column using a vacuum manifold. The dried glycans were labeled with 4-ABEE (ethyl 4-aminobenzoate) by reductive amination by adding 25 µL derivatizing solution (90:10 MeOH: HAc containing 35 mM ABEE and 100 mM 2-PB) to the dried glycans, and incubating at 65° C. for 2 hours. Excess ABEE was removed by adding 1 mL ethyl ether, vortexing and discarding the ether. After a second ether extraction, the sample was briefly put in the SpeedVac to remove any residual ether. The labeled glycans were then run on the HPLC and eluted between 20-25% acetonitrile from an Agilent C8 reverse phase column. This fraction was vacuum-dried, redissolved in 50 µL of 0.1% TFA and run on the Waters Q-TOF LC-ESI-MS for glycan analysis. The derivatized glycans eluted from the C18 reverse phase column on the Q-TOF MS at about 20-25% acetonitrile in 0.2% formic acid. The mass spectrometer was scanned in MS-only mode from m/z 150-2000 every second to acquire the derivatized glycan profile data. FIG. 1 summarizes these results, and depicts a graph of the relative abundance of various glycoprotein derived glycan structures present in a fraction of a gastrointestinal lavage fluid. As shown in FIG. 1, some glycoprotein derived glycan structures include particular modifications that are associated with truncation of the chains. These modifications may be due to bacterial activity present in the GLF sample as it is known that bacteria can digest and consume glycans from proteins. However, such modifications can also be associated with disease, especially cancer where aberrant glycosylation has been linked to the disease.

The foregoing analysis demonstrates that a large number of glycans can be detected in samples obtained using a GLF.

Example 10—Detection of Metabolites in Samples Obtained Using a GLF

In this analysis, the ability of metabolites to be detected in samples obtained using a GLF was assessed. To identify and analyze target molecules, including metabolites, in a GLF, a magnesium citrate-based lavage composition was administered to human subjects, and the resultant GLF was analyzed for metabolites such as cholic acid and other bile salts. The resultant GLF was collected from the subjects as part of a colonoscopy procedure.

3 ml GLF was centrifuged at max speed for 20 minutes and the supernatant acidified with 0.1% TFA. The supernatant was applied to a C18 SPE column (Waters Sep-Pak), washed with 3 volumes of 0.1% TFA, and eluted with 50% ACN in 0.1% TFA. The elutant was dried by centrifugal lyophilization and re-dissolved in 500 µl 0.1% TFA.

Figure 2:
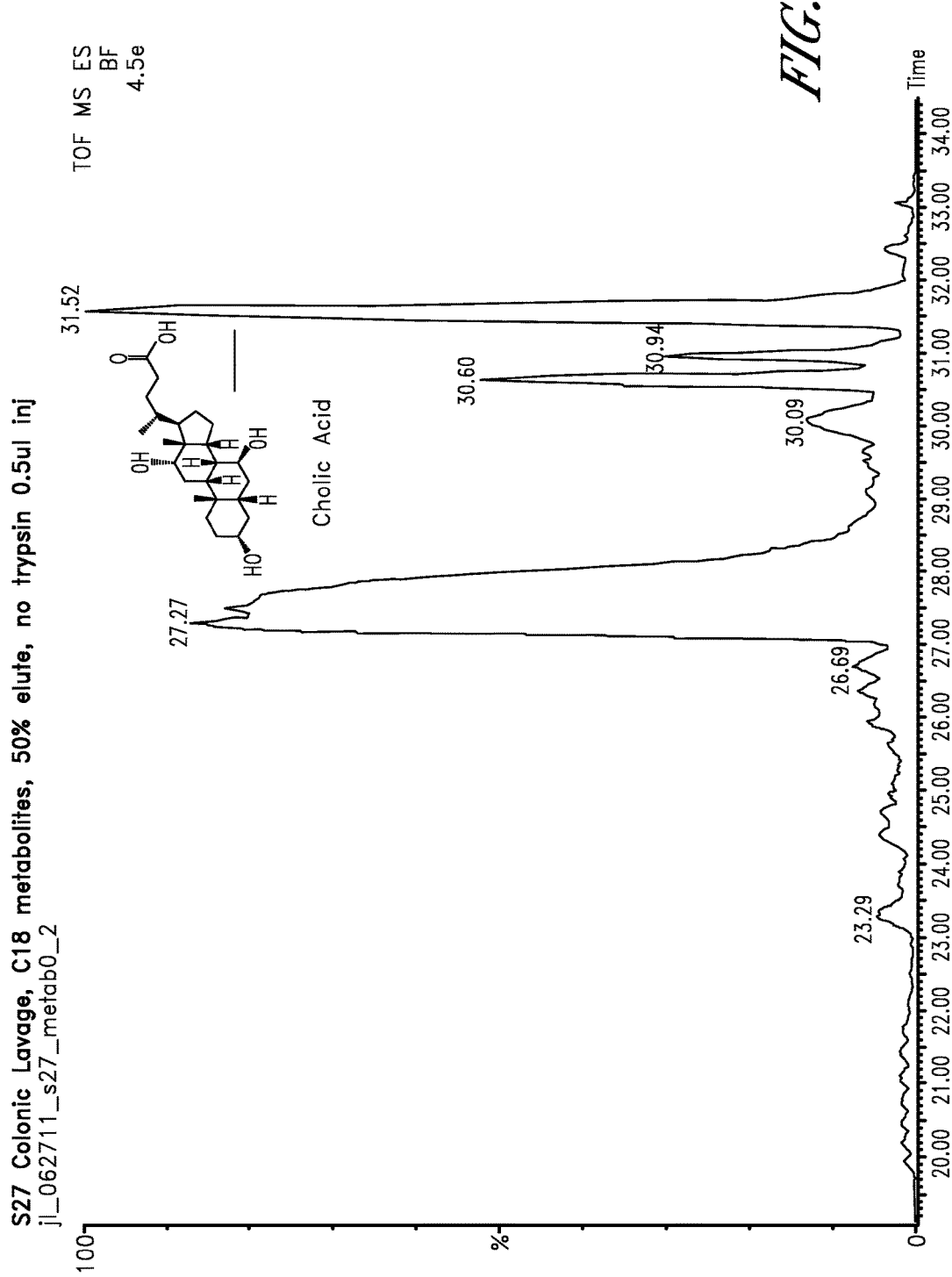
FIG. 2 depicts a graph of the relative abundance of compounds, including metabolites such as cholic acid, present in a fraction of a gastrointestinal lavage fluid. Data were acquired on a Waters Q-TOF mass spectrometer using input from an LC system, and using MassLynx software. The MS scanned over the mass range from m/z 100 m/z to 2000 every second.
Figure 3:
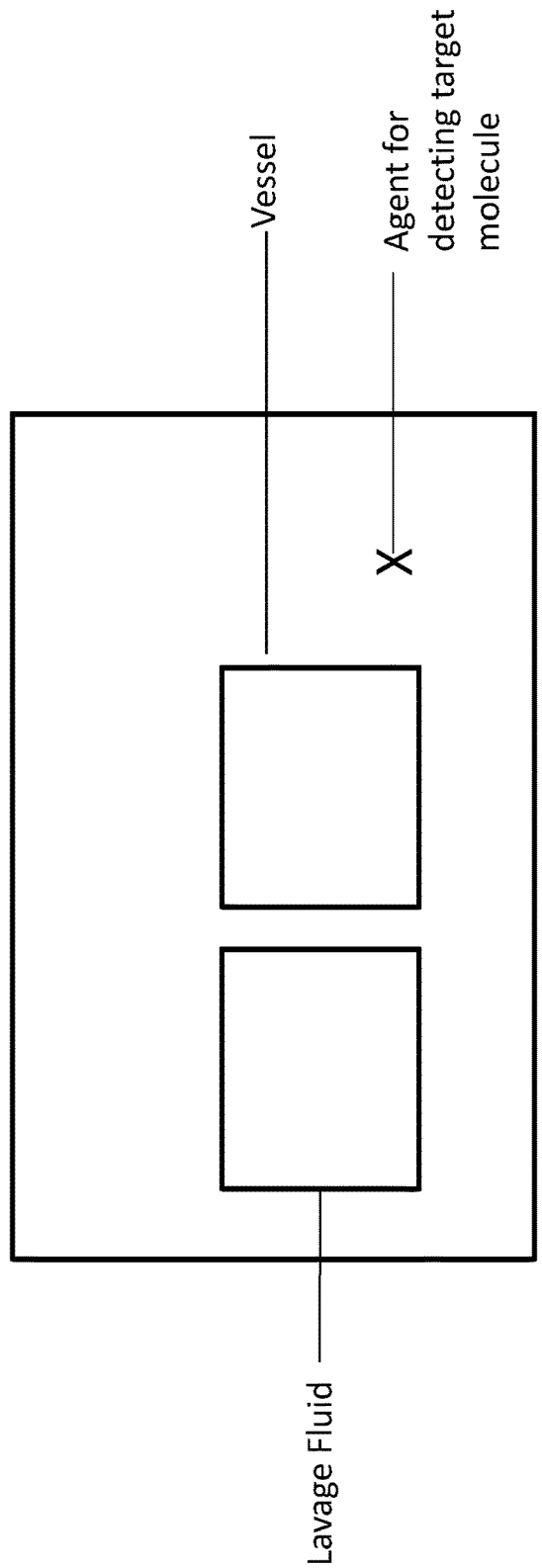
FIG. 3 depicts a kit according to the invention.

Data were acquired on a Waters Q-TOF mass spectrometer using input from an LC system. The A solvent contained 3% of B and 0.2% formic acid in water. The B solvent contained 3% of A and 0.2% formic acid in acetonitrile. Solvents were HPLC grade from Fisher. The starting solvent was 5% B and remained for 5 min and then changed to 40% by 25 min, 90% by 30 min, and then reset to 5% at 36. The MS scanned over the mass range from m/z 100 m/z to 2000 every second. Data were acquired using the standard MassLynx software. The eluting compounds with the cholic acid peak marked are summarized in FIG. 2. A similar profile of peaks was observed on the Orbitrap instrument where the cholic acid peak was identified using a standard and MS/MS data. Metabolites including cholic acid were identified.

The foregoing analysis demonstrates that metabolites can be detected in samples obtained using a GLF.

The term "comprising" as used herein is synonymous with "including," "containing," or "characterized by," and is inclusive or open-ended and does not exclude additional, unrecited elements or method steps.

All numbers expressing quantities of ingredients, reaction conditions, and so forth used in the specification are to be understood as being modified in all instances by the term "about." Accordingly, unless indicated to the contrary, the numerical parameters set forth herein are approximations that may vary depending upon the desired properties sought to be obtained. At the very least, and not as an attempt to limit the application of the doctrine of equivalents to the scope of any claims in any application claiming priority to the present application, each numerical parameter should be construed in light of the number of significant digits and ordinary rounding approaches.

The above description discloses several methods and materials of the present invention. This invention is susceptible to modifications in the methods and materials, as well as alterations in the fabrication methods and equipment. Such modifications will become apparent to those skilled in the art from a consideration of this disclosure or practice of the invention disclosed herein. Consequently, it is not intended that this invention be limited to the specific embodiments disclosed herein, but that it cover all modifications and alternatives coming within the true scope and spirit of the invention.

REFERENCES

Each of the following references is incorporated by reference herein in its entirety.

Pancreatic Juice References

Chen, R., S. Pan, et al. (2007). "Comparison of pancreas juice proteins from cancer versus pancreatitis using quantitative proteomic analysis." Pancreas 34(1): 70-9.

Chen, R., S. Pan, et al. (2010). "Elevated level of anterior gradient-2 in pancreatic juice from patients with pre-malignant pancreatic neoplasia." Mol Cancer 9: 149.

Chen, R., S. Pan, et al. (2006). "Quantitative proteomic profiling of pancreatic cancer juice." Proteomics 6(13): 3871-9.

Gao, J., F. Zhu, et al. (2010). "Identification of pancreatic juice proteins as biomarkers of pancreatic cancer." Oncol Rep 23(6): 1683-92.

Gomez-Lazaro, M., C. Rinn, et al. (2010). "Proteomic analysis of zymogen granules." Expert Rev Proteomics 7(5): 735-47.

Gronborg, M., J. Bunkenborg, et al. (2004). "Comprehensive proteomic analysis of human pancreatic juice." J Proteome Res 3(5): 1042-55.

Paulo, J. A., L. S. Lee, et al. (2010). "Identification of pancreas-specific proteins in endoscopically (endoscopic pancreatic function test) collected pancreatic fluid with liquid chromatography—tandem mass spectrometry." Pancreas 39(6): 889-96.

Zhou, L., Z. Lu, et al. (2007). "Comparative proteomic analysis of human pancreatic juice: methodological study." Proteomics 7(8): 1345-55.

Cancer References

Akakura, N., M. Kobayashi, et al. (2001). "Constitutive expression of hypoxia-inducible factor-1alpha renders pancreatic cancer cells resistant to apoptosis induced by hypoxia and nutrient deprivation." Cancer Res 61(17): 6548-54.

Bark, C. J. (1980). "Mitochondrial Creatine Kinase." Journal of the American Medical Association 243(20): 2058-2060.

Belinsky, G. S., T. V. Rajan, et al. (2007). "Expression of secretory phospholipase A2 in colon tumor cells potentiates tumor growth." Mol Carcinog 46(2): 106-16.

Bresalier, R. S., J. C. Byrd, et al. (2004). "A circulating ligand for galectin-3 is a haptoglobin-related glycoprotein elevated in individuals with colon cancer." Gastroenterology 127(3): 741-8.

Cavard, C., B. Terris, et al. (2006). "Overexpression of regenerating islet-derived 1 alpha and 3 alpha genes in human primary liver tumors with beta-catenin mutations." Oncogene 25(4): 599-608.

Cui, L., F. Li, et al. (2010). "Screening and Verification of Differentially Expressed Proteins from Pancreatic Cancer Tissue." Chinese Journal of Chemistry 28(6): 884-890.

DeSouza, L., G. Diehl, et al. (2005). "Search for cancer markers from endometrial tissues using differentially labeled tags iTRAQ and cICAT with multidimensional liquid chromatography and tandem mass spectrometry." J Proteome Res 4(2): 377-86.

Egea, L., L. Aguilera, et al. (2007). "Role of secreted glyceraldehyde-3-phosphate dehydrogenase in the infection mechanism of enterohemorrhagic and enteropathogenic *Escherichia coli*: interaction of the extracellular enzyme with human plasminogen and fibrinogen." Int J Biochem Cell Biol 39(6): 1190-203.

Fentz, A. K., M. Sporl, et al. (2007). "Detection of colorectal adenoma and cancer based on transthyretin and C3a-desArg serum levels." Proteomics Clin Appl 1(6): 536-44.

Friess, H., J. Ding, et al. (2003). "Microarray-based identification of differentially expressed growth- and metastasis-associated genes in pancreatic cancer." Cell Mol Life Sci 60(6): 1180-99.

Gao, J., F. Zhu, et al. (2010). "Identification of pancreatic juice proteins as biomarkers of pancreatic cancer." Oncol Rep 23(6): 1683-92.

Gazi, M. H., M. He, et al. (2008). "Downregulation of IgG Fc binding protein (Fc gammaBP) in prostate cancer." Cancer Biol Ther 7(1): 70-5.

Gerstel, D., F. Wegwitz, et al. (2011). "CEACAM1 creates a pro-angiogenic tumor microenvironment that supports tumor vessel maturation." Oncogene.

Grisendi, S., C. Mecucci, et al. (2006). "Nucleophosmin and cancer." Nat Rev Cancer 6(7): 493-505.

Gu, N., T. Adachi, et al. (2006). "Sucrase-isomaltase gene expression is inhibited by mutant hepatocyte nuclear factor (HNF)-1alpha and mutant HNF-1beta in Caco-2 cells." J Nutr Sci Vitaminol (Tokyo) 52(2): 105-12.

Harding, T. C., M. Nguyen, et al. (2006). Humoral immue response induced to filamin B in patients with metastatic hormone-refractory prostate cancer (HRPC) treated with a GM-CSF-transduced allogeneic prostate cancer vaccine (GVAX®). AACR.

Hockla, A., D. C. Radisky, et al. (2010). "Mesotrypsin promotes malignant growth of breast cancer cells through shedding of CD109." Breast Cancer Res Treat 124(1): 27-38.

Huang, K. C., D. C. Park, et al. (2006). "Selenium binding protein 1 in ovarian cancer." Int J Cancer 118(10): 2433-40.

Jiang, H. B., M. Xu, et al. (2008). "Pancreatic stellate cells promote proliferation and invasiveness of human pancreatic cancer cells via galectin-3." World J Gastroenterol 14(13): 2023-8.

Kang, J. U., S. H. Koo, et al. (2010). "AMY2A: a possible tumor-suppressor gene of 1p21.1 loss in gastric carcinoma." Int J Oncol 36(6): 1429-35.

Kim, G. E., H. I. Bae, et al. (2002). "Aberrant expression of MUC5AC and MUC6 gastric mucins and sialyl Tn antigen in intraepithelial neoplasms of the pancreas." Gastroenterology 123(4): 1052-60.

Kim, Y. S., J. A. Jung, et al. (2011). "Galectin-3 binding protein promotes cell motility in colon cancer by stimulating the shedding of protein tyrosine phosphatase kappa by proprotein convertase 5." Biochem Biophys Res Commun 404(1): 96-102.

Kipps, T. J., E. Tomhave, et al. (1988). "Autoantibody-associated kappa light chain variable region gene expressed in chronic lymphocytic leukemia with little or no somatic mutation. Implications for etiology and immunotherapy." J Exp Med 167(3): 840-52.

Kobayashi, D., S. Koshida, et al. (2007). "Olfactomedin 4 promotes S-phase transition in proliferation of pancreatic cancer cells." Cancer Sci 98(3): 334-40.

Kos, J., M. Krasovec, et al. (2000). "Cysteine proteinase inhibitors stefin A, stefin B, and cystatin C in sera from patients with colorectal cancer: relation to prognosis." Clin Cancer Res 6(2): 505-11.

Koshida, S., D. Kobayashi, et al. (2007). "Specific overexpression of OLFM4(GW112/HGC-1) mRNA in colon, breast and lung cancer tissues detected using quantitative analysis." Cancer Sci 98(3): 315-20.

Koyama, I., S. Komine, et al. (2001). "alpha-Amylase expressed in human liver is encoded by the AMY-2B gene identified in tumorous tissues." Clin Chim Acta 309(1): 73-83.

Krasnov, G. S., N. Oparina, et al. (2009). "[Colorectal cancer 2D-proteomics: identification of altered protein expression]." Mol Biol (Mosk) 43(2): 348-56.

Kuopio, T., A. Kankaanranta, et al. (1998). "Cysteine proteinase inhibitor cystatin A in breast cancer." Cancer Res 58(3): 432-6.

Kuramitsu, Y. and K. Nakamura (2006). "Proteomic analysis of cancer tissues: shedding light on carcinogenesis and possible biomarkers." Proteomics 6(20): 5650-61.

Liang, X., J. Zhao, et al. (2006). "Quantification of membrane and membrane-bound proteins in normal and malignant breast cancer cells isolated from the same patient with primary breast carcinoma." J Proteome Res 5(10): 2632-41.

Lin, H. H., C. J. Liao, et al. (2011). "Lipocalin-2-induced cytokine production enhances endometrial carcinoma cell survival and migration." Int J Biol Sci 7(1): 74-86.

Lottaz, D., C. A. Maurer, et al. (1999). "Nonpolarized secretion of human meprin alpha in colorectal cancer generates an increased proteolytic potential in the stroma." Cancer Res 59(5): 1127-33.

Mahadevan, N. R., J. Rodvold, et al. (2011). "ER stress drives Lipocalin 2 upregulation in prostate cancer cells in an NF-kappaB-dependent manner." BMC Cancer 11: 229.

Maher, D. M., B. K. Gupta, et al. (2011). "Mucin 13: structure, function, and potential roles in cancer pathogenesis." Mol Cancer Res 9(5): 531-7.

Matsugi, S., T. Hamada, et al. (2007). "Serum carboxypeptidase A activity as a biomarker for early-stage pancreatic carcinoma." Clin Chim Acta 378(1-2): 147-53.

Miao, Q., Y. Sun, et al. (2008). "Chymotrypsin B cached in rat liver lysosomes and involved in apoptotic regulation through a mitochondrial pathway." J Biol Chem 283(13): 8218-28.

Millar, E. K., P. H. Graham, et al. (2009). "Prediction of local recurrence, distant metastases, and death after breast-conserving therapy in early-stage invasive breast cancer using a five-biomarker panel." J Clin Oncol 27(28): 4701-8.

Mohammad, H. S., K. Kurokohchi, et al. (2008). "Annexin A2 expression and phosphorylation are up-regulated in hepatocellular carcinoma." Int J Oncol 33(6): 1157-63.

Normandin, K., B. Peant, et al. (2010). "Protease inhibitor SERPINA1 expression in epithelial ovarian cancer." Clin Exp Metastasis 27(1): 55-69.

Park, H. U., J. W. Kim, et al. (2003). "Aberrant expression of MUC3 and MUC4 membrane-associated mucins and sialyl Le(x) antigen in pancreatic intraepithelial neoplasia." Pancreas 26(3): e48-54.

Pham, T. M., Y. Fujino, et al. (2009). "Relationship between serum levels of superoxide dismutase activity and subsequent risk of cancer mortality: Findings from a nested case-control study within the Japan Collaborative Cohort Study." Asian Pac J Cancer Prev 10 Suppl: 69-73.

Rosty, C., L. Christa, et al. (2002). "Identification of hepatocarcinoma-intestine-pancreas/pancreatitis-associated protein I as a biomarker for pancreatic ductal adenocarcinoma by protein biochip technology." Cancer Res 62(6): 1868-75.

Sasaki, K., K. Sato, et al. (2002). "Peptidomics-based approach reveals the secretion of the 29-residue COOH-terminal fragment of the putative tumor suppressor protein DMBT1 from pancreatic adenocarcinoma cell lines." Cancer Res 62(17): 4894-8.

Sato, N., N. Fukushima, et al. (2004). "Gene expression profiling identifies genes associated with invasive intraductal papillary mucinous neoplasms of the pancreas." Am J Pathol 164(3): 903-14.

Shimada, S., K. Yamaguchi, et al. (2002). "Pancreatic elastase IIIA and its variants are expressed in pancreatic carcinoma cells." Int J Mol Med 10(5): 599-603.

Shin, Y. K., B. C. Yoo, et al. (2009). "Upregulation of glycolytic enzymes in proteins secreted from human colon cancer cells with 5-fluorouracil resistance." Electrophoresis 30(12): 2182-92.

Silvers, A. L., L. Lin, et al. (2010). "Decreased selenium-binding protein 1 in esophageal adenocarcinoma results from posttranscriptional and epigenetic regulation and affects chemosensitivity." Clin Cancer Res 16(7): 2009-21.

Sved, P., K. F. Scott, et al. (2004). "Oncogenic action of secreted phospholipase A2 in prostate cancer." Cancer Res 64(19): 6934-40.

Tamesa, M. S., Y. Kuramitsu, et al. (2009). "Detection of autoantibodies against cyclophilin A and triosephosphate isomerase in sera from breast cancer patients by proteomic analysis." Electrophoresis 30(12): 2168-81.

Terris, B., E. Blayeri, et al. (2002). "Characterization of gene expression profiles in intraductal papillary-mucinous tumors of the pancreas." Am J Pathol 160(5): 1745-54.

Tomita, N., A. Horii, et al. (1989). "A novel type of human alpha-amylase produced in lung carcinoid tumor." Gene 76(1): 11-8.

van Gisbergen, K. P., C. A. Aarnoudse, et al. (2005). "Dendritic cells recognize tumor-specific glycosylation of carcinoembryonic antigen on colorectal cancer cells through dendritic cell-specific intercellular adhesion molecule-3-grabbing nonintegrin." Cancer Res 65(13): 5935-44.

Vilen, S. T., P. Nyberg, et al. (2008). "Intracellular co-localization of trypsin-2 and matrix metalloprotease-9: possible proteolytic cascade of trypsin-2, MMP-9 and enterokinase in carcinoma." Exp Cell Res 314(4): 914-26.

Wang, H., W. Sha, et al. (2011). "Effect of chymotrypsin C and related proteins on pancreatic cancer cell migration." Acta Biochim Biophys Sin (Shanghai) 43(5): 362-71.

Wang, Y., H. Jiang, et al. (2010). "Alpha 1 antichymotrypsin is aberrantly expressed during melanoma progression and predicts poor survival for patients with metastatic melanoma." Pigment Cell Melanoma Res 23(4): 575-8.

Wolf, M., I. Clark-Lewis, et al. (2003). "Cathepsin D specifically cleaves the chemokines macrophage inflammatory protein-1 alpha, macrophage inflammatory protein-1 beta, and SLC that are expressed in human breast cancer." Am J Pathol 162(4): 1183-90.

Xiao, J., W. N. Lee, et al. (2010). "Profiling pancreatic cancer-secreted proteome using 15N amino acids and serum-free media." Pancreas 39(1): e17-23.

Yamamoto, H., M. Tanaka, et al. (1984). "Intestinal-type alkaline phosphatase produced by human hepatoblastoma cell line HUH-6 clone 5." Cancer Res 44(1): 339-44.

Yamamura, H., M. Tatsuta, et al. (1989). "Effectiveness of discriminant analysis of serum CA 19-9 and elastase 1 in diagnosis of pancreatic carcinoma." Pancreas 4(4): 401-5.

Yamashiro, Y., K. Takei, et al. (2010). "Ectopic coexpression of keratin 8 and 18 promotes invasion of transformed keratinocytes and is induced in patients with cutaneous squamous cell carcinoma." Biochem Biophys Res Commun 399(3): 365-72.

Yang, X. R., Y. Xu, et al. (2008). "Cytokeratin 10 and cytokeratin 19: predictive markers for poor prognosis in hepatocellular carcinoma patients after curative resection." Clin Cancer Res 14(12): 3850-9.

Zhang, J., W. G. Dong, et al. (2011). "Reduced selenium-binding protein 1 is associated with poor survival rate in gastric carcinoma." Med Oncol 28(2): 481-7.

Zhang, P., C. Zhang, et al. (2010). "The expression of selenium-binding protein 1 is decreased in uterine leiomyoma." Diagn Pathol 5: 80.

Zheng, H., H. Takahashi, et al. (2006). "MUC6 down-regulation correlates with gastric carcinoma progression and a poor prognosis: an immunohistochemical study with tissue microarrays." J Cancer Res Clin Oncol 132 (12): 817-23.

Zhou, H., M. E. Ortiz-Pallardo, et al. (2000). "Is heterozygous alpha-1-antitrypsin deficiency type PIZ a risk factor for primary liver carcinoma?" Cancer 88(12): 2668-76.

All references cited herein, including but not limited to published and unpublished applications, patents, and literature references, are incorporated herein by reference in their entirety and are hereby made a part of this specification. To the extent publications and patents or patent applications incorporated by reference contradict the disclosure contained in the specification, the specification is intended to supersede and/or take precedence over any such contradictory material.

What is claimed is:

1. A method for detecting a target molecule associated with the presence of pancreatic cancer or predisposition to pancreatic cancer in gastrointestinal lavage fluid derived from a mammalian subject, the method comprising:
   orally administering a lavage composition to the subject, thereby inducing purgation of the subject's gastrointestinal system;
   obtaining from the subject a sample comprising gastrointestinal lavage fluid produced by the oral administration of the lavage composition; and
   detecting the target molecule in the gastrointestinal lavage fluid using mass spectrometry or an immunoassay, wherein the target molecule is a pancreas-derived polypeptide and is not a cell.

2. The method of claim 1, wherein the lavage composition comprises (i) an ingredient selected from the group consisting of polyethylene glycol, magnesium sulfate, sodium sulfate, potassium sulfate, magnesium citrate, ascorbic acid, sodium picosulfate, bisacodyl, sodium phosphate, sennoside and a combination thereof; or (ii) a solution comprising a sodium, potassium or magnesium salt of sulfate, bicarbonate, chloride, phosphate or citrate, or a combination thereof.

3. A kit for detecting a target molecule associated with the presence of pancreatic cancer or predisposition to pancreatic cancer in gastrointestinal lavage fluid derived from a mammalian subject, and for diagnosing pancreatic cancer or predisposition to pancreatic cancer in the subject, the kit comprising:
   an oral lavage composition suitable for inducing purgation of the subject's gastrointestinal system;
   a vessel for collecting the sample comprising gastrointestinal lavage fluid produced by the oral administration of the lavage composition to the subject; and
   an agent for detecting the target molecule in the gastrointestinal lavage fluid using mass spectrometry or an immunoassay, wherein the target molecule is a pancreas-derived polypeptide and is not a cell.

4. The kit of claim 3, further comprising at least one of a protease inhibitor, an enzyme inhibitor or a denaturant.

5. The kit of claim 3, wherein the lavage composition (i) comprises an ingredient selected from the group consisting of polyethylene glycol, magnesium sulfate, sodium sulfate, potassium sulfate, magnesium citrate, ascorbic acid, sodium picosulfate, bisacodyl, sodium phosphate, sennoside and a combination thereof; (ii) comprises a solution comprising a sodium, potassium or magnesium salt of sulfate, bicarbonate, chloride, phosphate or citrate, or a combination thereof; or (iii) is selected from the group consisting of a composition comprising polyethylene glycol with an electrolyte solution, a composition comprising polyethylene glycol with an electrolyte solution and bisacodyl, and a composition comprising sodium sulfate, magnesium sulfate, and potassium sulfate.

6. The method of claim 1, wherein the lavage composition is selected from the group consisting of a composition comprising polyethylene glycol with an electrolyte solution; a composition comprising polyethylene glycol with an electrolyte solution and bisacodyl; and a composition comprising sodium sulfate, magnesium sulfate, and potassium sulfate.

7. The method of claim 1, wherein the lavage composition comprises at least one of an osmotic agent or a laxative.

8. The method of claim 7, wherein the lavage composition comprises a laxative selected from the group consisting of aloe, bisacodyl, casanthranol, cascara aromatic fluid extract, cascara sagrada bark, cascada sagrada extract, cascara sagrada fluid extract, castor oil, danthron, dehydrocholic acid, phenolphthalein, sennoside A, sennoside B, picosulfate and a combination thereof.

9. The method of claim 1, wherein the gastrointestinal lavage fluid is obtained non-invasively.

10. The method of claim 9, wherein the gastrointestinal lavage fluid is obtained by non-invasive self-collection by the subject.

11. The method of claim 1, wherein the gastrointestinal lavage fluid is obtained as part of a colonoscopy procedure.

12. The method of claim 1, further comprising (i) exposing the sample to a material to stabilize or preserve the target molecule or (ii) adjusting the pH of the sample to stabilize or preserve the target molecule.

13. The method of claim 12, wherein the material comprises at least one of an enzyme inhibitor, a protease inhibitor or a denaturant.

14. The method of claim 1, wherein the subject's gastrointestinal system is partially purged.

15. The method of claim 1, wherein the subject's gastrointestinal system is cleansed.

16. A method for diagnosing pancreatic cancer or predisposition to pancreatic cancer in a mammalian subject by detecting a target molecule associated with the presence of pancreatic cancer or predisposition to pancreatic cancer, the method comprising:
orally administering a lavage composition to the subject, thereby inducing purgation of the subject's gastrointestinal system;
obtaining from the subject a sample comprising gastrointestinal lavage fluid produced by the oral administration of the lavage composition; and
detecting a target molecule in the gastrointestinal lavage fluid using mass spectrometry or an immunoassay;
wherein the target molecule is a pancreas-derived polypeptide and is not a cell.

17. The method of claim 16, wherein the lavage composition comprises (i) an ingredient selected from the group consisting of polyethylene glycol, magnesium sulfate, sodium sulfate, potassium sulfate, magnesium citrate, ascorbic acid, sodium picosulfate, bisacodyl, sodium phosphate, sennoside and a combination thereof; or (ii) a solution comprising a sodium, potassium or magnesium salt of sulfate, bicarbonate, chloride, phosphate or citrate, or a combination thereof.

18. The method of claim 16, wherein the lavage composition comprises at least one of an osmotic agent or a laxative.

19. The method of claim 18, wherein the lavage composition comprises a laxative selected from the group consisting of aloe, bisacodyl, casanthranol, cascara aromatic fluid extract, cascara sagrada bark, cascada sagrada extract, cascara sagrada fluid extract, castor oil, danthron, dehydrocholic acid, phenolphthalein, sennoside A, sennoside B, picosulfate and a combination thereof.

20. The method of claim 16, wherein the gastrointestinal lavage fluid is obtained non-invasively.

21. The method of claim 20, wherein the gastrointestinal lavage fluid is obtained by non-invasive self-collection by the subject.

22. The method of claim 16, wherein the gastrointestinal lavage fluid is obtained as part of a colonoscopy procedure.

23. The method of claim 16, further comprising (i) exposing the sample to a material to stabilize or preserve the target molecule or (ii) adjusting the pH of the sample to stabilize or preserve the target molecule.

24. The method of claim 23, wherein the material comprises at least one of an enzyme inhibitor, a protease inhibitor or a denaturant.

25. The method of claim 16, wherein the subject's gastrointestinal system is partially purged.

26. The method of claim 16, wherein the subject's gastrointestinal system is cleansed.

27. The method of claim 16, wherein the lavage composition is selected from the group consisting of a composition comprising polyethylene glycol with an electrolyte solution; a composition comprising polyethylene glycol with an electrolyte solution and bisacodyl; and a composition comprising sodium sulfate, magnesium sulfate, and potassium sulfate.

28. The method of claim 1, comprising detecting at least 5, 10, 20, 30, 50 or 100 target molecules in the gastrointestinal lavage fluid.

29. The kit of claim 3, comprising agents for detecting at least 5, 10, 20, 30, 50 or 100 target molecules in the gastrointestinal lavage fluid.

30. The method of claim 16, comprising detecting at least 5, 10, 20, 30, 50 or 100 target molecules in the gastrointestinal lavage fluid.

* * * * *

UNITED STATES PATENT AND TRADEMARK OFFICE
CERTIFICATE OF CORRECTION

| | |
|---|---|
| PATENT NO. | : 10,226,238 B2 |
| APPLICATION NO. | : 14/344399 |
| DATED | : March 12, 2019 |
| INVENTOR(S) | : Pannell et al. |

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 268 days.

Signed and Sealed this
Thirty-first Day of December, 2019

Andrei Iancu
*Director of the United States Patent and Trademark Office*

SEQUENCE LISTING

<160> NUMBER OF SEQ ID NOS: 804

<210> SEQ ID NO 1
<211> LENGTH: 7
<212> TYPE: PRT
<213> ORGANISM: Homo Sapiens
<220> FEATURE:
<221> NAME/KEY: PEPTIDE
<222> LOCATION: (1)...(5)
<223> OTHER INFORMATION: pancreatic lipase precursor

<400> SEQUENCE: 1

Tyr Lys Val Ser Val Thr Leu
 1               5

<210> SEQ ID NO 2
<211> LENGTH: 10
<212> TYPE: PRT
<213> ORGANISM: Homo Sapiens
<220> FEATURE:
<221> NAME/KEY: PEPTIDE
<222> LOCATION: (1)...(10)
<223> OTHER INFORMATION: pancreatic lipase precursor

<400> SEQUENCE: 2

Gly Ala His Ala Ala Gly Glu Ala Gly Arg
 1               5                  10

<210> SEQ ID NO 3
<211> LENGTH: 9
<212> TYPE: PRT
<213> ORGANISM: Homo Sapiens
<220> FEATURE:
<221> NAME/KEY: PEPTIDE
<222> LOCATION: (1)...(5)
<223> OTHER INFORMATION: pancreatic lipase precursor

<400> SEQUENCE: 3

Ile Ile Val Glu Thr Asn Val Gly Lys
 1               5

<210> SEQ ID NO 4
<211> LENGTH: 9
<212> TYPE: PRT
<213> ORGANISM: Homo Sapiens
<220> FEATURE:
<221> NAME/KEY: PEPTIDE
<222> LOCATION: (1)...(5)
<223> OTHER INFORMATION: pancreatic lipase precursor

<400> SEQUENCE: 4

Ile Leu Val Ser Leu Phe Gly Asn Lys
 1               5

<210> SEQ ID NO 5
<211> LENGTH: 10
<212> TYPE: PRT
<213> ORGANISM: Homo Sapiens
<220> FEATURE:
<221> NAME/KEY: PEPTIDE
<222> LOCATION: (1)...(10)
<223> OTHER INFORMATION: pancreatic lipase precursor

<400> SEQUENCE: 5

Tyr Lys Val Ser Val Thr Leu Ser Gly Lys
 1               5                  10

<210> SEQ ID NO 6

```
<211> LENGTH: 12
<212> TYPE: PRT
<213> ORGANISM: Homo Sapiens
<220> FEATURE:
<221> NAME/KEY: PEPTIDE
<222> LOCATION: (1)...(10)
<223> OTHER INFORMATION: pancreatic lipase precursor

<400> SEQUENCE: 6

Ser Leu Gly Ala His Ala Ala Gly Glu Ala Gly Arg
1               5                   10

<210> SEQ ID NO 7
<211> LENGTH: 10
<212> TYPE: PRT
<213> ORGANISM: Homo Sapiens
<220> FEATURE:
<221> NAME/KEY: PEPTIDE
<222> LOCATION: (1)...(10)
<223> OTHER INFORMATION: pancreatic lipase precursor

<400> SEQUENCE: 7

Ala Ser Tyr Asn Val Phe Thr Ala Asn Lys
1               5                   10

<210> SEQ ID NO 8
<211> LENGTH: 11
<212> TYPE: PRT
<213> ORGANISM: Homo Sapiens
<220> FEATURE:
<221> NAME/KEY: PEPTIDE
<222> LOCATION: (1)...(10)
<223> OTHER INFORMATION: pancreatic lipase precursor

<400> SEQUENCE: 8

Leu Gly Phe Gly Met Ser Gln Val Val Gly His
1               5                   10

<210> SEQ ID NO 9
<211> LENGTH: 10
<212> TYPE: PRT
<213> ORGANISM: Homo Sapiens
<220> FEATURE:
<221> NAME/KEY: PEPTIDE
<222> LOCATION: (1)...(10)
<223> OTHER INFORMATION: pancreatic lipase precursor

<400> SEQUENCE: 9

Asn Asn Val Ile Asn Pro Thr Leu Pro Arg
1               5                   10

<210> SEQ ID NO 10
<211> LENGTH: 10
<212> TYPE: PRT
<213> ORGANISM: Homo Sapiens
<220> FEATURE:
<221> NAME/KEY: PEPTIDE
<222> LOCATION: (1)...(10)
<223> OTHER INFORMATION: pancreatic lipase precursor

<400> SEQUENCE: 10

Asp Ile Asp Gly Ile Trp Glu Gly Thr Arg
1               5                   10

<210> SEQ ID NO 11
<211> LENGTH: 11
<212> TYPE: PRT
<213> ORGANISM: Homo Sapiens
<220> FEATURE:
```

```
<221> NAME/KEY: PEPTIDE
<222> LOCATION: (1)...(10)
<223> OTHER INFORMATION: pancreatic lipase precursor

<400> SEQUENCE: 11

Leu Asp Thr Gly Asp Ala Ser Asn Phe Ala Arg
1               5                   10

<210> SEQ ID NO 12
<211> LENGTH: 11
<212> TYPE: PRT
<213> ORGANISM: Homo Sapiens
<220> FEATURE:
<221> NAME/KEY: PEPTIDE
<222> LOCATION: (1)...(10)
<223> OTHER INFORMATION: pancreatic lipase precursor

<400> SEQUENCE: 12

Thr Gly Tyr Thr Gln Ala Ser Gln Asn Ile Arg
1               5                   10

<210> SEQ ID NO 13
<211> LENGTH: 11
<212> TYPE: PRT
<213> ORGANISM: Homo Sapiens
<220> FEATURE:
<221> NAME/KEY: PEPTIDE
<222> LOCATION: (1)...(10)
<223> OTHER INFORMATION: pancreatic lipase precursor

<400> SEQUENCE: 13

Val Asp Ile Asp Gly Ile Trp Glu Gly Thr Arg
1               5                   10

<210> SEQ ID NO 14
<211> LENGTH: 14
<212> TYPE: PRT
<213> ORGANISM: Homo Sapiens
<220> FEATURE:
<221> NAME/KEY: PEPTIDE
<222> LOCATION: (1)...(10)
<223> OTHER INFORMATION: pancreatic lipase precursor

<400> SEQUENCE: 14

Gly His Ser Leu Gly Ala His Ala Ala Gly Glu Ala Gly Arg
1               5                   10

<210> SEQ ID NO 15
<211> LENGTH: 11
<212> TYPE: PRT
<213> ORGANISM: Homo Sapiens
<220> FEATURE:
<221> NAME/KEY: PEPTIDE
<222> LOCATION: (1)...(10)
<223> OTHER INFORMATION: pancreatic lipase precursor

<400> SEQUENCE: 15

Tyr Asn Asn Val Ile Asn Pro Thr Leu Pro Arg
1               5                   10

<210> SEQ ID NO 16
<211> LENGTH: 11
<212> TYPE: PRT
<213> ORGANISM: Homo Sapiens
<220> FEATURE:
<221> NAME/KEY: PEPTIDE
<222> LOCATION: (1)...(10)
<223> OTHER INFORMATION: pancreatic lipase precursor
```

```
<400> SEQUENCE: 16

Thr Asn Glu Asn Pro Asn Asn Phe Gln Glu Val
1               5                   10

<210> SEQ ID NO 17
<211> LENGTH: 11
<212> TYPE: PRT
<213> ORGANISM: Homo Sapiens
<220> FEATURE:
<221> NAME/KEY: PEPTIDE
<222> LOCATION: (1)...(10)
<223> OTHER INFORMATION: pancreatic lipase precursor

<400> SEQUENCE: 17

Gln Phe Asn Phe Cys Ser Pro Glu Thr Val Arg
1               5                   10

<210> SEQ ID NO 18
<211> LENGTH: 12
<212> TYPE: PRT
<213> ORGANISM: Homo Sapiens
<220> FEATURE:
<221> NAME/KEY: PEPTIDE
<222> LOCATION: (1)...(10)
<223> OTHER INFORMATION: pancreatic lipase precursor

<400> SEQUENCE: 18

Tyr Leu Asp Thr Gly Asp Ala Ser Asn Phe Ala Arg
1               5                   10

<210> SEQ ID NO 19
<211> LENGTH: 13
<212> TYPE: PRT
<213> ORGANISM: Homo Sapiens
<220> FEATURE:
<221> NAME/KEY: PEPTIDE
<222> LOCATION: (1)...(10)
<223> OTHER INFORMATION: pancreatic lipase precursor

<400> SEQUENCE: 19

Pro Asn Leu Gly Phe Gly Met Ser Gln Val Val Gly His
1               5                   10

<210> SEQ ID NO 20
<211> LENGTH: 12
<212> TYPE: PRT
<213> ORGANISM: Homo Sapiens
<220> FEATURE:
<221> NAME/KEY: PEPTIDE
<222> LOCATION: (1)...(10)
<223> OTHER INFORMATION: pancreatic lipase precursor

<400> SEQUENCE: 20

Ile Val Asp Ile Asp Gly Ile Trp Glu Gly Thr Arg
1               5                   10

<210> SEQ ID NO 21
<211> LENGTH: 12
<212> TYPE: PRT
<213> ORGANISM: Homo Sapiens
<220> FEATURE:
<221> NAME/KEY: PEPTIDE
<222> LOCATION: (1)...(10)
<223> OTHER INFORMATION: pancreatic lipase precursor

<400> SEQUENCE: 21

Gly Phe Ile Asp Lys Gly Glu Glu Asn Trp Leu Ala
1               5                   10
```

<210> SEQ ID NO 22
<211> LENGTH: 13
<212> TYPE: PRT
<213> ORGANISM: Homo Sapiens
<220> FEATURE:
<221> NAME/KEY: PEPTIDE
<222> LOCATION: (1)...(10)
<223> OTHER INFORMATION: pancreatic lipase precursor

<400> SEQUENCE: 22

Leu Gly Cys Phe Ser Asp Asp Ser Pro Trp Ser Gly Ile
1               5                   10

<210> SEQ ID NO 23
<211> LENGTH: 12
<212> TYPE: PRT
<213> ORGANISM: Homo Sapiens
<220> FEATURE:
<221> NAME/KEY: PEPTIDE
<222> LOCATION: (1)...(10)
<223> OTHER INFORMATION: pancreatic lipase precursor

<400> SEQUENCE: 23

Val Glu Ser Val Asn Cys Ile Cys Val Asp Trp Lys
1               5                   10

<210> SEQ ID NO 24
<211> LENGTH: 13
<212> TYPE: PRT
<213> ORGANISM: Homo Sapiens
<220> FEATURE:
<221> NAME/KEY: PEPTIDE
<222> LOCATION: (1)...(10)
<223> OTHER INFORMATION: pancreatic lipase precursor

<400> SEQUENCE: 24

Asp Ser Asp Val Asp Val Gly Asp Leu Gln Met Val Lys
1               5                   10

<210> SEQ ID NO 25
<211> LENGTH: 12
<212> TYPE: PRT
<213> ORGANISM: Homo Sapiens
<220> FEATURE:
<221> NAME/KEY: PEPTIDE
<222> LOCATION: (1)...(10)
<223> OTHER INFORMATION: pancreatic lipase precursor

<400> SEQUENCE: 25

His Gly Phe Ile Asp Lys Gly Glu Glu Asn Trp Leu
1               5                   10

<210> SEQ ID NO 26
<211> LENGTH: 13
<212> TYPE: PRT
<213> ORGANISM: Homo Sapiens
<220> FEATURE:
<221> NAME/KEY: PEPTIDE
<222> LOCATION: (1)...(10)
<223> OTHER INFORMATION: pancreatic lipase precursor

<400> SEQUENCE: 26

Phe Tyr Leu Asp Thr Gly Asp Ala Ser Asn Phe Ala Arg
1               5                   10

<210> SEQ ID NO 27
<211> LENGTH: 14

```
<212> TYPE: PRT
<213> ORGANISM: Homo Sapiens
<220> FEATURE:
<221> NAME/KEY: PEPTIDE
<222> LOCATION: (1)...(10)
<223> OTHER INFORMATION: pancreatic lipase precursor

<400> SEQUENCE: 27

Ser Asp Asp Ser Pro Trp Ser Gly Ile Thr Glu Arg Pro Leu
1               5                   10

<210> SEQ ID NO 28
<211> LENGTH: 13
<212> TYPE: PRT
<213> ORGANISM: Homo Sapiens
<220> FEATURE:
<221> NAME/KEY: PEPTIDE
<222> LOCATION: (1)...(10)
<223> OTHER INFORMATION: pancreatic lipase precursor

<400> SEQUENCE: 28

Thr Glu Arg Pro Leu His Ile Leu Pro Trp Ser Pro Lys
1               5                   10

<210> SEQ ID NO 29
<211> LENGTH: 14
<212> TYPE: PRT
<213> ORGANISM: Homo Sapiens
<220> FEATURE:
<221> NAME/KEY: PEPTIDE
<222> LOCATION: (1)...(10)
<223> OTHER INFORMATION: pancreatic lipase precursor

<400> SEQUENCE: 29

Ser Gln Ile Val Asp Ile Asp Gly Ile Trp Glu Gly Thr Arg
1               5                   10

<210> SEQ ID NO 30
<211> LENGTH: 13
<212> TYPE: PRT
<213> ORGANISM: Homo Sapiens
<220> FEATURE:
<221> NAME/KEY: PEPTIDE
<222> LOCATION: (1)...(10)
<223> OTHER INFORMATION: pancreatic lipase precursor

<400> SEQUENCE: 30

Ile Trp Tyr Asn Asn Val Ile Asn Pro Thr Leu Pro Arg
1               5                   10

<210> SEQ ID NO 31
<211> LENGTH: 15
<212> TYPE: PRT
<213> ORGANISM: Homo Sapiens
<220> FEATURE:
<221> NAME/KEY: PEPTIDE
<222> LOCATION: (1)...(15)
<223> OTHER INFORMATION: pancreatic lipase precursor

<400> SEQUENCE: 31

Leu Asp Phe Phe Pro Asn Gly Gly Val Glu Met Pro Gly Cys Lys
1               5                   10                  15

<210> SEQ ID NO 32
<211> LENGTH: 14
<212> TYPE: PRT
<213> ORGANISM: Homo Sapiens
<220> FEATURE:
<221> NAME/KEY: PEPTIDE
```

-continued

<222> LOCATION: (1)...(10)
<223> OTHER INFORMATION: pancreatic lipase precursor

<400> SEQUENCE: 32

Ile Ile His Gly Phe Ile Asp Lys Gly Glu Glu Asn Trp Leu
1               5                   10

<210> SEQ ID NO 33
<211> LENGTH: 15
<212> TYPE: PRT
<213> ORGANISM: Homo Sapiens
<220> FEATURE:
<221> NAME/KEY: PEPTIDE
<222> LOCATION: (1)...(15)
<223> OTHER INFORMATION: pancreatic lipase precursor

<400> SEQUENCE: 33

His Ser Asn Glu Phe Asp Ser Asp Val Asp Val Gly Asp Leu Gln
1               5                   10                  15

<210> SEQ ID NO 34
<211> LENGTH: 15
<212> TYPE: PRT
<213> ORGANISM: Homo Sapiens
<220> FEATURE:
<221> NAME/KEY: PEPTIDE
<222> LOCATION: (1)...(15)
<223> OTHER INFORMATION: pancreatic lipase precursor

<400> SEQUENCE: 34

Glu Phe Asp Ser Asp Val Asp Val Gly Asp Leu Gln Met Val Lys
1               5                   10                  15

<210> SEQ ID NO 35
<211> LENGTH: 16
<212> TYPE: PRT
<213> ORGANISM: Homo Sapiens
<220> FEATURE:
<221> NAME/KEY: PEPTIDE
<222> LOCATION: (1)...(15)
<223> OTHER INFORMATION: pancreatic lipase precursor

<400> SEQUENCE: 35

Tyr Thr Asp Ser Ile Val Asn Pro Asp Gly Phe Ala Gly Phe Pro Cys
1               5                   10                  15

<210> SEQ ID NO 36
<211> LENGTH: 17
<212> TYPE: PRT
<213> ORGANISM: Homo Sapiens
<220> FEATURE:
<221> NAME/KEY: PEPTIDE
<222> LOCATION: (1)...(15)
<223> OTHER INFORMATION: pancreatic lipase precursor

<400> SEQUENCE: 36

Asp Val Ile His Thr Asp Gly Ala Pro Ile Val Pro Asn Leu Gly Phe
1               5                   10                  15

Gly

<210> SEQ ID NO 37
<211> LENGTH: 14
<212> TYPE: PRT
<213> ORGANISM: Homo Sapiens
<220> FEATURE:
<221> NAME/KEY: PEPTIDE
<222> LOCATION: (1)...(10)
<223> OTHER INFORMATION: pancreatic lipase precursor

```
<400> SEQUENCE: 37

Phe Ile Trp Tyr Asn Asn Val Ile Asn Pro Thr Leu Pro Arg
1               5                   10

<210> SEQ ID NO 38
<211> LENGTH: 16
<212> TYPE: PRT
<213> ORGANISM: Homo Sapiens
<220> FEATURE:
<221> NAME/KEY: PEPTIDE
<222> LOCATION: (1)...(15)
<223> OTHER INFORMATION: pancreatic lipase precursor

<400> SEQUENCE: 38

Leu Gly Cys Phe Ser Asp Asp Ser Pro Trp Ser Gly Ile Thr Glu Arg
1               5                   10                  15

<210> SEQ ID NO 39
<211> LENGTH: 17
<212> TYPE: PRT
<213> ORGANISM: Homo Sapiens
<220> FEATURE:
<221> NAME/KEY: PEPTIDE
<222> LOCATION: (1)...(15)
<223> OTHER INFORMATION: pancreatic lipase precursor

<400> SEQUENCE: 39

Gly His Leu Asp Phe Phe Pro Asn Gly Gly Val Glu Met Pro Gly Cys
1               5                   10                  15

Lys

<210> SEQ ID NO 40
<211> LENGTH: 16
<212> TYPE: PRT
<213> ORGANISM: Homo Sapiens
<220> FEATURE:
<221> NAME/KEY: PEPTIDE
<222> LOCATION: (1)...(15)
<223> OTHER INFORMATION: pancreatic lipase precursor

<400> SEQUENCE: 40

Asn Glu Phe Asp Ser Asp Val Asp Val Gly Asp Leu Gln Met Val Lys
1               5                   10                  15

<210> SEQ ID NO 41
<211> LENGTH: 15
<212> TYPE: PRT
<213> ORGANISM: Homo Sapiens
<220> FEATURE:
<221> NAME/KEY: PEPTIDE
<222> LOCATION: (1)...(15)
<223> OTHER INFORMATION: pancreatic lipase precursor

<400> SEQUENCE: 41

Phe Ile Ile His Gly Phe Ile Asp Lys Gly Glu Glu Asn Trp Leu
1               5                   10                  15

<210> SEQ ID NO 42
<211> LENGTH: 16
<212> TYPE: PRT
<213> ORGANISM: Homo Sapiens
<220> FEATURE:
<221> NAME/KEY: PEPTIDE
<222> LOCATION: (1)...(15)
<223> OTHER INFORMATION: pancreatic lipase precursor

<400> SEQUENCE: 42
```

Gly Phe Ile Asp Lys Gly Glu Glu Asn Trp Leu Ala Asn Val Cys Lys
 1               5                  10                  15

<210> SEQ ID NO 43
<211> LENGTH: 16
<212> TYPE: PRT
<213> ORGANISM: Homo Sapiens
<220> FEATURE:
<221> NAME/KEY: PEPTIDE
<222> LOCATION: (1)...(15)
<223> OTHER INFORMATION: pancreatic lipase precursor

<400> SEQUENCE: 43

Ser Gly Ile Thr Glu Arg Pro Leu His Ile Leu Pro Trp Ser Pro Lys
 1               5                  10                  15

<210> SEQ ID NO 44
<211> LENGTH: 18
<212> TYPE: PRT
<213> ORGANISM: Homo Sapiens
<220> FEATURE:
<221> NAME/KEY: PEPTIDE
<222> LOCATION: (1)...(15)
<223> OTHER INFORMATION: pancreatic lipase precursor

<400> SEQUENCE: 44

His Thr Asp Gly Ala Pro Ile Val Pro Asn Leu Gly Phe Gly Met Ser
 1               5                  10                  15

Gln Val

<210> SEQ ID NO 45
<211> LENGTH: 18
<212> TYPE: PRT
<213> ORGANISM: Homo Sapiens
<220> FEATURE:
<221> NAME/KEY: PEPTIDE
<222> LOCATION: (1)...(15)
<223> OTHER INFORMATION: pancreatic lipase precursor

<400> SEQUENCE: 45

Asp Val Ile His Thr Asp Gly Ala Pro Ile Val Pro Asn Leu Gly Phe
 1               5                  10                  15

Gly Met

<210> SEQ ID NO 46
<211> LENGTH: 18
<212> TYPE: PRT
<213> ORGANISM: Homo Sapiens
<220> FEATURE:
<221> NAME/KEY: PEPTIDE
<222> LOCATION: (1)...(15)
<223> OTHER INFORMATION: pancreatic lipase precursor

<400> SEQUENCE: 46

Asn Phe Gln Glu Val Ala Ala Asp Ser Ser Ile Ser Gly Ser Asn
 1               5                  10                  15

Phe Lys

<210> SEQ ID NO 47
<211> LENGTH: 17
<212> TYPE: PRT
<213> ORGANISM: Homo Sapiens
<220> FEATURE:
<221> NAME/KEY: PEPTIDE
<222> LOCATION: (1)...(15)
<223> OTHER INFORMATION: pancreatic lipase precursor

<400> SEQUENCE: 47

Ser Asn Glu Phe Asp Ser Asp Val Asp Val Gly Asp Leu Gln Met Val
1               5                   10                  15

Lys

<210> SEQ ID NO 48
<211> LENGTH: 16
<212> TYPE: PRT
<213> ORGANISM: Homo Sapiens
<220> FEATURE:
<221> NAME/KEY: PEPTIDE
<222> LOCATION: (1)...(15)
<223> OTHER INFORMATION: pancreatic lipase precursor

<400> SEQUENCE: 48

Gln Phe Asn Phe Cys Ser Pro Glu Thr Val Arg Glu Glu Val Leu Leu
1               5                   10                  15

<210> SEQ ID NO 49
<211> LENGTH: 17
<212> TYPE: PRT
<213> ORGANISM: Homo Sapiens
<220> FEATURE:
<221> NAME/KEY: PEPTIDE
<222> LOCATION: (1)...(15)
<223> OTHER INFORMATION: pancreatic lipase precursor

<400> SEQUENCE: 49

Asn Ile Leu Ser Gln Ile Val Asp Ile Asp Gly Ile Trp Glu Gly Thr
1               5                   10                  15

Arg

<210> SEQ ID NO 50
<211> LENGTH: 19
<212> TYPE: PRT
<213> ORGANISM: Homo Sapiens
<220> FEATURE:
<221> NAME/KEY: PEPTIDE
<222> LOCATION: (1)...(15)
<223> OTHER INFORMATION: pancreatic lipase precursor

<400> SEQUENCE: 50

His Thr Asp Gly Ala Pro Ile Val Pro Asn Leu Gly Phe Gly Met Ser
1               5                   10                  15

Gln Val Val

<210> SEQ ID NO 51
<211> LENGTH: 19
<212> TYPE: PRT
<213> ORGANISM: Homo Sapiens
<220> FEATURE:
<221> NAME/KEY: PEPTIDE
<222> LOCATION: (1)...(15)
<223> OTHER INFORMATION: pancreatic lipase precursor

<400> SEQUENCE: 51

Asp Val Ile His Thr Asp Gly Ala Pro Ile Val Pro Asn Leu Gly Phe
1               5                   10                  15

Gly Met Ser

<210> SEQ ID NO 52
<211> LENGTH: 18
<212> TYPE: PRT
<213> ORGANISM: Homo Sapiens

```
<220> FEATURE:
<221> NAME/KEY: PEPTIDE
<222> LOCATION: (1)...(15)
<223> OTHER INFORMATION: pancreatic lipase precursor

<400> SEQUENCE: 52

Leu Gly Cys Phe Ser Asp Asp Ser Pro Trp Ser Gly Ile Thr Glu Arg
1               5                   10                  15

Pro Leu

<210> SEQ ID NO 53
<211> LENGTH: 18
<212> TYPE: PRT
<213> ORGANISM: Homo Sapiens
<220> FEATURE:
<221> NAME/KEY: PEPTIDE
<222> LOCATION: (1)...(15)
<223> OTHER INFORMATION: pancreatic lipase precursor

<400> SEQUENCE: 53

His Ser Asn Glu Phe Asp Ser Asp Val Asp Val Gly Asp Leu Gln Met
1               5                   10                  15

Val Lys

<210> SEQ ID NO 54
<211> LENGTH: 19
<212> TYPE: PRT
<213> ORGANISM: Homo Sapiens
<220> FEATURE:
<221> NAME/KEY: PEPTIDE
<222> LOCATION: (1)...(15)
<223> OTHER INFORMATION: pancreatic lipase precursor

<400> SEQUENCE: 54

Ile Thr Gly Leu Asp Pro Ala Glu Pro Cys Phe Gln Gly Thr Pro Glu
1               5                   10                  15

Leu Val Arg

<210> SEQ ID NO 55
<211> LENGTH: 18
<212> TYPE: PRT
<213> ORGANISM: Homo Sapiens
<220> FEATURE:
<221> NAME/KEY: PEPTIDE
<222> LOCATION: (1)...(15)
<223> OTHER INFORMATION: pancreatic lipase precursor

<400> SEQUENCE: 55

Lys Asn Ile Leu Ser Gln Ile Val Asp Ile Asp Gly Ile Trp Glu Gly
1               5                   10                  15

Thr Arg

<210> SEQ ID NO 56
<211> LENGTH: 20
<212> TYPE: PRT
<213> ORGANISM: Homo Sapiens
<220> FEATURE:
<221> NAME/KEY: PEPTIDE
<222> LOCATION: (1)...(20)
<223> OTHER INFORMATION: pancreatic lipase precursor

<400> SEQUENCE: 56

Asp Val Ile His Thr Asp Gly Ala Pro Ile Val Pro Asn Leu Gly Phe
1               5                   10                  15

Gly Met Ser Gln
```

```
                    20

<210> SEQ ID NO 57
<211> LENGTH: 18
<212> TYPE: PRT
<213> ORGANISM: Homo Sapiens
<220> FEATURE:
<221> NAME/KEY: PEPTIDE
<222> LOCATION: (1)...(15)
<223> OTHER INFORMATION: pancreatic lipase precursor

<400> SEQUENCE: 57

Phe Ile Ile His Gly Phe Ile Asp Lys Gly Glu Glu Asn Trp Leu Ala
 1               5                  10                  15

Asn Val

<210> SEQ ID NO 58
<211> LENGTH: 21
<212> TYPE: PRT
<213> ORGANISM: Homo Sapiens
<220> FEATURE:
<221> NAME/KEY: PEPTIDE
<222> LOCATION: (1)...(20)
<223> OTHER INFORMATION: pancreatic lipase precursor

<400> SEQUENCE: 58

His Thr Asp Gly Ala Pro Ile Val Pro Asn Leu Gly Phe Gly Met Ser
 1               5                  10                  15

Gln Val Val Gly His
              20

<210> SEQ ID NO 59
<211> LENGTH: 20
<212> TYPE: PRT
<213> ORGANISM: Homo Sapiens
<220> FEATURE:
<221> NAME/KEY: PEPTIDE
<222> LOCATION: (1)...(20)
<223> OTHER INFORMATION: pancreatic lipase precursor

<400> SEQUENCE: 59

Phe Ile Ile His Gly Phe Ile Asp Lys Gly Glu Glu Asn Trp Leu Ala
 1               5                  10                  15

Asn Val Cys Lys
              20

<210> SEQ ID NO 60
<211> LENGTH: 22
<212> TYPE: PRT
<213> ORGANISM: Homo Sapiens
<220> FEATURE:
<221> NAME/KEY: PEPTIDE
<222> LOCATION: (1)...(20)
<223> OTHER INFORMATION: pancreatic lipase precursor

<400> SEQUENCE: 60

Glu Asn Pro Asn Asn Phe Gln Glu Val Ala Ala Asp Ser Ser Ser Ile
 1               5                  10                  15

Ser Gly Ser Asn Phe Lys
              20

<210> SEQ ID NO 61
<211> LENGTH: 22
<212> TYPE: PRT
<213> ORGANISM: Homo Sapiens
<220> FEATURE:
```

```
<221> NAME/KEY: PEPTIDE
<222> LOCATION: (1)...(20)
<223> OTHER INFORMATION: pancreatic lipase precursor

<400> SEQUENCE: 61

Gly Thr Leu Lys Pro Asp Ser Thr His Ser Asn Glu Phe Asp Ser Asp
 1               5                  10                  15

Val Asp Val Gly Asp Leu
            20

<210> SEQ ID NO 62
<211> LENGTH: 21
<212> TYPE: PRT
<213> ORGANISM: Homo Sapiens
<220> FEATURE:
<221> NAME/KEY: PEPTIDE
<222> LOCATION: (1)...(20)
<223> OTHER INFORMATION: pancreatic lipase precursor

<400> SEQUENCE: 62

Gln Phe Asn Phe Cys Ser Pro Glu Thr Val Arg Glu Glu Val Leu Leu
 1               5                  10                  15

Thr Leu Thr Pro Cys
            20

<210> SEQ ID NO 63
<211> LENGTH: 23
<212> TYPE: PRT
<213> ORGANISM: Homo Sapiens
<220> FEATURE:
<221> NAME/KEY: PEPTIDE
<222> LOCATION: (1)...(20)
<223> OTHER INFORMATION: pancreatic lipase precursor

<400> SEQUENCE: 63

Asn Glu Asn Pro Asn Asn Phe Gln Glu Val Ala Ala Asp Ser Ser Ser
 1               5                  10                  15

Ile Ser Gly Ser Asn Phe Lys
            20

<210> SEQ ID NO 64
<211> LENGTH: 24
<212> TYPE: PRT
<213> ORGANISM: Homo Sapiens
<220> FEATURE:
<221> NAME/KEY: PEPTIDE
<222> LOCATION: (1)...(20)
<223> OTHER INFORMATION: pancreatic lipase precursor

<400> SEQUENCE: 64

Asp Val Ile His Thr Asp Gly Ala Pro Ile Val Pro Asn Leu Gly Phe
 1               5                  10                  15

Gly Met Ser Gln Val Val Gly His
            20

<210> SEQ ID NO 65
<211> LENGTH: 23
<212> TYPE: PRT
<213> ORGANISM: Homo Sapiens
<220> FEATURE:
<221> NAME/KEY: PEPTIDE
<222> LOCATION: (1)...(20)
<223> OTHER INFORMATION: pancreatic lipase precursor

<400> SEQUENCE: 65

Gly Thr Leu Lys Pro Asp Ser Thr His Ser Asn Glu Phe Asp Ser Asp
```

```
                1               5                  10                 15

Val Asp Val Gly Asp Leu Gln
            20

<210> SEQ ID NO 66
<211> LENGTH: 22
<212> TYPE: PRT
<213> ORGANISM: Homo Sapiens
<220> FEATURE:
<221> NAME/KEY: PEPTIDE
<222> LOCATION: (1)...(20)
<223> OTHER INFORMATION: pancreatic lipase precursor

<400> SEQUENCE: 66

Ser Asp Asp Ser Pro Trp Ser Gly Ile Thr Glu Arg Pro Leu His Ile
1               5                   10                  15

Leu Pro Trp Ser Pro Lys
            20

<210> SEQ ID NO 67
<211> LENGTH: 24
<212> TYPE: PRT
<213> ORGANISM: Homo Sapiens
<220> FEATURE:
<221> NAME/KEY: PEPTIDE
<222> LOCATION: (1)...(20)
<223> OTHER INFORMATION: pancreatic lipase precursor

<400> SEQUENCE: 67

Thr Asn Glu Asn Pro Asn Asn Phe Gln Glu Val Ala Ala Asp Ser Ser
1               5                   10                  15

Ser Ile Ser Gly Ser Asn Phe Lys
            20

<210> SEQ ID NO 68
<211> LENGTH: 24
<212> TYPE: PRT
<213> ORGANISM: Homo Sapiens
<220> FEATURE:
<221> NAME/KEY: PEPTIDE
<222> LOCATION: (1)...(20)
<223> OTHER INFORMATION: pancreatic lipase precursor

<400> SEQUENCE: 68

Lys Gly Thr Leu Lys Pro Asp Ser Thr His Ser Asn Glu Phe Asp Ser
1               5                   10                  15

Asp Val Asp Val Gly Asp Leu Gln
            20

<210> SEQ ID NO 69
<211> LENGTH: 24
<212> TYPE: PRT
<213> ORGANISM: Homo Sapiens
<220> FEATURE:
<221> NAME/KEY: PEPTIDE
<222> LOCATION: (1)...(20)
<223> OTHER INFORMATION: pancreatic lipase precursor

<400> SEQUENCE: 69

Gly Thr Leu Lys Pro Asp Ser Thr His Ser Asn Glu Phe Asp Ser Asp
1               5                   10                  15

Val Asp Val Gly Asp Leu Gln Met
            20

<210> SEQ ID NO 70
```

```
<211> LENGTH: 26
<212> TYPE: PRT
<213> ORGANISM: Homo Sapiens
<220> FEATURE:
<221> NAME/KEY: PEPTIDE
<222> LOCATION: (1)...(25)
<223> OTHER INFORMATION: pancreatic lipase precursor

<400> SEQUENCE: 70

Phe Val Asp Val Ile His Thr Asp Gly Ala Pro Ile Val Pro Asn Leu
 1               5                  10                  15

Gly Phe Gly Met Ser Gln Val Val Gly His
            20                  25

<210> SEQ ID NO 71
<211> LENGTH: 25
<212> TYPE: PRT
<213> ORGANISM: Homo Sapiens
<220> FEATURE:
<221> NAME/KEY: PEPTIDE
<222> LOCATION: (1)...(25)
<223> OTHER INFORMATION: pancreatic lipase precursor

<400> SEQUENCE: 71

Tyr Thr Asn Glu Asn Pro Asn Asn Phe Gln Glu Val Ala Ala Asp Ser
 1               5                  10                  15

Ser Ser Ile Ser Gly Ser Asn Phe Lys
            20                  25

<210> SEQ ID NO 72
<211> LENGTH: 26
<212> TYPE: PRT
<213> ORGANISM: Homo Sapiens
<220> FEATURE:
<221> NAME/KEY: PEPTIDE
<222> LOCATION: (1)...(25)
<223> OTHER INFORMATION: pancreatic lipase precursor

<400> SEQUENCE: 72

Leu Gly Phe Gly Met Ser Gln Val Val Gly His Leu Asp Phe Phe Pro
 1               5                  10                  15

Asn Gly Gly Val Glu Met Pro Gly Cys Lys
            20                  25

<210> SEQ ID NO 73
<211> LENGTH: 26
<212> TYPE: PRT
<213> ORGANISM: Homo Sapiens
<220> FEATURE:
<221> NAME/KEY: PEPTIDE
<222> LOCATION: (1)...(25)
<223> OTHER INFORMATION: pancreatic lipase precursor

<400> SEQUENCE: 73

Leu Tyr Thr Asn Glu Asn Pro Asn Asn Phe Gln Glu Val Ala Ala Asp
 1               5                  10                  15

Ser Ser Ser Ile Ser Gly Ser Asn Phe Lys
            20                  25

<210> SEQ ID NO 74
<211> LENGTH: 26
<212> TYPE: PRT
<213> ORGANISM: Homo Sapiens
<220> FEATURE:
<221> NAME/KEY: PEPTIDE
<222> LOCATION: (1)...(25)
<223> OTHER INFORMATION: pancreatic lipase precursor
```

<400> SEQUENCE: 74

Gly Thr Leu Lys Pro Asp Ser Thr His Ser Asn Glu Phe Asp Ser Asp
1               5                   10                  15

Val Asp Val Gly Asp Leu Gln Met Val Lys
            20                  25

<210> SEQ ID NO 75
<211> LENGTH: 26
<212> TYPE: PRT
<213> ORGANISM: Homo Sapiens
<220> FEATURE:
<221> NAME/KEY: PEPTIDE
<222> LOCATION: (1)...(25)
<223> OTHER INFORMATION: pancreatic lipase precursor

<400> SEQUENCE: 75

Leu Gly Cys Phe Ser Asp Asp Ser Pro Trp Ser Gly Ile Thr Glu Arg
1               5                   10                  15

Pro Leu His Ile Leu Pro Trp Ser Pro Lys
            20                  25

<210> SEQ ID NO 76
<211> LENGTH: 28
<212> TYPE: PRT
<213> ORGANISM: Homo Sapiens
<220> FEATURE:
<221> NAME/KEY: PEPTIDE
<222> LOCATION: (1)...(25)
<223> OTHER INFORMATION: pancreatic lipase precursor

<400> SEQUENCE: 76

Phe Leu Leu Tyr Thr Asn Glu Asn Pro Asn Asn Phe Gln Glu Val Ala
1               5                   10                  15

Ala Asp Ser Ser Ser Ile Ser Gly Ser Asn Phe Lys
            20                  25

<210> SEQ ID NO 77
<211> LENGTH: 29
<212> TYPE: PRT
<213> ORGANISM: Homo Sapiens
<220> FEATURE:
<221> NAME/KEY: PEPTIDE
<222> LOCATION: (1)...(25)
<223> OTHER INFORMATION: pancreatic lipase precursor

<400> SEQUENCE: 77

Ile Val Gly Ala Glu Val Ala Tyr Phe Val Glu Phe Leu Gln Ser Ala
1               5                   10                  15

Phe Gly Tyr Ser Pro Ser Asn Val His Val Ile Gly His
            20                  25

<210> SEQ ID NO 78
<211> LENGTH: 8
<212> TYPE: PRT
<213> ORGANISM: Homo Sapiens
<220> FEATURE:
<221> NAME/KEY: PEPTIDE
<222> LOCATION: (1)...(5)
<223> OTHER INFORMATION: pancreatic amylase alpha 2A precursor

<400> SEQUENCE: 78

Ser Gly Asn Glu Asp Glu Phe Arg
1               5

```
<210> SEQ ID NO 79
<211> LENGTH: 9
<212> TYPE: PRT
<213> ORGANISM: Homo Sapiens
<220> FEATURE:
<221> NAME/KEY: PEPTIDE
<222> LOCATION: (1)...(5)
<223> OTHER INFORMATION: pancreatic amylase alpha 2A precursor

<400> SEQUENCE: 79

Ser Gly Trp Asp Phe Asn Asp Gly Lys
 1               5

<210> SEQ ID NO 80
<211> LENGTH: 9
<212> TYPE: PRT
<213> ORGANISM: Homo Sapiens
<220> FEATURE:
<221> NAME/KEY: PEPTIDE
<222> LOCATION: (1)...(5)
<223> OTHER INFORMATION: pancreatic amylase alpha 2A precursor

<400> SEQUENCE: 80

Ile Tyr Val Asp Ala Val Ile Asn His
 1               5

<210> SEQ ID NO 81
<211> LENGTH: 9
<212> TYPE: PRT
<213> ORGANISM: Homo Sapiens
<220> FEATURE:
<221> NAME/KEY: PEPTIDE
<222> LOCATION: (1)...(5)
<223> OTHER INFORMATION: pancreatic amylase alpha 2A precursor

<400> SEQUENCE: 81

Ile Ala Glu Tyr Met Asn His Leu Ile
 1               5

<210> SEQ ID NO 82
<211> LENGTH: 10
<212> TYPE: PRT
<213> ORGANISM: Homo Sapiens
<220> FEATURE:
<221> NAME/KEY: PEPTIDE
<222> LOCATION: (1)...(10)
<223> OTHER INFORMATION: pancreatic amylase alpha 2A precursor

<400> SEQUENCE: 82

Pro Phe Ile Ala Ile His Ala Glu Ser Lys
 1               5                  10

<210> SEQ ID NO 83
<211> LENGTH: 11
<212> TYPE: PRT
<213> ORGANISM: Homo Sapiens
<220> FEATURE:
<221> NAME/KEY: PEPTIDE
<222> LOCATION: (1)...(10)
<223> OTHER INFORMATION: pancreatic amylase alpha 2A precursor

<400> SEQUENCE: 83

Glu Val Ile Asp Leu Gly Gly Glu Pro Ile Lys
 1               5                  10

<210> SEQ ID NO 84
<211> LENGTH: 11
<212> TYPE: PRT
<213> ORGANISM: Homo Sapiens
```

```
<220> FEATURE:
<221> NAME/KEY: PEPTIDE
<222> LOCATION: (1)...(10)
<223> OTHER INFORMATION: pancreatic amylase alpha 2A precursor

<400> SEQUENCE: 84

Leu Thr Gly Leu Leu Asp Leu Ala Leu Glu Lys
1               5                   10

<210> SEQ ID NO 85
<211> LENGTH: 10
<212> TYPE: PRT
<213> ORGANISM: Homo Sapiens
<220> FEATURE:
<221> NAME/KEY: PEPTIDE
<222> LOCATION: (1)...(10)
<223> OTHER INFORMATION: pancreatic amylase alpha 2A precursor

<400> SEQUENCE: 85

Asp Leu Ala Leu Glu Lys Asp Tyr Val Arg
1               5                   10

<210> SEQ ID NO 86
<211> LENGTH: 10
<212> TYPE: PRT
<213> ORGANISM: Homo Sapiens
<220> FEATURE:
<221> NAME/KEY: PEPTIDE
<222> LOCATION: (1)...(10)
<223> OTHER INFORMATION: pancreatic amylase alpha 2A precursor

<400> SEQUENCE: 86

Trp Val Asp Ile Ala Leu Glu Cys Glu Arg
1               5                   10

<210> SEQ ID NO 87
<211> LENGTH: 11
<212> TYPE: PRT
<213> ORGANISM: Homo Sapiens
<220> FEATURE:
<221> NAME/KEY: PEPTIDE
<222> LOCATION: (1)...(10)
<223> OTHER INFORMATION: pancreatic amylase alpha 2A precursor

<400> SEQUENCE: 87

Met Ala Val Gly Phe Met Leu Ala His Pro Tyr
1               5                   10

<210> SEQ ID NO 88
<211> LENGTH: 10
<212> TYPE: PRT
<213> ORGANISM: Homo Sapiens
<220> FEATURE:
<221> NAME/KEY: PEPTIDE
<222> LOCATION: (1)...(10)
<223> OTHER INFORMATION: pancreatic amylase alpha 2A precursor

<400> SEQUENCE: 88

Thr Ser Ile Val His Leu Phe Glu Trp Arg
1               5                   10

<210> SEQ ID NO 89
<211> LENGTH: 12
<212> TYPE: PRT
<213> ORGANISM: Homo Sapiens
<220> FEATURE:
<221> NAME/KEY: PEPTIDE
<222> LOCATION: (1)...(10)
<223> OTHER INFORMATION: pancreatic amylase alpha 2A precursor
```

<400> SEQUENCE: 89

Gln Glu Val Ile Asp Leu Gly Gly Glu Pro Ile Lys
1               5                   10

<210> SEQ ID NO 90
<211> LENGTH: 12
<212> TYPE: PRT
<213> ORGANISM: Homo Sapiens
<220> FEATURE:
<221> NAME/KEY: PEPTIDE
<222> LOCATION: (1)...(10)
<223> OTHER INFORMATION: pancreatic amylase alpha 2A precursor

<400> SEQUENCE: 90

Asn His Leu Ile Asp Ile Gly Val Ala Gly Phe Arg
1               5                   10

<210> SEQ ID NO 91
<211> LENGTH: 11
<212> TYPE: PRT
<213> ORGANISM: Homo Sapiens
<220> FEATURE:
<221> NAME/KEY: PEPTIDE
<222> LOCATION: (1)...(10)
<223> OTHER INFORMATION: pancreatic amylase alpha 2A precursor

<400> SEQUENCE: 91

Leu Asp Leu Ala Leu Glu Lys Asp Tyr Val Arg
1               5                   10

<210> SEQ ID NO 92
<211> LENGTH: 12
<212> TYPE: PRT
<213> ORGANISM: Homo Sapiens
<220> FEATURE:
<221> NAME/KEY: PEPTIDE
<222> LOCATION: (1)...(10)
<223> OTHER INFORMATION: pancreatic amylase alpha 2A precursor

<400> SEQUENCE: 92

Asn Ser Asn Trp Phe Pro Ala Gly Ser Lys Pro Phe
1               5                   10

<210> SEQ ID NO 93
<211> LENGTH: 14
<212> TYPE: PRT
<213> ORGANISM: Homo Sapiens
<220> FEATURE:
<221> NAME/KEY: PEPTIDE
<222> LOCATION: (1)...(10)
<223> OTHER INFORMATION: pancreatic amylase alpha 2A precursor

<400> SEQUENCE: 93

Gly Phe Gly Gly Val Gln Val Ser Pro Pro Asn Glu Asn Val
1               5                   10

<210> SEQ ID NO 94
<211> LENGTH: 13
<212> TYPE: PRT
<213> ORGANISM: Homo Sapiens
<220> FEATURE:
<221> NAME/KEY: PEPTIDE
<222> LOCATION: (1)...(10)
<223> OTHER INFORMATION: pancreatic amylase alpha 2A precursor

<400> SEQUENCE: 94

Ala His Phe Ser Ile Ser Asn Ser Ala Glu Asp Pro Phe

```
1               5                   10
```

<210> SEQ ID NO 95
<211> LENGTH: 12
<212> TYPE: PRT
<213> ORGANISM: Homo Sapiens
<220> FEATURE:
<221> NAME/KEY: PEPTIDE
<222> LOCATION: (1)...(10)
<223> OTHER INFORMATION: pancreatic amylase alpha 2A precursor

<400> SEQUENCE: 95

```
Ala Leu Val Phe Val Asp Asn His Asp Asn Gln Arg
1               5                   10
```

<210> SEQ ID NO 96
<211> LENGTH: 13
<212> TYPE: PRT
<213> ORGANISM: Homo Sapiens
<220> FEATURE:
<221> NAME/KEY: PEPTIDE
<222> LOCATION: (1)...(10)
<223> OTHER INFORMATION: pancreatic amylase alpha 2A precursor

<400> SEQUENCE: 96

```
Met Asn His Leu Ile Asp Ile Gly Val Ala Gly Phe Arg
1               5                   10
```

<210> SEQ ID NO 97
<211> LENGTH: 13
<212> TYPE: PRT
<213> ORGANISM: Homo Sapiens
<220> FEATURE:
<221> NAME/KEY: PEPTIDE
<222> LOCATION: (1)...(10)
<223> OTHER INFORMATION: pancreatic amylase alpha 2A precursor

<400> SEQUENCE: 97

```
Ile Tyr Val Asp Ala Val Ile Asn His Met Cys Gly Asn
1               5                   10
```

<210> SEQ ID NO 98
<211> LENGTH: 15
<212> TYPE: PRT
<213> ORGANISM: Homo Sapiens
<220> FEATURE:
<221> NAME/KEY: PEPTIDE
<222> LOCATION: (1)...(15)
<223> OTHER INFORMATION: pancreatic amylase alpha 2A precursor

<400> SEQUENCE: 98

```
Gly Phe Gly Gly Val Gln Val Ser Pro Pro Asn Glu Asn Val Ala
1               5                   10                  15
```

<210> SEQ ID NO 99
<211> LENGTH: 14
<212> TYPE: PRT
<213> ORGANISM: Homo Sapiens
<220> FEATURE:
<221> NAME/KEY: PEPTIDE
<222> LOCATION: (1)...(10)
<223> OTHER INFORMATION: pancreatic amylase alpha 2A precursor

<400> SEQUENCE: 99

```
Ser Ile Ser Asn Ser Ala Glu Asp Pro Phe Ile Ala Ile His
1               5                   10
```

<210> SEQ ID NO 100

<211> LENGTH: 13
<212> TYPE: PRT
<213> ORGANISM: Homo Sapiens
<220> FEATURE:
<221> NAME/KEY: PEPTIDE
<222> LOCATION: (1)...(10)
<223> OTHER INFORMATION: pancreatic amylase alpha 2A precursor

<400> SEQUENCE: 100

Gly Leu Leu Asp Leu Ala Leu Glu Lys Asp Tyr Val Arg
1               5                   10

<210> SEQ ID NO 101
<211> LENGTH: 13
<212> TYPE: PRT
<213> ORGANISM: Homo Sapiens
<220> FEATURE:
<221> NAME/KEY: PEPTIDE
<222> LOCATION: (1)...(10)
<223> OTHER INFORMATION: pancreatic amylase alpha 2A precursor

<400> SEQUENCE: 101

Asn Trp Gly Glu Gly Trp Gly Phe Val Pro Ser Asp Arg
1               5                   10

<210> SEQ ID NO 102
<211> LENGTH: 14
<212> TYPE: PRT
<213> ORGANISM: Homo Sapiens
<220> FEATURE:
<221> NAME/KEY: PEPTIDE
<222> LOCATION: (1)...(10)
<223> OTHER INFORMATION: pancreatic amylase alpha 2A precursor

<400> SEQUENCE: 102

Ile Tyr Gln Glu Val Ile Asp Leu Gly Gly Glu Pro Ile Lys
1               5                   10

<210> SEQ ID NO 103
<211> LENGTH: 14
<212> TYPE: PRT
<213> ORGANISM: Homo Sapiens
<220> FEATURE:
<221> NAME/KEY: PEPTIDE
<222> LOCATION: (1)...(10)
<223> OTHER INFORMATION: pancreatic amylase alpha 2A precursor

<400> SEQUENCE: 103

Asn Leu Asn Ser Asn Trp Phe Pro Ala Gly Ser Lys Pro Phe
1               5                   10

<210> SEQ ID NO 104
<211> LENGTH: 14
<212> TYPE: PRT
<213> ORGANISM: Homo Sapiens
<220> FEATURE:
<221> NAME/KEY: PEPTIDE
<222> LOCATION: (1)...(10)
<223> OTHER INFORMATION: pancreatic amylase alpha 2A precursor

<400> SEQUENCE: 104

Thr Gly Leu Leu Asp Leu Ala Leu Glu Lys Asp Tyr Val Arg
1               5                   10

<210> SEQ ID NO 105
<211> LENGTH: 16
<212> TYPE: PRT
<213> ORGANISM: Homo Sapiens
<220> FEATURE:

```
<221> NAME/KEY: PEPTIDE
<222> LOCATION: (1)...(15)
<223> OTHER INFORMATION: pancreatic amylase alpha 2A precursor

<400> SEQUENCE: 105

Gly His Gly Ala Gly Gly Ala Ser Ile Leu Thr Phe Trp Asp Ala Arg
 1               5                  10                  15

<210> SEQ ID NO 106
<211> LENGTH: 15
<212> TYPE: PRT
<213> ORGANISM: Homo Sapiens
<220> FEATURE:
<221> NAME/KEY: PEPTIDE
<222> LOCATION: (1)...(15)
<223> OTHER INFORMATION: pancreatic amylase alpha 2A precursor

<400> SEQUENCE: 106

Phe Ser Ile Ser Asn Ser Ala Glu Asp Pro Phe Ile Ala Ile His
 1               5                  10                  15

<210> SEQ ID NO 107
<211> LENGTH: 17
<212> TYPE: PRT
<213> ORGANISM: Homo Sapiens
<220> FEATURE:
<221> NAME/KEY: PEPTIDE
<222> LOCATION: (1)...(15)
<223> OTHER INFORMATION: pancreatic amylase alpha 2A precursor

<400> SEQUENCE: 107

Ser Ala Gly Thr Ser Ser Thr Cys Gly Ser Tyr Phe Asn Pro Gly Ser
 1               5                  10                  15

Arg

<210> SEQ ID NO 108
<211> LENGTH: 15
<212> TYPE: PRT
<213> ORGANISM: Homo Sapiens
<220> FEATURE:
<221> NAME/KEY: PEPTIDE
<222> LOCATION: (1)...(15)
<223> OTHER INFORMATION: pancreatic amylase alpha 2A precursor

<400> SEQUENCE: 108

Leu His Asn Leu Asn Ser Asn Trp Phe Pro Ala Gly Ser Lys Pro
 1               5                  10                  15

<210> SEQ ID NO 109
<211> LENGTH: 15
<212> TYPE: PRT
<213> ORGANISM: Homo Sapiens
<220> FEATURE:
<221> NAME/KEY: PEPTIDE
<222> LOCATION: (1)...(15)
<223> OTHER INFORMATION: pancreatic amylase alpha 2A precursor

<400> SEQUENCE: 109

Leu Thr Gly Leu Leu Asp Leu Ala Leu Glu Lys Asp Tyr Val Arg
 1               5                  10                  15

<210> SEQ ID NO 110
<211> LENGTH: 15
<212> TYPE: PRT
<213> ORGANISM: Homo Sapiens
<220> FEATURE:
<221> NAME/KEY: PEPTIDE
<222> LOCATION: (1)...(15)
```

```
<223> OTHER INFORMATION: pancreatic amylase alpha 2A precursor

<400> SEQUENCE: 110

Thr Asn Trp Tyr Asp Asn Gly Ser Asn Gln Val Ala Phe Gly Arg
  1               5                  10                  15

<210> SEQ ID NO 111
<211> LENGTH: 15
<212> TYPE: PRT
<213> ORGANISM: Homo Sapiens
<220> FEATURE:
<221> NAME/KEY: PEPTIDE
<222> LOCATION: (1)...(15)
<223> OTHER INFORMATION: pancreatic amylase alpha 2A precursor

<400> SEQUENCE: 111

Glu Tyr Met Asn His Leu Ile Asp Ile Gly Val Ala Gly Phe Arg
  1               5                  10                  15

<210> SEQ ID NO 112
<211> LENGTH: 16
<212> TYPE: PRT
<213> ORGANISM: Homo Sapiens
<220> FEATURE:
<221> NAME/KEY: PEPTIDE
<222> LOCATION: (1)...(15)
<223> OTHER INFORMATION: pancreatic amylase alpha 2A precursor

<400> SEQUENCE: 112

Thr Gly Ser Gly Asp Ile Glu Asn Tyr Asn Asp Ala Thr Gln Val Arg
  1               5                  10                  15

<210> SEQ ID NO 113
<211> LENGTH: 15
<212> TYPE: PRT
<213> ORGANISM: Homo Sapiens
<220> FEATURE:
<221> NAME/KEY: PEPTIDE
<222> LOCATION: (1)...(15)
<223> OTHER INFORMATION: pancreatic amylase alpha 2A precursor

<400> SEQUENCE: 113

Ala Ile Leu Asp Lys Leu His Asn Leu Asn Ser Asn Trp Phe Pro
  1               5                  10                  15

<210> SEQ ID NO 114
<211> LENGTH: 16
<212> TYPE: PRT
<213> ORGANISM: Homo Sapiens
<220> FEATURE:
<221> NAME/KEY: PEPTIDE
<222> LOCATION: (1)...(15)
<223> OTHER INFORMATION: pancreatic amylase alpha 2A precursor

<400> SEQUENCE: 114

Ala Glu Tyr Met Asn His Leu Ile Asp Ile Gly Val Ala Gly Phe Arg
  1               5                  10                  15

<210> SEQ ID NO 115
<211> LENGTH: 16
<212> TYPE: PRT
<213> ORGANISM: Homo Sapiens
<220> FEATURE:
<221> NAME/KEY: PEPTIDE
<222> LOCATION: (1)...(15)
<223> OTHER INFORMATION: pancreatic amylase alpha 2A precursor

<400> SEQUENCE: 115
```

```
Asp Phe Pro Ala Val Pro Tyr Ser Gly Trp Asp Phe Asn Asp Gly Lys
1               5                   10                  15
```

<210> SEQ ID NO 116
<211> LENGTH: 16
<212> TYPE: PRT
<213> ORGANISM: Homo Sapiens
<220> FEATURE:
<221> NAME/KEY: PEPTIDE
<222> LOCATION: (1)...(15)
<223> OTHER INFORMATION: pancreatic amylase alpha 2A precursor

<400> SEQUENCE: 116

```
Pro Phe Ile Tyr Gln Glu Val Ile Asp Leu Gly Gly Glu Pro Ile Lys
1               5                   10                  15
```

<210> SEQ ID NO 117
<211> LENGTH: 16
<212> TYPE: PRT
<213> ORGANISM: Homo Sapiens
<220> FEATURE:
<221> NAME/KEY: PEPTIDE
<222> LOCATION: (1)...(15)
<223> OTHER INFORMATION: pancreatic amylase alpha 2A precursor

<400> SEQUENCE: 117

```
Leu His Asn Leu Asn Ser Asn Trp Phe Pro Ala Gly Ser Lys Pro Phe
1               5                   10                  15
```

<210> SEQ ID NO 118
<211> LENGTH: 19
<212> TYPE: PRT
<213> ORGANISM: Homo Sapiens
<220> FEATURE:
<221> NAME/KEY: PEPTIDE
<222> LOCATION: (1)...(15)
<223> OTHER INFORMATION: pancreatic amylase alpha 2A precursor

<400> SEQUENCE: 118

```
Ala Val Ser Ala Gly Thr Ser Ser Thr Cys Gly Ser Tyr Phe Asn Pro
1               5                   10                  15

Gly Ser Arg
```

<210> SEQ ID NO 119
<211> LENGTH: 17
<212> TYPE: PRT
<213> ORGANISM: Homo Sapiens
<220> FEATURE:
<221> NAME/KEY: PEPTIDE
<222> LOCATION: (1)...(15)
<223> OTHER INFORMATION: pancreatic amylase alpha 2A precursor

<400> SEQUENCE: 119

```
Ala His Phe Ser Ile Ser Asn Ser Ala Glu Asp Pro Phe Ile Ala Ile
1               5                   10                  15

His
```

<210> SEQ ID NO 120
<211> LENGTH: 18
<212> TYPE: PRT
<213> ORGANISM: Homo Sapiens
<220> FEATURE:
<221> NAME/KEY: PEPTIDE
<222> LOCATION: (1)...(15)
<223> OTHER INFORMATION: pancreatic amylase alpha 2A precursor

<400> SEQUENCE: 120

Ser Ile Ser Asn Ser Ala Glu Asp Pro Phe Ile Ala Ile His Ala Glu
1               5                   10                  15

Ser Lys

<210> SEQ ID NO 121
<211> LENGTH: 17
<212> TYPE: PRT
<213> ORGANISM: Homo Sapiens
<220> FEATURE:
<221> NAME/KEY: PEPTIDE
<222> LOCATION: (1)...(15)
<223> OTHER INFORMATION: pancreatic amylase alpha 2A precursor

<400> SEQUENCE: 121

Ile Ala Glu Tyr Met Asn His Leu Ile Asp Ile Gly Val Ala Gly Phe
1               5                   10                  15

Arg

<210> SEQ ID NO 122
<211> LENGTH: 19
<212> TYPE: PRT
<213> ORGANISM: Homo Sapiens
<220> FEATURE:
<221> NAME/KEY: PEPTIDE
<222> LOCATION: (1)...(15)
<223> OTHER INFORMATION: pancreatic amylase alpha 2A precursor

<400> SEQUENCE: 122

Ser Ile Ser Asn Ser Ala Glu Asp Pro Phe Ile Ala Ile His Ala Glu
1               5                   10                  15

Ser Lys Leu

<210> SEQ ID NO 123
<211> LENGTH: 18
<212> TYPE: PRT
<213> ORGANISM: Homo Sapiens
<220> FEATURE:
<221> NAME/KEY: PEPTIDE
<222> LOCATION: (1)...(15)
<223> OTHER INFORMATION: pancreatic amylase alpha 2A precursor

<400> SEQUENCE: 123

Glu Val Thr Ile Asn Pro Asp Thr Thr Cys Gly Asn Asp Trp Val Cys
1               5                   10                  15

Glu His

<210> SEQ ID NO 124
<211> LENGTH: 19
<212> TYPE: PRT
<213> ORGANISM: Homo Sapiens
<220> FEATURE:
<221> NAME/KEY: PEPTIDE
<222> LOCATION: (1)...(15)
<223> OTHER INFORMATION: pancreatic amylase alpha 2A precursor

<400> SEQUENCE: 124

Ser Lys Ile Ala Glu Tyr Met Asn His Leu Ile Asp Ile Gly Val Ala
1               5                   10                  15

Gly Phe Arg

<210> SEQ ID NO 125
<211> LENGTH: 19
<212> TYPE: PRT
<213> ORGANISM: Homo Sapiens
<220> FEATURE:

```
<221> NAME/KEY: PEPTIDE
<222> LOCATION: (1)...(15)
<223> OTHER INFORMATION: pancreatic amylase alpha 2A precursor

<400> SEQUENCE: 125

Glu Val Thr Ile Asn Pro Asp Thr Thr Cys Gly Asn Asp Trp Val Cys
1               5                   10                  15

Glu His Arg

<210> SEQ ID NO 126
<211> LENGTH: 21
<212> TYPE: PRT
<213> ORGANISM: Homo Sapiens
<220> FEATURE:
<221> NAME/KEY: PEPTIDE
<222> LOCATION: (1)...(20)
<223> OTHER INFORMATION: pancreatic amylase alpha 2A precursor

<400> SEQUENCE: 126

Ala His Phe Ser Ile Ser Asn Ser Ala Glu Asp Pro Phe Ile Ala Ile
1               5                   10                  15

His Ala Glu Ser Lys
            20

<210> SEQ ID NO 127
<211> LENGTH: 21
<212> TYPE: PRT
<213> ORGANISM: Homo Sapiens
<220> FEATURE:
<221> NAME/KEY: PEPTIDE
<222> LOCATION: (1)...(20)
<223> OTHER INFORMATION: pancreatic amylase alpha 2A precursor

<400> SEQUENCE: 127

Ala Ile Leu Asp Lys Leu His Asn Leu Asn Ser Asn Trp Phe Pro Ala
1               5                   10                  15

Gly Ser Lys Pro Phe
            20

<210> SEQ ID NO 128
<211> LENGTH: 21
<212> TYPE: PRT
<213> ORGANISM: Homo Sapiens
<220> FEATURE:
<221> NAME/KEY: PEPTIDE
<222> LOCATION: (1)...(20)
<223> OTHER INFORMATION: pancreatic amylase alpha 2A precursor

<400> SEQUENCE: 128

Asn Val Val Asp Gly Gln Pro Phe Thr Asn Trp Tyr Asp Asn Gly Ser
1               5                   10                  15

Asn Gln Val Ala Phe
            20

<210> SEQ ID NO 129
<211> LENGTH: 22
<212> TYPE: PRT
<213> ORGANISM: Homo Sapiens
<220> FEATURE:
<221> NAME/KEY: PEPTIDE
<222> LOCATION: (1)...(20)
<223> OTHER INFORMATION: pancreatic amylase alpha 2A precursor

<400> SEQUENCE: 129

Ala His Phe Ser Ile Ser Asn Ser Ala Glu Asp Pro Phe Ile Ala Ile
1               5                   10                  15
```

His Ala Glu Ser Lys Leu
            20

<210> SEQ ID NO 130
<211> LENGTH: 22
<212> TYPE: PRT
<213> ORGANISM: Homo Sapiens
<220> FEATURE:
<221> NAME/KEY: PEPTIDE
<222> LOCATION: (1)...(20)
<223> OTHER INFORMATION: pancreatic amylase alpha 2A precursor

<400> SEQUENCE: 130

Gln Phe Gln Asn Gly Asn Asp Val Asn Asp Trp Val Gly Pro Pro Asn
 1               5                  10                  15

Asn Asn Gly Val Ile Lys
            20

<210> SEQ ID NO 131
<211> LENGTH: 25
<212> TYPE: PRT
<213> ORGANISM: Homo Sapiens
<220> FEATURE:
<221> NAME/KEY: PEPTIDE
<222> LOCATION: (1)...(25)
<223> OTHER INFORMATION: pancreatic amylase alpha 2A precursor

<400> SEQUENCE: 131

Asn His Met Cys Gly Asn Ala Val Ser Ala Gly Thr Ser Ser Thr Cys
 1               5                  10                  15

Gly Ser Tyr Phe Asn Pro Gly Ser Arg
            20                  25

<210> SEQ ID NO 132
<211> LENGTH: 23
<212> TYPE: PRT
<213> ORGANISM: Homo Sapiens
<220> FEATURE:
<221> NAME/KEY: PEPTIDE
<222> LOCATION: (1)...(20)
<223> OTHER INFORMATION: pancreatic amylase alpha 2A precursor

<400> SEQUENCE: 132

Gly Phe Gly Gly Val Gln Val Ser Pro Pro Asn Glu Asn Val Ala Ile
 1               5                  10                  15

Tyr Asn Pro Phe Arg Pro Trp
            20

<210> SEQ ID NO 133
<211> LENGTH: 23
<212> TYPE: PRT
<213> ORGANISM: Homo Sapiens
<220> FEATURE:
<221> NAME/KEY: PEPTIDE
<222> LOCATION: (1)...(20)
<223> OTHER INFORMATION: pancreatic amylase alpha 2A precursor

<400> SEQUENCE: 133

Asn Val Val Asp Gly Gln Pro Phe Thr Asn Trp Tyr Asp Asn Gly Ser
 1               5                  10                  15

Asn Gln Val Ala Phe Gly Arg
            20

<210> SEQ ID NO 134
<211> LENGTH: 26

```
<212> TYPE: PRT
<213> ORGANISM: Homo Sapiens
<220> FEATURE:
<221> NAME/KEY: PEPTIDE
<222> LOCATION: (1)...(25)
<223> OTHER INFORMATION: pancreatic amylase alpha 2A precursor

<400> SEQUENCE: 134

Ile Asn His Met Cys Gly Asn Ala Val Ser Ala Gly Thr Ser Ser Thr
1               5                   10                  15
Cys Gly Ser Tyr Phe Asn Pro Gly Ser Arg
            20                  25

<210> SEQ ID NO 135
<211> LENGTH: 32
<212> TYPE: PRT
<213> ORGANISM: Homo Sapiens
<220> FEATURE:
<221> NAME/KEY: PEPTIDE
<222> LOCATION: (1)...(30)
<223> OTHER INFORMATION: pancreatic amylase alpha 2A precursor

<400> SEQUENCE: 135

Ile Tyr Val Asp Ala Val Ile Asn His Met Cys Gly Asn Ala Val Ser
1               5                   10                  15
Ala Gly Thr Ser Ser Thr Cys Gly Ser Tyr Phe Asn Pro Gly Ser Arg
            20                  25                  30

<210> SEQ ID NO 136
<211> LENGTH: 30
<212> TYPE: PRT
<213> ORGANISM: Homo Sapiens
<220> FEATURE:
<221> NAME/KEY: PEPTIDE
<222> LOCATION: (1)...(30)
<223> OTHER INFORMATION: pancreatic amylase alpha 2A precursor

<400> SEQUENCE: 136

Leu His Asn Leu Asn Ser Asn Trp Phe Pro Ala Gly Ser Lys Pro Phe
1               5                   10                  15
Ile Tyr Gln Glu Val Ile Asp Leu Gly Gly Glu Pro Ile Lys
            20                  25                  30

<210> SEQ ID NO 137
<211> LENGTH: 35
<212> TYPE: PRT
<213> ORGANISM: Homo Sapiens
<220> FEATURE:
<221> NAME/KEY: PEPTIDE
<222> LOCATION: (1)...(35)
<223> OTHER INFORMATION: pancreatic amylase alpha 2A precursor

<400> SEQUENCE: 137

Ala Ile Leu Asp Lys Leu His Asn Leu Asn Ser Asn Trp Phe Pro Ala
1               5                   10                  15
Gly Ser Lys Pro Phe Ile Tyr Gln Glu Val Ile Asp Leu Gly Gly Glu
            20                  25                  30
Pro Ile Lys
        35

<210> SEQ ID NO 138
<211> LENGTH: 11
<212> TYPE: PRT
<213> ORGANISM: Homo Sapiens
<220> FEATURE:
<221> NAME/KEY: PEPTIDE
```

```
<222> LOCATION: (1)...(10)
<223> OTHER INFORMATION: amylase, pancreatic, alpha-2B precursor

<400> SEQUENCE: 138

Leu Val Gly Leu Leu Asp Leu Ala Leu Glu Lys
1               5                   10

<210> SEQ ID NO 139
<211> LENGTH: 13
<212> TYPE: PRT
<213> ORGANISM: Homo Sapiens
<220> FEATURE:
<221> NAME/KEY: PEPTIDE
<222> LOCATION: (1)...(10)
<223> OTHER INFORMATION: amylase, pancreatic, alpha-2B precursor

<400> SEQUENCE: 139

Asn Trp Gly Glu Gly Trp Gly Phe Met Pro Ser Asp Arg
1               5                   10

<210> SEQ ID NO 140
<211> LENGTH: 26
<212> TYPE: PRT
<213> ORGANISM: Homo Sapiens
<220> FEATURE:
<221> NAME/KEY: PEPTIDE
<222> LOCATION: (1)...(25)
<223> OTHER INFORMATION: amylase, pancreatic, alpha-2B precursor

<400> SEQUENCE: 140

Gly Phe Gly Gly Val Gln Val Ser Pro Pro Asn Glu Asn Val Ala Ile
1               5                   10                  15

His Asn Pro Phe Arg Pro Trp Trp Glu Arg
            20                  25

<210> SEQ ID NO 141
<211> LENGTH: 32
<212> TYPE: PRT
<213> ORGANISM: Homo Sapiens
<220> FEATURE:
<221> NAME/KEY: PEPTIDE
<222> LOCATION: (1)...(30)
<223> OTHER INFORMATION: amylase, pancreatic, alpha-2B precursor

<400> SEQUENCE: 141

Ile Tyr Val Asp Ala Val Ile Asn His Met Ser Gly Asn Ala Val Ser
1               5                   10                  15

Ala Gly Thr Ser Ser Thr Cys Gly Ser Tyr Phe Asn Pro Gly Ser Arg
            20                  25                  30

<210> SEQ ID NO 142
<211> LENGTH: 11
<212> TYPE: PRT
<213> ORGANISM: Homo Sapiens
<220> FEATURE:
<221> NAME/KEY: PEPTIDE
<222> LOCATION: (1)...(10)
<223> OTHER INFORMATION: salivary amylase alpha 1A precursor

<400> SEQUENCE: 142

Leu Ser Gly Leu Leu Asp Leu Ala Leu Gly Lys
1               5                   10

<210> SEQ ID NO 143
<211> LENGTH: 16
<212> TYPE: PRT
<213> ORGANISM: Homo Sapiens
```

-continued

```
<220> FEATURE:
<221> NAME/KEY: PEPTIDE
<222> LOCATION: (1)...(15)
<223> OTHER INFORMATION: salivary amylase alpha 1A precursor

<400> SEQUENCE: 143

Asp Val Asn Asp Trp Val Gly Pro Pro Asn Asp Asn Gly Val Thr Lys
1               5                   10                  15

<210> SEQ ID NO 144
<211> LENGTH: 7
<212> TYPE: PRT
<213> ORGANISM: Homo Sapiens
<220> FEATURE:
<221> NAME/KEY: PEPTIDE
<222> LOCATION: (1)...(5)
<223> OTHER INFORMATION: elastase 3A, pancreatic preproprotein

<400> SEQUENCE: 144

Leu Pro Val Val Asp Tyr Lys
1               5

<210> SEQ ID NO 145
<211> LENGTH: 8
<212> TYPE: PRT
<213> ORGANISM: Homo Sapiens
<220> FEATURE:
<221> NAME/KEY: PEPTIDE
<222> LOCATION: (1)...(5)
<223> OTHER INFORMATION: elastase 3A, pancreatic preproprotein

<400> SEQUENCE: 145

Gly Asn Asp Ile Ala Leu Ile Lys
1               5

<210> SEQ ID NO 146
<211> LENGTH: 7
<212> TYPE: PRT
<213> ORGANISM: Homo Sapiens
<220> FEATURE:
<221> NAME/KEY: PEPTIDE
<222> LOCATION: (1)...(5)
<223> OTHER INFORMATION: elastase 3A, pancreatic preproprotein

<400> SEQUENCE: 146

Asp Trp Ile Glu Glu Thr Ile
1               5

<210> SEQ ID NO 147
<211> LENGTH: 10
<212> TYPE: PRT
<213> ORGANISM: Homo Sapiens
<220> FEATURE:
<221> NAME/KEY: PEPTIDE
<222> LOCATION: (1)...(10)
<223> OTHER INFORMATION: elastase 3A, pancreatic preproprotein

<400> SEQUENCE: 147

Ser Ala Gln Leu Gly Asp Ala Val Gln Leu
1               5                   10

<210> SEQ ID NO 148
<211> LENGTH: 9
<212> TYPE: PRT
<213> ORGANISM: Homo Sapiens
<220> FEATURE:
<221> NAME/KEY: PEPTIDE
<222> LOCATION: (1)...(5)
<223> OTHER INFORMATION: elastase 3A, pancreatic preproprotein
```

<400> SEQUENCE: 148

Leu Gly Glu Tyr Asn Leu Ala Val Lys
 1               5

<210> SEQ ID NO 149
<211> LENGTH: 10
<212> TYPE: PRT
<213> ORGANISM: Homo Sapiens
<220> FEATURE:
<221> NAME/KEY: PEPTIDE
<222> LOCATION: (1)...(10)
<223> OTHER INFORMATION: elastase 3A, pancreatic preproprotein

<400> SEQUENCE: 149

Pro Pro Ala Gly Asp Ile Leu Pro Asn Lys
 1               5                  10

<210> SEQ ID NO 150
<211> LENGTH: 10
<212> TYPE: PRT
<213> ORGANISM: Homo Sapiens
<220> FEATURE:
<221> NAME/KEY: PEPTIDE
<222> LOCATION: (1)...(10)
<223> OTHER INFORMATION: elastase 3A, pancreatic preproprotein

<400> SEQUENCE: 150

Thr Met Val Cys Ala Gly Gly Tyr Ile Arg
 1               5                  10

<210> SEQ ID NO 151
<211> LENGTH: 11
<212> TYPE: PRT
<213> ORGANISM: Homo Sapiens
<220> FEATURE:
<221> NAME/KEY: PEPTIDE
<222> LOCATION: (1)...(10)
<223> OTHER INFORMATION: elastase 3A, pancreatic preproprotein

<400> SEQUENCE: 151

Ser Ala Gln Leu Gly Asp Ala Val Gln Leu Ala
 1               5                  10

<210> SEQ ID NO 152
<211> LENGTH: 10
<212> TYPE: PRT
<213> ORGANISM: Homo Sapiens
<220> FEATURE:
<221> NAME/KEY: PEPTIDE
<222> LOCATION: (1)...(10)
<223> OTHER INFORMATION: elastase 3A, pancreatic preproprotein

<400> SEQUENCE: 152

Leu Tyr Thr Asn Gly Pro Leu Pro Asp Lys
 1               5                  10

<210> SEQ ID NO 153
<211> LENGTH: 10
<212> TYPE: PRT
<213> ORGANISM: Homo Sapiens
<220> FEATURE:
<221> NAME/KEY: PEPTIDE
<222> LOCATION: (1)...(10)
<223> OTHER INFORMATION: elastase 3A, pancreatic preproprotein

<400> SEQUENCE: 153

Thr Pro Cys Tyr Ile Thr Gly Trp Gly Arg

```
<210> SEQ ID NO 154
<211> LENGTH: 9
<212> TYPE: PRT
<213> ORGANISM: Homo Sapiens
<220> FEATURE:
<221> NAME/KEY: PEPTIDE
<222> LOCATION: (1)...(5)
<223> OTHER INFORMATION: elastase 3A, pancreatic preproprotein

<400> SEQUENCE: 154

Trp Asn Trp Trp Gly Ser Thr Val Lys
1               5

<210> SEQ ID NO 155
<211> LENGTH: 11
<212> TYPE: PRT
<213> ORGANISM: Homo Sapiens
<220> FEATURE:
<221> NAME/KEY: PEPTIDE
<222> LOCATION: (1)...(10)
<223> OTHER INFORMATION: elastase 3A, pancreatic preproprotein

<400> SEQUENCE: 155

Ile Ala Pro Asp Trp Val Val Thr Ala Gly His
1               5                   10

<210> SEQ ID NO 156
<211> LENGTH: 11
<212> TYPE: PRT
<213> ORGANISM: Homo Sapiens
<220> FEATURE:
<221> NAME/KEY: PEPTIDE
<222> LOCATION: (1)...(10)
<223> OTHER INFORMATION: elastase 3A, pancreatic preproprotein

<400> SEQUENCE: 156

Lys Thr Met Val Cys Ala Gly Gly Tyr Ile Arg
1               5                   10

<210> SEQ ID NO 157
<211> LENGTH: 10
<212> TYPE: PRT
<213> ORGANISM: Homo Sapiens
<220> FEATURE:
<221> NAME/KEY: PEPTIDE
<222> LOCATION: (1)...(10)
<223> OTHER INFORMATION: elastase 3A, pancreatic preproprotein

<400> SEQUENCE: 157

Asp Trp Ile Glu Glu Thr Ile Ala Ser His
1               5                   10

<210> SEQ ID NO 158
<211> LENGTH: 11
<212> TYPE: PRT
<213> ORGANISM: Homo Sapiens
<220> FEATURE:
<221> NAME/KEY: PEPTIDE
<222> LOCATION: (1)...(10)
<223> OTHER INFORMATION: elastase 3A, pancreatic preproprotein

<400> SEQUENCE: 158

Val Val Leu Gly Glu Tyr Asn Leu Ala Val Lys
1               5                   10

<210> SEQ ID NO 159
```

```
<211> LENGTH: 12
<212> TYPE: PRT
<213> ORGANISM: Homo Sapiens
<220> FEATURE:
<221> NAME/KEY: PEPTIDE
<222> LOCATION: (1)...(10)
<223> OTHER INFORMATION: elastase 3A, pancreatic preproprotein

<400> SEQUENCE: 159

Ser Leu Pro Pro Ala Gly Asp Ile Leu Pro Asn Lys
 1               5                  10

<210> SEQ ID NO 160
<211> LENGTH: 13
<212> TYPE: PRT
<213> ORGANISM: Homo Sapiens
<220> FEATURE:
<221> NAME/KEY: PEPTIDE
<222> LOCATION: (1)...(10)
<223> OTHER INFORMATION: elastase 3A, pancreatic preproprotein

<400> SEQUENCE: 160

Ala Ser Leu Pro Pro Ala Gly Asp Ile Leu Pro Asn Lys
 1               5                  10

<210> SEQ ID NO 161
<211> LENGTH: 13
<212> TYPE: PRT
<213> ORGANISM: Homo Sapiens
<220> FEATURE:
<221> NAME/KEY: PEPTIDE
<222> LOCATION: (1)...(10)
<223> OTHER INFORMATION: elastase 3A, pancreatic preproprotein

<400> SEQUENCE: 161

Ser Cys Val Ala Cys Gly Asn Asp Ile Ala Leu Ile Lys
 1               5                  10

<210> SEQ ID NO 162
<211> LENGTH: 11
<212> TYPE: PRT
<213> ORGANISM: Homo Sapiens
<220> FEATURE:
<221> NAME/KEY: PEPTIDE
<222> LOCATION: (1)...(10)
<223> OTHER INFORMATION: elastase 3A, pancreatic preproprotein

<400> SEQUENCE: 162

Val Ser Ala Phe Ile Asp Trp Ile Glu Glu Thr
 1               5                  10

<210> SEQ ID NO 163
<211> LENGTH: 11
<212> TYPE: PRT
<213> ORGANISM: Homo Sapiens
<220> FEATURE:
<221> NAME/KEY: PEPTIDE
<222> LOCATION: (1)...(10)
<223> OTHER INFORMATION: elastase 3A, pancreatic preproprotein

<400> SEQUENCE: 163

Ile Asp Trp Ile Glu Glu Thr Ile Ala Ser His
 1               5                  10

<210> SEQ ID NO 164
<211> LENGTH: 12
<212> TYPE: PRT
<213> ORGANISM: Homo Sapiens
<220> FEATURE:
```

```
<221> NAME/KEY: PEPTIDE
<222> LOCATION: (1)...(10)
<223> OTHER INFORMATION: elastase 3A, pancreatic preproprotein

<400> SEQUENCE: 164

Gln Val Val Leu Gly Glu Tyr Asn Leu Ala Val Lys
  1               5                  10

<210> SEQ ID NO 165
<211> LENGTH: 12
<212> TYPE: PRT
<213> ORGANISM: Homo Sapiens
<220> FEATURE:
<221> NAME/KEY: PEPTIDE
<222> LOCATION: (1)...(10)
<223> OTHER INFORMATION: elastase 3A, pancreatic preproprotein

<400> SEQUENCE: 165

Asn Cys Pro Thr Glu Asp Gly Gly Trp Gln Val His
  1               5                  10

<210> SEQ ID NO 166
<211> LENGTH: 12
<212> TYPE: PRT
<213> ORGANISM: Homo Sapiens
<220> FEATURE:
<221> NAME/KEY: PEPTIDE
<222> LOCATION: (1)...(10)
<223> OTHER INFORMATION: elastase 3A, pancreatic preproprotein

<400> SEQUENCE: 166

Leu Tyr Thr Asn Gly Pro Leu Pro Asp Lys Leu Gln
  1               5                  10

<210> SEQ ID NO 167
<211> LENGTH: 14
<212> TYPE: PRT
<213> ORGANISM: Homo Sapiens
<220> FEATURE:
<221> NAME/KEY: PEPTIDE
<222> LOCATION: (1)...(10)
<223> OTHER INFORMATION: elastase 3A, pancreatic preproprotein

<400> SEQUENCE: 167

Leu Ala Ser Leu Pro Pro Ala Gly Asp Ile Leu Pro Asn Lys
  1               5                  10

<210> SEQ ID NO 168
<211> LENGTH: 12
<212> TYPE: PRT
<213> ORGANISM: Homo Sapiens
<220> FEATURE:
<221> NAME/KEY: PEPTIDE
<222> LOCATION: (1)...(10)
<223> OTHER INFORMATION: elastase 3A, pancreatic preproprotein

<400> SEQUENCE: 168

Val Ser Ala Phe Ile Asp Trp Ile Glu Glu Thr Ile
  1               5                  10

<210> SEQ ID NO 169
<211> LENGTH: 13
<212> TYPE: PRT
<213> ORGANISM: Homo Sapiens
<220> FEATURE:
<221> NAME/KEY: PEPTIDE
<222> LOCATION: (1)...(10)
<223> OTHER INFORMATION: elastase 3A, pancreatic preproprotein
```

```
<400> SEQUENCE: 169

Thr Asn Gly Pro Leu Pro Asp Lys Leu Gln Gln Ala Arg
1               5                   10

<210> SEQ ID NO 170
<211> LENGTH: 12
<212> TYPE: PRT
<213> ORGANISM: Homo Sapiens
<220> FEATURE:
<221> NAME/KEY: PEPTIDE
<222> LOCATION: (1)...(10)
<223> OTHER INFORMATION: elastase 3A, pancreatic preproprotein

<400> SEQUENCE: 170

Phe Ile Asp Trp Ile Glu Glu Thr Ile Ala Ser His
1               5                   10

<210> SEQ ID NO 171
<211> LENGTH: 13
<212> TYPE: PRT
<213> ORGANISM: Homo Sapiens
<220> FEATURE:
<221> NAME/KEY: PEPTIDE
<222> LOCATION: (1)...(10)
<223> OTHER INFORMATION: elastase 3A, pancreatic preproprotein

<400> SEQUENCE: 171

Leu Tyr Thr Asn Gly Pro Leu Pro Asp Lys Leu Gln Gln
1               5                   10

<210> SEQ ID NO 172
<211> LENGTH: 14
<212> TYPE: PRT
<213> ORGANISM: Homo Sapiens
<220> FEATURE:
<221> NAME/KEY: PEPTIDE
<222> LOCATION: (1)...(10)
<223> OTHER INFORMATION: elastase 3A, pancreatic preproprotein

<400> SEQUENCE: 172

Asn Cys Pro Thr Glu Asp Gly Gly Trp Gln Val His Gly Val
1               5                   10

<210> SEQ ID NO 173
<211> LENGTH: 13
<212> TYPE: PRT
<213> ORGANISM: Homo Sapiens
<220> FEATURE:
<221> NAME/KEY: PEPTIDE
<222> LOCATION: (1)...(10)
<223> OTHER INFORMATION: elastase 3A, pancreatic preproprotein

<400> SEQUENCE: 173

Ala Phe Ile Asp Trp Ile Glu Glu Thr Ile Ala Ser His
1               5                   10

<210> SEQ ID NO 174
<211> LENGTH: 12
<212> TYPE: PRT
<213> ORGANISM: Homo Sapiens
<220> FEATURE:
<221> NAME/KEY: PEPTIDE
<222> LOCATION: (1)...(10)
<223> OTHER INFORMATION: elastase 3A, pancreatic preproprotein

<400> SEQUENCE: 174

Ser Trp Pro Trp Gln Val Ser Leu Gln Tyr Glu Lys
1               5                   10
```

<210> SEQ ID NO 175
<211> LENGTH: 15
<212> TYPE: PRT
<213> ORGANISM: Homo Sapiens
<220> FEATURE:
<221> NAME/KEY: PEPTIDE
<222> LOCATION: (1)...(15)
<223> OTHER INFORMATION: elastase 3A, pancreatic preproprotein

<400> SEQUENCE: 175

His Thr Cys Gly Gly Ser Leu Ile Ala Pro Asp Trp Val Val Thr
 1               5                  10                  15

<210> SEQ ID NO 176
<211> LENGTH: 15
<212> TYPE: PRT
<213> ORGANISM: Homo Sapiens
<220> FEATURE:
<221> NAME/KEY: PEPTIDE
<222> LOCATION: (1)...(15)
<223> OTHER INFORMATION: elastase 3A, pancreatic preproprotein

<400> SEQUENCE: 176

Asn Cys Pro Thr Glu Asp Gly Gly Trp Gln Val His Gly Val Thr
 1               5                  10                  15

<210> SEQ ID NO 177
<211> LENGTH: 15
<212> TYPE: PRT
<213> ORGANISM: Homo Sapiens
<220> FEATURE:
<221> NAME/KEY: PEPTIDE
<222> LOCATION: (1)...(15)
<223> OTHER INFORMATION: elastase 3A, pancreatic preproprotein

<400> SEQUENCE: 177

Leu Tyr Thr Asn Gly Pro Leu Pro Asp Lys Leu Gln Gln Ala Arg
 1               5                  10                  15

<210> SEQ ID NO 178
<211> LENGTH: 16
<212> TYPE: PRT
<213> ORGANISM: Homo Sapiens
<220> FEATURE:
<221> NAME/KEY: PEPTIDE
<222> LOCATION: (1)...(15)
<223> OTHER INFORMATION: elastase 3A, pancreatic preproprotein

<400> SEQUENCE: 178

Pro Thr Glu Asp Gly Gly Trp Gln Val His Gly Val Thr Ser Phe Val
 1               5                  10                  15

<210> SEQ ID NO 179
<211> LENGTH: 15
<212> TYPE: PRT
<213> ORGANISM: Homo Sapiens
<220> FEATURE:
<221> NAME/KEY: PEPTIDE
<222> LOCATION: (1)...(15)
<223> OTHER INFORMATION: elastase 3A, pancreatic preproprotein

<400> SEQUENCE: 179

Val Ser Ala Phe Ile Asp Trp Ile Glu Glu Thr Ile Ala Ser His
 1               5                  10                  15

<210> SEQ ID NO 180
<211> LENGTH: 15

```
<212> TYPE: PRT
<213> ORGANISM: Homo Sapiens
<220> FEATURE:
<221> NAME/KEY: PEPTIDE
<222> LOCATION: (1)...(15)
<223> OTHER INFORMATION: elastase 3A, pancreatic preproprotein

<400> SEQUENCE: 180

Gln Val Ile Pro Ile Asn Ser Glu Glu Leu Phe Val His Pro Leu
1               5                   10                  15

<210> SEQ ID NO 181
<211> LENGTH: 18
<212> TYPE: PRT
<213> ORGANISM: Homo Sapiens
<220> FEATURE:
<221> NAME/KEY: PEPTIDE
<222> LOCATION: (1)...(15)
<223> OTHER INFORMATION: elastase 3A, pancreatic preproprotein

<400> SEQUENCE: 181

His Thr Cys Gly Gly Ser Leu Ile Ala Pro Asp Trp Val Val Thr Ala
1               5                   10                  15

Gly His

<210> SEQ ID NO 182
<211> LENGTH: 16
<212> TYPE: PRT
<213> ORGANISM: Homo Sapiens
<220> FEATURE:
<221> NAME/KEY: PEPTIDE
<222> LOCATION: (1)...(15)
<223> OTHER INFORMATION: elastase 3A, pancreatic preproprotein

<400> SEQUENCE: 182

Asp Leu Thr Tyr Gln Val Val Leu Gly Glu Tyr Asn Leu Ala Val Lys
1               5                   10                  15

<210> SEQ ID NO 183
<211> LENGTH: 17
<212> TYPE: PRT
<213> ORGANISM: Homo Sapiens
<220> FEATURE:
<221> NAME/KEY: PEPTIDE
<222> LOCATION: (1)...(15)
<223> OTHER INFORMATION: elastase 3A, pancreatic preproprotein

<400> SEQUENCE: 183

Asn Cys Pro Thr Glu Asp Gly Gly Trp Gln Val His Gly Val Thr Ser
1               5                   10                  15

Phe

<210> SEQ ID NO 184
<211> LENGTH: 16
<212> TYPE: PRT
<213> ORGANISM: Homo Sapiens
<220> FEATURE:
<221> NAME/KEY: PEPTIDE
<222> LOCATION: (1)...(15)
<223> OTHER INFORMATION: elastase 3A, pancreatic preproprotein

<400> SEQUENCE: 184

Val Val His Gly Glu Asp Ala Val Pro Tyr Ser Trp Pro Trp Gln Val
1               5                   10                  15

<210> SEQ ID NO 185
<211> LENGTH: 18
```

```
<212> TYPE: PRT
<213> ORGANISM: Homo Sapiens
<220> FEATURE:
<221> NAME/KEY: PEPTIDE
<222> LOCATION: (1)...(15)
<223> OTHER INFORMATION: elastase 3A, pancreatic preproprotein

<400> SEQUENCE: 185

Asn Cys Pro Thr Glu Asp Gly Gly Trp Gln Val His Gly Val Thr Ser
1               5                   10                  15

Phe Val

<210> SEQ ID NO 186
<211> LENGTH: 20
<212> TYPE: PRT
<213> ORGANISM: Homo Sapiens
<220> FEATURE:
<221> NAME/KEY: PEPTIDE
<222> LOCATION: (1)...(20)
<223> OTHER INFORMATION: elastase 3A, pancreatic preproprotein

<400> SEQUENCE: 186

Ser Gly Ser Phe Tyr His Thr Cys Gly Gly Ser Leu Ile Ala Pro Asp
1               5                   10                  15

Trp Val Val Thr
            20

<210> SEQ ID NO 187
<211> LENGTH: 19
<212> TYPE: PRT
<213> ORGANISM: Homo Sapiens
<220> FEATURE:
<221> NAME/KEY: PEPTIDE
<222> LOCATION: (1)...(15)
<223> OTHER INFORMATION: elastase 3A, pancreatic preproprotein

<400> SEQUENCE: 187

Glu Gly Pro Glu Gln Val Ile Pro Ile Asn Ser Glu Glu Leu Phe Val
1               5                   10                  15

His Pro Leu

<210> SEQ ID NO 188
<211> LENGTH: 21
<212> TYPE: PRT
<213> ORGANISM: Homo Sapiens
<220> FEATURE:
<221> NAME/KEY: PEPTIDE
<222> LOCATION: (1)...(20)
<223> OTHER INFORMATION: elastase 3A, pancreatic preproprotein

<400> SEQUENCE: 188

Ser Gly Ser Phe Tyr His Thr Cys Gly Gly Ser Leu Ile Ala Pro Asp
1               5                   10                  15

Trp Val Val Thr Ala
            20

<210> SEQ ID NO 189
<211> LENGTH: 23
<212> TYPE: PRT
<213> ORGANISM: Homo Sapiens
<220> FEATURE:
<221> NAME/KEY: PEPTIDE
<222> LOCATION: (1)...(20)
<223> OTHER INFORMATION: elastase 3A, pancreatic preproprotein

<400> SEQUENCE: 189
```

Ser Ala Gln Leu Gly Asp Ala Val Gln Leu Ala Ser Leu Pro Pro Ala
1               5                   10                  15

Gly Asp Ile Leu Pro Asn Lys
            20

<210> SEQ ID NO 190
<211> LENGTH: 22
<212> TYPE: PRT
<213> ORGANISM: Homo Sapiens
<220> FEATURE:
<221> NAME/KEY: PEPTIDE
<222> LOCATION: (1)...(20)
<223> OTHER INFORMATION: elastase 3A, pancreatic preproprotein

<400> SEQUENCE: 190

His Thr Cys Gly Gly Ser Leu Ile Ala Pro Asp Trp Val Val Thr Ala
1               5                   10                  15

Gly His Cys Ile Ser Arg
            20

<210> SEQ ID NO 191
<211> LENGTH: 23
<212> TYPE: PRT
<213> ORGANISM: Homo Sapiens
<220> FEATURE:
<221> NAME/KEY: PEPTIDE
<222> LOCATION: (1)...(20)
<223> OTHER INFORMATION: elastase 3A, pancreatic preproprotein

<400> SEQUENCE: 191

Ser Gly Ser Phe Tyr His Thr Cys Gly Gly Ser Leu Ile Ala Pro Asp
1               5                   10                  15

Trp Val Val Thr Ala Gly His
            20

<210> SEQ ID NO 192
<211> LENGTH: 22
<212> TYPE: PRT
<213> ORGANISM: Homo Sapiens
<220> FEATURE:
<221> NAME/KEY: PEPTIDE
<222> LOCATION: (1)...(20)
<223> OTHER INFORMATION: elastase 3A, pancreatic preproprotein

<400> SEQUENCE: 192

Val Val His Gly Glu Asp Ala Val Pro Tyr Ser Trp Pro Trp Gln Val
1               5                   10                  15

Ser Leu Gln Tyr Glu Lys
            20

<210> SEQ ID NO 193
<211> LENGTH: 33
<212> TYPE: PRT
<213> ORGANISM: Homo Sapiens
<220> FEATURE:
<221> NAME/KEY: PEPTIDE
<222> LOCATION: (1)...(30)
<223> OTHER INFORMATION: elastase 3A, pancreatic preproprotein

<400> SEQUENCE: 193

Ser Ala Gln Leu Gly Asp Ala Val Gln Leu Ala Ser Leu Pro Pro Ala
1               5                   10                  15

Gly Asp Ile Leu Pro Asn Lys Thr Pro Cys Tyr Ile Thr Gly Trp Gly
            20                  25                  30

Arg

```
<210> SEQ ID NO 194
<211> LENGTH: 9
<212> TYPE: PRT
<213> ORGANISM: Homo Sapiens
<220> FEATURE:
<221> NAME/KEY: PEPTIDE
<222> LOCATION: (1)...(5)
<223> OTHER INFORMATION: elastase 3B, pancreatic preproprotein

<400> SEQUENCE: 194

Val Ser Ala Phe Gly Cys Asn Thr Arg
1               5

<210> SEQ ID NO 195
<211> LENGTH: 10
<212> TYPE: PRT
<213> ORGANISM: Homo Sapiens
<220> FEATURE:
<221> NAME/KEY: PEPTIDE
<222> LOCATION: (1)...(10)
<223> OTHER INFORMATION: elastase 3B, pancreatic preproprotein

<400> SEQUENCE: 195

Thr Met Val Cys Ala Gly Gly Asp Ile Arg
1               5                   10

<210> SEQ ID NO 196
<211> LENGTH: 9
<212> TYPE: PRT
<213> ORGANISM: Homo Sapiens
<220> FEATURE:
<221> NAME/KEY: PEPTIDE
<222> LOCATION: (1)...(5)
<223> OTHER INFORMATION: elastase 3B, pancreatic preproprotein

<400> SEQUENCE: 196

Gln Val Val Leu Gly Glu Tyr Asp Arg
1               5

<210> SEQ ID NO 197
<211> LENGTH: 10
<212> TYPE: PRT
<213> ORGANISM: Homo Sapiens
<220> FEATURE:
<221> NAME/KEY: PEPTIDE
<222> LOCATION: (1)...(10)
<223> OTHER INFORMATION: elastase 3B, pancreatic preproprotein

<400> SEQUENCE: 197

Asn Ser Gly Asp Leu Phe Val His Pro Leu
1               5                   10

<210> SEQ ID NO 198
<211> LENGTH: 9
<212> TYPE: PRT
<213> ORGANISM: Homo Sapiens
<220> FEATURE:
<221> NAME/KEY: PEPTIDE
<222> LOCATION: (1)...(5)
<223> OTHER INFORMATION: elastase 3B, pancreatic preproprotein

<400> SEQUENCE: 198

Trp Asn Trp Trp Gly Ser Ser Val Lys
1               5

<210> SEQ ID NO 199
<211> LENGTH: 12
```

```
<212> TYPE: PRT
<213> ORGANISM: Homo Sapiens
<220> FEATURE:
<221> NAME/KEY: PEPTIDE
<222> LOCATION: (1)...(10)
<223> OTHER INFORMATION: elastase 3B, pancreatic preproprotein

<400> SEQUENCE: 199

Thr Asn Gly Pro Leu Pro Asp Lys Leu Gln Glu Ala
1               5                   10

<210> SEQ ID NO 200
<211> LENGTH: 11
<212> TYPE: PRT
<213> ORGANISM: Homo Sapiens
<220> FEATURE:
<221> NAME/KEY: PEPTIDE
<222> LOCATION: (1)...(10)
<223> OTHER INFORMATION: elastase 3B, pancreatic preproprotein

<400> SEQUENCE: 200

Thr Tyr Gln Val Val Leu Gly Glu Tyr Asp Arg
1               5                   10

<210> SEQ ID NO 201
<211> LENGTH: 14
<212> TYPE: PRT
<213> ORGANISM: Homo Sapiens
<220> FEATURE:
<221> NAME/KEY: PEPTIDE
<222> LOCATION: (1)...(10)
<223> OTHER INFORMATION: elastase 3B, pancreatic preproprotein

<400> SEQUENCE: 201

Leu Tyr Thr Asn Gly Pro Leu Pro Asp Lys Leu Gln Glu Ala
1               5                   10

<210> SEQ ID NO 202
<211> LENGTH: 14
<212> TYPE: PRT
<213> ORGANISM: Homo Sapiens
<220> FEATURE:
<221> NAME/KEY: PEPTIDE
<222> LOCATION: (1)...(10)
<223> OTHER INFORMATION: elastase 3B, pancreatic preproprotein

<400> SEQUENCE: 202

Leu Gln Glu Ala Leu Leu Pro Val Val Asp Tyr Glu His Cys
1               5                   10

<210> SEQ ID NO 203
<211> LENGTH: 15
<212> TYPE: PRT
<213> ORGANISM: Homo Sapiens
<220> FEATURE:
<221> NAME/KEY: PEPTIDE
<222> LOCATION: (1)...(15)
<223> OTHER INFORMATION: elastase 3B, pancreatic preproprotein

<400> SEQUENCE: 203

Gln Val Ile Pro Ile Asn Ser Gly Asp Leu Phe Val His Pro Leu
1               5                   10                  15

<210> SEQ ID NO 204
<211> LENGTH: 16
<212> TYPE: PRT
<213> ORGANISM: Homo Sapiens
<220> FEATURE:
<221> NAME/KEY: PEPTIDE
```

```
<222> LOCATION: (1)..(15)
<223> OTHER INFORMATION: elastase 3B, pancreatic preproprotein

<400> SEQUENCE: 204

Leu Gln Glu Ala Leu Leu Pro Val Val Asp Tyr Glu His Cys Ser Arg
 1               5                  10                  15

<210> SEQ ID NO 205
<211> LENGTH: 18
<212> TYPE: PRT
<213> ORGANISM: Homo Sapiens
<220> FEATURE:
<221> NAME/KEY: PEPTIDE
<222> LOCATION: (1)..(15)
<223> OTHER INFORMATION: elastase 3B, pancreatic preproprotein

<400> SEQUENCE: 205

Glu Gly Pro Glu Gln Val Ile Pro Ile Asn Ser Gly Asp Leu Phe Val
 1               5                  10                  15

His Pro

<210> SEQ ID NO 206
<211> LENGTH: 19
<212> TYPE: PRT
<213> ORGANISM: Homo Sapiens
<220> FEATURE:
<221> NAME/KEY: PEPTIDE
<222> LOCATION: (1)..(15)
<223> OTHER INFORMATION: elastase 3B, pancreatic preproprotein

<400> SEQUENCE: 206

Glu Gly Pro Glu Gln Val Ile Pro Ile Asn Ser Gly Asp Leu Phe Val
 1               5                  10                  15

His Pro Leu

<210> SEQ ID NO 207
<211> LENGTH: 22
<212> TYPE: PRT
<213> ORGANISM: Homo Sapiens
<220> FEATURE:
<221> NAME/KEY: PEPTIDE
<222> LOCATION: (1)..(20)
<223> OTHER INFORMATION: elastase 3B, pancreatic preproprotein

<400> SEQUENCE: 207

Ser Leu Pro Pro Ala Gly Asp Ile Leu Pro Asn Glu Thr Pro Cys Tyr
 1               5                  10                  15

Ile Thr Gly Trp Gly Arg
            20

<210> SEQ ID NO 208
<211> LENGTH: 23
<212> TYPE: PRT
<213> ORGANISM: Homo Sapiens
<220> FEATURE:
<221> NAME/KEY: PEPTIDE
<222> LOCATION: (1)..(20)
<223> OTHER INFORMATION: elastase 3B, pancreatic preproprotein

<400> SEQUENCE: 208

Ala Ser Leu Pro Pro Ala Gly Asp Ile Leu Pro Asn Glu Thr Pro Cys
 1               5                  10                  15

Tyr Ile Thr Gly Trp Gly Arg
            20
```

-continued

```
<210> SEQ ID NO 209
<211> LENGTH: 22
<212> TYPE: PRT
<213> ORGANISM: Homo Sapiens
<220> FEATURE:
<221> NAME/KEY: PEPTIDE
<222> LOCATION: (1)...(20)
<223> OTHER INFORMATION: elastase 3B, pancreatic preproprotein

<400> SEQUENCE: 209

Val Val Asn Gly Glu Asp Ala Val Pro Tyr Ser Trp Pro Trp Gln Val
 1               5                  10                  15

Ser Leu Gln Tyr Glu Lys
            20

<210> SEQ ID NO 210
<211> LENGTH: 26
<212> TYPE: PRT
<213> ORGANISM: Homo Sapiens
<220> FEATURE:
<221> NAME/KEY: PEPTIDE
<222> LOCATION: (1)...(25)
<223> OTHER INFORMATION: elastase 3B, pancreatic preproprotein

<400> SEQUENCE: 210

Leu Tyr Thr Asn Gly Pro Leu Pro Asp Lys Leu Gln Glu Ala Leu Leu
 1               5                  10                  15

Pro Val Val Asp Tyr Glu His Cys Ser Arg
            20                  25

<210> SEQ ID NO 211
<211> LENGTH: 33
<212> TYPE: PRT
<213> ORGANISM: Homo Sapiens
<220> FEATURE:
<221> NAME/KEY: PEPTIDE
<222> LOCATION: (1)...(30)
<223> OTHER INFORMATION: elastase 3B, pancreatic preproprotein

<400> SEQUENCE: 211

Ser Ala Gln Leu Gly Asp Ala Val Gln Leu Ala Ser Leu Pro Pro Ala
 1               5                  10                  15

Gly Asp Ile Leu Pro Asn Glu Thr Pro Cys Tyr Ile Thr Gly Trp Gly
            20                  25                  30

Arg

<210> SEQ ID NO 212
<211> LENGTH: 10
<212> TYPE: PRT
<213> ORGANISM: Homo Sapiens
<220> FEATURE:
<221> NAME/KEY: PEPTIDE
<222> LOCATION: (1)...(10)
<223> OTHER INFORMATION: protease, serine, 2 preproprotein

<400> SEQUENCE: 212

Leu Ser Ser Pro Ala Val Ile Asn Ser Arg
 1               5                  10

<210> SEQ ID NO 213
<211> LENGTH: 10
<212> TYPE: PRT
<213> ORGANISM: Homo Sapiens
<220> FEATURE:
<221> NAME/KEY: PEPTIDE
<222> LOCATION: (1)...(10)
<223> OTHER INFORMATION: protease, serine, 2 preproprotein
```

```
<400> SEQUENCE: 213

Thr Leu Asp Asn Asp Ile Leu Leu Ile Lys
1               5                   10

<210> SEQ ID NO 214
<211> LENGTH: 9
<212> TYPE: PRT
<213> ORGANISM: Homo Sapiens
<220> FEATURE:
<221> NAME/KEY: PEPTIDE
<222> LOCATION: (1)...(5)
<223> OTHER INFORMATION: protease, serine, 2 preproprotein

<400> SEQUENCE: 214

Val Tyr Asn Tyr Val Asp Trp Ile Lys
1               5

<210> SEQ ID NO 215
<211> LENGTH: 11
<212> TYPE: PRT
<213> ORGANISM: Homo Sapiens
<220> FEATURE:
<221> NAME/KEY: PEPTIDE
<222> LOCATION: (1)...(10)
<223> OTHER INFORMATION: protease, serine, 2 preproprotein

<400> SEQUENCE: 215

Glu Gly Asn Glu Gln Phe Ile Asn Ala Ala Lys
1               5                   10

<210> SEQ ID NO 216
<211> LENGTH: 12
<212> TYPE: PRT
<213> ORGANISM: Homo Sapiens
<220> FEATURE:
<221> NAME/KEY: PEPTIDE
<222> LOCATION: (1)...(10)
<223> OTHER INFORMATION: protease, serine, 2 preproprotein

<400> SEQUENCE: 216

Asp Ala Pro Val Leu Ser Gln Ala Glu Cys Glu Ala
1               5                   10

<210> SEQ ID NO 217
<211> LENGTH: 11
<212> TYPE: PRT
<213> ORGANISM: Homo Sapiens
<220> FEATURE:
<221> NAME/KEY: PEPTIDE
<222> LOCATION: (1)...(10)
<223> OTHER INFORMATION: protease, serine, 2 preproprotein

<400> SEQUENCE: 217

Gln Val Ser Leu Asn Ser Gly Tyr His Phe Cys
1               5                   10

<210> SEQ ID NO 218
<211> LENGTH: 10
<212> TYPE: PRT
<213> ORGANISM: Homo Sapiens
<220> FEATURE:
<221> NAME/KEY: PEPTIDE
<222> LOCATION: (1)...(10)
<223> OTHER INFORMATION: protease, serine, 2 preproprotein

<400> SEQUENCE: 218

Asn Tyr Val Asp Trp Ile Lys Asp Thr Ile
```

```
<210> SEQ ID NO 219
<211> LENGTH: 12
<212> TYPE: PRT
<213> ORGANISM: Homo Sapiens
<220> FEATURE:
<221> NAME/KEY: PEPTIDE
<222> LOCATION: (1)...(10)
<223> OTHER INFORMATION: protease, serine, 2 preproprotein

<400> SEQUENCE: 219

Leu Glu Gly Asn Glu Gln Phe Ile Asn Ala Ala Lys
 1               5                  10

<210> SEQ ID NO 220
<211> LENGTH: 13
<212> TYPE: PRT
<213> ORGANISM: Homo Sapiens
<220> FEATURE:
<221> NAME/KEY: PEPTIDE
<222> LOCATION: (1)...(10)
<223> OTHER INFORMATION: protease, serine, 2 preproprotein

<400> SEQUENCE: 220

Leu Asp Ala Pro Val Leu Ser Gln Ala Glu Cys Glu Ala
 1               5                  10

<210> SEQ ID NO 221
<211> LENGTH: 13
<212> TYPE: PRT
<213> ORGANISM: Homo Sapiens
<220> FEATURE:
<221> NAME/KEY: PEPTIDE
<222> LOCATION: (1)...(10)
<223> OTHER INFORMATION: protease, serine, 2 preproprotein

<400> SEQUENCE: 221

Val Leu Glu Gly Asn Glu Gln Phe Ile Asn Ala Ala Lys
 1               5                  10

<210> SEQ ID NO 222
<211> LENGTH: 14
<212> TYPE: PRT
<213> ORGANISM: Homo Sapiens
<220> FEATURE:
<221> NAME/KEY: PEPTIDE
<222> LOCATION: (1)...(10)
<223> OTHER INFORMATION: protease, serine, 2 preproprotein

<400> SEQUENCE: 222

Ser Leu Asn Ser Gly Tyr His Phe Cys Gly Gly Ser Leu Ile
 1               5                  10

<210> SEQ ID NO 223
<211> LENGTH: 13
<212> TYPE: PRT
<213> ORGANISM: Homo Sapiens
<220> FEATURE:
<221> NAME/KEY: PEPTIDE
<222> LOCATION: (1)...(10)
<223> OTHER INFORMATION: protease, serine, 2 preproprotein

<400> SEQUENCE: 223

Ser Glu Gln Trp Val Val Ser Ala Gly His Cys Tyr Lys
 1               5                  10

<210> SEQ ID NO 224
```

```
<211> LENGTH: 12
<212> TYPE: PRT
<213> ORGANISM: Homo Sapiens
<220> FEATURE:
<221> NAME/KEY: PEPTIDE
<222> LOCATION: (1)...(10)
<223> OTHER INFORMATION: protease, serine, 2 preproprotein

<400> SEQUENCE: 224

Val Tyr Asn Tyr Val Asp Trp Ile Lys Asp Thr Ile
 1               5                  10

<210> SEQ ID NO 225
<211> LENGTH: 14
<212> TYPE: PRT
<213> ORGANISM: Homo Sapiens
<220> FEATURE:
<221> NAME/KEY: PEPTIDE
<222> LOCATION: (1)...(10)
<223> OTHER INFORMATION: protease, serine, 2 preproprotein

<400> SEQUENCE: 225

Glu Val Leu Glu Gly Asn Glu Gln Phe Ile Asn Ala Ala Lys
 1               5                  10

<210> SEQ ID NO 226
<211> LENGTH: 14
<212> TYPE: PRT
<213> ORGANISM: Homo Sapiens
<220> FEATURE:
<221> NAME/KEY: PEPTIDE
<222> LOCATION: (1)...(10)
<223> OTHER INFORMATION: protease, serine, 2 preproprotein

<400> SEQUENCE: 226

Asn Tyr Val Asp Trp Ile Lys Asp Thr Ile Ala Ala Asn Ser
 1               5                  10

<210> SEQ ID NO 227
<211> LENGTH: 15
<212> TYPE: PRT
<213> ORGANISM: Homo Sapiens
<220> FEATURE:
<221> NAME/KEY: PEPTIDE
<222> LOCATION: (1)...(15)
<223> OTHER INFORMATION: protease, serine, 2 preproprotein

<400> SEQUENCE: 227

Ile Thr Asn Asn Met Phe Cys Val Gly Phe Leu Glu Gly Gly Lys
 1               5                  10                  15

<210> SEQ ID NO 228
<211> LENGTH: 16
<212> TYPE: PRT
<213> ORGANISM: Homo Sapiens
<220> FEATURE:
<221> NAME/KEY: PEPTIDE
<222> LOCATION: (1)...(15)
<223> OTHER INFORMATION: protease, serine, 2 preproprotein

<400> SEQUENCE: 228

Gln Val Ser Leu Asn Ser Gly Tyr His Phe Cys Gly Gly Ser Leu Ile
 1               5                  10                  15

<210> SEQ ID NO 229
<211> LENGTH: 15
<212> TYPE: PRT
<213> ORGANISM: Homo Sapiens
<220> FEATURE:
```

```
<221> NAME/KEY: PEPTIDE
<222> LOCATION: (1)...(15)
<223> OTHER INFORMATION: protease, serine, 2 preproprotein

<400> SEQUENCE: 229

Leu Gly Glu His Asn Ile Glu Val Leu Glu Gly Asn Glu Gln Phe
1               5                   10                  15

<210> SEQ ID NO 230
<211> LENGTH: 17
<212> TYPE: PRT
<213> ORGANISM: Homo Sapiens
<220> FEATURE:
<221> NAME/KEY: PEPTIDE
<222> LOCATION: (1)...(15)
<223> OTHER INFORMATION: protease, serine, 2 preproprotein

<400> SEQUENCE: 230

Asp Ala Pro Val Leu Ser Gln Ala Glu Cys Glu Ala Ser Tyr Pro Gly
1               5                   10                  15
Lys

<210> SEQ ID NO 231
<211> LENGTH: 16
<212> TYPE: PRT
<213> ORGANISM: Homo Sapiens
<220> FEATURE:
<221> NAME/KEY: PEPTIDE
<222> LOCATION: (1)...(15)
<223> OTHER INFORMATION: protease, serine, 2 preproprotein

<400> SEQUENCE: 231

Asn Ile Glu Val Leu Glu Gly Asn Glu Gln Phe Ile Asn Ala Ala Lys
1               5                   10                  15

<210> SEQ ID NO 232
<211> LENGTH: 16
<212> TYPE: PRT
<213> ORGANISM: Homo Sapiens
<220> FEATURE:
<221> NAME/KEY: PEPTIDE
<222> LOCATION: (1)...(15)
<223> OTHER INFORMATION: protease, serine, 2 preproprotein

<400> SEQUENCE: 232

Leu Gly Glu His Asn Ile Glu Val Leu Glu Gly Asn Glu Gln Phe Ile
1               5                   10                  15

<210> SEQ ID NO 233
<211> LENGTH: 16
<212> TYPE: PRT
<213> ORGANISM: Homo Sapiens
<220> FEATURE:
<221> NAME/KEY: PEPTIDE
<222> LOCATION: (1)...(15)
<223> OTHER INFORMATION: protease, serine, 2 preproprotein

<400> SEQUENCE: 233

Val Tyr Asn Tyr Val Asp Trp Ile Lys Asp Thr Ile Ala Ala Asn Ser
1               5                   10                  15

<210> SEQ ID NO 234
<211> LENGTH: 18
<212> TYPE: PRT
<213> ORGANISM: Homo Sapiens
<220> FEATURE:
<221> NAME/KEY: PEPTIDE
<222> LOCATION: (1)...(15)
```

<223> OTHER INFORMATION: protease, serine, 2 preproprotein

<400> SEQUENCE: 234

Leu Asp Ala Pro Val Leu Ser Gln Ala Glu Cys Glu Ala Ser Tyr Pro
1               5                   10                  15

Gly Lys

<210> SEQ ID NO 235
<211> LENGTH: 20
<212> TYPE: PRT
<213> ORGANISM: Homo Sapiens
<220> FEATURE:
<221> NAME/KEY: PEPTIDE
<222> LOCATION: (1)...(20)
<223> OTHER INFORMATION: protease, serine, 2 preproprotein

<400> SEQUENCE: 235

Asp Ser Cys Gln Gly Asp Ser Gly Gly Pro Val Val Ser Asn Gly Glu
1               5                   10                  15

Leu Gln Gly Ile
            20

<210> SEQ ID NO 236
<211> LENGTH: 17
<212> TYPE: PRT
<213> ORGANISM: Homo Sapiens
<220> FEATURE:
<221> NAME/KEY: PEPTIDE
<222> LOCATION: (1)...(15)
<223> OTHER INFORMATION: protease, serine, 2 preproprotein

<400> SEQUENCE: 236

Leu Gly Glu His Asn Ile Glu Val Leu Glu Gly Asn Glu Gln Phe Ile
1               5                   10                  15

Asn

<210> SEQ ID NO 237
<211> LENGTH: 21
<212> TYPE: PRT
<213> ORGANISM: Homo Sapiens
<220> FEATURE:
<221> NAME/KEY: PEPTIDE
<222> LOCATION: (1)...(20)
<223> OTHER INFORMATION: protease, serine, 2 preproprotein

<400> SEQUENCE: 237

Asp Ser Cys Gln Gly Asp Ser Gly Gly Pro Val Val Ser Asn Gly Glu
1               5                   10                  15

Leu Gln Gly Ile Val
            20

<210> SEQ ID NO 238
<211> LENGTH: 18
<212> TYPE: PRT
<213> ORGANISM: Homo Sapiens
<220> FEATURE:
<221> NAME/KEY: PEPTIDE
<222> LOCATION: (1)...(15)
<223> OTHER INFORMATION: protease, serine, 2 preproprotein

<400> SEQUENCE: 238

Leu Gly Glu His Asn Ile Glu Val Leu Glu Gly Asn Glu Gln Phe Ile
1               5                   10                  15

Asn Ala

<210> SEQ ID NO 239
<211> LENGTH: 18
<212> TYPE: PRT
<213> ORGANISM: Homo Sapiens
<220> FEATURE:
<221> NAME/KEY: PEPTIDE
<222> LOCATION: (1)...(15)
<223> OTHER INFORMATION: protease, serine, 2 preproprotein

<400> SEQUENCE: 239

Glu His Asn Ile Glu Val Leu Glu Gly Asn Glu Gln Phe Ile Asn Ala
 1               5                  10                  15

Ala Lys

<210> SEQ ID NO 240
<211> LENGTH: 19
<212> TYPE: PRT
<213> ORGANISM: Homo Sapiens
<220> FEATURE:
<221> NAME/KEY: PEPTIDE
<222> LOCATION: (1)...(15)
<223> OTHER INFORMATION: protease, serine, 2 preproprotein

<400> SEQUENCE: 240

Leu Gly Glu His Asn Ile Glu Val Leu Glu Gly Asn Glu Gln Phe Ile
 1               5                  10                  15

Asn Ala Ala

<210> SEQ ID NO 241
<211> LENGTH: 20
<212> TYPE: PRT
<213> ORGANISM: Homo Sapiens
<220> FEATURE:
<221> NAME/KEY: PEPTIDE
<222> LOCATION: (1)...(20)
<223> OTHER INFORMATION: protease, serine, 2 preproprotein

<400> SEQUENCE: 241

Gln Cys Leu Asp Ala Pro Val Leu Ser Gln Ala Glu Cys Glu Ala Ser
 1               5                  10                  15

Tyr Pro Gly Lys
            20

<210> SEQ ID NO 242
<211> LENGTH: 19
<212> TYPE: PRT
<213> ORGANISM: Homo Sapiens
<220> FEATURE:
<221> NAME/KEY: PEPTIDE
<222> LOCATION: (1)...(15)
<223> OTHER INFORMATION: protease, serine, 2 preproprotein

<400> SEQUENCE: 242

Gly Glu His Asn Ile Glu Val Leu Glu Gly Asn Glu Gln Phe Ile Asn
 1               5                  10                  15

Ala Ala Lys

<210> SEQ ID NO 243
<211> LENGTH: 22
<212> TYPE: PRT
<213> ORGANISM: Homo Sapiens
<220> FEATURE:
<221> NAME/KEY: PEPTIDE
<222> LOCATION: (1)...(20)
<223> OTHER INFORMATION: protease, serine, 2 preproprotein

```
<400> SEQUENCE: 243

Val Ser Ala Ile Ser Leu Pro Thr Ala Pro Pro Ala Ala Gly Thr Glu
 1               5                  10                  15

Ser Leu Ile Ser Gly Trp
            20

<210> SEQ ID NO 244
<211> LENGTH: 22
<212> TYPE: PRT
<213> ORGANISM: Homo Sapiens
<220> FEATURE:
<221> NAME/KEY: PEPTIDE
<222> LOCATION: (1)...(20)
<223> OTHER INFORMATION: protease, serine, 2 preproprotein

<400> SEQUENCE: 244

Ser Leu Pro Thr Ala Pro Pro Ala Ala Gly Thr Glu Ser Leu Ile Ser
 1               5                  10                  15

Gly Trp Gly Asn Thr Leu
            20

<210> SEQ ID NO 245
<211> LENGTH: 20
<212> TYPE: PRT
<213> ORGANISM: Homo Sapiens
<220> FEATURE:
<221> NAME/KEY: PEPTIDE
<222> LOCATION: (1)...(20)
<223> OTHER INFORMATION: protease, serine, 2 preproprotein

<400> SEQUENCE: 245

Leu Gly Glu His Asn Ile Glu Val Leu Glu Gly Asn Glu Gln Phe Ile
 1               5                  10                  15

Asn Ala Ala Lys
            20

<210> SEQ ID NO 246
<211> LENGTH: 23
<212> TYPE: PRT
<213> ORGANISM: Homo Sapiens
<220> FEATURE:
<221> NAME/KEY: PEPTIDE
<222> LOCATION: (1)...(20)
<223> OTHER INFORMATION: protease, serine, 2 preproprotein

<400> SEQUENCE: 246

Ser Leu Pro Thr Ala Pro Pro Ala Ala Gly Thr Glu Ser Leu Ile Ser
 1               5                  10                  15

Gly Trp Gly Asn Thr Leu Ser
            20

<210> SEQ ID NO 247
<211> LENGTH: 26
<212> TYPE: PRT
<213> ORGANISM: Homo Sapiens
<220> FEATURE:
<221> NAME/KEY: PEPTIDE
<222> LOCATION: (1)...(25)
<223> OTHER INFORMATION: protease, serine, 2 preproprotein

<400> SEQUENCE: 247

Val Ser Ala Ile Ser Leu Pro Thr Ala Pro Pro Ala Ala Gly Thr Glu
 1               5                  10                  15

Ser Leu Ile Ser Gly Trp Gly Asn Thr Leu
            20                  25
```

```
<210> SEQ ID NO 248
<211> LENGTH: 8
<212> TYPE: PRT
<213> ORGANISM: Homo Sapiens
<220> FEATURE:
<221> NAME/KEY: PEPTIDE
<222> LOCATION: (1)...(5)
<223> OTHER INFORMATION: chymotrypsin B2

<400> SEQUENCE: 248

Asn Asn Asp Ile Thr Leu Leu Lys
 1               5

<210> SEQ ID NO 249
<211> LENGTH: 10
<212> TYPE: PRT
<213> ORGANISM: Homo Sapiens
<220> FEATURE:
<221> NAME/KEY: PEPTIDE
<222> LOCATION: (1)...(10)
<223> OTHER INFORMATION: chymotrypsin B2

<400> SEQUENCE: 249

Thr Val Asn Asn Asp Ile Thr Leu Leu Lys
 1               5                  10

<210> SEQ ID NO 250
<211> LENGTH: 11
<212> TYPE: PRT
<213> ORGANISM: Homo Sapiens
<220> FEATURE:
<221> NAME/KEY: PEPTIDE
<222> LOCATION: (1)...(10)
<223> OTHER INFORMATION: chymotrypsin B2

<400> SEQUENCE: 250

Ala Leu Pro Leu Leu Ser Asn Ala Glu Cys Lys
 1               5                  10

<210> SEQ ID NO 251
<211> LENGTH: 12
<212> TYPE: PRT
<213> ORGANISM: Homo Sapiens
<220> FEATURE:
<221> NAME/KEY: PEPTIDE
<222> LOCATION: (1)...(10)
<223> OTHER INFORMATION: chymotrypsin B2

<400> SEQUENCE: 251

Thr Pro Asp Lys Leu Gln Gln Ala Ala Leu Pro Leu
 1               5                  10

<210> SEQ ID NO 252
<211> LENGTH: 12
<212> TYPE: PRT
<213> ORGANISM: Homo Sapiens
<220> FEATURE:
<221> NAME/KEY: PEPTIDE
<222> LOCATION: (1)...(10)
<223> OTHER INFORMATION: chymotrypsin B2

<400> SEQUENCE: 252

Gly Glu Phe Asp Gln Gly Ser Asp Glu Glu Asn Ile
 1               5                  10

<210> SEQ ID NO 253
<211> LENGTH: 14
```

```
<212> TYPE: PRT
<213> ORGANISM: Homo Sapiens
<220> FEATURE:
<221> NAME/KEY: PEPTIDE
<222> LOCATION: (1)...(10)
<223> OTHER INFORMATION: chymotrypsin B2

<400> SEQUENCE: 253

Thr Pro Asp Lys Leu Gln Gln Ala Ala Leu Pro Leu Leu Ser
1               5                   10

<210> SEQ ID NO 254
<211> LENGTH: 14
<212> TYPE: PRT
<213> ORGANISM: Homo Sapiens
<220> FEATURE:
<221> NAME/KEY: PEPTIDE
<222> LOCATION: (1)...(10)
<223> OTHER INFORMATION: chymotrypsin B2

<400> SEQUENCE: 254

Ser Glu Asp Trp Val Val Thr Ala Ala His Cys Gly Val Arg
1               5                   10

<210> SEQ ID NO 255
<211> LENGTH: 14
<212> TYPE: PRT
<213> ORGANISM: Homo Sapiens
<220> FEATURE:
<221> NAME/KEY: PEPTIDE
<222> LOCATION: (1)...(10)
<223> OTHER INFORMATION: chymotrypsin B2

<400> SEQUENCE: 255

Phe Ser Ile Leu Thr Val Asn Asn Asp Ile Thr Leu Leu Lys
1               5                   10

<210> SEQ ID NO 256
<211> LENGTH: 15
<212> TYPE: PRT
<213> ORGANISM: Homo Sapiens
<220> FEATURE:
<221> NAME/KEY: PEPTIDE
<222> LOCATION: (1)...(15)
<223> OTHER INFORMATION: chymotrypsin B2

<400> SEQUENCE: 256

Leu Gln Gln Ala Ala Leu Pro Leu Leu Ser Asn Ala Glu Cys Lys
1               5                   10                  15

<210> SEQ ID NO 257
<211> LENGTH: 15
<212> TYPE: PRT
<213> ORGANISM: Homo Sapiens
<220> FEATURE:
<221> NAME/KEY: PEPTIDE
<222> LOCATION: (1)...(15)
<223> OTHER INFORMATION: chymotrypsin B2

<400> SEQUENCE: 257

Asp Gly Ala Trp Thr Leu Val Gly Ile Val Ser Trp Gly Ser Arg
1               5                   10                  15

<210> SEQ ID NO 258
<211> LENGTH: 14
<212> TYPE: PRT
<213> ORGANISM: Homo Sapiens
<220> FEATURE:
<221> NAME/KEY: PEPTIDE
```

```
<222> LOCATION: (1)...(10)
<223> OTHER INFORMATION: chymotrypsin B2

<400> SEQUENCE: 258

Phe Asp Gln Gly Ser Asp Glu Glu Asn Ile Gln Val Leu Lys
 1               5                  10

<210> SEQ ID NO 259
<211> LENGTH: 15
<212> TYPE: PRT
<213> ORGANISM: Homo Sapiens
<220> FEATURE:
<221> NAME/KEY: PEPTIDE
<222> LOCATION: (1)...(15)
<223> OTHER INFORMATION: chymotrypsin B2

<400> SEQUENCE: 259

Gly Glu Phe Asp Gln Gly Ser Asp Glu Glu Asn Ile Gln Val Leu
 1               5                  10                  15

<210> SEQ ID NO 260
<211> LENGTH: 15
<212> TYPE: PRT
<213> ORGANISM: Homo Sapiens
<220> FEATURE:
<221> NAME/KEY: PEPTIDE
<222> LOCATION: (1)...(15)
<223> OTHER INFORMATION: chymotrypsin B2

<400> SEQUENCE: 260

Glu Phe Asp Gln Gly Ser Asp Glu Glu Asn Ile Gln Val Leu Lys
 1               5                  10                  15

<210> SEQ ID NO 261
<211> LENGTH: 16
<212> TYPE: PRT
<213> ORGANISM: Homo Sapiens
<220> FEATURE:
<221> NAME/KEY: PEPTIDE
<222> LOCATION: (1)...(15)
<223> OTHER INFORMATION: chymotrypsin B2

<400> SEQUENCE: 261

Gly Glu Phe Asp Gln Gly Ser Asp Glu Glu Asn Ile Gln Val Leu Lys
 1               5                  10                  15

<210> SEQ ID NO 262
<211> LENGTH: 17
<212> TYPE: PRT
<213> ORGANISM: Homo Sapiens
<220> FEATURE:
<221> NAME/KEY: PEPTIDE
<222> LOCATION: (1)...(15)
<223> OTHER INFORMATION: chymotrypsin B2

<400> SEQUENCE: 262

Ala Gly Glu Phe Asp Gln Gly Ser Asp Glu Glu Asn Ile Gln Val Leu
 1               5                  10                  15

Lys

<210> SEQ ID NO 263
<211> LENGTH: 21
<212> TYPE: PRT
<213> ORGANISM: Homo Sapiens
<220> FEATURE:
<221> NAME/KEY: PEPTIDE
<222> LOCATION: (1)...(20)
<223> OTHER INFORMATION: chymotrypsin B2
```

<400> SEQUENCE: 263

Ala Gly Ala Ser Gly Val Ser Ser Cys Met Gly Asp Ser Gly Gly Pro
1               5                   10                  15

Leu Val Cys Gln Lys
            20

<210> SEQ ID NO 264
<211> LENGTH: 18
<212> TYPE: PRT
<213> ORGANISM: Homo Sapiens
<220> FEATURE:
<221> NAME/KEY: PEPTIDE
<222> LOCATION: (1)...(15)
<223> OTHER INFORMATION: chymotrypsin B2

<400> SEQUENCE: 264

Val Ala Gly Glu Phe Asp Gln Gly Ser Asp Glu Glu Asn Ile Gln Val
1               5                   10                  15

Leu Lys

<210> SEQ ID NO 265
<211> LENGTH: 19
<212> TYPE: PRT
<213> ORGANISM: Homo Sapiens
<220> FEATURE:
<221> NAME/KEY: PEPTIDE
<222> LOCATION: (1)...(15)
<223> OTHER INFORMATION: chymotrypsin B2

<400> SEQUENCE: 265

Thr Pro Asp Lys Leu Gln Gln Ala Ala Leu Pro Leu Leu Ser Asn Ala
1               5                   10                  15

Glu Cys Lys

<210> SEQ ID NO 266
<211> LENGTH: 19
<212> TYPE: PRT
<213> ORGANISM: Homo Sapiens
<220> FEATURE:
<221> NAME/KEY: PEPTIDE
<222> LOCATION: (1)...(15)
<223> OTHER INFORMATION: chymotrypsin B2

<400> SEQUENCE: 266

Val Val Ala Gly Glu Phe Asp Gln Gly Ser Asp Glu Glu Asn Ile Gln
1               5                   10                  15

Val Leu Lys

<210> SEQ ID NO 267
<211> LENGTH: 20
<212> TYPE: PRT
<213> ORGANISM: Homo Sapiens
<220> FEATURE:
<221> NAME/KEY: PEPTIDE
<222> LOCATION: (1)...(20)
<223> OTHER INFORMATION: chymotrypsin B2

<400> SEQUENCE: 267

Thr Pro Asp Lys Leu Gln Gln Ala Ala Leu Pro Leu Leu Ser Asn Ala
1               5                   10                  15

Glu Cys Lys Lys
            20

```
<210> SEQ ID NO 268
<211> LENGTH: 21
<212> TYPE: PRT
<213> ORGANISM: Homo Sapiens
<220> FEATURE:
<221> NAME/KEY: PEPTIDE
<222> LOCATION: (1)...(20)
<223> OTHER INFORMATION: chymotrypsin B2

<400> SEQUENCE: 268

Ile Val Asn Gly Glu Asp Ala Val Pro Gly Ser Trp Pro Trp Gln Val
 1               5                  10                  15
Ser Leu Gln Asp Lys
            20

<210> SEQ ID NO 269
<211> LENGTH: 23
<212> TYPE: PRT
<213> ORGANISM: Homo Sapiens
<220> FEATURE:
<221> NAME/KEY: PEPTIDE
<222> LOCATION: (1)...(20)
<223> OTHER INFORMATION: chymotrypsin B2

<400> SEQUENCE: 269

Thr Ser Asp Val Val Ala Gly Glu Phe Asp Gln Gly Ser Asp Glu
 1               5                  10                  15
Glu Asn Ile Gln Val Leu Lys
            20

<210> SEQ ID NO 270
<211> LENGTH: 24
<212> TYPE: PRT
<213> ORGANISM: Homo Sapiens
<220> FEATURE:
<221> NAME/KEY: PEPTIDE
<222> LOCATION: (1)...(20)
<223> OTHER INFORMATION: chymotrypsin B2

<400> SEQUENCE: 270

Tyr Asn Ala Asn Lys Thr Pro Asp Lys Leu Gln Gln Ala Ala Leu Pro
 1               5                  10                  15
Leu Leu Ser Asn Ala Glu Cys Lys
            20

<210> SEQ ID NO 271
<211> LENGTH: 25
<212> TYPE: PRT
<213> ORGANISM: Homo Sapiens
<220> FEATURE:
<221> NAME/KEY: PEPTIDE
<222> LOCATION: (1)...(25)
<223> OTHER INFORMATION: chymotrypsin B2

<400> SEQUENCE: 271

Tyr Asn Ala Asn Lys Thr Pro Asp Lys Leu Gln Gln Ala Ala Leu Pro
 1               5                  10                  15
Leu Leu Ser Asn Ala Glu Cys Lys Lys
            20                  25

<210> SEQ ID NO 272
<211> LENGTH: 26
<212> TYPE: PRT
<213> ORGANISM: Homo Sapiens
<220> FEATURE:
<221> NAME/KEY: PEPTIDE
<222> LOCATION: (1)...(25)
```

```
<223> OTHER INFORMATION: chymotrypsin B2

<400> SEQUENCE: 272

Val Phe Lys Asn Pro Lys Phe Ser Ile Leu Thr Val Asn Asn Asp Ile
1               5                   10                  15

Thr Leu Leu Lys Leu Ala Thr Pro Ala Arg
            20                  25

<210> SEQ ID NO 273
<211> LENGTH: 27
<212> TYPE: PRT
<213> ORGANISM: Homo Sapiens
<220> FEATURE:
<221> NAME/KEY: PEPTIDE
<222> LOCATION: (1)...(25)
<223> OTHER INFORMATION: chymotrypsin B2

<400> SEQUENCE: 273

Thr Lys Tyr Asn Ala Asn Lys Thr Pro Asp Lys Leu Gln Gln Ala Ala
1               5                   10                  15

Leu Pro Leu Leu Ser Asn Ala Glu Cys Lys Lys
            20                  25

<210> SEQ ID NO 274
<211> LENGTH: 30
<212> TYPE: PRT
<213> ORGANISM: Homo Sapiens
<220> FEATURE:
<221> NAME/KEY: PEPTIDE
<222> LOCATION: (1)...(30)
<223> OTHER INFORMATION: chymotrypsin B2

<400> SEQUENCE: 274

Phe Ser Gln Thr Val Ser Ala Val Cys Leu Pro Ser Ala Asp Asp
1               5                   10                  15

Phe Pro Ala Gly Thr Leu Cys Ala Thr Thr Gly Trp Gly Lys
            20                  25                  30

<210> SEQ ID NO 275
<211> LENGTH: 8
<212> TYPE: PRT
<213> ORGANISM: Homo Sapiens
<220> FEATURE:
<221> NAME/KEY: PEPTIDE
<222> LOCATION: (1)...(5)
<223> OTHER INFORMATION: serine proteinase inhibitor, clade A, member 1

<400> SEQUENCE: 275

Leu Gly Gln Leu Gly Ile Thr Lys
1               5

<210> SEQ ID NO 276
<211> LENGTH: 9
<212> TYPE: PRT
<213> ORGANISM: Homo Sapiens
<220> FEATURE:
<221> NAME/KEY: PEPTIDE
<222> LOCATION: (1)...(5)
<223> OTHER INFORMATION: serine proteinase inhibitor, clade A, member 1

<400> SEQUENCE: 276

Ser Val Leu Gly Gln Leu Gly Ile Thr
1               5

<210> SEQ ID NO 277
<211> LENGTH: 7
```

```
<212> TYPE: PRT
<213> ORGANISM: Homo Sapiens
<220> FEATURE:
<221> NAME/KEY: PEPTIDE
<222> LOCATION: (1)...(5)
<223> OTHER INFORMATION: serine proteinase inhibitor, clade A, member 1

<400> SEQUENCE: 277

Phe Asn Lys Pro Phe Val Phe
 1               5

<210> SEQ ID NO 278
<211> LENGTH: 10
<212> TYPE: PRT
<213> ORGANISM: Homo Sapiens
<220> FEATURE:
<221> NAME/KEY: PEPTIDE
<222> LOCATION: (1)...(10)
<223> OTHER INFORMATION: serine proteinase inhibitor, clade A, member 1

<400> SEQUENCE: 278

Ser Val Leu Gly Gln Leu Gly Ile Thr Lys
 1               5                  10

<210> SEQ ID NO 279
<211> LENGTH: 9
<212> TYPE: PRT
<213> ORGANISM: Homo Sapiens
<220> FEATURE:
<221> NAME/KEY: PEPTIDE
<222> LOCATION: (1)...(5)
<223> OTHER INFORMATION: serine proteinase inhibitor, clade A, member 1

<400> SEQUENCE: 279

Leu Ser Ser Trp Val Leu Leu Met Lys
 1               5

<210> SEQ ID NO 280
<211> LENGTH: 10
<212> TYPE: PRT
<213> ORGANISM: Homo Sapiens
<220> FEATURE:
<221> NAME/KEY: PEPTIDE
<222> LOCATION: (1)...(10)
<223> OTHER INFORMATION: serine proteinase inhibitor, clade A, member 1

<400> SEQUENCE: 280

Leu Ser Ile Thr Gly Thr Tyr Asp Leu Lys
 1               5                  10

<210> SEQ ID NO 281
<211> LENGTH: 10
<212> TYPE: PRT
<213> ORGANISM: Homo Sapiens
<220> FEATURE:
<221> NAME/KEY: PEPTIDE
<222> LOCATION: (1)...(10)
<223> OTHER INFORMATION: serine proteinase inhibitor, clade A, member 1

<400> SEQUENCE: 281

Lys Leu Ser Ser Trp Val Leu Leu Met Lys
 1               5                  10

<210> SEQ ID NO 282
<211> LENGTH: 10
<212> TYPE: PRT
<213> ORGANISM: Homo Sapiens
<220> FEATURE:
<221> NAME/KEY: PEPTIDE
```

```
<222> LOCATION: (1)...(10)
<223> OTHER INFORMATION: serine proteinase inhibitor, clade A, member 1

<400> SEQUENCE: 282

Leu Ala Glu Phe Ala Phe Ser Leu Tyr Arg
 1               5                  10

<210> SEQ ID NO 283
<211> LENGTH: 10
<212> TYPE: PRT
<213> ORGANISM: Homo Sapiens
<220> FEATURE:
<221> NAME/KEY: PEPTIDE
<222> LOCATION: (1)...(10)
<223> OTHER INFORMATION: serine proteinase inhibitor, clade A, member 1

<400> SEQUENCE: 283

Val Phe Leu Met Ile Glu Gln Asn Thr Lys
 1               5                  10

<210> SEQ ID NO 284
<211> LENGTH: 12
<212> TYPE: PRT
<213> ORGANISM: Homo Sapiens
<220> FEATURE:
<221> NAME/KEY: PEPTIDE
<222> LOCATION: (1)...(10)
<223> OTHER INFORMATION: serine proteinase inhibitor, clade A, member 1

<400> SEQUENCE: 284

Thr Gly Asn Gly Leu Phe Leu Ser Glu Gly Leu Lys
 1               5                  10

<210> SEQ ID NO 285
<211> LENGTH: 12
<212> TYPE: PRT
<213> ORGANISM: Homo Sapiens
<220> FEATURE:
<221> NAME/KEY: PEPTIDE
<222> LOCATION: (1)...(10)
<223> OTHER INFORMATION: serine proteinase inhibitor, clade A, member 1

<400> SEQUENCE: 285

Asp Leu Ser Gly Val Thr Glu Glu Ala Pro Leu Lys
 1               5                  10

<210> SEQ ID NO 286
<211> LENGTH: 11
<212> TYPE: PRT
<213> ORGANISM: Homo Sapiens
<220> FEATURE:
<221> NAME/KEY: PEPTIDE
<222> LOCATION: (1)...(10)
<223> OTHER INFORMATION: serine proteinase inhibitor, clade A, member 1

<400> SEQUENCE: 286

Leu Val Asp Lys Phe Leu Glu Asp Val Lys Lys
 1               5                  10

<210> SEQ ID NO 287
<211> LENGTH: 12
<212> TYPE: PRT
<213> ORGANISM: Homo Sapiens
<220> FEATURE:
<221> NAME/KEY: PEPTIDE
<222> LOCATION: (1)...(10)
<223> OTHER INFORMATION: serine proteinase inhibitor, clade A, member 1

<400> SEQUENCE: 287
```

```
Thr Leu Asn Gln Pro Asp Ser Gln Leu Gln Leu Thr
1               5                   10

<210> SEQ ID NO 288
<211> LENGTH: 13
<212> TYPE: PRT
<213> ORGANISM: Homo Sapiens
<220> FEATURE:
<221> NAME/KEY: PEPTIDE
<222> LOCATION: (1)...(10)
<223> OTHER INFORMATION: serine proteinase inhibitor, clade A, member 1

<400> SEQUENCE: 288

His Leu Glu Asn Glu Leu Thr His Asp Ile Ile Thr Lys
1               5                   10

<210> SEQ ID NO 289
<211> LENGTH: 16
<212> TYPE: PRT
<213> ORGANISM: Homo Sapiens
<220> FEATURE:
<221> NAME/KEY: PEPTIDE
<222> LOCATION: (1)...(15)
<223> OTHER INFORMATION: serine proteinase inhibitor, clade A, member 1

<400> SEQUENCE: 289

Ser Asn Gly Ala Asp Leu Ser Gly Val Thr Glu Glu Ala Pro Leu Lys
1               5                   10                  15

<210> SEQ ID NO 290
<211> LENGTH: 14
<212> TYPE: PRT
<213> ORGANISM: Homo Sapiens
<220> FEATURE:
<221> NAME/KEY: PEPTIDE
<222> LOCATION: (1)...(10)
<223> OTHER INFORMATION: serine proteinase inhibitor, clade A, member 1

<400> SEQUENCE: 290

Ile Thr Pro Asn Leu Ala Glu Phe Ala Phe Ser Leu Tyr Arg
1               5                   10

<210> SEQ ID NO 291
<211> LENGTH: 17
<212> TYPE: PRT
<213> ORGANISM: Homo Sapiens
<220> FEATURE:
<221> NAME/KEY: PEPTIDE
<222> LOCATION: (1)...(15)
<223> OTHER INFORMATION: serine proteinase inhibitor, clade A, member 1

<400> SEQUENCE: 291

Val Phe Ser Asn Gly Ala Asp Leu Ser Gly Val Thr Glu Glu Ala Pro
1               5                   10                  15

Leu

<210> SEQ ID NO 292
<211> LENGTH: 15
<212> TYPE: PRT
<213> ORGANISM: Homo Sapiens
<220> FEATURE:
<221> NAME/KEY: PEPTIDE
<222> LOCATION: (1)...(15)
<223> OTHER INFORMATION: serine proteinase inhibitor, clade A, member 1

<400> SEQUENCE: 292

Leu Gln His Leu Glu Asn Glu Leu Thr His Asp Ile Ile Thr Lys
```

```
<210> SEQ ID NO 293
<211> LENGTH: 18
<212> TYPE: PRT
<213> ORGANISM: Homo Sapiens
<220> FEATURE:
<221> NAME/KEY: PEPTIDE
<222> LOCATION: (1)...(15)
<223> OTHER INFORMATION: serine proteinase inhibitor, clade A, member 1

<400> SEQUENCE: 293

Val Phe Ser Asn Gly Ala Asp Leu Ser Gly Val Thr Glu Glu Ala Pro
 1               5                  10                  15

Leu Lys

<210> SEQ ID NO 294
<211> LENGTH: 15
<212> TYPE: PRT
<213> ORGANISM: Homo Sapiens
<220> FEATURE:
<221> NAME/KEY: PEPTIDE
<222> LOCATION: (1)...(15)
<223> OTHER INFORMATION: serine proteinase inhibitor, clade A, member 1

<400> SEQUENCE: 294

Phe Asn Lys Pro Phe Val Phe Leu Met Ile Glu Gln Asn Thr Lys
 1               5                  10                  15

<210> SEQ ID NO 295
<211> LENGTH: 16
<212> TYPE: PRT
<213> ORGANISM: Homo Sapiens
<220> FEATURE:
<221> NAME/KEY: PEPTIDE
<222> LOCATION: (1)...(15)
<223> OTHER INFORMATION: serine proteinase inhibitor, clade A, member 1

<400> SEQUENCE: 295

Asp Thr Glu Glu Glu Asp Phe His Val Asp Gln Val Thr Thr Val Lys
 1               5                  10                  15

<210> SEQ ID NO 296
<211> LENGTH: 18
<212> TYPE: PRT
<213> ORGANISM: Homo Sapiens
<220> FEATURE:
<221> NAME/KEY: PEPTIDE
<222> LOCATION: (1)...(15)
<223> OTHER INFORMATION: serine proteinase inhibitor, clade A, member 1

<400> SEQUENCE: 296

Leu Tyr His Ser Glu Ala Phe Thr Val Asn Phe Gly Asp Thr Glu Glu
 1               5                  10                  15

Ala Lys

<210> SEQ ID NO 297
<211> LENGTH: 17
<212> TYPE: PRT
<213> ORGANISM: Homo Sapiens
<220> FEATURE:
<221> NAME/KEY: PEPTIDE
<222> LOCATION: (1)...(15)
<223> OTHER INFORMATION: serine proteinase inhibitor, clade A, member 1

<400> SEQUENCE: 297

Glu Leu Asp Arg Asp Thr Val Phe Ala Leu Val Asn Tyr Ile Phe Phe
 1               5                  10                  15
```

```
                1               5                   10                  15
Lys

<210> SEQ ID NO 298
<211> LENGTH: 21
<212> TYPE: PRT
<213> ORGANISM: Homo Sapiens
<220> FEATURE:
<221> NAME/KEY: PEPTIDE
<222> LOCATION: (1)...(20)
<223> OTHER INFORMATION: serine proteinase inhibitor, clade A, member 1

<400> SEQUENCE: 298

Val Phe Ser Asn Gly Ala Asp Leu Ser Gly Val Thr Glu Glu Ala Pro
1               5                   10                  15

Leu Lys Leu Ser Lys
            20

<210> SEQ ID NO 299
<211> LENGTH: 19
<212> TYPE: PRT
<213> ORGANISM: Homo Sapiens
<220> FEATURE:
<221> NAME/KEY: PEPTIDE
<222> LOCATION: (1)...(15)
<223> OTHER INFORMATION: serine proteinase inhibitor, clade A, member 1

<400> SEQUENCE: 299

Leu Tyr His Ser Glu Ala Phe Thr Val Asn Phe Gly Asp Thr Glu Glu
1               5                   10                  15

Ala Lys Lys

<210> SEQ ID NO 300
<211> LENGTH: 20
<212> TYPE: PRT
<213> ORGANISM: Homo Sapiens
<220> FEATURE:
<221> NAME/KEY: PEPTIDE
<222> LOCATION: (1)...(20)
<223> OTHER INFORMATION: serine proteinase inhibitor, clade A, member 1

<400> SEQUENCE: 300

Lys Leu Tyr His Ser Glu Ala Phe Thr Val Asn Phe Gly Asp Thr Glu
1               5                   10                  15

Glu Ala Lys Lys
            20

<210> SEQ ID NO 301
<211> LENGTH: 24
<212> TYPE: PRT
<213> ORGANISM: Homo Sapiens
<220> FEATURE:
<221> NAME/KEY: PEPTIDE
<222> LOCATION: (1)...(20)
<223> OTHER INFORMATION: serine proteinase inhibitor, clade A, member 1

<400> SEQUENCE: 301

Thr Leu Asn Gln Pro Asp Ser Gln Leu Gln Leu Thr Thr Gly Asn Gly
1               5                   10                  15

Leu Phe Leu Ser Glu Gly Leu Lys
            20

<210> SEQ ID NO 302
<211> LENGTH: 23
<212> TYPE: PRT
```

```
<213> ORGANISM: Homo Sapiens
<220> FEATURE:
<221> NAME/KEY: PEPTIDE
<222> LOCATION: (1)...(20)
<223> OTHER INFORMATION: serine proteinase inhibitor, clade A, member 1

<400> SEQUENCE: 302

Phe Phe Leu Pro Asp Glu Gly Lys Leu Gln His Leu Glu Asn Glu Leu
 1               5                  10                  15

Thr His Asp Ile Ile Thr Lys
            20

<210> SEQ ID NO 303
<211> LENGTH: 23
<212> TYPE: PRT
<213> ORGANISM: Homo Sapiens
<220> FEATURE:
<221> NAME/KEY: PEPTIDE
<222> LOCATION: (1)...(20)
<223> OTHER INFORMATION: serine proteinase inhibitor, clade A, member 1

<400> SEQUENCE: 303

Ile Val Asp Leu Val Lys Glu Leu Asp Arg Asp Thr Val Phe Ala Leu
 1               5                  10                  15

Val Asn Tyr Ile Phe Phe Lys
            20

<210> SEQ ID NO 304
<211> LENGTH: 26
<212> TYPE: PRT
<213> ORGANISM: Homo Sapiens
<220> FEATURE:
<221> NAME/KEY: PEPTIDE
<222> LOCATION: (1)...(25)
<223> OTHER INFORMATION: serine proteinase inhibitor, clade A, member 1

<400> SEQUENCE: 304

Gly Lys Trp Glu Arg Pro Phe Glu Val Lys Asp Thr Glu Glu Glu Asp
 1               5                  10                  15

Phe His Val Asp Gln Val Thr Thr Val Lys
            20                  25

<210> SEQ ID NO 305
<211> LENGTH: 8
<212> TYPE: PRT
<213> ORGANISM: Homo Sapiens
<220> FEATURE:
<221> NAME/KEY: PEPTIDE
<222> LOCATION: (1)...(5)
<223> OTHER INFORMATION: elastase 2A preproprotein

<400> SEQUENCE: 305

Gly Asn Asp Ile Ala Leu Leu Lys
 1               5

<210> SEQ ID NO 306
<211> LENGTH: 8
<212> TYPE: PRT
<213> ORGANISM: Homo Sapiens
<220> FEATURE:
<221> NAME/KEY: PEPTIDE
<222> LOCATION: (1)...(5)
<223> OTHER INFORMATION: elastase 2A preproprotein

<400> SEQUENCE: 306

Pro Asp Val Leu Gln Gln Gly Arg
 1               5
```

<210> SEQ ID NO 307
<211> LENGTH: 10
<212> TYPE: PRT
<213> ORGANISM: Homo Sapiens
<220> FEATURE:
<221> NAME/KEY: PEPTIDE
<222> LOCATION: (1)...(10)
<223> OTHER INFORMATION: elastase 2A preproprotein

<400> SEQUENCE: 307

Leu Ala Asn Pro Val Ser Leu Thr Asp Lys
1               5                   10

<210> SEQ ID NO 308
<211> LENGTH: 11
<212> TYPE: PRT
<213> ORGANISM: Homo Sapiens
<220> FEATURE:
<221> NAME/KEY: PEPTIDE
<222> LOCATION: (1)...(10)
<223> OTHER INFORMATION: elastase 2A preproprotein

<400> SEQUENCE: 308

Glu Ser Gly Ser Leu Ala Val Ser Val Ser Lys
1               5                   10

<210> SEQ ID NO 309
<211> LENGTH: 12
<212> TYPE: PRT
<213> ORGANISM: Homo Sapiens
<220> FEATURE:
<221> NAME/KEY: PEPTIDE
<222> LOCATION: (1)...(10)
<223> OTHER INFORMATION: elastase 2A preproprotein

<400> SEQUENCE: 309

Ala Glu Ser Gly Ser Leu Ala Val Ser Val Ser Lys
1               5                   10

<210> SEQ ID NO 310
<211> LENGTH: 11
<212> TYPE: PRT
<213> ORGANISM: Homo Sapiens
<220> FEATURE:
<221> NAME/KEY: PEPTIDE
<222> LOCATION: (1)...(10)
<223> OTHER INFORMATION: elastase 2A preproprotein

<400> SEQUENCE: 310

Leu Ala Asn Pro Val Ser Leu Thr Asp Lys Ile
1               5                   10

<210> SEQ ID NO 311
<211> LENGTH: 11
<212> TYPE: PRT
<213> ORGANISM: Homo Sapiens
<220> FEATURE:
<221> NAME/KEY: PEPTIDE
<222> LOCATION: (1)...(10)
<223> OTHER INFORMATION: elastase 2A preproprotein

<400> SEQUENCE: 311

Ser Ser Ser Ala Trp Trp Gly Ser Ser Val Lys
1               5                   10

<210> SEQ ID NO 312
<211> LENGTH: 11

```
<212> TYPE: PRT
<213> ORGANISM: Homo Sapiens
<220> FEATURE:
<221> NAME/KEY: PEPTIDE
<222> LOCATION: (1)...(10)
<223> OTHER INFORMATION: elastase 2A preproprotein

<400> SEQUENCE: 312

His Asn Leu Tyr Val Ala Glu Ser Gly Ser Leu
1               5                   10

<210> SEQ ID NO 313
<211> LENGTH: 13
<212> TYPE: PRT
<213> ORGANISM: Homo Sapiens
<220> FEATURE:
<221> NAME/KEY: PEPTIDE
<222> LOCATION: (1)...(10)
<223> OTHER INFORMATION: elastase 2A preproprotein

<400> SEQUENCE: 313

Val Ala Glu Ser Gly Ser Leu Ala Val Ser Val Ser Lys
1               5                   10

<210> SEQ ID NO 314
<211> LENGTH: 12
<212> TYPE: PRT
<213> ORGANISM: Homo Sapiens
<220> FEATURE:
<221> NAME/KEY: PEPTIDE
<222> LOCATION: (1)...(10)
<223> OTHER INFORMATION: elastase 2A preproprotein

<400> SEQUENCE: 314

Leu Ala Asn Pro Val Ser Leu Thr Asp Lys Ile Gln
1               5                   10

<210> SEQ ID NO 315
<211> LENGTH: 11
<212> TYPE: PRT
<213> ORGANISM: Homo Sapiens
<220> FEATURE:
<221> NAME/KEY: PEPTIDE
<222> LOCATION: (1)...(10)
<223> OTHER INFORMATION: elastase 2A preproprotein

<400> SEQUENCE: 315

Val Ser Asn Tyr Ile Asp Trp Ile Asn Ser Val
1               5                   10

<210> SEQ ID NO 316
<211> LENGTH: 12
<212> TYPE: PRT
<213> ORGANISM: Homo Sapiens
<220> FEATURE:
<221> NAME/KEY: PEPTIDE
<222> LOCATION: (1)...(10)
<223> OTHER INFORMATION: elastase 2A preproprotein

<400> SEQUENCE: 316

Trp Gln Val His Gly Ile Val Ser Phe Gly Ser Arg
1               5                   10

<210> SEQ ID NO 317
<211> LENGTH: 13
<212> TYPE: PRT
<213> ORGANISM: Homo Sapiens
<220> FEATURE:
<221> NAME/KEY: PEPTIDE
```

```
<222> LOCATION: (1)...(10)
<223> OTHER INFORMATION: elastase 2A preproprotein

<400> SEQUENCE: 317

Thr Cys Ser Ser Ser Ala Trp Trp Gly Ser Ser Val Lys
  1               5                  10

<210> SEQ ID NO 318
<211> LENGTH: 13
<212> TYPE: PRT
<213> ORGANISM: Homo Sapiens
<220> FEATURE:
<221> NAME/KEY: PEPTIDE
<222> LOCATION: (1)...(10)
<223> OTHER INFORMATION: elastase 2A preproprotein

<400> SEQUENCE: 318

Leu Ala Asn Pro Val Ser Leu Thr Asp Lys Ile Gln Leu
  1               5                  10

<210> SEQ ID NO 319
<211> LENGTH: 12
<212> TYPE: PRT
<213> ORGANISM: Homo Sapiens
<220> FEATURE:
<221> NAME/KEY: PEPTIDE
<222> LOCATION: (1)...(10)
<223> OTHER INFORMATION: elastase 2A preproprotein

<400> SEQUENCE: 319

Val Ser Asn Tyr Ile Asp Trp Ile Asn Ser Val Ile
  1               5                  10

<210> SEQ ID NO 320
<211> LENGTH: 14
<212> TYPE: PRT
<213> ORGANISM: Homo Sapiens
<220> FEATURE:
<221> NAME/KEY: PEPTIDE
<222> LOCATION: (1)...(10)
<223> OTHER INFORMATION: elastase 2A preproprotein

<400> SEQUENCE: 320

Val Val Gly Gly Glu Glu Ala Arg Pro Asn Ser Trp Pro Trp
  1               5                  10

<210> SEQ ID NO 321
<211> LENGTH: 15
<212> TYPE: PRT
<213> ORGANISM: Homo Sapiens
<220> FEATURE:
<221> NAME/KEY: PEPTIDE
<222> LOCATION: (1)...(15)
<223> OTHER INFORMATION: elastase 2A preproprotein

<400> SEQUENCE: 321

Leu Gln Thr Asn Gly Ala Val Pro Asp Val Leu Gln Gln Gly Arg
  1               5                  10                  15

<210> SEQ ID NO 322
<211> LENGTH: 15
<212> TYPE: PRT
<213> ORGANISM: Homo Sapiens
<220> FEATURE:
<221> NAME/KEY: PEPTIDE
<222> LOCATION: (1)...(15)
<223> OTHER INFORMATION: elastase 2A preproprotein

<400> SEQUENCE: 322
```

```
<210> SEQ ID NO 323
<211> LENGTH: 15
<212> TYPE: PRT
<213> ORGANISM: Homo Sapiens
<220> FEATURE:
<221> NAME/KEY: PEPTIDE
<222> LOCATION: (1)...(15)
<223> OTHER INFORMATION: elastase 2A preproprotein

<400> SEQUENCE: 323
```

Val Gly Gly Glu Glu Ala Arg Pro Asn Ser Trp Pro Trp Gln Val
1               5                   10                  15

```
<210> SEQ ID NO 323
<211> LENGTH: 15
<212> TYPE: PRT
<213> ORGANISM: Homo Sapiens
<220> FEATURE:
<221> NAME/KEY: PEPTIDE
<222> LOCATION: (1)...(15)
<223> OTHER INFORMATION: elastase 2A preproprotein

<400> SEQUENCE: 323
```

Val Ser Asn Tyr Ile Asp Trp Ile Asn Ser Val Ile Ala Asn Asn
1               5                   10                  15

```
<210> SEQ ID NO 324
<211> LENGTH: 17
<212> TYPE: PRT
<213> ORGANISM: Homo Sapiens
<220> FEATURE:
<221> NAME/KEY: PEPTIDE
<222> LOCATION: (1)...(15)
<223> OTHER INFORMATION: elastase 2A preproprotein

<400> SEQUENCE: 324
```

His Asn Leu Tyr Val Ala Glu Ser Gly Ser Leu Ala Val Ser Val Ser
1               5                   10                  15

Lys

```
<210> SEQ ID NO 325
<211> LENGTH: 16
<212> TYPE: PRT
<213> ORGANISM: Homo Sapiens
<220> FEATURE:
<221> NAME/KEY: PEPTIDE
<222> LOCATION: (1)...(15)
<223> OTHER INFORMATION: elastase 2A preproprotein

<400> SEQUENCE: 325
```

Val Val Gly Gly Glu Glu Ala Arg Pro Asn Ser Trp Pro Trp Gln Val
1               5                   10                  15

```
<210> SEQ ID NO 326
<211> LENGTH: 17
<212> TYPE: PRT
<213> ORGANISM: Homo Sapiens
<220> FEATURE:
<221> NAME/KEY: PEPTIDE
<222> LOCATION: (1)...(15)
<223> OTHER INFORMATION: elastase 2A preproprotein

<400> SEQUENCE: 326
```

Val Val Gly Gly Glu Glu Ala Arg Pro Asn Ser Trp Pro Trp Gln Val
1               5                   10                  15

Ser

```
<210> SEQ ID NO 327
<211> LENGTH: 25
<212> TYPE: PRT
<213> ORGANISM: Homo Sapiens
<220> FEATURE:
<221> NAME/KEY: PEPTIDE
<222> LOCATION: (1)...(25)
<223> OTHER INFORMATION: elastase 2A preproprotein

<400> SEQUENCE: 327
```

```
Val Val Gly Gly Glu Glu Ala Arg Pro Asn Ser Trp Pro Trp Gln Val
1               5                   10                  15

Ser Leu Gln Tyr Ser Ser Asn Gly Lys
            20                  25
```

<210> SEQ ID NO 328
<211> LENGTH: 26
<212> TYPE: PRT
<213> ORGANISM: Homo Sapiens
<220> FEATURE:
<221> NAME/KEY: PEPTIDE
<222> LOCATION: (1)...(25)
<223> OTHER INFORMATION: elastase 2A preproprotein

<400> SEQUENCE: 328

```
Ile Gln Leu Ala Cys Leu Pro Pro Ala Gly Thr Ile Leu Pro Asn Asn
1               5                   10                  15

Tyr Pro Cys Tyr Val Thr Gly Trp Gly Arg
            20                  25
```

<210> SEQ ID NO 329
<211> LENGTH: 26
<212> TYPE: PRT
<213> ORGANISM: Homo Sapiens
<220> FEATURE:
<221> NAME/KEY: PEPTIDE
<222> LOCATION: (1)...(25)
<223> OTHER INFORMATION: elastase 2A preproprotein

<400> SEQUENCE: 329

```
Trp Tyr His Thr Cys Gly Gly Ser Leu Ile Ala Asn Ser Trp Val Leu
1               5                   10                  15

Thr Ala Ala His Cys Ile Ser Ser Ser Arg
            20                  25
```

<210> SEQ ID NO 330
<211> LENGTH: 31
<212> TYPE: PRT
<213> ORGANISM: Homo Sapiens
<220> FEATURE:
<221> NAME/KEY: PEPTIDE
<222> LOCATION: (1)...(30)
<223> OTHER INFORMATION: elastase 2A preproprotein

<400> SEQUENCE: 330

```
Thr Ser Met Ile Cys Ala Gly Gly Asp Gly Val Ile Ser Ser Cys Asn
1               5                   10                  15

Gly Asp Ser Gly Gly Pro Leu Asn Cys Gln Ala Ser Asp Gly Arg
            20                  25                  30
```

<210> SEQ ID NO 331
<211> LENGTH: 36
<212> TYPE: PRT
<213> ORGANISM: Homo Sapiens
<220> FEATURE:
<221> NAME/KEY: PEPTIDE
<222> LOCATION: (1)...(35)
<223> OTHER INFORMATION: elastase 2A preproprotein

<400> SEQUENCE: 331

```
Leu Ala Asn Pro Val Ser Leu Thr Asp Lys Ile Gln Leu Ala Cys Leu
1               5                   10                  15

Pro Pro Ala Gly Thr Ile Leu Pro Asn Asn Tyr Pro Cys Tyr Val Thr
            20                  25                  30
```

```
Gly Trp Gly Arg
        35

<210> SEQ ID NO 332
<211> LENGTH: 7
<212> TYPE: PRT
<213> ORGANISM: Homo Sapiens
<220> FEATURE:
<221> NAME/KEY: PEPTIDE
<222> LOCATION: (1)...(5)
<223> OTHER INFORMATION: pancreatic carboxypeptidase B1 preproprotein

<400> SEQUENCE: 332

Ala Leu Ala Asp Phe Ile Arg
1               5

<210> SEQ ID NO 333
<211> LENGTH: 8
<212> TYPE: PRT
<213> ORGANISM: Homo Sapiens
<220> FEATURE:
<221> NAME/KEY: PEPTIDE
<222> LOCATION: (1)...(5)
<223> OTHER INFORMATION: pancreatic carboxypeptidase B1 preproprotein

<400> SEQUENCE: 333

Met Asp Cys Gly Phe His Ala Arg
1               5

<210> SEQ ID NO 334
<211> LENGTH: 8
<212> TYPE: PRT
<213> ORGANISM: Homo Sapiens
<220> FEATURE:
<221> NAME/KEY: PEPTIDE
<222> LOCATION: (1)...(5)
<223> OTHER INFORMATION: pancreatic carboxypeptidase B1 preproprotein

<400> SEQUENCE: 334

Tyr Ser Phe Thr Phe Glu Leu Arg
1               5

<210> SEQ ID NO 335
<211> LENGTH: 10
<212> TYPE: PRT
<213> ORGANISM: Homo Sapiens
<220> FEATURE:
<221> NAME/KEY: PEPTIDE
<222> LOCATION: (1)...(10)
<223> OTHER INFORMATION: pancreatic carboxypeptidase B1 preproprotein

<400> SEQUENCE: 335

Ser Val Ile Gly Thr Thr Phe Glu Gly Arg
1               5                   10

<210> SEQ ID NO 336
<211> LENGTH: 11
<212> TYPE: PRT
<213> ORGANISM: Homo Sapiens
<220> FEATURE:
<221> NAME/KEY: PEPTIDE
<222> LOCATION: (1)...(10)
<223> OTHER INFORMATION: pancreatic carboxypeptidase B1 preproprotein

<400> SEQUENCE: 336

Ala Thr Cys Glu Glu Thr Phe Leu Ala Ile Lys
1               5                   10
```

```
<210> SEQ ID NO 337
<211> LENGTH: 11
<212> TYPE: PRT
<213> ORGANISM: Homo Sapiens
<220> FEATURE:
<221> NAME/KEY: PEPTIDE
<222> LOCATION: (1)...(10)
<223> OTHER INFORMATION: pancreatic carboxypeptidase B1 preproprotein

<400> SEQUENCE: 337

Glu Ile Gln Val Thr Glu Leu Leu Asp Lys Leu
1               5                   10

<210> SEQ ID NO 338
<211> LENGTH: 12
<212> TYPE: PRT
<213> ORGANISM: Homo Sapiens
<220> FEATURE:
<221> NAME/KEY: PEPTIDE
<222> LOCATION: (1)...(10)
<223> OTHER INFORMATION: pancreatic carboxypeptidase B1 preproprotein

<400> SEQUENCE: 338

Ala Glu Asp Thr Val Thr Val Glu Asn Val Leu Lys
1               5                   10

<210> SEQ ID NO 339
<211> LENGTH: 11
<212> TYPE: PRT
<213> ORGANISM: Homo Sapiens
<220> FEATURE:
<221> NAME/KEY: PEPTIDE
<222> LOCATION: (1)...(10)
<223> OTHER INFORMATION: pancreatic carboxypeptidase B1 preproprotein

<400> SEQUENCE: 339

Tyr Gly Phe Leu Leu Pro Glu Ser Gln Ile Arg
1               5                   10

<210> SEQ ID NO 340
<211> LENGTH: 13
<212> TYPE: PRT
<213> ORGANISM: Homo Sapiens
<220> FEATURE:
<221> NAME/KEY: PEPTIDE
<222> LOCATION: (1)...(10)
<223> OTHER INFORMATION: pancreatic carboxypeptidase B1 preproprotein

<400> SEQUENCE: 340

Leu Gly Glu Asn Asn Ala Glu Leu Asn Ala Leu Ala Lys
1               5                   10

<210> SEQ ID NO 341
<211> LENGTH: 13
<212> TYPE: PRT
<213> ORGANISM: Homo Sapiens
<220> FEATURE:
<221> NAME/KEY: PEPTIDE
<222> LOCATION: (1)...(10)
<223> OTHER INFORMATION: pancreatic carboxypeptidase B1 preproprotein

<400> SEQUENCE: 341

Asn Phe Asp Ala Gly Trp Cys Glu Ile Gly Ala Ser Arg
1               5                   10

<210> SEQ ID NO 342
<211> LENGTH: 12
<212> TYPE: PRT
<213> ORGANISM: Homo Sapiens
```

<220> FEATURE:
<221> NAME/KEY: PEPTIDE
<222> LOCATION: (1)...(10)
<223> OTHER INFORMATION: pancreatic carboxypeptidase B1 preproprotein

<400> SEQUENCE: 342

Leu Asn Ile Asp Gly Tyr Ile Tyr Thr Trp Thr Lys
 1               5                  10

<210> SEQ ID NO 343
<211> LENGTH: 14
<212> TYPE: PRT
<213> ORGANISM: Homo Sapiens
<220> FEATURE:
<221> NAME/KEY: PEPTIDE
<222> LOCATION: (1)...(10)
<223> OTHER INFORMATION: pancreatic carboxypeptidase B1 preproprotein

<400> SEQUENCE: 343

Ala Gly Gly Ser Asp Asp Trp Ala Tyr Asp Gln Gly Ile Arg
 1               5                  10

<210> SEQ ID NO 344
<211> LENGTH: 13
<212> TYPE: PRT
<213> ORGANISM: Homo Sapiens
<220> FEATURE:
<221> NAME/KEY: PEPTIDE
<222> LOCATION: (1)...(10)
<223> OTHER INFORMATION: pancreatic carboxypeptidase B1 preproprotein

<400> SEQUENCE: 344

Glu Trp Ile Ser Pro Ala Phe Cys Gln Trp Phe Val Arg
 1               5                  10

<210> SEQ ID NO 345
<211> LENGTH: 15
<212> TYPE: PRT
<213> ORGANISM: Homo Sapiens
<220> FEATURE:
<221> NAME/KEY: PEPTIDE
<222> LOCATION: (1)...(15)
<223> OTHER INFORMATION: pancreatic carboxypeptidase B1 preproprotein

<400> SEQUENCE: 345

Trp Thr Gln Gln Val Ala Thr Glu Asn Pro Ala Leu Ile Ser Arg
 1               5                  10                  15

<210> SEQ ID NO 346
<211> LENGTH: 17
<212> TYPE: PRT
<213> ORGANISM: Homo Sapiens
<220> FEATURE:
<221> NAME/KEY: PEPTIDE
<222> LOCATION: (1)...(15)
<223> OTHER INFORMATION: pancreatic carboxypeptidase B1 preproprotein

<400> SEQUENCE: 346

Ala Gly Gln Asn Lys Pro Ala Ile Phe Met Asp Cys Gly Phe His Ala
 1               5                  10                  15
Arg

<210> SEQ ID NO 347
<211> LENGTH: 15
<212> TYPE: PRT
<213> ORGANISM: Homo Sapiens
<220> FEATURE:
<221> NAME/KEY: PEPTIDE

```
<222> LOCATION: (1)...(15)
<223> OTHER INFORMATION: pancreatic carboxypeptidase B1 preproprotein

<400> SEQUENCE: 347

Tyr Asn Lys Trp Glu Thr Ile Glu Ala Trp Thr Gln Gln Val Ala
 1               5                  10                  15

<210> SEQ ID NO 348
<211> LENGTH: 17
<212> TYPE: PRT
<213> ORGANISM: Homo Sapiens
<220> FEATURE:
<221> NAME/KEY: PEPTIDE
<222> LOCATION: (1)...(15)
<223> OTHER INFORMATION: pancreatic carboxypeptidase B1 preproprotein

<400> SEQUENCE: 348

Glu Ala Trp Thr Gln Gln Val Ala Thr Glu Asn Pro Ala Leu Ile Ser
 1               5                  10                  15

Arg

<210> SEQ ID NO 349
<211> LENGTH: 19
<212> TYPE: PRT
<213> ORGANISM: Homo Sapiens
<220> FEATURE:
<221> NAME/KEY: PEPTIDE
<222> LOCATION: (1)...(15)
<223> OTHER INFORMATION: pancreatic carboxypeptidase B1 preproprotein

<400> SEQUENCE: 349

Thr Ile Tyr Pro Ala Ala Gly Gly Ser Asp Asp Trp Ala Tyr Asp Gln
 1               5                  10                  15

Gly Ile Arg

<210> SEQ ID NO 350
<211> LENGTH: 19
<212> TYPE: PRT
<213> ORGANISM: Homo Sapiens
<220> FEATURE:
<221> NAME/KEY: PEPTIDE
<222> LOCATION: (1)...(15)
<223> OTHER INFORMATION: pancreatic carboxypeptidase B1 preproprotein

<400> SEQUENCE: 350

Asn Pro Cys Asp Glu Thr Tyr Cys Gly Pro Ala Ala Glu Ser Glu Lys
 1               5                  10                  15

Glu Thr Lys

<210> SEQ ID NO 351
<211> LENGTH: 20
<212> TYPE: PRT
<213> ORGANISM: Homo Sapiens
<220> FEATURE:
<221> NAME/KEY: PEPTIDE
<222> LOCATION: (1)...(20)
<223> OTHER INFORMATION: pancreatic carboxypeptidase B1 preproprotein

<400> SEQUENCE: 351

Tyr Asn Lys Trp Glu Thr Ile Glu Ala Trp Thr Gln Gln Val Ala Thr
 1               5                  10                  15

Glu Asn Pro Ala
            20

<210> SEQ ID NO 352
```

```
<211> LENGTH: 22
<212> TYPE: PRT
<213> ORGANISM: Homo Sapiens
<220> FEATURE:
<221> NAME/KEY: PEPTIDE
<222> LOCATION: (1)...(20)
<223> OTHER INFORMATION: pancreatic carboxypeptidase B1 preproprotein

<400> SEQUENCE: 352

Tyr Asn Lys Trp Glu Thr Ile Glu Ala Trp Thr Gln Gln Val Ala Thr
1               5                   10                  15

Glu Asn Pro Ala Leu Ile
            20

<210> SEQ ID NO 353
<211> LENGTH: 26
<212> TYPE: PRT
<213> ORGANISM: Homo Sapiens
<220> FEATURE:
<221> NAME/KEY: PEPTIDE
<222> LOCATION: (1)...(25)
<223> OTHER INFORMATION: pancreatic carboxypeptidase B1 preproprotein

<400> SEQUENCE: 353

Thr Tyr Gly Pro Gly Ala Thr Thr Ile Tyr Pro Ala Ala Gly Gly Ser
1               5                   10                  15

Asp Asp Trp Ala Tyr Asp Gln Gly Ile Arg
            20                  25

<210> SEQ ID NO 354
<211> LENGTH: 24
<212> TYPE: PRT
<213> ORGANISM: Homo Sapiens
<220> FEATURE:
<221> NAME/KEY: PEPTIDE
<222> LOCATION: (1)...(20)
<223> OTHER INFORMATION: pancreatic carboxypeptidase B1 preproprotein

<400> SEQUENCE: 354

Tyr Asn Lys Trp Glu Thr Ile Glu Ala Trp Thr Gln Gln Val Ala Thr
1               5                   10                  15

Glu Asn Pro Ala Leu Ile Ser Arg
            20

<210> SEQ ID NO 355
<211> LENGTH: 27
<212> TYPE: PRT
<213> ORGANISM: Homo Sapiens
<220> FEATURE:
<221> NAME/KEY: PEPTIDE
<222> LOCATION: (1)...(25)
<223> OTHER INFORMATION: pancreatic carboxypeptidase B1 preproprotein

<400> SEQUENCE: 355

Tyr Thr Tyr Gly Pro Gly Ala Thr Thr Ile Tyr Pro Ala Ala Gly Gly
1               5                   10                  15

Ser Asp Asp Trp Ala Tyr Asp Gln Gly Ile Arg
            20                  25

<210> SEQ ID NO 356
<211> LENGTH: 10
<212> TYPE: PRT
<213> ORGANISM: Homo Sapiens
<220> FEATURE:
<221> NAME/KEY: PEPTIDE
<222> LOCATION: (1)...(10)
<223> OTHER INFORMATION: protease, serine, 1 preproprotein
```

```
<400> SEQUENCE: 356

Leu Asp Ala Pro Val Leu Ser Gln Ala Lys
1               5                   10

<210> SEQ ID NO 357
<211> LENGTH: 12
<212> TYPE: PRT
<213> ORGANISM: Homo Sapiens
<220> FEATURE:
<221> NAME/KEY: PEPTIDE
<222> LOCATION: (1)...(10)
<223> OTHER INFORMATION: protease, serine, 1 preproprotein

<400> SEQUENCE: 357

Ser Leu Pro Thr Ala Pro Pro Ala Thr Gly Thr Lys
1               5                   10

<210> SEQ ID NO 358
<211> LENGTH: 10
<212> TYPE: PRT
<213> ORGANISM: Homo Sapiens
<220> FEATURE:
<221> NAME/KEY: PEPTIDE
<222> LOCATION: (1)...(10)
<223> OTHER INFORMATION: protease, serine, 1 preproprotein

<400> SEQUENCE: 358

Thr Leu Asn Asn Asp Ile Met Leu Ile Lys
1               5                   10

<210> SEQ ID NO 359
<211> LENGTH: 11
<212> TYPE: PRT
<213> ORGANISM: Homo Sapiens
<220> FEATURE:
<221> NAME/KEY: PEPTIDE
<222> LOCATION: (1)...(10)
<223> OTHER INFORMATION: protease, serine, 1 preproprotein

<400> SEQUENCE: 359

Lys Thr Leu Asn Asn Asp Ile Met Leu Ile Lys
1               5                   10

<210> SEQ ID NO 360
<211> LENGTH: 16
<212> TYPE: PRT
<213> ORGANISM: Homo Sapiens
<220> FEATURE:
<221> NAME/KEY: PEPTIDE
<222> LOCATION: (1)...(15)
<223> OTHER INFORMATION: protease, serine, 1 preproprotein

<400> SEQUENCE: 360

Val Ser Thr Ile Ser Leu Pro Thr Ala Pro Pro Ala Thr Gly Thr Lys
1               5                   10                  15

<210> SEQ ID NO 361
<211> LENGTH: 17
<212> TYPE: PRT
<213> ORGANISM: Homo Sapiens
<220> FEATURE:
<221> NAME/KEY: PEPTIDE
<222> LOCATION: (1)...(15)
<223> OTHER INFORMATION: protease, serine, 1 preproprotein

<400> SEQUENCE: 361

Asn Gly Gln Leu Gln Gly Val Val Ser Trp Gly Asp Gly Cys Ala Gln
```

```
                1               5                  10                  15
Lys

<210> SEQ ID NO 362
<211> LENGTH: 11
<212> TYPE: PRT
<213> ORGANISM: Homo Sapiens
<220> FEATURE:
<221> NAME/KEY: PEPTIDE
<222> LOCATION: (1)...(10)
<223> OTHER INFORMATION: deleted in malignant brain tumors 1 isoform c
      precursor

<400> SEQUENCE: 362

Thr Ala Gly Pro Glu Ser Ser Leu Ala Leu Arg
1               5                  10

<210> SEQ ID NO 363
<211> LENGTH: 11
<212> TYPE: PRT
<213> ORGANISM: Homo Sapiens
<220> FEATURE:
<221> NAME/KEY: PEPTIDE
<222> LOCATION: (1)...(10)
<223> OTHER INFORMATION: deleted in malignant brain tumors 1 isoform c
      precursor

<400> SEQUENCE: 363

Gly Ser Gly Pro Ile Val Leu Asp Asp Val Arg
1               5                  10

<210> SEQ ID NO 364
<211> LENGTH: 12
<212> TYPE: PRT
<213> ORGANISM: Homo Sapiens
<220> FEATURE:
<221> NAME/KEY: PEPTIDE
<222> LOCATION: (1)...(10)
<223> OTHER INFORMATION: deleted in malignant brain tumors 1 isoform c
      precursor

<400> SEQUENCE: 364

Ser Thr Ala Gly Pro Glu Ser Ser Leu Ala Leu Arg
1               5                  10

<210> SEQ ID NO 365
<211> LENGTH: 12
<212> TYPE: PRT
<213> ORGANISM: Homo Sapiens
<220> FEATURE:
<221> NAME/KEY: PEPTIDE
<222> LOCATION: (1)...(10)
<223> OTHER INFORMATION: deleted in malignant brain tumors 1 isoform c
      precursor

<400> SEQUENCE: 365

Ser Thr Val Gly Ser Glu Ser Ser Leu Ala Leu Arg
1               5                  10

<210> SEQ ID NO 366
<211> LENGTH: 12
<212> TYPE: PRT
<213> ORGANISM: Homo Sapiens
<220> FEATURE:
<221> NAME/KEY: PEPTIDE
<222> LOCATION: (1)...(10)
<223> OTHER INFORMATION: deleted in malignant brain tumors 1 isoform c
      precursor
```

```
<400> SEQUENCE: 366

Gln Gly Ser Gly Pro Ile Val Leu Asp Asp Val Arg
1               5                   10

<210> SEQ ID NO 367
<211> LENGTH: 13
<212> TYPE: PRT
<213> ORGANISM: Homo Sapiens
<220> FEATURE:
<221> NAME/KEY: PEPTIDE
<222> LOCATION: (1)...(10)
<223> OTHER INFORMATION: deleted in malignant brain tumors 1 isoform c
      precursor

<400> SEQUENCE: 367

Ala Ser Thr Ala Gly Pro Glu Ser Ser Leu Ala Leu Arg
1               5                   10

<210> SEQ ID NO 368
<211> LENGTH: 13
<212> TYPE: PRT
<213> ORGANISM: Homo Sapiens
<220> FEATURE:
<221> NAME/KEY: PEPTIDE
<222> LOCATION: (1)...(10)
<223> OTHER INFORMATION: deleted in malignant brain tumors 1 isoform c
      precursor

<400> SEQUENCE: 368

Gly Gln Gly Ser Gly Pro Ile Val Leu Asp Asp Val Arg
1               5                   10

<210> SEQ ID NO 369
<211> LENGTH: 13
<212> TYPE: PRT
<213> ORGANISM: Homo Sapiens
<220> FEATURE:
<221> NAME/KEY: PEPTIDE
<222> LOCATION: (1)...(10)
<223> OTHER INFORMATION: deleted in malignant brain tumors 1 isoform c
      precursor

<400> SEQUENCE: 369

Gly Ser Phe Thr Ser Ser Ser Asn Phe Met Ser Ile Arg
1               5                   10

<210> SEQ ID NO 370
<211> LENGTH: 13
<212> TYPE: PRT
<213> ORGANISM: Homo Sapiens
<220> FEATURE:
<221> NAME/KEY: PEPTIDE
<222> LOCATION: (1)...(10)
<223> OTHER INFORMATION: deleted in malignant brain tumors 1 isoform c
      precursor

<400> SEQUENCE: 370

Asp Asp Thr Tyr Gly Pro Tyr Ser Ser Pro Ser Leu Arg
1               5                   10

<210> SEQ ID NO 371
<211> LENGTH: 14
<212> TYPE: PRT
<213> ORGANISM: Homo Sapiens
<220> FEATURE:
<221> NAME/KEY: PEPTIDE
<222> LOCATION: (1)...(10)
<223> OTHER INFORMATION: deleted in malignant brain tumors 1 isoform c
      precursor
```

```
<400> SEQUENCE: 371

Phe Gly Gln Gly Ser Gly Pro Ile Val Leu Asp Asp Val Arg
 1               5                  10

<210> SEQ ID NO 372
<211> LENGTH: 15
<212> TYPE: PRT
<213> ORGANISM: Homo Sapiens
<220> FEATURE:
<221> NAME/KEY: PEPTIDE
<222> LOCATION: (1)...(15)
<223> OTHER INFORMATION: deleted in malignant brain tumors 1 isoform c
      precursor

<400> SEQUENCE: 372

Gln Leu Gly Cys Gly Trp Ala Thr Ser Ala Pro Gly Asn Ala Arg
 1               5                  10                  15

<210> SEQ ID NO 373
<211> LENGTH: 15
<212> TYPE: PRT
<213> ORGANISM: Homo Sapiens
<220> FEATURE:
<221> NAME/KEY: PEPTIDE
<222> LOCATION: (1)...(15)
<223> OTHER INFORMATION: deleted in malignant brain tumors 1 isoform c
      precursor

<400> SEQUENCE: 373

Gln Leu Gly Cys Gly Trp Ala Met Ser Ala Pro Gly Asn Ala Arg
 1               5                  10                  15

<210> SEQ ID NO 374
<211> LENGTH: 15
<212> TYPE: PRT
<213> ORGANISM: Homo Sapiens
<220> FEATURE:
<221> NAME/KEY: PEPTIDE
<222> LOCATION: (1)...(15)
<223> OTHER INFORMATION: deleted in malignant brain tumors 1 isoform c
      precursor

<400> SEQUENCE: 374

Gln Leu Gly Cys Gly Trp Ala Met Leu Ala Pro Gly Asn Ala Arg
 1               5                  10                  15

<210> SEQ ID NO 375
<211> LENGTH: 15
<212> TYPE: PRT
<213> ORGANISM: Homo Sapiens
<220> FEATURE:
<221> NAME/KEY: PEPTIDE
<222> LOCATION: (1)...(15)
<223> OTHER INFORMATION: deleted in malignant brain tumors 1 isoform c
      precursor

<400> SEQUENCE: 375

Gln Phe Gly Gln Gly Ser Gly Pro Ile Val Leu Asp Asp Val Arg
 1               5                  10                  15

<210> SEQ ID NO 376
<211> LENGTH: 16
<212> TYPE: PRT
<213> ORGANISM: Homo Sapiens
<220> FEATURE:
<221> NAME/KEY: PEPTIDE
<222> LOCATION: (1)...(15)
<223> OTHER INFORMATION: deleted in malignant brain tumors 1 isoform c
``` precursor

<400> SEQUENCE: 376

Ala Gln Phe Gly Gln Gly Ser Gly Pro Ile Val Leu Asp Asp Val Arg
1               5                   10                  15

<210> SEQ ID NO 377
<211> LENGTH: 21
<212> TYPE: PRT
<213> ORGANISM: Homo Sapiens
<220> FEATURE:
<221> NAME/KEY: PEPTIDE
<222> LOCATION: (1)...(20)
<223> OTHER INFORMATION: deleted in malignant brain tumors 1 isoform c
      precursor

<400> SEQUENCE: 377

Ser Ala Pro Gly Asn Ala Gln Phe Gly Gln Gly Ser Gly Pro Ile Val
1               5                   10                  15

Leu Asp Asp Val Arg
            20

<210> SEQ ID NO 378
<211> LENGTH: 21
<212> TYPE: PRT
<213> ORGANISM: Homo Sapiens
<220> FEATURE:
<221> NAME/KEY: PEPTIDE
<222> LOCATION: (1)...(20)
<223> OTHER INFORMATION: deleted in malignant brain tumors 1 isoform c
      precursor

<400> SEQUENCE: 378

Ser Ala Pro Gly Asn Ala Trp Phe Gly Gln Gly Ser Gly Pro Ile Ala
1               5                   10                  15

Leu Asp Asp Val Arg
            20

<210> SEQ ID NO 379
<211> LENGTH: 21
<212> TYPE: PRT
<213> ORGANISM: Homo Sapiens
<220> FEATURE:
<221> NAME/KEY: PEPTIDE
<222> LOCATION: (1)...(20)
<223> OTHER INFORMATION: deleted in malignant brain tumors 1 isoform c
      precursor

<400> SEQUENCE: 379

Gly Ser Trp Gly Thr Val Cys Asp Asp Ser Trp Asp Thr Ser Asp Ala
1               5                   10                  15

Asn Val Val Cys Arg
            20

<210> SEQ ID NO 380
<211> LENGTH: 23
<212> TYPE: PRT
<213> ORGANISM: Homo Sapiens
<220> FEATURE:
<221> NAME/KEY: PEPTIDE
<222> LOCATION: (1)...(20)
<223> OTHER INFORMATION: deleted in malignant brain tumors 1 isoform c
      precursor

<400> SEQUENCE: 380

Ala Met Ser Ala Pro Gly Asn Ala Gln Phe Gly Gln Gly Ser Gly Pro
1               5                   10                  15

```
Ile Val Leu Asp Asp Val Arg
            20

<210> SEQ ID NO 381
<211> LENGTH: 21
<212> TYPE: PRT
<213> ORGANISM: Homo Sapiens
<220> FEATURE:
<221> NAME/KEY: PEPTIDE
<222> LOCATION: (1)...(20)
<223> OTHER INFORMATION: deleted in malignant brain tumors 1 isoform c
      precursor

<400> SEQUENCE: 381

Gly Ser Trp Gly Thr Val Cys Asp Asp Ser Trp Asp Thr Asn Asp Ala
1               5                   10                  15

Asn Val Val Cys Arg
            20

<210> SEQ ID NO 382
<211> LENGTH: 23
<212> TYPE: PRT
<213> ORGANISM: Homo Sapiens
<220> FEATURE:
<221> NAME/KEY: PEPTIDE
<222> LOCATION: (1)...(20)
<223> OTHER INFORMATION: deleted in malignant brain tumors 1 isoform c
      precursor

<400> SEQUENCE: 382

Ala Met Ser Ala Pro Gly Asn Ala Trp Phe Gly Gln Gly Ser Gly Pro
1               5                   10                  15

Ile Ala Leu Asp Asp Val Arg
            20

<210> SEQ ID NO 383
<211> LENGTH: 21
<212> TYPE: PRT
<213> ORGANISM: Homo Sapiens
<220> FEATURE:
<221> NAME/KEY: PEPTIDE
<222> LOCATION: (1)...(20)
<223> OTHER INFORMATION: deleted in malignant brain tumors 1 isoform c
      precursor

<400> SEQUENCE: 383

Gly Ser Trp Gly Thr Val Cys Asp Asp Tyr Trp Asp Thr Asn Asp Ala
1               5                   10                  15

Asn Val Val Cys Arg
            20

<210> SEQ ID NO 384
<211> LENGTH: 25
<212> TYPE: PRT
<213> ORGANISM: Homo Sapiens
<220> FEATURE:
<221> NAME/KEY: PEPTIDE
<222> LOCATION: (1)...(25)
<223> OTHER INFORMATION: deleted in malignant brain tumors 1 isoform c
      precursor

<400> SEQUENCE: 384

Gly Trp Ala Met Ser Ala Pro Gly Asn Ala Gln Phe Gly Gln Gly Ser
1               5                   10                  15

Gly Pro Ile Val Leu Asp Asp Val Arg
            20                  25
```

```
<210> SEQ ID NO 385
<211> LENGTH: 29
<212> TYPE: PRT
<213> ORGANISM: Homo Sapiens
<220> FEATURE:
<221> NAME/KEY: PEPTIDE
<222> LOCATION: (1)...(25)
<223> OTHER INFORMATION: deleted in malignant brain tumors 1 isoform c
      precursor

<400> SEQUENCE: 385

Gln Leu Gly Cys Gly Trp Ala Met Ser Ala Pro Gly Asn Ala Gln Phe
1               5                   10                  15

Gly Gln Gly Ser Gly Pro Ile Val Leu Asp Asp Val Arg
            20                  25

<210> SEQ ID NO 386
<211> LENGTH: 10
<212> TYPE: PRT
<213> ORGANISM: Homo Sapiens
<220> FEATURE:
<221> NAME/KEY: PEPTIDE
<222> LOCATION: (1)...(10)
<223> OTHER INFORMATION: RecName: Full=Ig alpha-1 chain C region

<400> SEQUENCE: 386

Trp Leu Gln Gly Ser Gln Glu Leu Pro Arg
1               5                   10

<210> SEQ ID NO 387
<211> LENGTH: 11
<212> TYPE: PRT
<213> ORGANISM: Homo Sapiens
<220> FEATURE:
<221> NAME/KEY: PEPTIDE
<222> LOCATION: (1)...(10)
<223> OTHER INFORMATION: RecName: Full=Ig alpha-1 chain C region

<400> SEQUENCE: 387

Asn Glu Leu Val Thr Leu Thr Cys Leu Ala Arg
1               5                   10

<210> SEQ ID NO 388
<211> LENGTH: 11
<212> TYPE: PRT
<213> ORGANISM: Homo Sapiens
<220> FEATURE:
<221> NAME/KEY: PEPTIDE
<222> LOCATION: (1)...(10)
<223> OTHER INFORMATION: RecName: Full=Ig alpha-1 chain C region

<400> SEQUENCE: 388

Leu Ser Leu His Arg Pro Ala Leu Glu Asp Leu
1               5                   10

<210> SEQ ID NO 389
<211> LENGTH: 12
<212> TYPE: PRT
<213> ORGANISM: Homo Sapiens
<220> FEATURE:
<221> NAME/KEY: PEPTIDE
<222> LOCATION: (1)...(10)
<223> OTHER INFORMATION: RecName: Full=Ig alpha-1 chain C region

<400> SEQUENCE: 389

Thr Phe Thr Cys Thr Ala Ala Tyr Pro Glu Ser Lys
1               5                   10
```

<210> SEQ ID NO 390
<211> LENGTH: 12
<212> TYPE: PRT
<213> ORGANISM: Homo Sapiens
<220> FEATURE:
<221> NAME/KEY: PEPTIDE
<222> LOCATION: (1)...(10)
<223> OTHER INFORMATION: RecName: Full=Ig alpha-1 chain C region

<400> SEQUENCE: 390

Leu Asn Glu Leu Val Thr Leu Thr Cys Leu Ala Arg
1               5                   10

<210> SEQ ID NO 391
<211> LENGTH: 13
<212> TYPE: PRT
<213> ORGANISM: Homo Sapiens
<220> FEATURE:
<221> NAME/KEY: PEPTIDE
<222> LOCATION: (1)...(10)
<223> OTHER INFORMATION: RecName: Full=Ig alpha-1 chain C region

<400> SEQUENCE: 391

Asn Phe Pro Pro Ser Gln Asp Ala Ser Gly Asp Leu Tyr
1               5                   10

<210> SEQ ID NO 392
<211> LENGTH: 13
<212> TYPE: PRT
<213> ORGANISM: Homo Sapiens
<220> FEATURE:
<221> NAME/KEY: PEPTIDE
<222> LOCATION: (1)...(10)
<223> OTHER INFORMATION: RecName: Full=Ig alpha-1 chain C region

<400> SEQUENCE: 392

Ala Leu Asn Glu Leu Val Thr Leu Thr Cys Leu Ala Arg
1               5                   10

<210> SEQ ID NO 393
<211> LENGTH: 14
<212> TYPE: PRT
<213> ORGANISM: Homo Sapiens
<220> FEATURE:
<221> NAME/KEY: PEPTIDE
<222> LOCATION: (1)...(10)
<223> OTHER INFORMATION: RecName: Full=Ig alpha-1 chain C region

<400> SEQUENCE: 393

Ser Val Thr Trp Ser Glu Ser Gly Gln Gly Val Thr Ala Arg
1               5                   10

<210> SEQ ID NO 394
<211> LENGTH: 15
<212> TYPE: PRT
<213> ORGANISM: Homo Sapiens
<220> FEATURE:
<221> NAME/KEY: PEPTIDE
<222> LOCATION: (1)...(15)
<223> OTHER INFORMATION: RecName: Full=Ig alpha-1 chain C region

<400> SEQUENCE: 394

Asp Ala Ser Gly Val Thr Phe Thr Trp Thr Pro Ser Ser Gly Lys
1               5                   10                  15

<210> SEQ ID NO 395
<211> LENGTH: 17

```
<212> TYPE: PRT
<213> ORGANISM: Homo Sapiens
<220> FEATURE:
<221> NAME/KEY: PEPTIDE
<222> LOCATION: (1)...(15)
<223> OTHER INFORMATION: RecName: Full=Ig alpha-1 chain C region

<400> SEQUENCE: 395

Thr Thr Ser Ser Gln Leu Thr Leu Pro Ala Thr Gln Cys Leu Ala Gly
1               5                   10                  15
Lys

<210> SEQ ID NO 396
<211> LENGTH: 17
<212> TYPE: PRT
<213> ORGANISM: Homo Sapiens
<220> FEATURE:
<221> NAME/KEY: PEPTIDE
<222> LOCATION: (1)...(15)
<223> OTHER INFORMATION: RecName: Full=Ig alpha-1 chain C region

<400> SEQUENCE: 396

Ser Val Ser Ser Val Leu Pro Gly Cys Ala Glu Pro Trp Asn His Gly
1               5                   10                  15
Lys

<210> SEQ ID NO 397
<211> LENGTH: 17
<212> TYPE: PRT
<213> ORGANISM: Homo Sapiens
<220> FEATURE:
<221> NAME/KEY: PEPTIDE
<222> LOCATION: (1)...(15)
<223> OTHER INFORMATION: RecName: Full=Ig alpha-1 chain C region

<400> SEQUENCE: 397

Gln Glu Pro Ser Gln Gly Thr Thr Thr Phe Ala Val Thr Ser Ile Leu
1               5                   10                  15
Arg

<210> SEQ ID NO 398
<211> LENGTH: 17
<212> TYPE: PRT
<213> ORGANISM: Homo Sapiens
<220> FEATURE:
<221> NAME/KEY: PEPTIDE
<222> LOCATION: (1)...(15)
<223> OTHER INFORMATION: RecName: Full=Ig alpha-1 chain C region

<400> SEQUENCE: 398

His Tyr Thr Asn Pro Ser Gln Asp Val Thr Val Pro Cys Pro Val Pro
1               5                   10                  15
Ser

<210> SEQ ID NO 399
<211> LENGTH: 19
<212> TYPE: PRT
<213> ORGANISM: Homo Sapiens
<220> FEATURE:
<221> NAME/KEY: PEPTIDE
<222> LOCATION: (1)...(15)
<223> OTHER INFORMATION: RecName: Full=Ig alpha-1 chain C region

<400> SEQUENCE: 399

Ser Arg Gln Glu Pro Ser Gln Gly Thr Thr Thr Phe Ala Val Thr Ser
1               5                   10                  15
```

Ile Leu Arg

<210> SEQ ID NO 400
<211> LENGTH: 19
<212> TYPE: PRT
<213> ORGANISM: Homo Sapiens
<220> FEATURE:
<221> NAME/KEY: PEPTIDE
<222> LOCATION: (1)...(15)
<223> OTHER INFORMATION: RecName: Full=Ig alpha-1 chain C region

<400> SEQUENCE: 400

Ser Gly Asn Thr Phe Arg Pro Glu Val His Leu Leu Pro Pro Pro Ser
1               5                   10                  15

Glu Glu Leu

<210> SEQ ID NO 401
<211> LENGTH: 21
<212> TYPE: PRT
<213> ORGANISM: Homo Sapiens
<220> FEATURE:
<221> NAME/KEY: PEPTIDE
<222> LOCATION: (1)...(20)
<223> OTHER INFORMATION: RecName: Full=Ig alpha-1 chain C region

<400> SEQUENCE: 401

Lys Gly Asp Thr Phe Ser Cys Met Val Gly His Glu Ala Leu Pro Leu
1               5                   10                  15

Ala Phe Thr Gln Lys
            20

<210> SEQ ID NO 402
<211> LENGTH: 21
<212> TYPE: PRT
<213> ORGANISM: Homo Sapiens
<220> FEATURE:
<221> NAME/KEY: PEPTIDE
<222> LOCATION: (1)...(20)
<223> OTHER INFORMATION: RecName: Full=Ig alpha-1 chain C region

<400> SEQUENCE: 402

Ser Gly Asn Thr Phe Arg Pro Glu Val His Leu Leu Pro Pro Pro Ser
1               5                   10                  15

Glu Glu Leu Ala Leu
            20

<210> SEQ ID NO 403
<211> LENGTH: 27
<212> TYPE: PRT
<213> ORGANISM: Homo Sapiens
<220> FEATURE:
<221> NAME/KEY: PEPTIDE
<222> LOCATION: (1)...(25)
<223> OTHER INFORMATION: RecName: Full=Ig alpha-1 chain C region

<400> SEQUENCE: 403

Ser Gly Asn Thr Phe Arg Pro Glu Val His Leu Leu Pro Pro Pro Ser
1               5                   10                  15

Glu Glu Leu Ala Leu Asn Glu Leu Val Thr Leu
            20                  25

<210> SEQ ID NO 404
<211> LENGTH: 28
<212> TYPE: PRT
<213> ORGANISM: Homo Sapiens

```
<220> FEATURE:
<221> NAME/KEY: PEPTIDE
<222> LOCATION: (1)...(25)
<223> OTHER INFORMATION: RecName: Full=Ig alpha-1 chain C region

<400> SEQUENCE: 404

Ser Gly Asn Thr Phe Arg Pro Glu Val His Leu Leu Pro Pro Ser
 1               5                  10                  15

Glu Glu Leu Ala Leu Asn Glu Leu Val Thr Leu Thr
            20                  25

<210> SEQ ID NO 405
<211> LENGTH: 30
<212> TYPE: PRT
<213> ORGANISM: Homo Sapiens
<220> FEATURE:
<221> NAME/KEY: PEPTIDE
<222> LOCATION: (1)...(30)
<223> OTHER INFORMATION: RecName: Full=Ig alpha-1 chain C region

<400> SEQUENCE: 405

Asn Phe Pro Pro Ser Gln Asp Ala Ser Gly Asp Leu Tyr Thr Thr Ser
 1               5                  10                  15

Ser Gln Leu Thr Leu Pro Ala Thr Gln Cys Leu Ala Gly Lys
            20                  25                  30

<210> SEQ ID NO 406
<211> LENGTH: 8
<212> TYPE: PRT
<213> ORGANISM: Homo Sapiens
<220> FEATURE:
<221> NAME/KEY: PEPTIDE
<222> LOCATION: (1)...(5)
<223> OTHER INFORMATION: carboxypeptidase A1 precursor

<400> SEQUENCE: 406

Phe Asn Tyr Gly Ser Ile Ile Lys
 1               5

<210> SEQ ID NO 407
<211> LENGTH: 9
<212> TYPE: PRT
<213> ORGANISM: Homo Sapiens
<220> FEATURE:
<221> NAME/KEY: PEPTIDE
<222> LOCATION: (1)...(5)
<223> OTHER INFORMATION: carboxypeptidase A1 precursor

<400> SEQUENCE: 407

Phe Ala Asn Ser Glu Val Glu Val Lys
 1               5

<210> SEQ ID NO 408
<211> LENGTH: 12
<212> TYPE: PRT
<213> ORGANISM: Homo Sapiens
<220> FEATURE:
<221> NAME/KEY: PEPTIDE
<222> LOCATION: (1)...(10)
<223> OTHER INFORMATION: carboxypeptidase A1 precursor

<400> SEQUENCE: 408

Ile Gln Ile Gly Asn Thr Tyr Glu Gly Arg Pro Ile
 1               5                  10

<210> SEQ ID NO 409
<211> LENGTH: 13
```

```
<212> TYPE: PRT
<213> ORGANISM: Homo Sapiens
<220> FEATURE:
<221> NAME/KEY: PEPTIDE
<222> LOCATION: (1)...(10)
<223> OTHER INFORMATION: carboxypeptidase A1 precursor

<400> SEQUENCE: 409

Lys Ile Thr Gln Asp Tyr Gly Gln Asp Ala Ala Phe Thr
1               5                   10

<210> SEQ ID NO 410
<211> LENGTH: 13
<212> TYPE: PRT
<213> ORGANISM: Homo Sapiens
<220> FEATURE:
<221> NAME/KEY: PEPTIDE
<222> LOCATION: (1)...(10)
<223> OTHER INFORMATION: carboxypeptidase A1 precursor

<400> SEQUENCE: 410

Ser Ile Val Asp Phe Val Lys Asp His Gly Asn Ile Lys
1               5                   10

<210> SEQ ID NO 411
<211> LENGTH: 13
<212> TYPE: PRT
<213> ORGANISM: Homo Sapiens
<220> FEATURE:
<221> NAME/KEY: PEPTIDE
<222> LOCATION: (1)...(10)
<223> OTHER INFORMATION: carboxypeptidase A1 precursor

<400> SEQUENCE: 411

Glu Trp Val Thr Gln Ala Ser Gly Val Trp Phe Ala Lys
1               5                   10

<210> SEQ ID NO 412
<211> LENGTH: 13
<212> TYPE: PRT
<213> ORGANISM: Homo Sapiens
<220> FEATURE:
<221> NAME/KEY: PEPTIDE
<222> LOCATION: (1)...(10)
<223> OTHER INFORMATION: carboxypeptidase A1 precursor

<400> SEQUENCE: 412

Arg Pro Ala Ile Trp Ile Asp Thr Gly Ile His Ser Arg
1               5                   10

<210> SEQ ID NO 413
<211> LENGTH: 15
<212> TYPE: PRT
<213> ORGANISM: Homo Sapiens
<220> FEATURE:
<221> NAME/KEY: PEPTIDE
<222> LOCATION: (1)...(15)
<223> OTHER INFORMATION: carboxypeptidase A1 precursor

<400> SEQUENCE: 413

Ser His Thr Ala Gly Ser Leu Cys Ile Gly Val Asp Pro Asn Arg
1               5                   10                  15

<210> SEQ ID NO 414
<211> LENGTH: 15
<212> TYPE: PRT
<213> ORGANISM: Homo Sapiens
<220> FEATURE:
<221> NAME/KEY: PEPTIDE
```

<222> LOCATION: (1)...(15)
<223> OTHER INFORMATION: carboxypeptidase A1 precursor

<400> SEQUENCE: 414

Tyr Gly Phe Leu Leu Pro Ala Ser Gln Ile Ile Pro Thr Ala Lys
 1               5                  10                  15

<210> SEQ ID NO 415
<211> LENGTH: 13
<212> TYPE: PRT
<213> ORGANISM: Homo Sapiens
<220> FEATURE:
<221> NAME/KEY: PEPTIDE
<222> LOCATION: (1)...(10)
<223> OTHER INFORMATION: carboxypeptidase A1 precursor

<400> SEQUENCE: 415

His Thr Leu Glu Glu Ile Tyr Asp Phe Leu Asp Leu Leu
 1               5                  10

<210> SEQ ID NO 416
<211> LENGTH: 14
<212> TYPE: PRT
<213> ORGANISM: Homo Sapiens
<220> FEATURE:
<221> NAME/KEY: PEPTIDE
<222> LOCATION: (1)...(10)
<223> OTHER INFORMATION: carboxypeptidase A1 precursor

<400> SEQUENCE: 416

Ile Gln Ile Gly Asn Thr Tyr Glu Gly Arg Pro Ile Tyr Val
 1               5                  10

<210> SEQ ID NO 417
<211> LENGTH: 15
<212> TYPE: PRT
<213> ORGANISM: Homo Sapiens
<220> FEATURE:
<221> NAME/KEY: PEPTIDE
<222> LOCATION: (1)...(15)
<223> OTHER INFORMATION: carboxypeptidase A1 precursor

<400> SEQUENCE: 417

Thr Glu Pro Val Pro Asp Gln Asp Glu Leu Asp Gln Leu Ser Lys
 1               5                  10                  15

<210> SEQ ID NO 418
<211> LENGTH: 16
<212> TYPE: PRT
<213> ORGANISM: Homo Sapiens
<220> FEATURE:
<221> NAME/KEY: PEPTIDE
<222> LOCATION: (1)...(15)
<223> OTHER INFORMATION: carboxypeptidase A1 precursor

<400> SEQUENCE: 418

Gln Ala Ser Gly Ser Thr Ile Asp Trp Thr Tyr Ser Gln Gly Ile Lys
 1               5                  10                  15

<210> SEQ ID NO 419
<211> LENGTH: 16
<212> TYPE: PRT
<213> ORGANISM: Homo Sapiens
<220> FEATURE:
<221> NAME/KEY: PEPTIDE
<222> LOCATION: (1)...(15)
<223> OTHER INFORMATION: carboxypeptidase A1 precursor

<400> SEQUENCE: 419

Asp Phe Leu Asp Leu Leu Val Ala Glu Asn Pro His Leu Val Ser Lys
1               5                   10                  15

<210> SEQ ID NO 420
<211> LENGTH: 16
<212> TYPE: PRT
<213> ORGANISM: Homo Sapiens
<220> FEATURE:
<221> NAME/KEY: PEPTIDE
<222> LOCATION: (1)...(15)
<223> OTHER INFORMATION: carboxypeptidase A1 precursor

<400> SEQUENCE: 420

Lys Thr Glu Pro Val Pro Asp Gln Asp Glu Leu Asp Gln Leu Ser Lys
1               5                   10                  15

<210> SEQ ID NO 421
<211> LENGTH: 16
<212> TYPE: PRT
<213> ORGANISM: Homo Sapiens
<220> FEATURE:
<221> NAME/KEY: PEPTIDE
<222> LOCATION: (1)...(15)
<223> OTHER INFORMATION: carboxypeptidase A1 precursor

<400> SEQUENCE: 421

Ile Gln Ile Gly Asn Thr Tyr Glu Gly Arg Pro Ile Tyr Val Leu Lys
1               5                   10                  15

<210> SEQ ID NO 422
<211> LENGTH: 18
<212> TYPE: PRT
<213> ORGANISM: Homo Sapiens
<220> FEATURE:
<221> NAME/KEY: PEPTIDE
<222> LOCATION: (1)...(15)
<223> OTHER INFORMATION: carboxypeptidase A1 precursor

<400> SEQUENCE: 422

Gly Tyr Lys Thr Glu Pro Val Pro Asp Gln Asp Glu Leu Asp Gln Leu
1               5                   10                  15

Ser Lys

<210> SEQ ID NO 423
<211> LENGTH: 19
<212> TYPE: PRT
<213> ORGANISM: Homo Sapiens
<220> FEATURE:
<221> NAME/KEY: PEPTIDE
<222> LOCATION: (1)...(15)
<223> OTHER INFORMATION: carboxypeptidase A1 precursor

<400> SEQUENCE: 423

Ala Ile Tyr Gln Ala Ser Gly Ser Thr Ile Asp Trp Thr Tyr Ser Gln
1               5                   10                  15

Gly Ile Lys

<210> SEQ ID NO 424
<211> LENGTH: 20
<212> TYPE: PRT
<213> ORGANISM: Homo Sapiens
<220> FEATURE:
<221> NAME/KEY: PEPTIDE
<222> LOCATION: (1)...(20)
<223> OTHER INFORMATION: carboxypeptidase A1 precursor

<400> SEQUENCE: 424

```
Glu Glu Ile Tyr Asp Phe Leu Asp Leu Leu Val Ala Glu Asn Pro His
  1               5                  10                  15

Leu Val Ser Lys
         20
```

<210> SEQ ID NO 425
<211> LENGTH: 22
<212> TYPE: PRT
<213> ORGANISM: Homo Sapiens
<220> FEATURE:
<221> NAME/KEY: PEPTIDE
<222> LOCATION: (1)...(20)
<223> OTHER INFORMATION: carboxypeptidase A1 precursor

<400> SEQUENCE: 425

```
Thr Leu Glu Glu Ile Tyr Asp Phe Leu Asp Leu Leu Val Ala Glu Asn
  1               5                  10                  15

Pro His Leu Val Ser Lys
             20
```

<210> SEQ ID NO 426
<211> LENGTH: 23
<212> TYPE: PRT
<213> ORGANISM: Homo Sapiens
<220> FEATURE:
<221> NAME/KEY: PEPTIDE
<222> LOCATION: (1)...(20)
<223> OTHER INFORMATION: carboxypeptidase A1 precursor

<400> SEQUENCE: 426

```
Ala Ile Leu Asp Thr Leu Asp Ile Phe Leu Glu Ile Val Thr Asn Pro
  1               5                  10                  15

Asp Gly Phe Ala Phe Thr His
             20
```

<210> SEQ ID NO 427
<211> LENGTH: 23
<212> TYPE: PRT
<213> ORGANISM: Homo Sapiens
<220> FEATURE:
<221> NAME/KEY: PEPTIDE
<222> LOCATION: (1)...(20)
<223> OTHER INFORMATION: carboxypeptidase A1 precursor

<400> SEQUENCE: 427

```
His Thr Leu Glu Glu Ile Tyr Asp Phe Leu Asp Leu Leu Val Ala Glu
  1               5                  10                  15

Asn Pro His Leu Val Ser Lys
             20
```

<210> SEQ ID NO 428
<211> LENGTH: 24
<212> TYPE: PRT
<213> ORGANISM: Homo Sapiens
<220> FEATURE:
<221> NAME/KEY: PEPTIDE
<222> LOCATION: (1)...(20)
<223> OTHER INFORMATION: carboxypeptidase A1 precursor

<400> SEQUENCE: 428

```
Tyr His Thr Leu Glu Glu Ile Tyr Asp Phe Leu Asp Leu Leu Val Ala
  1               5                  10                  15

Glu Asn Pro His Leu Val Ser Lys
             20
```

```
<210> SEQ ID NO 429
<211> LENGTH: 33
<212> TYPE: PRT
<213> ORGANISM: Homo Sapiens
<220> FEATURE:
<221> NAME/KEY: PEPTIDE
<222> LOCATION: (1)...(30)
<223> OTHER INFORMATION: carboxypeptidase A1 precursor

<400> SEQUENCE: 429

Ser Thr Asp Thr Phe Asn Tyr Ala Thr Tyr His Thr Leu Glu Glu Ile
 1               5                  10                  15

Tyr Asp Phe Leu Asp Leu Leu Val Ala Glu Asn Pro His Leu Val Ser
            20                  25                  30

Lys

<210> SEQ ID NO 430
<211> LENGTH: 9
<212> TYPE: PRT
<213> ORGANISM: Homo Sapiens
<220> FEATURE:
<221> NAME/KEY: PEPTIDE
<222> LOCATION: (1)...(5)
<223> OTHER INFORMATION: regenerating islet-derived 1 alpha precursor

<400> SEQUENCE: 430

Ser Val Leu Thr Gln Ala Glu Gly Ala
 1               5

<210> SEQ ID NO 431
<211> LENGTH: 9
<212> TYPE: PRT
<213> ORGANISM: Homo Sapiens
<220> FEATURE:
<221> NAME/KEY: PEPTIDE
<222> LOCATION: (1)...(5)
<223> OTHER INFORMATION: regenerating islet-derived 1 alpha precursor

<400> SEQUENCE: 431

Trp His Trp Ser Ser Gly Ser Leu Val
 1               5

<210> SEQ ID NO 432
<211> LENGTH: 11
<212> TYPE: PRT
<213> ORGANISM: Homo Sapiens
<220> FEATURE:
<221> NAME/KEY: PEPTIDE
<222> LOCATION: (1)...(10)
<223> OTHER INFORMATION: regenerating islet-derived 1 alpha precursor

<400> SEQUENCE: 432

Val Ser Leu Thr Ser Ser Thr Gly Phe Gln Lys
 1               5                  10

<210> SEQ ID NO 433
<211> LENGTH: 11
<212> TYPE: PRT
<213> ORGANISM: Homo Sapiens
<220> FEATURE:
<221> NAME/KEY: PEPTIDE
<222> LOCATION: (1)...(10)
<223> OTHER INFORMATION: regenerating islet-derived 1 alpha precursor

<400> SEQUENCE: 433

Ile Ser Cys Pro Glu Gly Thr Asn Ala Tyr Arg
 1               5                  10
```

<210> SEQ ID NO 434
<211> LENGTH: 12
<212> TYPE: PRT
<213> ORGANISM: Homo Sapiens
<220> FEATURE:
<221> NAME/KEY: PEPTIDE
<222> LOCATION: (1)...(10)
<223> OTHER INFORMATION: regenerating islet-derived 1 alpha precursor

<400> SEQUENCE: 434

Gln Ala Glu Gly Ala Phe Val Ala Ser Leu Ile Lys
1               5                   10

<210> SEQ ID NO 435
<211> LENGTH: 13
<212> TYPE: PRT
<213> ORGANISM: Homo Sapiens
<220> FEATURE:
<221> NAME/KEY: PEPTIDE
<222> LOCATION: (1)...(10)
<223> OTHER INFORMATION: regenerating islet-derived 1 alpha precursor

<400> SEQUENCE: 435

Thr Gln Ala Glu Gly Ala Phe Val Ala Ser Leu Ile Lys
1               5                   10

<210> SEQ ID NO 436
<211> LENGTH: 12
<212> TYPE: PRT
<213> ORGANISM: Homo Sapiens
<220> FEATURE:
<221> NAME/KEY: PEPTIDE
<222> LOCATION: (1)...(10)
<223> OTHER INFORMATION: regenerating islet-derived 1 alpha precursor

<400> SEQUENCE: 436

Trp His Trp Ser Ser Gly Ser Leu Val Ser Tyr Lys
1               5                   10

<210> SEQ ID NO 437
<211> LENGTH: 14
<212> TYPE: PRT
<213> ORGANISM: Homo Sapiens
<220> FEATURE:
<221> NAME/KEY: PEPTIDE
<222> LOCATION: (1)...(10)
<223> OTHER INFORMATION: regenerating islet-derived 1 alpha precursor

<400> SEQUENCE: 437

Leu Thr Gln Ala Glu Gly Ala Phe Val Ala Ser Leu Ile Lys
1               5                   10

<210> SEQ ID NO 438
<211> LENGTH: 12
<212> TYPE: PRT
<213> ORGANISM: Homo Sapiens
<220> FEATURE:
<221> NAME/KEY: PEPTIDE
<222> LOCATION: (1)...(10)
<223> OTHER INFORMATION: regenerating islet-derived 1 alpha precursor

<400> SEQUENCE: 438

Trp Lys Asp Val Pro Cys Glu Asp Lys Phe Ser Phe
1               5                   10

<210> SEQ ID NO 439
<211> LENGTH: 13

<212> TYPE: PRT
<213> ORGANISM: Homo Sapiens
<220> FEATURE:
<221> NAME/KEY: PEPTIDE
<222> LOCATION: (1)...(10)
<223> OTHER INFORMATION: regenerating islet-derived 1 alpha precursor

<400> SEQUENCE: 439

Asp Val Pro Cys Glu Asp Lys Phe Ser Phe Val Cys Lys
1               5                   10

<210> SEQ ID NO 440
<211> LENGTH: 13
<212> TYPE: PRT
<213> ORGANISM: Homo Sapiens
<220> FEATURE:
<221> NAME/KEY: PEPTIDE
<222> LOCATION: (1)...(10)
<223> OTHER INFORMATION: regenerating islet-derived 1 alpha precursor

<400> SEQUENCE: 440

Trp Lys Asp Val Pro Cys Glu Asp Lys Phe Ser Phe Val
1               5                   10

<210> SEQ ID NO 441
<211> LENGTH: 16
<212> TYPE: PRT
<213> ORGANISM: Homo Sapiens
<220> FEATURE:
<221> NAME/KEY: PEPTIDE
<222> LOCATION: (1)...(15)
<223> OTHER INFORMATION: regenerating islet-derived 1 alpha precursor

<400> SEQUENCE: 441

Ser Val Leu Thr Gln Ala Glu Gly Ala Phe Val Ala Ser Leu Ile Lys
1               5                   10                  15

<210> SEQ ID NO 442
<211> LENGTH: 14
<212> TYPE: PRT
<213> ORGANISM: Homo Sapiens
<220> FEATURE:
<221> NAME/KEY: PEPTIDE
<222> LOCATION: (1)...(10)
<223> OTHER INFORMATION: regenerating islet-derived 1 alpha precursor

<400> SEQUENCE: 442

Phe Asn Glu Asp Arg Glu Thr Trp Val Asp Ala Asp Leu Tyr
1               5                   10

<210> SEQ ID NO 443
<211> LENGTH: 17
<212> TYPE: PRT
<213> ORGANISM: Homo Sapiens
<220> FEATURE:
<221> NAME/KEY: PEPTIDE
<222> LOCATION: (1)...(15)
<223> OTHER INFORMATION: regenerating islet-derived 1 alpha precursor

<400> SEQUENCE: 443

Glu Ser Gly Thr Asp Asp Phe Asn Val Trp Ile Gly Leu His Asp Pro
1               5                   10                  15

Lys

<210> SEQ ID NO 444
<211> LENGTH: 18
<212> TYPE: PRT
<213> ORGANISM: Homo Sapiens

```
<220> FEATURE:
<221> NAME/KEY: PEPTIDE
<222> LOCATION: (1)...(15)
<223> OTHER INFORMATION: regenerating islet-derived 1 alpha precursor

<400> SEQUENCE: 444

Glu Ser Gly Thr Asp Asp Phe Asn Val Trp Ile Gly Leu His Asp Pro
1               5                   10                  15
Lys Lys

<210> SEQ ID NO 445
<211> LENGTH: 9
<212> TYPE: PRT
<213> ORGANISM: Homo Sapiens
<220> FEATURE:
<221> NAME/KEY: PEPTIDE
<222> LOCATION: (1)...(5)
<223> OTHER INFORMATION: polymeric immunoglobulin receptor precursor

<400> SEQUENCE: 445

Phe Ser Val Val Ile Asn Gln Leu Arg
1               5

<210> SEQ ID NO 446
<211> LENGTH: 10
<212> TYPE: PRT
<213> ORGANISM: Homo Sapiens
<220> FEATURE:
<221> NAME/KEY: PEPTIDE
<222> LOCATION: (1)...(10)
<223> OTHER INFORMATION: polymeric immunoglobulin receptor precursor

<400> SEQUENCE: 446

Lys Ser Pro Ile Phe Gly Pro Glu Glu Val
1               5                   10

<210> SEQ ID NO 447
<211> LENGTH: 11
<212> TYPE: PRT
<213> ORGANISM: Homo Sapiens
<220> FEATURE:
<221> NAME/KEY: PEPTIDE
<222> LOCATION: (1)...(10)
<223> OTHER INFORMATION: polymeric immunoglobulin receptor precursor

<400> SEQUENCE: 447

Leu Val Ser Leu Thr Leu Asn Leu Val Thr Arg
1               5                   10

<210> SEQ ID NO 448
<211> LENGTH: 11
<212> TYPE: PRT
<213> ORGANISM: Homo Sapiens
<220> FEATURE:
<221> NAME/KEY: PEPTIDE
<222> LOCATION: (1)...(10)
<223> OTHER INFORMATION: polymeric immunoglobulin receptor precursor

<400> SEQUENCE: 448

Ala Asp Glu Gly Trp Tyr Trp Cys Gly Val Lys
1               5                   10

<210> SEQ ID NO 449
<211> LENGTH: 12
<212> TYPE: PRT
<213> ORGANISM: Homo Sapiens
<220> FEATURE:
<221> NAME/KEY: PEPTIDE
```

-continued

```
<222> LOCATION: (1)...(10)
<223> OTHER INFORMATION: polymeric immunoglobulin receptor precursor

<400> SEQUENCE: 449

Asn Ala Asp Leu Gln Val Leu Lys Pro Glu Pro Glu
1               5                  10

<210> SEQ ID NO 450
<211> LENGTH: 13
<212> TYPE: PRT
<213> ORGANISM: Homo Sapiens
<220> FEATURE:
<221> NAME/KEY: PEPTIDE
<222> LOCATION: (1)...(10)
<223> OTHER INFORMATION: polymeric immunoglobulin receptor precursor

<400> SEQUENCE: 450

Ile Thr Leu Ile Ser Ser Glu Gly Tyr Val Ser Ser Lys
1               5                  10

<210> SEQ ID NO 451
<211> LENGTH: 13
<212> TYPE: PRT
<213> ORGANISM: Homo Sapiens
<220> FEATURE:
<221> NAME/KEY: PEPTIDE
<222> LOCATION: (1)...(10)
<223> OTHER INFORMATION: polymeric immunoglobulin receptor precursor

<400> SEQUENCE: 451

Lys Ser Pro Ile Phe Gly Pro Glu Glu Val Asn Ser Val
1               5                  10

<210> SEQ ID NO 452
<211> LENGTH: 15
<212> TYPE: PRT
<213> ORGANISM: Homo Sapiens
<220> FEATURE:
<221> NAME/KEY: PEPTIDE
<222> LOCATION: (1)...(15)
<223> OTHER INFORMATION: polymeric immunoglobulin receptor precursor

<400> SEQUENCE: 452

Gly Val Ala Gly Gly Ser Val Ala Val Leu Cys Pro Tyr Asn Arg
1               5                  10                  15

<210> SEQ ID NO 453
<211> LENGTH: 14
<212> TYPE: PRT
<213> ORGANISM: Homo Sapiens
<220> FEATURE:
<221> NAME/KEY: PEPTIDE
<222> LOCATION: (1)...(10)
<223> OTHER INFORMATION: polymeric immunoglobulin receptor precursor

<400> SEQUENCE: 453

Asn Ala Asp Leu Gln Val Leu Lys Pro Glu Pro Glu Leu Val
1               5                  10

<210> SEQ ID NO 454
<211> LENGTH: 16
<212> TYPE: PRT
<213> ORGANISM: Homo Sapiens
<220> FEATURE:
<221> NAME/KEY: PEPTIDE
<222> LOCATION: (1)...(15)
<223> OTHER INFORMATION: polymeric immunoglobulin receptor precursor

<400> SEQUENCE: 454
```

```
Gly Gly Cys Ile Thr Leu Ile Ser Ser Glu Gly Tyr Val Ser Ser Lys
1               5                   10                  15
```

<210> SEQ ID NO 455
<211> LENGTH: 16
<212> TYPE: PRT
<213> ORGANISM: Homo Sapiens
<220> FEATURE:
<221> NAME/KEY: PEPTIDE
<222> LOCATION: (1)...(15)
<223> OTHER INFORMATION: polymeric immunoglobulin receptor precursor

<400> SEQUENCE: 455

```
Gln Ser Ser Gly Glu Asn Cys Asp Val Val Asn Thr Leu Gly Lys
1               5                   10                  15
```

<210> SEQ ID NO 456
<211> LENGTH: 14
<212> TYPE: PRT
<213> ORGANISM: Homo Sapiens
<220> FEATURE:
<221> NAME/KEY: PEPTIDE
<222> LOCATION: (1)...(10)
<223> OTHER INFORMATION: polymeric immunoglobulin receptor precursor

<400> SEQUENCE: 456

```
Val Leu Lys Pro Glu Pro Glu Leu Val Tyr Glu Asp Leu Arg
1               5                   10
```

<210> SEQ ID NO 457
<211> LENGTH: 16
<212> TYPE: PRT
<213> ORGANISM: Homo Sapiens
<220> FEATURE:
<221> NAME/KEY: PEPTIDE
<222> LOCATION: (1)...(15)
<223> OTHER INFORMATION: polymeric immunoglobulin receptor precursor

<400> SEQUENCE: 457

```
Lys Ser Pro Ile Phe Gly Pro Glu Glu Val Asn Ser Val Glu Gly Asn
1               5                   10                  15
```

<210> SEQ ID NO 458
<211> LENGTH: 17
<212> TYPE: PRT
<213> ORGANISM: Homo Sapiens
<220> FEATURE:
<221> NAME/KEY: PEPTIDE
<222> LOCATION: (1)...(15)
<223> OTHER INFORMATION: polymeric immunoglobulin receptor precursor

<400> SEQUENCE: 458

```
Ser Pro Ile Phe Gly Pro Glu Glu Val Asn Ser Val Glu Gly Asn Ser
1               5                   10                  15

Val
```

<210> SEQ ID NO 459
<211> LENGTH: 17
<212> TYPE: PRT
<213> ORGANISM: Homo Sapiens
<220> FEATURE:
<221> NAME/KEY: PEPTIDE
<222> LOCATION: (1)...(15)
<223> OTHER INFORMATION: polymeric immunoglobulin receptor precursor

<400> SEQUENCE: 459

```
Tyr Leu Cys Gly Ala His Ser Asp Gly Gln Leu Gln Glu Gly Ser Pro
1               5                   10                  15
```

```
                1               5                  10                  15

Ile

<210> SEQ ID NO 460
<211> LENGTH: 18
<212> TYPE: PRT
<213> ORGANISM: Homo Sapiens
<220> FEATURE:
<221> NAME/KEY: PEPTIDE
<222> LOCATION: (1)...(15)
<223> OTHER INFORMATION: polymeric immunoglobulin receptor precursor

<400> SEQUENCE: 460

Lys Ser Pro Ile Phe Gly Pro Glu Glu Val Asn Ser Val Glu Gly Asn
 1               5                  10                  15

Ser Val

<210> SEQ ID NO 461
<211> LENGTH: 20
<212> TYPE: PRT
<213> ORGANISM: Homo Sapiens
<220> FEATURE:
<221> NAME/KEY: PEPTIDE
<222> LOCATION: (1)...(20)
<223> OTHER INFORMATION: polymeric immunoglobulin receptor precursor

<400> SEQUENCE: 461

Leu Ser Asp Ala Gly Gln Tyr Leu Cys Gln Ala Gly Asp Asp Ser Asn
 1               5                  10                  15

Ser Asn Lys Lys
            20

<210> SEQ ID NO 462
<211> LENGTH: 20
<212> TYPE: PRT
<213> ORGANISM: Homo Sapiens
<220> FEATURE:
<221> NAME/KEY: PEPTIDE
<222> LOCATION: (1)...(20)
<223> OTHER INFORMATION: polymeric immunoglobulin receptor precursor

<400> SEQUENCE: 462

Ile Leu Leu Asn Pro Gln Asp Lys Asp Gly Ser Phe Ser Val Val Ile
 1               5                  10                  15

Thr Gly Leu Arg
            20

<210> SEQ ID NO 463
<211> LENGTH: 21
<212> TYPE: PRT
<213> ORGANISM: Homo Sapiens
<220> FEATURE:
<221> NAME/KEY: PEPTIDE
<222> LOCATION: (1)...(20)
<223> OTHER INFORMATION: polymeric immunoglobulin receptor precursor

<400> SEQUENCE: 463

Lys Ser Pro Ile Phe Gly Pro Glu Glu Val Asn Ser Val Glu Gly Asn
 1               5                  10                  15

Ser Val Ser Ile Thr
            20

<210> SEQ ID NO 464
<211> LENGTH: 19
<212> TYPE: PRT
```

```
<213> ORGANISM: Homo Sapiens
<220> FEATURE:
<221> NAME/KEY: PEPTIDE
<222> LOCATION: (1)...(15)
<223> OTHER INFORMATION: polymeric immunoglobulin receptor precursor

<400> SEQUENCE: 464

Asn Ala Asp Leu Gln Val Leu Lys Pro Glu Pro Glu Leu Val Tyr Glu
 1               5                  10                  15

Asp Leu Arg

<210> SEQ ID NO 465
<211> LENGTH: 31
<212> TYPE: PRT
<213> ORGANISM: Homo Sapiens
<220> FEATURE:
<221> NAME/KEY: PEPTIDE
<222> LOCATION: (1)...(30)
<223> OTHER INFORMATION: polymeric immunoglobulin receptor precursor

<400> SEQUENCE: 465

Lys Ser Pro Ile Phe Gly Pro Glu Glu Val Asn Ser Val Glu Gly Asn
 1               5                  10                  15

Ser Val Ser Ile Thr Cys Tyr Tyr Pro Pro Thr Ser Val Asn Arg
            20                  25                  30

<210> SEQ ID NO 466
<211> LENGTH: 15
<212> TYPE: PRT
<213> ORGANISM: Homo Sapiens
<220> FEATURE:
<221> NAME/KEY: PEPTIDE
<222> LOCATION: (1)...(15)
<223> OTHER INFORMATION: RecName: Full=Ig alpha-2 chain C region

<400> SEQUENCE: 466

Asp Ala Ser Gly Ala Thr Phe Thr Trp Thr Pro Ser Ser Gly Lys
 1               5                  10                  15

<210> SEQ ID NO 467
<211> LENGTH: 17
<212> TYPE: PRT
<213> ORGANISM: Homo Sapiens
<220> FEATURE:
<221> NAME/KEY: PEPTIDE
<222> LOCATION: (1)...(15)
<223> OTHER INFORMATION: RecName: Full=Ig alpha-2 chain C region

<400> SEQUENCE: 467

Thr Thr Ser Ser Gln Leu Thr Leu Pro Ala Thr Gln Cys Pro Asp Gly
 1               5                  10                  15

Lys

<210> SEQ ID NO 468
<211> LENGTH: 25
<212> TYPE: PRT
<213> ORGANISM: Homo Sapiens
<220> FEATURE:
<221> NAME/KEY: PEPTIDE
<222> LOCATION: (1)...(25)
<223> OTHER INFORMATION: RecName: Full=Ig alpha-2 chain C region

<400> SEQUENCE: 468

His Tyr Thr Asn Pro Ser Gln Asp Val Thr Val Pro Cys Pro Val Pro
 1               5                  10                  15

Pro Pro Pro Pro Cys Cys His Pro Arg
```

<210> SEQ ID NO 469
<211> LENGTH: 30
<212> TYPE: PRT
<213> ORGANISM: Homo Sapiens
<220> FEATURE:
<221> NAME/KEY: PEPTIDE
<222> LOCATION: (1)...(30)
<223> OTHER INFORMATION: RecName: Full=Ig alpha-2 chain C region

<400> SEQUENCE: 469

Asn Phe Pro Pro Ser Gln Asp Ala Ser Gly Asp Leu Tyr Thr Thr Ser
1               5                   10                  15

Ser Gln Leu Thr Leu Pro Ala Thr Gln Cys Pro Asp Gly Lys
            20                  25                  30

<210> SEQ ID NO 470
<211> LENGTH: 11
<212> TYPE: PRT
<213> ORGANISM: Homo Sapiens
<220> FEATURE:
<221> NAME/KEY: PEPTIDE
<222> LOCATION: (1)...(10)
<223> OTHER INFORMATION: membrane alanine aminopeptidase precursor

<400> SEQUENCE: 470

Ser Glu Leu Phe Asp Ala Ile Ser Tyr Ser Lys
1               5                   10

<210> SEQ ID NO 471
<211> LENGTH: 11
<212> TYPE: PRT
<213> ORGANISM: Homo Sapiens
<220> FEATURE:
<221> NAME/KEY: PEPTIDE
<222> LOCATION: (1)...(10)
<223> OTHER INFORMATION: membrane alanine aminopeptidase precursor

<400> SEQUENCE: 471

Phe Ile Val Ser Glu Phe Asp Tyr Val Glu Lys
1               5                   10

<210> SEQ ID NO 472
<211> LENGTH: 12
<212> TYPE: PRT
<213> ORGANISM: Homo Sapiens
<220> FEATURE:
<221> NAME/KEY: PEPTIDE
<222> LOCATION: (1)...(10)
<223> OTHER INFORMATION: membrane alanine aminopeptidase precursor

<400> SEQUENCE: 472

Met Leu Ser Ser Phe Leu Ser Glu Asp Val Phe Lys
1               5                   10

<210> SEQ ID NO 473
<211> LENGTH: 11
<212> TYPE: PRT
<213> ORGANISM: Homo Sapiens
<220> FEATURE:
<221> NAME/KEY: PEPTIDE
<222> LOCATION: (1)...(10)
<223> OTHER INFORMATION: membrane alanine aminopeptidase precursor

<400> SEQUENCE: 473

Gln Gln Gln Asp Tyr Trp Leu Ile Asp Val Arg
1               5                   10

```
<210> SEQ ID NO 474
<211> LENGTH: 12
<212> TYPE: PRT
<213> ORGANISM: Homo Sapiens
<220> FEATURE:
<221> NAME/KEY: PEPTIDE
<222> LOCATION: (1)...(10)
<223> OTHER INFORMATION: membrane alanine aminopeptidase precursor

<400> SEQUENCE: 474

Tyr Leu Ser Tyr Thr Leu Asn Pro Asp Leu Ile Arg
 1               5                  10

<210> SEQ ID NO 475
<211> LENGTH: 12
<212> TYPE: PRT
<213> ORGANISM: Homo Sapiens
<220> FEATURE:
<221> NAME/KEY: PEPTIDE
<222> LOCATION: (1)...(10)
<223> OTHER INFORMATION: membrane alanine aminopeptidase precursor

<400> SEQUENCE: 475

Glu Val Val Leu Gln Trp Phe Thr Glu Asn Ser Lys
 1               5                  10

<210> SEQ ID NO 476
<211> LENGTH: 16
<212> TYPE: PRT
<213> ORGANISM: Homo Sapiens
<220> FEATURE:
<221> NAME/KEY: PEPTIDE
<222> LOCATION: (1)...(15)
<223> OTHER INFORMATION: membrane alanine aminopeptidase precursor

<400> SEQUENCE: 476

Glu Asn Ser Leu Leu Phe Asp Pro Leu Ser Ser Ser Ser Ser Asn Lys
 1               5                  10                  15

<210> SEQ ID NO 477
<211> LENGTH: 15
<212> TYPE: PRT
<213> ORGANISM: Homo Sapiens
<220> FEATURE:
<221> NAME/KEY: PEPTIDE
<222> LOCATION: (1)...(15)
<223> OTHER INFORMATION: membrane alanine aminopeptidase precursor

<400> SEQUENCE: 477

Phe Ser Thr Glu Tyr Glu Leu Gln Gln Leu Glu Gln Phe Lys Lys
 1               5                  10                  15

<210> SEQ ID NO 478
<211> LENGTH: 16
<212> TYPE: PRT
<213> ORGANISM: Homo Sapiens
<220> FEATURE:
<221> NAME/KEY: PEPTIDE
<222> LOCATION: (1)...(15)
<223> OTHER INFORMATION: membrane alanine aminopeptidase precursor

<400> SEQUENCE: 478

Gln Tyr Met Pro Trp Glu Ala Ala Leu Ser Ser Leu Ser Tyr Phe Lys
 1               5                  10                  15

<210> SEQ ID NO 479
<211> LENGTH: 16
```

```
<212> TYPE: PRT
<213> ORGANISM: Homo Sapiens
<220> FEATURE:
<221> NAME/KEY: PEPTIDE
<222> LOCATION: (1)...(15)
<223> OTHER INFORMATION: membrane alanine aminopeptidase precursor

<400> SEQUENCE: 479

Gln Trp Met Glu Asn Pro Asn Asn Pro Ile His Pro Asn Leu Arg
 1               5                  10                  15

<210> SEQ ID NO 480
<211> LENGTH: 16
<212> TYPE: PRT
<213> ORGANISM: Homo Sapiens
<220> FEATURE:
<221> NAME/KEY: PEPTIDE
<222> LOCATION: (1)...(15)
<223> OTHER INFORMATION: membrane alanine aminopeptidase precursor

<400> SEQUENCE: 480

Arg Phe Ser Thr Glu Tyr Glu Leu Gln Gln Leu Glu Gln Phe Lys Lys
 1               5                  10                  15

<210> SEQ ID NO 481
<211> LENGTH: 21
<212> TYPE: PRT
<213> ORGANISM: Homo Sapiens
<220> FEATURE:
<221> NAME/KEY: PEPTIDE
<222> LOCATION: (1)...(20)
<223> OTHER INFORMATION: membrane alanine aminopeptidase precursor

<400> SEQUENCE: 481

Gly Val Gly Gly Ser Gln Pro Pro Asp Ile Asp Lys Thr Glu Leu Val
 1               5                  10                  15

Glu Pro Thr Glu Tyr
            20

<210> SEQ ID NO 482
<211> LENGTH: 28
<212> TYPE: PRT
<213> ORGANISM: Homo Sapiens
<220> FEATURE:
<221> NAME/KEY: PEPTIDE
<222> LOCATION: (1)...(25)
<223> OTHER INFORMATION: membrane alanine aminopeptidase precursor

<400> SEQUENCE: 482

Ser Leu Gly Ile Leu Gly Ile Leu Leu Gly Val Ala Ala Val Cys Thr
 1               5                  10                  15

Ile Ile Ala Leu Ser Val Val Tyr Ser Gln Glu Lys
            20                  25

<210> SEQ ID NO 483
<211> LENGTH: 30
<212> TYPE: PRT
<213> ORGANISM: Homo Sapiens
<220> FEATURE:
<221> NAME/KEY: PEPTIDE
<222> LOCATION: (1)...(30)
<223> OTHER INFORMATION: membrane alanine aminopeptidase precursor

<400> SEQUENCE: 483

Ser Leu Gly Ile Leu Gly Ile Leu Leu Gly Val Ala Ala Val Cys Thr
 1               5                  10                  15

Ile Ile Ala Leu Ser Val Val Tyr Ser Gln Glu Lys Asn Lys
```

```
                    20                  25                  30

<210> SEQ ID NO 484
<211> LENGTH: 36
<212> TYPE: PRT
<213> ORGANISM: Homo Sapiens
<220> FEATURE:
<221> NAME/KEY: PEPTIDE
<222> LOCATION: (1)...(35)
<223> OTHER INFORMATION: membrane alanine aminopeptidase precursor

<400> SEQUENCE: 484

Ala Lys Gly Phe Tyr Ile Ser Lys Ser Leu Gly Ile Leu Gly Ile Leu
 1               5                  10                  15

Leu Gly Val Ala Ala Val Cys Thr Ile Ile Ala Leu Ser Val Val Tyr
                20                  25                  30

Ser Gln Glu Lys
        35

<210> SEQ ID NO 485
<211> LENGTH: 36
<212> TYPE: PRT
<213> ORGANISM: Homo Sapiens
<220> FEATURE:
<221> NAME/KEY: PEPTIDE
<222> LOCATION: (1)...(35)
<223> OTHER INFORMATION: membrane alanine aminopeptidase precursor

<400> SEQUENCE: 485

Gly Phe Tyr Ile Ser Lys Ser Leu Gly Ile Leu Gly Ile Leu Leu Gly
 1               5                  10                  15

Val Ala Ala Val Cys Thr Ile Ile Ala Leu Ser Val Val Tyr Ser Gln
                20                  25                  30

Glu Lys Asn Lys
        35

<210> SEQ ID NO 486
<211> LENGTH: 38
<212> TYPE: PRT
<213> ORGANISM: Homo Sapiens
<220> FEATURE:
<221> NAME/KEY: PEPTIDE
<222> LOCATION: (1)...(35)
<223> OTHER INFORMATION: membrane alanine aminopeptidase precursor

<400> SEQUENCE: 486

Ala Lys Gly Phe Tyr Ile Ser Lys Ser Leu Gly Ile Leu Gly Ile Leu
 1               5                  10                  15

Leu Gly Val Ala Ala Val Cys Thr Ile Ile Ala Leu Ser Val Val Tyr
                20                  25                  30

Ser Gln Glu Lys Asn Lys
        35

<210> SEQ ID NO 487
<211> LENGTH: 8
<212> TYPE: PRT
<213> ORGANISM: Homo Sapiens
<220> FEATURE:
<221> NAME/KEY: PEPTIDE
<222> LOCATION: (1)...(5)
<223> OTHER INFORMATION: keratin 1

<400> SEQUENCE: 487

Ile Glu Ile Ser Glu Leu Asn Arg
 1               5
```

<210> SEQ ID NO 488
<211> LENGTH: 10
<212> TYPE: PRT
<213> ORGANISM: Homo Sapiens
<220> FEATURE:
<221> NAME/KEY: PEPTIDE
<222> LOCATION: (1)...(10)
<223> OTHER INFORMATION: keratin 1

<400> SEQUENCE: 488

Tyr Glu Glu Leu Gln Ile Thr Ala Gly Arg
1               5                   10

<210> SEQ ID NO 489
<211> LENGTH: 11
<212> TYPE: PRT
<213> ORGANISM: Homo Sapiens
<220> FEATURE:
<221> NAME/KEY: PEPTIDE
<222> LOCATION: (1)...(10)
<223> OTHER INFORMATION: keratin 1

<400> SEQUENCE: 489

Leu Ala Leu Asp Leu Glu Ile Ala Thr Tyr Arg
1               5                   10

<210> SEQ ID NO 490
<211> LENGTH: 10
<212> TYPE: PRT
<213> ORGANISM: Homo Sapiens
<220> FEATURE:
<221> NAME/KEY: PEPTIDE
<222> LOCATION: (1)...(10)
<223> OTHER INFORMATION: keratin 1

<400> SEQUENCE: 490

Asn Met Gln Asp Met Val Glu Asp Tyr Arg
1               5                   10

<210> SEQ ID NO 491
<211> LENGTH: 12
<212> TYPE: PRT
<213> ORGANISM: Homo Sapiens
<220> FEATURE:
<221> NAME/KEY: PEPTIDE
<222> LOCATION: (1)...(10)
<223> OTHER INFORMATION: keratin 1

<400> SEQUENCE: 491

Ser Leu Asp Leu Asp Ser Ile Ile Ala Glu Val Lys
1               5                   10

<210> SEQ ID NO 492
<211> LENGTH: 12
<212> TYPE: PRT
<213> ORGANISM: Homo Sapiens
<220> FEATURE:
<221> NAME/KEY: PEPTIDE
<222> LOCATION: (1)...(10)
<223> OTHER INFORMATION: keratin 1

<400> SEQUENCE: 492

Leu Asn Asp Leu Glu Asp Ala Leu Gln Gln Ala Lys
1               5                   10

<210> SEQ ID NO 493
<211> LENGTH: 12

```
<212> TYPE: PRT
<213> ORGANISM: Homo Sapiens
<220> FEATURE:
<221> NAME/KEY: PEPTIDE
<222> LOCATION: (1)...(10)
<223> OTHER INFORMATION: keratin 1

<400> SEQUENCE: 493

Ser Leu Asn Asn Gln Phe Ala Ser Phe Ile Asp Lys
1               5                   10

<210> SEQ ID NO 494
<211> LENGTH: 12
<212> TYPE: PRT
<213> ORGANISM: Homo Sapiens
<220> FEATURE:
<221> NAME/KEY: PEPTIDE
<222> LOCATION: (1)...(10)
<223> OTHER INFORMATION: keratin 1

<400> SEQUENCE: 494

Trp Glu Leu Leu Gln Gln Val Asp Thr Ser Thr Arg
1               5                   10

<210> SEQ ID NO 495
<211> LENGTH: 12
<212> TYPE: PRT
<213> ORGANISM: Homo Sapiens
<220> FEATURE:
<221> NAME/KEY: PEPTIDE
<222> LOCATION: (1)...(10)
<223> OTHER INFORMATION: keratin 1

<400> SEQUENCE: 495

Phe Leu Glu Gln Gln Asn Gln Val Leu Gln Thr Lys
1               5                   10

<210> SEQ ID NO 496
<211> LENGTH: 14
<212> TYPE: PRT
<213> ORGANISM: Homo Sapiens
<220> FEATURE:
<221> NAME/KEY: PEPTIDE
<222> LOCATION: (1)...(10)
<223> OTHER INFORMATION: keratin 1

<400> SEQUENCE: 496

Asn Lys Leu Asn Asp Leu Glu Asp Ala Leu Gln Gln Ala Lys
1               5                   10

<210> SEQ ID NO 497
<211> LENGTH: 15
<212> TYPE: PRT
<213> ORGANISM: Homo Sapiens
<220> FEATURE:
<221> NAME/KEY: PEPTIDE
<222> LOCATION: (1)...(15)
<223> OTHER INFORMATION: keratin 1

<400> SEQUENCE: 497

Gln Ile Ser Asn Leu Gln Gln Ser Ile Ser Asp Ala Glu Gln Arg
1               5                   10                  15

<210> SEQ ID NO 498
<211> LENGTH: 16
<212> TYPE: PRT
<213> ORGANISM: Homo Sapiens
<220> FEATURE:
<221> NAME/KEY: PEPTIDE
```

```
<222> LOCATION: (1)...(15)
<223> OTHER INFORMATION: keratin 1

<400> SEQUENCE: 498

Thr His Asn Leu Glu Pro Tyr Phe Glu Ser Phe Ile Asn Asn Leu Arg
 1               5                  10                  15

<210> SEQ ID NO 499
<211> LENGTH: 19
<212> TYPE: PRT
<213> ORGANISM: Homo Sapiens
<220> FEATURE:
<221> NAME/KEY: PEPTIDE
<222> LOCATION: (1)...(15)
<223> OTHER INFORMATION: keratin 1

<400> SEQUENCE: 499

Asn Lys Leu Asn Asp Leu Glu Asp Ala Leu Gln Gln Ala Lys Glu Asp
 1               5                  10                  15

Leu Ala Arg

<210> SEQ ID NO 500
<211> LENGTH: 21
<212> TYPE: PRT
<213> ORGANISM: Homo Sapiens
<220> FEATURE:
<221> NAME/KEY: PEPTIDE
<222> LOCATION: (1)...(20)
<223> OTHER INFORMATION: keratin 1

<400> SEQUENCE: 500

Ser Leu Asp Leu Asp Ser Ile Ile Ala Glu Val Lys Ala Gln Tyr Glu
 1               5                  10                  15

Asp Ile Ala Gln Lys
            20

<210> SEQ ID NO 501
<211> LENGTH: 26
<212> TYPE: PRT
<213> ORGANISM: Homo Sapiens
<220> FEATURE:
<221> NAME/KEY: PEPTIDE
<222> LOCATION: (1)...(25)
<223> OTHER INFORMATION: keratin 1

<400> SEQUENCE: 501

Met Ser Gly Glu Cys Ala Pro Asn Val Ser Val Ser Val Ser Thr Ser
 1               5                  10                  15

His Thr Thr Ile Ser Gly Gly Gly Ser Arg
            20                  25

<210> SEQ ID NO 502
<211> LENGTH: 7
<212> TYPE: PRT
<213> ORGANISM: Homo Sapiens
<220> FEATURE:
<221> NAME/KEY: PEPTIDE
<222> LOCATION: (1)...(5)
<223> OTHER INFORMATION: chymotrypsin C preproprotein

<400> SEQUENCE: 502

Ile Asp Trp Trp Gly Phe Arg
 1               5

<210> SEQ ID NO 503
<211> LENGTH: 11
```

```
<212> TYPE: PRT
<213> ORGANISM: Homo Sapiens
<220> FEATURE:
<221> NAME/KEY: PEPTIDE
<222> LOCATION: (1)...(10)
<223> OTHER INFORMATION: chymotrypsin C preproprotein

<400> SEQUENCE: 503

Thr Met Val Cys Ala Gly Gly Asp Gly Val Ile
1               5                   10

<210> SEQ ID NO 504
<211> LENGTH: 8
<212> TYPE: PRT
<213> ORGANISM: Homo Sapiens
<220> FEATURE:
<221> NAME/KEY: PEPTIDE
<222> LOCATION: (1)...(5)
<223> OTHER INFORMATION: chymotrypsin C preproprotein

<400> SEQUENCE: 504

Pro His Ser Trp Pro Trp Gln Ile
1               5

<210> SEQ ID NO 505
<211> LENGTH: 11
<212> TYPE: PRT
<213> ORGANISM: Homo Sapiens
<220> FEATURE:
<221> NAME/KEY: PEPTIDE
<222> LOCATION: (1)...(10)
<223> OTHER INFORMATION: chymotrypsin C preproprotein

<400> SEQUENCE: 505

Asp Tyr Pro Cys Tyr Val Thr Gly Trp Gly Arg
1               5                   10

<210> SEQ ID NO 506
<211> LENGTH: 11
<212> TYPE: PRT
<213> ORGANISM: Homo Sapiens
<220> FEATURE:
<221> NAME/KEY: PEPTIDE
<222> LOCATION: (1)...(10)
<223> OTHER INFORMATION: chymotrypsin C preproprotein

<400> SEQUENCE: 506

Val Ser Ala Tyr Ile Asp Trp Ile Asn Glu Lys
1               5                   10

<210> SEQ ID NO 507
<211> LENGTH: 14
<212> TYPE: PRT
<213> ORGANISM: Homo Sapiens
<220> FEATURE:
<221> NAME/KEY: PEPTIDE
<222> LOCATION: (1)...(10)
<223> OTHER INFORMATION: chymotrypsin C preproprotein

<400> SEQUENCE: 507

Leu Gln Gln Gly Leu Gln Pro Val Val Asp His Ala Thr Cys
1               5                   10

<210> SEQ ID NO 508
<211> LENGTH: 16
<212> TYPE: PRT
<213> ORGANISM: Homo Sapiens
<220> FEATURE:
<221> NAME/KEY: PEPTIDE
```

<222> LOCATION: (1)..(15)
<223> OTHER INFORMATION: chymotrypsin C preproprotein

<400> SEQUENCE: 508

Thr Asn Gly Pro Ile Ala Asp Lys Leu Gln Gln Gly Leu Gln Pro Val
1               5                   10                  15

<210> SEQ ID NO 509
<211> LENGTH: 16
<212> TYPE: PRT
<213> ORGANISM: Homo Sapiens
<220> FEATURE:
<221> NAME/KEY: PEPTIDE
<222> LOCATION: (1)..(15)
<223> OTHER INFORMATION: chymotrypsin C preproprotein

<400> SEQUENCE: 509

Leu Gln Gln Gly Leu Gln Pro Val Val Asp His Ala Thr Cys Ser Arg
1               5                   10                  15

<210> SEQ ID NO 510
<211> LENGTH: 16
<212> TYPE: PRT
<213> ORGANISM: Homo Sapiens
<220> FEATURE:
<221> NAME/KEY: PEPTIDE
<222> LOCATION: (1)..(15)
<223> OTHER INFORMATION: chymotrypsin C preproprotein

<400> SEQUENCE: 510

Val Val Gly Gly Glu Asp Ala Arg Pro His Ser Trp Pro Trp Gln Ile
1               5                   10                  15

<210> SEQ ID NO 511
<211> LENGTH: 18
<212> TYPE: PRT
<213> ORGANISM: Homo Sapiens
<220> FEATURE:
<221> NAME/KEY: PEPTIDE
<222> LOCATION: (1)..(15)
<223> OTHER INFORMATION: chymotrypsin C preproprotein

<400> SEQUENCE: 511

Ser Asp Thr Ile Gln Val Ala Cys Leu Pro Glu Lys Asp Ser Leu Leu
1               5                   10                  15

Pro Lys

<210> SEQ ID NO 512
<211> LENGTH: 18
<212> TYPE: PRT
<213> ORGANISM: Homo Sapiens
<220> FEATURE:
<221> NAME/KEY: PEPTIDE
<222> LOCATION: (1)..(15)
<223> OTHER INFORMATION: chymotrypsin C preproprotein

<400> SEQUENCE: 512

Leu Trp Thr Asn Gly Pro Ile Ala Asp Lys Leu Gln Gln Gly Leu Gln
1               5                   10                  15

Pro Val

<210> SEQ ID NO 513
<211> LENGTH: 24
<212> TYPE: PRT
<213> ORGANISM: Homo Sapiens
<220> FEATURE:
<221> NAME/KEY: PEPTIDE

```
<222> LOCATION: (1)...(20)
<223> OTHER INFORMATION: chymotrypsin C preproprotein

<400> SEQUENCE: 513

His Thr Cys Gly Gly Thr Leu Ile Ala Ser Asn Phe Val Leu Thr Ala
1               5                   10                  15

Ala His Cys Ile Ser Asn Thr Arg
            20

<210> SEQ ID NO 514
<211> LENGTH: 23
<212> TYPE: PRT
<213> ORGANISM: Homo Sapiens
<220> FEATURE:
<221> NAME/KEY: PEPTIDE
<222> LOCATION: (1)...(20)
<223> OTHER INFORMATION: chymotrypsin C preproprotein

<400> SEQUENCE: 514

Asn Asn Leu Glu Val Glu Asp Glu Glu Gly Ser Leu Phe Val Gly Val
1               5                   10                  15

Asp Thr Ile His Val His Lys
            20

<210> SEQ ID NO 515
<211> LENGTH: 24
<212> TYPE: PRT
<213> ORGANISM: Homo Sapiens
<220> FEATURE:
<221> NAME/KEY: PEPTIDE
<222> LOCATION: (1)...(20)
<223> OTHER INFORMATION: chymotrypsin C preproprotein

<400> SEQUENCE: 515

Asn Asn Leu Glu Val Glu Asp Glu Glu Gly Ser Leu Phe Val Gly Val
1               5                   10                  15

Asp Thr Ile His Val His Lys Arg
            20

<210> SEQ ID NO 516
<211> LENGTH: 25
<212> TYPE: PRT
<213> ORGANISM: Homo Sapiens
<220> FEATURE:
<221> NAME/KEY: PEPTIDE
<222> LOCATION: (1)...(25)
<223> OTHER INFORMATION: chymotrypsin C preproprotein

<400> SEQUENCE: 516

Leu Ala Glu His Val Glu Leu Ser Asp Thr Ile Gln Val Ala Cys Leu
1               5                   10                  15

Pro Glu Lys Asp Ser Leu Leu Pro Lys
            20                  25

<210> SEQ ID NO 517
<211> LENGTH: 26
<212> TYPE: PRT
<213> ORGANISM: Homo Sapiens
<220> FEATURE:
<221> NAME/KEY: PEPTIDE
<222> LOCATION: (1)...(25)
<223> OTHER INFORMATION: chymotrypsin C preproprotein

<400> SEQUENCE: 517

Leu Trp Thr Asn Gly Pro Ile Ala Asp Lys Leu Gln Gln Gly Leu Gln
1               5                   10                  15
```

```
Pro Val Val Asp His Ala Thr Cys Ser Arg
            20                  25

<210> SEQ ID NO 518
<211> LENGTH: 9
<212> TYPE: PRT
<213> ORGANISM: Homo Sapiens
<220> FEATURE:
<221> NAME/KEY: PEPTIDE
<222> LOCATION: (1)...(5)
<223> OTHER INFORMATION: carcinoembryonic antigen-related cell adhesion
      molecule 5 preproprotein

<400> SEQUENCE: 518

Thr Leu Thr Leu Leu Ser Val Thr Arg
1               5

<210> SEQ ID NO 519
<211> LENGTH: 11
<212> TYPE: PRT
<213> ORGANISM: Homo Sapiens
<220> FEATURE:
<221> NAME/KEY: PEPTIDE
<222> LOCATION: (1)...(10)
<223> OTHER INFORMATION: carcinoembryonic antigen-related cell adhesion
      molecule 5 preproprotein

<400> SEQUENCE: 519

Thr Ile Thr Val Ser Ala Glu Leu Pro Lys Pro
1               5                   10

<210> SEQ ID NO 520
<211> LENGTH: 12
<212> TYPE: PRT
<213> ORGANISM: Homo Sapiens
<220> FEATURE:
<221> NAME/KEY: PEPTIDE
<222> LOCATION: (1)...(10)
<223> OTHER INFORMATION: carcinoembryonic antigen-related cell adhesion
      molecule 5 preproprotein

<400> SEQUENCE: 520

Thr Ile Thr Val Ser Ala Glu Leu Pro Lys Pro Ser
1               5                   10

<210> SEQ ID NO 521
<211> LENGTH: 13
<212> TYPE: PRT
<213> ORGANISM: Homo Sapiens
<220> FEATURE:
<221> NAME/KEY: PEPTIDE
<222> LOCATION: (1)...(10)
<223> OTHER INFORMATION: carcinoembryonic antigen-related cell adhesion
      molecule 5 preproprotein

<400> SEQUENCE: 521

Ser Asp Leu Val Asn Glu Glu Ala Thr Gly Gln Phe Arg
1               5                   10

<210> SEQ ID NO 522
<211> LENGTH: 14
<212> TYPE: PRT
<213> ORGANISM: Homo Sapiens
<220> FEATURE:
<221> NAME/KEY: PEPTIDE
<222> LOCATION: (1)...(10)
<223> OTHER INFORMATION: carcinoembryonic antigen-related cell adhesion
      molecule 5 preproprotein
```

```
<400> SEQUENCE: 522

Leu Thr Ile Glu Ser Thr Pro Phe Asn Val Ala Glu Gly Lys
 1               5                  10

<210> SEQ ID NO 523
<211> LENGTH: 15
<212> TYPE: PRT
<213> ORGANISM: Homo Sapiens
<220> FEATURE:
<221> NAME/KEY: PEPTIDE
<222> LOCATION: (1)...(15)
<223> OTHER INFORMATION: carcinoembryonic antigen-related cell adhesion
      molecule 5 preproprotein

<400> SEQUENCE: 523

Thr Thr Val Thr Thr Ile Thr Val Tyr Ala Glu Pro Pro Lys Pro
 1               5                  10                  15

<210> SEQ ID NO 524
<211> LENGTH: 15
<212> TYPE: PRT
<213> ORGANISM: Homo Sapiens
<220> FEATURE:
<221> NAME/KEY: PEPTIDE
<222> LOCATION: (1)...(15)
<223> OTHER INFORMATION: carcinoembryonic antigen-related cell adhesion
      molecule 5 preproprotein

<400> SEQUENCE: 524

Lys Leu Thr Ile Glu Ser Thr Pro Phe Asn Val Ala Glu Gly Lys
 1               5                  10                  15

<210> SEQ ID NO 525
<211> LENGTH: 16
<212> TYPE: PRT
<213> ORGANISM: Homo Sapiens
<220> FEATURE:
<221> NAME/KEY: PEPTIDE
<222> LOCATION: (1)...(15)
<223> OTHER INFORMATION: carcinoembryonic antigen-related cell adhesion
      molecule 5 preproprotein

<400> SEQUENCE: 525

Thr Thr Val Thr Thr Ile Thr Val Tyr Ala Glu Pro Pro Lys Pro Phe
 1               5                  10                  15

<210> SEQ ID NO 526
<211> LENGTH: 21
<212> TYPE: PRT
<213> ORGANISM: Homo Sapiens
<220> FEATURE:
<221> NAME/KEY: PEPTIDE
<222> LOCATION: (1)...(20)
<223> OTHER INFORMATION: carcinoembryonic antigen-related cell adhesion
      molecule 5 preproprotein

<400> SEQUENCE: 526

Gln Ile Ile Gly Tyr Val Ile Gly Thr Gln Gln Ala Thr Pro Gly Pro
 1               5                  10                  15

Ala Tyr Ser Gly Arg
            20

<210> SEQ ID NO 527
<211> LENGTH: 20
<212> TYPE: PRT
<213> ORGANISM: Homo Sapiens
<220> FEATURE:
<221> NAME/KEY: PEPTIDE
```

```
<222> LOCATION: (1)...(20)
<223> OTHER INFORMATION: carcinoembryonic antigen-related cell adhesion
      molecule 5 preproprotein

<400> SEQUENCE: 527

Glu Val Leu Leu Leu Val His Asn Leu Pro Gln His Leu Phe Gly Tyr
1               5                   10                  15

Ser Trp Tyr Lys
            20

<210> SEQ ID NO 528
<211> LENGTH: 26
<212> TYPE: PRT
<213> ORGANISM: Homo Sapiens
<220> FEATURE:
<221> NAME/KEY: PEPTIDE
<222> LOCATION: (1)...(25)
<223> OTHER INFORMATION: carcinoembryonic antigen-related cell adhesion
      molecule 5 preproprotein

<400> SEQUENCE: 528

Val Asp Gly Asn Arg Gln Ile Ile Gly Tyr Val Ile Gly Thr Gln Gln
1               5                   10                  15

Ala Thr Pro Gly Pro Ala Tyr Ser Gly Arg
            20                  25

<210> SEQ ID NO 529
<211> LENGTH: 8
<212> TYPE: PRT
<213> ORGANISM: Homo Sapiens
<220> FEATURE:
<221> NAME/KEY: PEPTIDE
<222> LOCATION: (1)...(5)
<223> OTHER INFORMATION: carboxypeptidase A2 (pancreatic) precursor

<400> SEQUENCE: 529

Tyr Gly Phe Leu Leu Pro Ala Arg
1               5

<210> SEQ ID NO 530
<211> LENGTH: 10
<212> TYPE: PRT
<213> ORGANISM: Homo Sapiens
<220> FEATURE:
<221> NAME/KEY: PEPTIDE
<222> LOCATION: (1)...(10)
<223> OTHER INFORMATION: carboxypeptidase A2 (pancreatic) precursor

<400> SEQUENCE: 530

Ser Gly Asn Phe Asn Phe Gly Ala Tyr His
1               5                   10

<210> SEQ ID NO 531
<211> LENGTH: 13
<212> TYPE: PRT
<213> ORGANISM: Homo Sapiens
<220> FEATURE:
<221> NAME/KEY: PEPTIDE
<222> LOCATION: (1)...(10)
<223> OTHER INFORMATION: carboxypeptidase A2 (pancreatic) precursor

<400> SEQUENCE: 531

Val Ser Gly Ser Leu Cys Val Gly Val Asp Pro Asn Arg
1               5                   10

<210> SEQ ID NO 532
<211> LENGTH: 13
```

```
<212> TYPE: PRT
<213> ORGANISM: Homo Sapiens
<220> FEATURE:
<221> NAME/KEY: PEPTIDE
<222> LOCATION: (1)...(10)
<223> OTHER INFORMATION: carboxypeptidase A2 (pancreatic) precursor

<400> SEQUENCE: 532

Leu Asp Asp Phe Asp Glu Leu Ser Glu Val Ala Gln Lys
1               5                   10

<210> SEQ ID NO 533
<211> LENGTH: 14
<212> TYPE: PRT
<213> ORGANISM: Homo Sapiens
<220> FEATURE:
<221> NAME/KEY: PEPTIDE
<222> LOCATION: (1)...(10)
<223> OTHER INFORMATION: carboxypeptidase A2 (pancreatic) precursor

<400> SEQUENCE: 533

Gln Ile Leu Pro Thr Ala Glu Glu Thr Trp Leu Gly Leu Lys
1               5                   10

<210> SEQ ID NO 534
<211> LENGTH: 14
<212> TYPE: PRT
<213> ORGANISM: Homo Sapiens
<220> FEATURE:
<221> NAME/KEY: PEPTIDE
<222> LOCATION: (1)...(10)
<223> OTHER INFORMATION: carboxypeptidase A2 (pancreatic) precursor

<400> SEQUENCE: 534

Glu Trp Val Thr Gln Ala Thr Ala Leu Trp Thr Ala Asn Lys
1               5                   10

<210> SEQ ID NO 535
<211> LENGTH: 16
<212> TYPE: PRT
<213> ORGANISM: Homo Sapiens
<220> FEATURE:
<221> NAME/KEY: PEPTIDE
<222> LOCATION: (1)...(15)
<223> OTHER INFORMATION: carboxypeptidase A2 (pancreatic) precursor

<400> SEQUENCE: 535

Leu Leu Pro Val Thr Asn Pro Asp Gly Tyr Val Phe Ser Gln Thr Lys
1               5                   10                  15

<210> SEQ ID NO 536
<211> LENGTH: 16
<212> TYPE: PRT
<213> ORGANISM: Homo Sapiens
<220> FEATURE:
<221> NAME/KEY: PEPTIDE
<222> LOCATION: (1)...(15)
<223> OTHER INFORMATION: carboxypeptidase A2 (pancreatic) precursor

<400> SEQUENCE: 536

Val Asn Ile Gly Ser Ser Phe Glu Asn Arg Pro Met Asn Val Leu Lys
1               5                   10                  15

<210> SEQ ID NO 537
<211> LENGTH: 19
<212> TYPE: PRT
<213> ORGANISM: Homo Sapiens
<220> FEATURE:
<221> NAME/KEY: PEPTIDE
```

```
<222> LOCATION: (1)...(15)
<223> OTHER INFORMATION: carboxypeptidase A2 (pancreatic) precursor

<400> SEQUENCE: 537

Phe Ser Thr Gly Gly Asp Lys Pro Ala Ile Trp Leu Asp Ala Gly Ile
1               5                   10                  15

His Ala Arg

<210> SEQ ID NO 538
<211> LENGTH: 32
<212> TYPE: PRT
<213> ORGANISM: Homo Sapiens
<220> FEATURE:
<221> NAME/KEY: PEPTIDE
<222> LOCATION: (1)...(30)
<223> OTHER INFORMATION: carboxypeptidase A2 (pancreatic) precursor

<400> SEQUENCE: 538

Asn Trp Asp Ala Gly Phe Gly Gly Pro Gly Ala Ser Ser Asn Pro Cys
1               5                   10                  15

Ser Asp Ser Tyr His Gly Pro Ser Ala Asn Ser Glu Val Glu Val Lys
            20                  25                  30

<210> SEQ ID NO 539
<211> LENGTH: 32
<212> TYPE: PRT
<213> ORGANISM: Homo Sapiens
<220> FEATURE:
<221> NAME/KEY: PEPTIDE
<222> LOCATION: (1)...(30)
<223> OTHER INFORMATION: carboxypeptidase A2 (pancreatic) precursor

<400> SEQUENCE: 539

Ser Gly Asn Phe Asn Phe Gly Ala Tyr His Thr Leu Glu Glu Ile Ser
1               5                   10                  15

Gln Glu Met Asp Asn Leu Val Ala Glu His Pro Gly Leu Val Ser Lys
            20                  25                  30

<210> SEQ ID NO 540
<211> LENGTH: 9
<212> TYPE: PRT
<213> ORGANISM: Homo Sapiens
<220> FEATURE:
<221> NAME/KEY: PEPTIDE
<222> LOCATION: (1)...(5)
<223> OTHER INFORMATION: phospholipase A2 group IB

<400> SEQUENCE: 540

Leu Asp Asn Pro Tyr Thr His Thr Tyr
1               5

<210> SEQ ID NO 541
<211> LENGTH: 10
<212> TYPE: PRT
<213> ORGANISM: Homo Sapiens
<220> FEATURE:
<221> NAME/KEY: PEPTIDE
<222> LOCATION: (1)...(10)
<223> OTHER INFORMATION: phospholipase A2 group IB

<400> SEQUENCE: 541

Phe Leu Leu Asp Asn Pro Tyr Thr His Thr
1               5                   10

<210> SEQ ID NO 542
<211> LENGTH: 10
```

```
<212> TYPE: PRT
<213> ORGANISM: Homo Sapiens
<220> FEATURE:
<221> NAME/KEY: PEPTIDE
<222> LOCATION: (1)...(10)
<223> OTHER INFORMATION: phospholipase A2 group IB

<400> SEQUENCE: 542

Leu Leu Asp Asn Pro Tyr Thr His Thr Tyr
 1               5                  10

<210> SEQ ID NO 543
<211> LENGTH: 11
<212> TYPE: PRT
<213> ORGANISM: Homo Sapiens
<220> FEATURE:
<221> NAME/KEY: PEPTIDE
<222> LOCATION: (1)...(10)
<223> OTHER INFORMATION: phospholipase A2 group IB

<400> SEQUENCE: 543

Leu Leu Asp Asn Pro Tyr Thr His Thr Tyr Ser
 1               5                  10

<210> SEQ ID NO 544
<211> LENGTH: 14
<212> TYPE: PRT
<213> ORGANISM: Homo Sapiens
<220> FEATURE:
<221> NAME/KEY: PEPTIDE
<222> LOCATION: (1)...(10)
<223> OTHER INFORMATION: phospholipase A2 group IB

<400> SEQUENCE: 544

Gly Leu Gly Gly Ser Gly Thr Pro Val Asp Glu Leu Asp Lys
 1               5                  10

<210> SEQ ID NO 545
<211> LENGTH: 11
<212> TYPE: PRT
<213> ORGANISM: Homo Sapien
<220> FEATURE:
<221> NAME/KEY: PEPTIDE
<222> LOCATION: (1)...(10)
<223> OTHER INFORMATION: phospholipase A2 group IB

<400> SEQUENCE: 545

Phe Leu Leu Asp Asn Pro Tyr Thr His Thr Tyr
 1               5                  10

<210> SEQ ID NO 546
<211> LENGTH: 15
<212> TYPE: PRT
<213> ORGANISM: Homo Sapiens
<220> FEATURE:
<221> NAME/KEY: PEPTIDE
<222> LOCATION: (1)...(15)
<223> OTHER INFORMATION: phospholipase A2 group IB

<400> SEQUENCE: 546

Cys Gly Leu Gly Gly Ser Gly Thr Pro Val Asp Glu Leu Asp Lys
 1               5                  10                  15

<210> SEQ ID NO 547
<211> LENGTH: 13
<212> TYPE: PRT
<213> ORGANISM: Homo Sapiens
<220> FEATURE:
<221> NAME/KEY: PEPTIDE
```

<222> LOCATION: (1)...(10)
<223> OTHER INFORMATION: phospholipase A2 group IB

<400> SEQUENCE: 547

Leu Leu Asp Asn Pro Tyr Thr His Thr Tyr Ser Tyr Ser
1               5                   10

<210> SEQ ID NO 548
<211> LENGTH: 13
<212> TYPE: PRT
<213> ORGANISM: Homo Sapiens
<220> FEATURE:
<221> NAME/KEY: PEPTIDE
<222> LOCATION: (1)...(10)
<223> OTHER INFORMATION: phospholipase A2 group IB

<400> SEQUENCE: 548

Phe Leu Leu Asp Asn Pro Tyr Thr His Thr Tyr Ser Tyr
1               5                   10

<210> SEQ ID NO 549
<211> LENGTH: 14
<212> TYPE: PRT
<213> ORGANISM: Homo Sapiens
<220> FEATURE:
<221> NAME/KEY: PEPTIDE
<222> LOCATION: (1)...(10)
<223> OTHER INFORMATION: phospholipase A2 group IB

<400> SEQUENCE: 549

Phe Leu Leu Asp Asn Pro Tyr Thr His Thr Tyr Ser Tyr Ser
1               5                   10

<210> SEQ ID NO 550
<211> LENGTH: 18
<212> TYPE: PRT
<213> ORGANISM: Homo Sapiens
<220> FEATURE:
<221> NAME/KEY: PEPTIDE
<222> LOCATION: (1)...(15)
<223> OTHER INFORMATION: phospholipase A2 group IB

<400> SEQUENCE: 550

Phe Leu Leu Asp Asn Pro Tyr Thr His Thr Tyr Ser Tyr Ser Cys Ser
1               5                   10                  15

Gly Ser

<210> SEQ ID NO 551
<211> LENGTH: 21
<212> TYPE: PRT
<213> ORGANISM: Homo Sapiens
<220> FEATURE:
<221> NAME/KEY: PEPTIDE
<222> LOCATION: (1)...(20)
<223> OTHER INFORMATION: phospholipase A2 group IB

<400> SEQUENCE: 551

Asn Lys Glu Cys Glu Ala Phe Ile Cys Asn Cys Asp Arg Asn Ala Ala
1               5                   10                  15

Ile Cys Phe Ser Lys
            20

<210> SEQ ID NO 552
<211> LENGTH: 25
<212> TYPE: PRT
<213> ORGANISM: Homo Sapiens
<220> FEATURE:

<221> NAME/KEY: PEPTIDE
<222> LOCATION: (1)...(25)
<223> OTHER INFORMATION: phospholipase A2 group IB

<400> SEQUENCE: 552

Phe Leu Leu Asp Asn Pro Tyr Thr His Thr Tyr Ser Tyr Ser Cys Ser
1               5                   10                  15

Gly Ser Ala Ile Thr Cys Ser Ser Lys
            20                  25

<210> SEQ ID NO 553
<211> LENGTH: 8
<212> TYPE: PRT
<213> ORGANISM: Homo Sapiens
<220> FEATURE:
<221> NAME/KEY: PEPTIDE
<222> LOCATION: (1)...(5)
<223> OTHER INFORMATION: RecName: Full=Ig kappa chain C region

<400> SEQUENCE: 553

Leu Leu Asn Asn Phe Tyr Pro Arg
1               5

<210> SEQ ID NO 554
<211> LENGTH: 10
<212> TYPE: PRT
<213> ORGANISM: Homo Sapiens
<220> FEATURE:
<221> NAME/KEY: PEPTIDE
<222> LOCATION: (1)...(10)
<223> OTHER INFORMATION: RecName: Full=Ig kappa chain C region

<400> SEQUENCE: 554

Ser Leu Ser Ser Thr Leu Thr Leu Ser Lys
1               5                   10

<210> SEQ ID NO 555
<211> LENGTH: 12
<212> TYPE: PRT
<213> ORGANISM: Homo Sapiens
<220> FEATURE:
<221> NAME/KEY: PEPTIDE
<222> LOCATION: (1)...(10)
<223> OTHER INFORMATION: RecName: Full=Ig kappa chain C region

<400> SEQUENCE: 555

Val Phe Ile Phe Pro Pro Ser Asp Glu Gln Leu Lys
1               5                   10

<210> SEQ ID NO 556
<211> LENGTH: 14
<212> TYPE: PRT
<213> ORGANISM: Homo Sapiens
<220> FEATURE:
<221> NAME/KEY: PEPTIDE
<222> LOCATION: (1)...(10)
<223> OTHER INFORMATION: RecName: Full=Ig kappa chain C region

<400> SEQUENCE: 556

Asp Ser Thr Tyr Ser Leu Ser Ser Thr Leu Thr Leu Ser Lys
1               5                   10

<210> SEQ ID NO 557
<211> LENGTH: 15
<212> TYPE: PRT
<213> ORGANISM: Homo Sapiens
<220> FEATURE:
<221> NAME/KEY: PEPTIDE

```
<222> LOCATION: (1)..(15)
<223> OTHER INFORMATION: RecName: Full=Ig kappa chain C region

<400> SEQUENCE: 557

Ala Cys Glu Val Thr His Gln Gly Leu Ser Ser Pro Val Thr Lys
1               5                   10                  15

<210> SEQ ID NO 558
<211> LENGTH: 15
<212> TYPE: PRT
<213> ORGANISM: Homo Sapiens
<220> FEATURE:
<221> NAME/KEY: PEPTIDE
<222> LOCATION: (1)..(15)
<223> OTHER INFORMATION: RecName: Full=Ig kappa chain C region

<400> SEQUENCE: 558

Val Tyr Ala Cys Glu Val Thr His Gln Gly Leu Ser Ser Pro Val
1               5                   10                  15

<210> SEQ ID NO 559
<211> LENGTH: 16
<212> TYPE: PRT
<213> ORGANISM: Homo Sapiens
<220> FEATURE:
<221> NAME/KEY: PEPTIDE
<222> LOCATION: (1)..(15)
<223> OTHER INFORMATION: RecName: Full=Ig kappa chain C region

<400> SEQUENCE: 559

Val Tyr Ala Cys Glu Val Thr His Gln Gly Leu Ser Ser Pro Val Thr
1               5                   10                  15

<210> SEQ ID NO 560
<211> LENGTH: 16
<212> TYPE: PRT
<213> ORGANISM: Homo Sapiens
<220> FEATURE:
<221> NAME/KEY: PEPTIDE
<222> LOCATION: (1)..(15)
<223> OTHER INFORMATION: RecName: Full=Ig kappa chain C region

<400> SEQUENCE: 560

Ser Gly Thr Ala Ser Val Val Cys Leu Leu Asn Asn Phe Tyr Pro Arg
1               5                   10                  15

<210> SEQ ID NO 561
<211> LENGTH: 17
<212> TYPE: PRT
<213> ORGANISM: Homo Sapiens
<220> FEATURE:
<221> NAME/KEY: PEPTIDE
<222> LOCATION: (1)..(15)
<223> OTHER INFORMATION: RecName: Full=Ig kappa chain C region

<400> SEQUENCE: 561

Val Tyr Ala Cys Glu Val Thr His Gln Gly Leu Ser Ser Pro Val Thr
1               5                   10                  15

Lys

<210> SEQ ID NO 562
<211> LENGTH: 18
<212> TYPE: PRT
<213> ORGANISM: Homo Sapiens
<220> FEATURE:
<221> NAME/KEY: PEPTIDE
<222> LOCATION: (1)..(15)
<223> OTHER INFORMATION: RecName: Full=Ig kappa chain C region
```

```
<400> SEQUENCE: 562

Thr Val Ala Ala Pro Ser Val Phe Ile Phe Pro Pro Ser Asp Glu Gln
1               5                   10                  15

Leu Lys

<210> SEQ ID NO 563
<211> LENGTH: 19
<212> TYPE: PRT
<213> ORGANISM: Homo Sapiens
<220> FEATURE:
<221> NAME/KEY: PEPTIDE
<222> LOCATION: (1)...(15)
<223> OTHER INFORMATION: RecName: Full=Ig kappa chain C region

<400> SEQUENCE: 563

His Lys Val Tyr Ala Cys Glu Val Thr His Gln Gly Leu Ser Ser Pro
1               5                   10                  15

Val Thr Lys

<210> SEQ ID NO 564
<211> LENGTH: 24
<212> TYPE: PRT
<213> ORGANISM: Homo Sapiens
<220> FEATURE:
<221> NAME/KEY: PEPTIDE
<222> LOCATION: (1)...(20)
<223> OTHER INFORMATION: RecName: Full=Ig kappa chain C region

<400> SEQUENCE: 564

Val Asp Asn Ala Leu Gln Ser Gly Asn Ser Gln Glu Ser Val Thr Glu
1               5                   10                  15

Gln Asp Ser Lys Asp Ser Thr Tyr
            20

<210> SEQ ID NO 565
<211> LENGTH: 27
<212> TYPE: PRT
<213> ORGANISM: Homo Sapiens
<220> FEATURE:
<221> NAME/KEY: PEPTIDE
<222> LOCATION: (1)...(25)
<223> OTHER INFORMATION: RecName: Full=Ig kappa chain C region

<400> SEQUENCE: 565

Val Asp Asn Ala Leu Gln Ser Gly Asn Ser Gln Glu Ser Val Thr Glu
1               5                   10                  15

Gln Asp Ser Lys Asp Ser Thr Tyr Ser Leu Ser
            20                  25

<210> SEQ ID NO 566
<211> LENGTH: 34
<212> TYPE: PRT
<213> ORGANISM: Homo Sapiens
<220> FEATURE:
<221> NAME/KEY: PEPTIDE
<222> LOCATION: (1)...(30)
<223> OTHER INFORMATION: RecName: Full=Ig kappa chain C region

<400> SEQUENCE: 566

Val Asp Asn Ala Leu Gln Ser Gly Asn Ser Gln Glu Ser Val Thr Glu
1               5                   10                  15

Gln Asp Ser Lys Asp Ser Thr Tyr Ser Leu Ser Ser Thr Leu Thr Leu
            20                  25                  30
```

Ser Lys

<210> SEQ ID NO 567
<211> LENGTH: 12
<212> TYPE: PRT
<213> ORGANISM: Homo Sapiens
<220> FEATURE:
<221> NAME/KEY: PEPTIDE
<222> LOCATION: (1)...(10)
<223> OTHER INFORMATION: glyceraldehyde-3-phosphate dehydrogenase

<400> SEQUENCE: 567

Val Val Asp Leu Met Ala His Met Ala Ser Lys Glu
 1               5                  10

<210> SEQ ID NO 568
<211> LENGTH: 15
<212> TYPE: PRT
<213> ORGANISM: Homo Sapiens
<220> FEATURE:
<221> NAME/KEY: PEPTIDE
<222> LOCATION: (1)...(15)
<223> OTHER INFORMATION: glyceraldehyde-3-phosphate dehydrogenase

<400> SEQUENCE: 568

Gly Ala Leu Gln Asn Ile Ile Pro Ala Ser Thr Gly Ala Ala Lys
 1               5                  10                  15

<210> SEQ ID NO 569
<211> LENGTH: 14
<212> TYPE: PRT
<213> ORGANISM: Homo Sapiens
<220> FEATURE:
<221> NAME/KEY: PEPTIDE
<222> LOCATION: (1)...(10)
<223> OTHER INFORMATION: glyceraldehyde-3-phosphate dehydrogenase

<400> SEQUENCE: 569

Val Pro Thr Ala Asn Val Ser Val Val Asp Leu Thr Cys Arg
 1               5                  10

<210> SEQ ID NO 570
<211> LENGTH: 12
<212> TYPE: PRT
<213> ORGANISM: Homo Sapiens
<220> FEATURE:
<221> NAME/KEY: PEPTIDE
<222> LOCATION: (1)...(10)
<223> OTHER INFORMATION: glyceraldehyde-3-phosphate dehydrogenase

<400> SEQUENCE: 570

Asn Asp Pro Phe Ile Asp Leu Asn Tyr Met Val Tyr
 1               5                  10

<210> SEQ ID NO 571
<211> LENGTH: 15
<212> TYPE: PRT
<213> ORGANISM: Homo Sapiens
<220> FEATURE:
<221> NAME/KEY: PEPTIDE
<222> LOCATION: (1)...(15)
<223> OTHER INFORMATION: glyceraldehyde-3-phosphate dehydrogenase

<400> SEQUENCE: 571

Arg Val Ile Ile Ser Ala Pro Ser Ala Asp Ala Pro Met Phe Val
 1               5                  10                  15

<210> SEQ ID NO 572

```
<211> LENGTH: 14
<212> TYPE: PRT
<213> ORGANISM: Homo Sapiens
<220> FEATURE:
<221> NAME/KEY: PEPTIDE
<222> LOCATION: (1)...(10)
<223> OTHER INFORMATION: glyceraldehyde-3-phosphate dehydrogenase

<400> SEQUENCE: 572

Leu Val Ile Asn Gly Asn Pro Ile Thr Ile Phe Gln Glu Arg
 1               5                  10

<210> SEQ ID NO 573
<211> LENGTH: 17
<212> TYPE: PRT
<213> ORGANISM: Homo Sapiens
<220> FEATURE:
<221> NAME/KEY: PEPTIDE
<222> LOCATION: (1)...(15)
<223> OTHER INFORMATION: glyceraldehyde-3-phosphate dehydrogenase

<400> SEQUENCE: 573

Ile Ile Ser Asn Ala Ser Cys Thr Thr Asn Cys Leu Ala Pro Leu Ala
 1               5                  10                  15

Lys

<210> SEQ ID NO 574
<211> LENGTH: 14
<212> TYPE: PRT
<213> ORGANISM: Homo Sapiens
<220> FEATURE:
<221> NAME/KEY: PEPTIDE
<222> LOCATION: (1)...(10)
<223> OTHER INFORMATION: glyceraldehyde-3-phosphate dehydrogenase

<400> SEQUENCE: 574

Leu Ile Ser Trp Tyr Asp Asn Glu Phe Gly Tyr Ser Asn Arg
 1               5                  10

<210> SEQ ID NO 575
<211> LENGTH: 19
<212> TYPE: PRT
<213> ORGANISM: Homo Sapiens
<220> FEATURE:
<221> NAME/KEY: PEPTIDE
<222> LOCATION: (1)...(15)
<223> OTHER INFORMATION: glyceraldehyde-3-phosphate dehydrogenase

<400> SEQUENCE: 575

Ser Ser Asp Phe Asn Ser Asp Thr His Ser Ser Thr Phe Asp Ala Gly
 1               5                  10                  15

Ala Gly Ile

<210> SEQ ID NO 576
<211> LENGTH: 18
<212> TYPE: PRT
<213> ORGANISM: Homo Sapiens
<220> FEATURE:
<221> NAME/KEY: PEPTIDE
<222> LOCATION: (1)...(15)
<223> OTHER INFORMATION: glyceraldehyde-3-phosphate dehydrogenase

<400> SEQUENCE: 576

Leu Val Ile Asn Gly Asn Pro Ile Thr Ile Phe Gln Glu Arg Asp Pro
 1               5                  10                  15

Ser Lys
```

```
<210> SEQ ID NO 577
<211> LENGTH: 24
<212> TYPE: PRT
<213> ORGANISM: Homo Sapiens
<220> FEATURE:
<221> NAME/KEY: PEPTIDE
<222> LOCATION: (1)...(20)
<223> OTHER INFORMATION: glyceraldehyde-3-phosphate dehydrogenase

<400> SEQUENCE: 577

Val Ile His Asp Asn Phe Gly Ile Val Glu Gly Leu Met Thr Thr Val
 1               5                   10                  15
His Ala Ile Thr Ala Thr Gln Lys
             20

<210> SEQ ID NO 578
<211> LENGTH: 28
<212> TYPE: PRT
<213> ORGANISM: Homo Sapiens
<220> FEATURE:
<221> NAME/KEY: PEPTIDE
<222> LOCATION: (1)...(25)
<223> OTHER INFORMATION: glyceraldehyde-3-phosphate dehydrogenase

<400> SEQUENCE: 578

Val Asp Ile Val Ala Ile Asn Asp Pro Phe Ile Asp Leu Asn Tyr Met
 1               5                   10                  15
Val Tyr Met Phe Gln Tyr Asp Ser Thr His Gly Lys
             20                  25

<210> SEQ ID NO 579
<211> LENGTH: 12
<212> TYPE: PRT
<213> ORGANISM: Homo Sapiens
<220> FEATURE:
<221> NAME/KEY: PEPTIDE
<222> LOCATION: (1)...(10)
<223> OTHER INFORMATION: filamin B, beta (actin binding protein 278)

<400> SEQUENCE: 579

Thr Gly Glu Glu Val Gly Phe Val Val Asp Ala Lys
 1               5                   10

<210> SEQ ID NO 580
<211> LENGTH: 12
<212> TYPE: PRT
<213> ORGANISM: Homo Sapiens
<220> FEATURE:
<221> NAME/KEY: PEPTIDE
<222> LOCATION: (1)...(10)
<223> OTHER INFORMATION: filamin B, beta (actin binding protein 278)

<400> SEQUENCE: 580

Phe Ala Ser Gln Glu Ile Pro Ala Ser Pro Phe Arg
 1               5                   10

<210> SEQ ID NO 581
<211> LENGTH: 15
<212> TYPE: PRT
<213> ORGANISM: Homo Sapiens
<220> FEATURE:
<221> NAME/KEY: PEPTIDE
<222> LOCATION: (1)...(15)
<223> OTHER INFORMATION: filamin B, beta (actin binding protein 278)

<400> SEQUENCE: 581

Ala Gly Pro Gly Thr Leu Ser Val Thr Ile Glu Gly Pro Ser Lys
```

-continued

```
1               5                    10                   15
```

```
<210> SEQ ID NO 582
<211> LENGTH: 14
<212> TYPE: PRT
<213> ORGANISM: Homo Sapiens
<220> FEATURE:
<221> NAME/KEY: PEPTIDE
<222> LOCATION: (1)...(10)
<223> OTHER INFORMATION: filamin B, beta (actin binding protein 278)

<400> SEQUENCE: 582

Val Leu Phe Ala Ser Gln Glu Ile Pro Ala Ser Pro Phe Arg
1               5                   10

<210> SEQ ID NO 583
<211> LENGTH: 15
<212> TYPE: PRT
<213> ORGANISM: Homo Sapiens
<220> FEATURE:
<221> NAME/KEY: PEPTIDE
<222> LOCATION: (1)...(15)
<223> OTHER INFORMATION: filamin B, beta (actin binding protein 278)

<400> SEQUENCE: 583

Ser Pro Phe Glu Val Gln Val Gly Pro Glu Ala Gly Met Gln Lys
1               5                   10                  15

<210> SEQ ID NO 584
<211> LENGTH: 17
<212> TYPE: PRT
<213> ORGANISM: Homo Sapiens
<220> FEATURE:
<221> NAME/KEY: PEPTIDE
<222> LOCATION: (1)...(15)
<223> OTHER INFORMATION: filamin B, beta (actin binding protein 278)

<400> SEQUENCE: 584

Ala Pro Leu Asn Val Gln Phe Asn Ser Pro Leu Pro Gly Asp Ala Val
1               5                   10                  15
Lys

<210> SEQ ID NO 585
<211> LENGTH: 18
<212> TYPE: PRT
<213> ORGANISM: Homo Sapiens
<220> FEATURE:
<221> NAME/KEY: PEPTIDE
<222> LOCATION: (1)...(15)
<223> OTHER INFORMATION: filamin B, beta (actin binding protein 278)

<400> SEQUENCE: 585

Tyr Met Ile Gly Val Thr Tyr Gly Gly Asp Asp Ile Pro Leu Ser Pro
1               5                   10                  15
Tyr Arg

<210> SEQ ID NO 586
<211> LENGTH: 22
<212> TYPE: PRT
<213> ORGANISM: Homo Sapiens
<220> FEATURE:
<221> NAME/KEY: PEPTIDE
<222> LOCATION: (1)...(20)
<223> OTHER INFORMATION: filamin B, beta (actin binding protein 278)

<400> SEQUENCE: 586

Ala Ile Val His Asp Asn Lys Asp Gly Thr Tyr Ala Val Thr Tyr Ile
```

```
                1               5                   10                  15
Pro Asp Lys Thr Gly Arg
            20

<210> SEQ ID NO 587
<211> LENGTH: 11
<212> TYPE: PRT
<213> ORGANISM: Homo Sapiens
<220> FEATURE:
<221> NAME/KEY: PEPTIDE
<222> LOCATION: (1)...(10)
<223> OTHER INFORMATION: transthyretin precursor

<400> SEQUENCE: 587

Pro Ala Ile Asn Val Ala Val His Val Phe Arg
  1               5                   10

<210> SEQ ID NO 588
<211> LENGTH: 13
<212> TYPE: PRT
<213> ORGANISM: Homo Sapiens
<220> FEATURE:
<221> NAME/KEY: PEPTIDE
<222> LOCATION: (1)...(10)
<223> OTHER INFORMATION: transthyretin precursor

<400> SEQUENCE: 588

Gly Ser Pro Ala Ile Asn Val Ala Val His Val Phe Arg
  1               5                   10

<210> SEQ ID NO 589
<211> LENGTH: 13
<212> TYPE: PRT
<213> ORGANISM: Homo Sapiens
<220> FEATURE:
<221> NAME/KEY: PEPTIDE
<222> LOCATION: (1)...(10)
<223> OTHER INFORMATION: transthyretin precursor

<400> SEQUENCE: 589

Ala Ala Asp Asp Thr Trp Glu Pro Phe Ala Ser Gly Lys
  1               5                   10

<210> SEQ ID NO 590
<211> LENGTH: 14
<212> TYPE: PRT
<213> ORGANISM: Homo Sapiens
<220> FEATURE:
<221> NAME/KEY: PEPTIDE
<222> LOCATION: (1)...(10)
<223> OTHER INFORMATION: transthyretin precursor

<400> SEQUENCE: 590

Lys Ala Ala Asp Asp Thr Trp Glu Pro Phe Ala Ser Gly Lys
  1               5                   10

<210> SEQ ID NO 591
<211> LENGTH: 14
<212> TYPE: PRT
<213> ORGANISM: Homo Sapiens
<220> FEATURE:
<221> NAME/KEY: PEPTIDE
<222> LOCATION: (1)...(10)
<223> OTHER INFORMATION: transthyretin precursor

<400> SEQUENCE: 591

Gly Leu Thr Thr Glu Glu Glu Phe Val Glu Gly Ile Tyr Lys
  1               5                   10
```

```
<210> SEQ ID NO 592
<211> LENGTH: 16
<212> TYPE: PRT
<213> ORGANISM: Homo Sapiens
<220> FEATURE:
<221> NAME/KEY: PEPTIDE
<222> LOCATION: (1)...(15)
<223> OTHER INFORMATION: transthyretin precursor

<400> SEQUENCE: 592

Arg Tyr Thr Ile Ala Ala Leu Leu Ser Pro Tyr Ser Tyr Ser Thr Thr
 1               5                  10                  15

<210> SEQ ID NO 593
<211> LENGTH: 17
<212> TYPE: PRT
<213> ORGANISM: Homo Sapiens
<220> FEATURE:
<221> NAME/KEY: PEPTIDE
<222> LOCATION: (1)...(15)
<223> OTHER INFORMATION: transthyretin precursor

<400> SEQUENCE: 593

Leu Leu Ser Pro Tyr Ser Tyr Ser Thr Thr Ala Val Val Thr Asn Pro
 1               5                  10                  15

Lys

<210> SEQ ID NO 594
<211> LENGTH: 18
<212> TYPE: PRT
<213> ORGANISM: Homo Sapiens
<220> FEATURE:
<221> NAME/KEY: PEPTIDE
<222> LOCATION: (1)...(15)
<223> OTHER INFORMATION: transthyretin precursor

<400> SEQUENCE: 594

Leu Leu Ser Pro Tyr Ser Tyr Ser Thr Thr Ala Val Val Thr Asn Pro
 1               5                  10                  15

Lys Glu

<210> SEQ ID NO 595
<211> LENGTH: 19
<212> TYPE: PRT
<213> ORGANISM: Homo Sapiens
<220> FEATURE:
<221> NAME/KEY: PEPTIDE
<222> LOCATION: (1)...(15)
<223> OTHER INFORMATION: transthyretin precursor

<400> SEQUENCE: 595

Ala Leu Leu Ser Pro Tyr Ser Tyr Ser Thr Thr Ala Val Val Thr Asn
 1               5                  10                  15

Pro Lys Glu

<210> SEQ ID NO 596
<211> LENGTH: 23
<212> TYPE: PRT
<213> ORGANISM: Homo Sapiens
<220> FEATURE:
<221> NAME/KEY: PEPTIDE
<222> LOCATION: (1)...(20)
<223> OTHER INFORMATION: transthyretin precursor

<400> SEQUENCE: 596
```

```
Ala Leu Gly Ile Ser Pro Phe His Glu His Ala Glu Val Val Phe Thr
1               5                   10                  15

Ala Asn Asp Ser Gly Pro Arg
            20
```

<210> SEQ ID NO 597
<211> LENGTH: 22
<212> TYPE: PRT
<213> ORGANISM: Homo Sapiens
<220> FEATURE:
<221> NAME/KEY: PEPTIDE
<222> LOCATION: (1)...(20)
<223> OTHER INFORMATION: transthyretin precursor

<400> SEQUENCE: 597

```
Thr Ser Glu Ser Gly Glu Leu His Gly Leu Thr Thr Glu Glu Glu Phe
1               5                   10                  15

Val Glu Gly Ile Tyr Lys
            20
```

<210> SEQ ID NO 598
<211> LENGTH: 9
<212> TYPE: PRT
<213> ORGANISM: Homo Sapiens
<220> FEATURE:
<221> NAME/KEY: PEPTIDE
<222> LOCATION: (1)...(5)
<223> OTHER INFORMATION: keratin 9

<400> SEQUENCE: 598

```
Thr Leu Leu Asp Ile Asp Asn Thr Arg
1               5
```

<210> SEQ ID NO 599
<211> LENGTH: 11
<212> TYPE: PRT
<213> ORGANISM: Homo Sapiens
<220> FEATURE:
<221> NAME/KEY: PEPTIDE
<222> LOCATION: (1)...(10)
<223> OTHER INFORMATION: keratin 9

<400> SEQUENCE: 599

```
Gln Gly Val Asp Ala Asp Ile Asn Gly Leu Arg
1               5                   10
```

<210> SEQ ID NO 600
<211> LENGTH: 10
<212> TYPE: PRT
<213> ORGANISM: Homo Sapiens
<220> FEATURE:
<221> NAME/KEY: PEPTIDE
<222> LOCATION: (1)...(10)
<223> OTHER INFORMATION: keratin 9

<400> SEQUENCE: 600

```
Ile Lys Phe Glu Met Glu Gln Asn Leu Arg
1               5                   10
```

<210> SEQ ID NO 601
<211> LENGTH: 14
<212> TYPE: PRT
<213> ORGANISM: Homo Sapiens
<220> FEATURE:
<221> NAME/KEY: PEPTIDE
<222> LOCATION: (1)...(10)
<223> OTHER INFORMATION: keratin 9

```
<400> SEQUENCE: 601

Val Gln Ala Leu Glu Glu Ala Asn Asn Asp Leu Glu Asn Lys
 1               5                  10

<210> SEQ ID NO 602
<211> LENGTH: 17
<212> TYPE: PRT
<213> ORGANISM: Homo Sapiens
<220> FEATURE:
<221> NAME/KEY: PEPTIDE
<222> LOCATION: (1)...(15)
<223> OTHER INFORMATION: keratin 9

<400> SEQUENCE: 602

Asn Leu Leu Glu Gly Gly Gln Glu Asp Phe Glu Ser Ser Gly Ala Gly
 1               5                  10                  15

Lys

<210> SEQ ID NO 603
<211> LENGTH: 16
<212> TYPE: PRT
<213> ORGANISM: Homo Sapiens
<220> FEATURE:
<221> NAME/KEY: PEPTIDE
<222> LOCATION: (1)...(15)
<223> OTHER INFORMATION: keratin 9

<400> SEQUENCE: 603

His Gly Val Gln Glu Leu Glu Ile Glu Leu Gln Ser Gln Leu Ser Lys
 1               5                  10                  15

<210> SEQ ID NO 604
<211> LENGTH: 17
<212> TYPE: PRT
<213> ORGANISM: Homo Sapiens
<220> FEATURE:
<221> NAME/KEY: PEPTIDE
<222> LOCATION: (1)...(15)
<223> OTHER INFORMATION: keratin 9

<400> SEQUENCE: 604

His Gly Val Gln Glu Leu Glu Ile Glu Leu Gln Ser Gln Leu Ser Lys
 1               5                  10                  15

Lys

<210> SEQ ID NO 605
<211> LENGTH: 21
<212> TYPE: PRT
<213> ORGANISM: Homo Sapiens
<220> FEATURE:
<221> NAME/KEY: PEPTIDE
<222> LOCATION: (1)...(20)
<223> OTHER INFORMATION: keratin 9

<400> SEQUENCE: 605

Leu Ala Ser Tyr Leu Asp Lys Val Gln Ala Leu Glu Glu Ala Asn Asn
 1               5                  10                  15

Asp Leu Glu Asn Lys
            20

<210> SEQ ID NO 606
<211> LENGTH: 23
<212> TYPE: PRT
<213> ORGANISM: Homo Sapiens
<220> FEATURE:
<221> NAME/KEY: PEPTIDE
```

```
<222> LOCATION: (1)...(20)
<223> OTHER INFORMATION: keratin 9

<400> SEQUENCE: 606

Glu Ile Glu Thr Tyr His Asn Leu Leu Glu Gly Gly Gln Glu Asp Phe
 1               5                  10                  15

Glu Ser Ser Gly Ala Gly Lys
            20

<210> SEQ ID NO 607
<211> LENGTH: 25
<212> TYPE: PRT
<213> ORGANISM: Homo Sapiens
<220> FEATURE:
<221> NAME/KEY: PEPTIDE
<222> LOCATION: (1)...(25)
<223> OTHER INFORMATION: keratin 9

<400> SEQUENCE: 607

Asn Tyr Ser Pro Tyr Tyr Asn Thr Ile Asp Asp Leu Lys Asp Gln Ile
 1               5                  10                  15

Val Asp Leu Thr Val Gly Asn Asn Lys
            20                  25

<210> SEQ ID NO 608
<211> LENGTH: 10
<212> TYPE: PRT
<213> ORGANISM: Homo Sapiens
<220> FEATURE:
<221> NAME/KEY: PEPTIDE
<222> LOCATION: (1)...(10)
<223> OTHER INFORMATION: mesotrypsin isoform 1 preproprotein

<400> SEQUENCE: 608

Thr Leu Asp Asn Asp Ile Met Leu Ile Lys
 1               5                  10

<210> SEQ ID NO 609
<211> LENGTH: 10
<212> TYPE: PRT
<213> ORGANISM: Homo Sapiens
<220> FEATURE:
<221> NAME/KEY: PEPTIDE
<222> LOCATION: (1)...(10)
<223> OTHER INFORMATION: serine (or cysteine) proteinase inhibitor,
      clade B
      (ovalbumin), member 6

<400> SEQUENCE: 609

Leu Val Leu Val Asn Ala Val Tyr Phe Arg
 1               5                  10

<210> SEQ ID NO 610
<211> LENGTH: 12
<212> TYPE: PRT
<213> ORGANISM: Homo Sapiens
<220> FEATURE:
<221> NAME/KEY: PEPTIDE
<222> LOCATION: (1)...(10)
<223> OTHER INFORMATION: serine (or cysteine) proteinase inhibitor,
      clade B
      (ovalbumin), member 6

<400> SEQUENCE: 610

Asn Leu Gly Met Thr Asp Ala Phe Glu Leu Gly Lys
 1               5                  10
```

```
<210> SEQ ID NO 611
<211> LENGTH: 15
<212> TYPE: PRT
<213> ORGANISM: Homo Sapiens
<220> FEATURE:
<221> NAME/KEY: PEPTIDE
<222> LOCATION: (1)...(15)
<223> OTHER INFORMATION: serine (or cysteine) proteinase inhibitor,
      clade B
      (ovalbumin), member 6

<400> SEQUENCE: 611

Ile Ala Glu Leu Leu Ser Pro Gly Ser Val Asp Pro Leu Thr Arg
 1               5                  10                  15

<210> SEQ ID NO 612
<211> LENGTH: 15
<212> TYPE: PRT
<213> ORGANISM: Homo Sapiens
<220> FEATURE:
<221> NAME/KEY: PEPTIDE
<222> LOCATION: (1)...(15)
<223> OTHER INFORMATION: serine (or cysteine) proteinase inhibitor,
      clade B
      (ovalbumin), member 6

<400> SEQUENCE: 612

Ala Asp Phe Ser Gly Met Ser Gln Thr Asp Leu Ser Leu Ser Lys
 1               5                  10                  15

<210> SEQ ID NO 613
<211> LENGTH: 15
<212> TYPE: PRT
<213> ORGANISM: Homo Sapiens
<220> FEATURE:
<221> NAME/KEY: PEPTIDE
<222> LOCATION: (1)...(15)
<223> OTHER INFORMATION: serine (or cysteine) proteinase inhibitor,
      clade B
      (ovalbumin), member 6

<400> SEQUENCE: 613

Gly Asn Thr Ala Ala Gln Met Ala Gln Ile Leu Ser Phe Asn Lys
 1               5                  10                  15

<210> SEQ ID NO 614
<211> LENGTH: 14
<212> TYPE: PRT
<213> ORGANISM: Homo Sapiens
<220> FEATURE:
<221> NAME/KEY: PEPTIDE
<222> LOCATION: (1)...(10)
<223> OTHER INFORMATION: serine (or cysteine) proteinase inhibitor,
      clade B
      (ovalbumin), member 6

<400> SEQUENCE: 614

Phe Lys Leu Glu Glu Ser Tyr Asp Met Glu Ser Val Leu Arg
 1               5                  10

<210> SEQ ID NO 615
<211> LENGTH: 16
<212> TYPE: PRT
<213> ORGANISM: Homo Sapiens
<220> FEATURE:
<221> NAME/KEY: PEPTIDE
<222> LOCATION: (1)...(15)
<223> OTHER INFORMATION: serine (or cysteine) proteinase inhibitor,
      clade B
      (ovalbumin), member 6
```

```
<400> SEQUENCE: 615

Glu Leu Asn Met Ile Ile Met Leu Pro Asp Glu Thr Thr Asp Leu Arg
1               5                   10                  15

<210> SEQ ID NO 616
<211> LENGTH: 20
<212> TYPE: PRT
<213> ORGANISM: Homo Sapiens
<220> FEATURE:
<221> NAME/KEY: PEPTIDE
<222> LOCATION: (1)...(20)
<223> OTHER INFORMATION: serine (or cysteine) proteinase inhibitor,
      clade B
      (ovalbumin), member 6

<400> SEQUENCE: 616

Ser Gly Gly Gly Gly Asp Ile His Gln Gly Phe Gln Ser Leu Leu Thr
1               5                   10                  15

Glu Val Asn Lys
            20

<210> SEQ ID NO 617
<211> LENGTH: 18
<212> TYPE: PRT
<213> ORGANISM: Homo Sapiens
<220> FEATURE:
<221> NAME/KEY: PEPTIDE
<222> LOCATION: (1)...(15)
<223> OTHER INFORMATION: serine (or cysteine) proteinase inhibitor,
      clade B
      (ovalbumin), member 6

<400> SEQUENCE: 617

Thr Tyr Ile Gly Glu Ile Phe Thr Gln Ile Leu Val Leu Pro Tyr Val
1               5                   10                  15

Gly Lys

<210> SEQ ID NO 618
<211> LENGTH: 13
<212> TYPE: PRT
<213> ORGANISM: Homo Sapiens
<220> FEATURE:
<221> NAME/KEY: PEPTIDE
<222> LOCATION: (1)...(10)
<223> OTHER INFORMATION: immunoglobulin light chain

<400> SEQUENCE: 618

Ser Asp Phe Tyr Pro Gly Ala Val Thr Val Ala Trp Lys
1               5                   10

<210> SEQ ID NO 619
<211> LENGTH: 13
<212> TYPE: PRT
<213> ORGANISM: Homo Sapiens
<220> FEATURE:
<221> NAME/KEY: PEPTIDE
<222> LOCATION: (1)...(10)
<223> OTHER INFORMATION: immunoglobulin light chain

<400> SEQUENCE: 619

Leu Phe Pro Pro Ser Ser Glu Glu Leu Gln Ala Asn Lys
1               5                   10

<210> SEQ ID NO 620
<211> LENGTH: 14
<212> TYPE: PRT
<213> ORGANISM: Homo Sapiens
```

```
-continued

<220> FEATURE:
<221> NAME/KEY: PEPTIDE
<222> LOCATION: (1)...(10)
<223> OTHER INFORMATION: immunoglobulin light chain

<400> SEQUENCE: 620

Ile Ser Asp Phe Tyr Pro Gly Ala Val Thr Val Ala Trp Lys
 1               5                  10

<210> SEQ ID NO 621
<211> LENGTH: 15
<212> TYPE: PRT
<213> ORGANISM: Homo Sapiens
<220> FEATURE:
<221> NAME/KEY: PEPTIDE
<222> LOCATION: (1)...(15)
<223> OTHER INFORMATION: immunoglobulin light chain

<400> SEQUENCE: 621

Ser Tyr Ser Cys Gln Val Thr His Glu Gly Ser Thr Val Glu Lys
 1               5                  10                  15

<210> SEQ ID NO 622
<211> LENGTH: 15
<212> TYPE: PRT
<213> ORGANISM: Homo Sapiens
<220> FEATURE:
<221> NAME/KEY: PEPTIDE
<222> LOCATION: (1)...(15)
<223> OTHER INFORMATION: immunoglobulin light chain

<400> SEQUENCE: 622

Leu Ile Ser Asp Phe Tyr Pro Gly Ala Val Thr Val Ala Trp Lys
 1               5                  10                  15

<210> SEQ ID NO 623
<211> LENGTH: 15
<212> TYPE: PRT
<213> ORGANISM: Homo Sapiens
<220> FEATURE:
<221> NAME/KEY: PEPTIDE
<222> LOCATION: (1)...(15)
<223> OTHER INFORMATION: immunoglobulin light chain

<400> SEQUENCE: 623

Tyr Ala Ala Ser Ser Tyr Leu Ser Leu Thr Pro Glu Gln Trp Lys
 1               5                  10                  15

<210> SEQ ID NO 624
<211> LENGTH: 19
<212> TYPE: PRT
<213> ORGANISM: Homo Sapiens
<220> FEATURE:
<221> NAME/KEY: PEPTIDE
<222> LOCATION: (1)...(15)
<223> OTHER INFORMATION: immunoglobulin light chain

<400> SEQUENCE: 624

Ala Ala Pro Ser Val Thr Leu Phe Pro Pro Ser Ser Glu Glu Leu Gln
 1               5                  10                  15

Ala Asn Lys

<210> SEQ ID NO 625
<211> LENGTH: 20
<212> TYPE: PRT
<213> ORGANISM: Homo Sapiens
<220> FEATURE:
<221> NAME/KEY: PEPTIDE
```

```
<222> LOCATION: (1)...(20)
<223> OTHER INFORMATION: immunoglobulin light chain

<400> SEQUENCE: 625

Ala Thr Leu Val Cys Leu Ile Ser Asp Phe Tyr Pro Gly Ala Val Thr
 1               5                  10                  15

Val Ala Trp Lys
         20

<210> SEQ ID NO 626
<211> LENGTH: 11
<212> TYPE: PRT
<213> ORGANISM: Homo Sapiens
<220> FEATURE:
<221> NAME/KEY: PEPTIDE
<222> LOCATION: (1)...(10)
<223> OTHER INFORMATION: pancreatitis-associated protein precursor

<400> SEQUENCE: 626

Ser Trp Thr Asp Ala Asp Leu Ala Cys Gln Lys
 1               5                  10

<210> SEQ ID NO 627
<211> LENGTH: 13
<212> TYPE: PRT
<213> ORGANISM: Homo Sapiens
<220> FEATURE:
<221> NAME/KEY: PEPTIDE
<222> LOCATION: (1)...(10)
<223> OTHER INFORMATION: pancreatitis-associated protein precursor

<400> SEQUENCE: 627

Ser Gly Ala Glu Gly Ser Phe Val Ser Ser Leu Val Lys
 1               5                  10

<210> SEQ ID NO 628
<211> LENGTH: 14
<212> TYPE: PRT
<213> ORGANISM: Homo Sapiens
<220> FEATURE:
<221> NAME/KEY: PEPTIDE
<222> LOCATION: (1)...(10)
<223> OTHER INFORMATION: pancreatitis-associated protein precursor

<400> SEQUENCE: 628

Leu Ser Gly Ala Glu Gly Ser Phe Val Ser Ser Leu Val Lys
 1               5                  10

<210> SEQ ID NO 629
<211> LENGTH: 16
<212> TYPE: PRT
<213> ORGANISM: Homo Sapiens
<220> FEATURE:
<221> NAME/KEY: PEPTIDE
<222> LOCATION: (1)...(15)
<223> OTHER INFORMATION: pancreatitis-associated protein precursor

<400> SEQUENCE: 629

Ser Val Leu Ser Gly Ala Glu Gly Ser Phe Val Ser Ser Leu Val Lys
 1               5                  10                  15

<210> SEQ ID NO 630
<211> LENGTH: 17
<212> TYPE: PRT
<213> ORGANISM: Homo Sapiens
<220> FEATURE:
<221> NAME/KEY: PEPTIDE
<222> LOCATION: (1)...(15)
```

<223> OTHER INFORMATION: pancreatitis-associated protein precursor

<400> SEQUENCE: 630

Val Ser Val Leu Ser Gly Ala Glu Gly Ser Phe Val Ser Ser Leu Val
1               5                   10                  15

Lys

<210> SEQ ID NO 631
<211> LENGTH: 18
<212> TYPE: PRT
<213> ORGANISM: Homo Sapiens
<220> FEATURE:
<221> NAME/KEY: PEPTIDE
<222> LOCATION: (1)...(15)
<223> OTHER INFORMATION: pancreatitis-associated protein precursor

<400> SEQUENCE: 631

Arg Pro Ser Gly Asn Leu Val Ser Val Leu Ser Gly Ala Glu Gly Ser
1               5                   10                  15

Phe Val

<210> SEQ ID NO 632
<211> LENGTH: 19
<212> TYPE: PRT
<213> ORGANISM: Homo Sapiens
<220> FEATURE:
<221> NAME/KEY: PEPTIDE
<222> LOCATION: (1)...(15)
<223> OTHER INFORMATION: pancreatitis-associated protein precursor

<400> SEQUENCE: 632

Gly Leu His Asp Pro Thr Gln Gly Thr Glu Pro Asn Gly Glu Gly Trp
1               5                   10                  15

Glu Trp Ser

<210> SEQ ID NO 633
<211> LENGTH: 22
<212> TYPE: PRT
<213> ORGANISM: Homo Sapiens
<220> FEATURE:
<221> NAME/KEY: PEPTIDE
<222> LOCATION: (1)...(20)
<223> OTHER INFORMATION: pancreatitis-associated protein precursor

<400> SEQUENCE: 633

Pro Ser Gly Asn Leu Val Ser Val Leu Ser Gly Ala Glu Gly Ser Phe
1               5                   10                  15

Val Ser Ser Leu Val Lys
            20

<210> SEQ ID NO 634
<211> LENGTH: 23
<212> TYPE: PRT
<213> ORGANISM: Homo Sapiens
<220> FEATURE:
<221> NAME/KEY: PEPTIDE
<222> LOCATION: (1)...(20)
<223> OTHER INFORMATION: pancreatitis-associated protein precursor

<400> SEQUENCE: 634

Arg Pro Ser Gly Asn Leu Val Ser Val Leu Ser Gly Ala Glu Gly Ser
1               5                   10                  15

Phe Val Ser Ser Leu Val Lys
            20

```
<210> SEQ ID NO 635
<211> LENGTH: 11
<212> TYPE: PRT
<213> ORGANISM: Homo Sapiens
<220> FEATURE:
<221> NAME/KEY: PEPTIDE
<222> LOCATION: (1)...(10)
<223> OTHER INFORMATION: serine (or cysteine) proteinase inhibitor,
      clade B
      (ovalbumin), member 1

<400> SEQUENCE: 635

Leu Gly Val Gln Asp Leu Phe Asn Ser Ser Lys
 1               5                  10

<210> SEQ ID NO 636
<211> LENGTH: 10
<212> TYPE: PRT
<213> ORGANISM: Homo Sapiens
<220> FEATURE:
<221> NAME/KEY: PEPTIDE
<222> LOCATION: (1)...(10)
<223> OTHER INFORMATION: serine (or cysteine) proteinase inhibitor,
      clade B
      (ovalbumin), member 1

<400> SEQUENCE: 636

Phe Ala Tyr Gly Tyr Ile Glu Asp Leu Lys
 1               5                  10

<210> SEQ ID NO 637
<211> LENGTH: 10
<212> TYPE: PRT
<213> ORGANISM: Homo Sapiens
<220> FEATURE:
<221> NAME/KEY: PEPTIDE
<222> LOCATION: (1)...(10)
<223> OTHER INFORMATION: serine (or cysteine) proteinase inhibitor,
      clade B
      (ovalbumin), member 1

<400> SEQUENCE: 637

Lys Ile Glu Glu Gln Leu Thr Leu Glu Lys
 1               5                  10

<210> SEQ ID NO 638
<211> LENGTH: 12
<212> TYPE: PRT
<213> ORGANISM: Homo Sapiens
<220> FEATURE:
<221> NAME/KEY: PEPTIDE
<222> LOCATION: (1)...(10)
<223> OTHER INFORMATION: serine (or cysteine) proteinase inhibitor,
      clade B
      (ovalbumin), member 1

<400> SEQUENCE: 638

Val Leu Glu Leu Pro Tyr Gln Gly Glu Glu Leu Ser
 1               5                  10

<210> SEQ ID NO 639
<211> LENGTH: 15
<212> TYPE: PRT
<213> ORGANISM: Homo Sapiens
<220> FEATURE:
<221> NAME/KEY: PEPTIDE
<222> LOCATION: (1)...(15)
<223> OTHER INFORMATION: serine (or cysteine) proteinase inhibitor,
      clade B
      (ovalbumin), member 1
```

```
<400> SEQUENCE: 639

Ile Pro Glu Leu Leu Ala Ser Gly Met Val Asp Asn Met Thr Lys
 1               5                  10                  15

<210> SEQ ID NO 640
<211> LENGTH: 15
<212> TYPE: PRT
<213> ORGANISM: Homo Sapiens
<220> FEATURE:
<221> NAME/KEY: PEPTIDE
<222> LOCATION: (1)...(15)
<223> OTHER INFORMATION: serine (or cysteine) proteinase inhibitor,
      clade B
      (ovalbumin), member 1

<400> SEQUENCE: 640

Ile Leu Leu Pro Asp Asp Ile Glu Asp Glu Ser Thr Gly Leu Lys
 1               5                  10                  15

<210> SEQ ID NO 641
<211> LENGTH: 19
<212> TYPE: PRT
<213> ORGANISM: Homo Sapiens
<220> FEATURE:
<221> NAME/KEY: PEPTIDE
<222> LOCATION: (1)...(15)
<223> OTHER INFORMATION: serine (or cysteine) proteinase inhibitor,
      clade B
      (ovalbumin), member 1

<400> SEQUENCE: 641

Thr Tyr Gly Ala Asp Leu Ala Ser Val Asp Phe Gln His Ala Ser Glu
 1               5                  10                  15

Asp Ala Arg

<210> SEQ ID NO 642
<211> LENGTH: 17
<212> TYPE: PRT
<213> ORGANISM: Homo Sapiens
<220> FEATURE:
<221> NAME/KEY: PEPTIDE
<222> LOCATION: (1)...(15)
<223> OTHER INFORMATION: serine (or cysteine) proteinase inhibitor,
      clade B
      (ovalbumin), member 1

<400> SEQUENCE: 642

Met Pro Glu Glu Asn Phe Thr Ala Asp His Pro Phe Leu Phe Phe Ile
 1               5                  10                  15

Arg

<210> SEQ ID NO 643
<211> LENGTH: 13
<212> TYPE: PRT
<213> ORGANISM: Homo Sapiens
<220> FEATURE:
<221> NAME/KEY: PEPTIDE
<222> LOCATION: (1)...(10)
<223> OTHER INFORMATION: triosephosphate isomerase 1 isoform 2

<400> SEQUENCE: 643

Ile Ile Tyr Gly Gly Ser Val Thr Gly Ala Thr Cys Lys
 1               5                  10

<210> SEQ ID NO 644
<211> LENGTH: 14
```

```
<212> TYPE: PRT
<213> ORGANISM: Homo Sapiens
<220> FEATURE:
<221> NAME/KEY: PEPTIDE
<222> LOCATION: (1)...(10)
<223> OTHER INFORMATION: triosephosphate isomerase 1 isoform 2

<400> SEQUENCE: 644

Gln Ser Leu Gly Glu Leu Ile Gly Thr Leu Asn Ala Ala Lys
1               5                   10

<210> SEQ ID NO 645
<211> LENGTH: 15
<212> TYPE: PRT
<213> ORGANISM: Homo Sapiens
<220> FEATURE:
<221> NAME/KEY: PEPTIDE
<222> LOCATION: (1)...(15)
<223> OTHER INFORMATION: triosephosphate isomerase 1 isoform 2

<400> SEQUENCE: 645

Lys Gln Ser Leu Gly Glu Leu Ile Gly Thr Leu Asn Ala Ala Lys
1               5                   10                  15

<210> SEQ ID NO 646
<211> LENGTH: 15
<212> TYPE: PRT
<213> ORGANISM: Homo Sapiens
<220> FEATURE:
<221> NAME/KEY: PEPTIDE
<222> LOCATION: (1)...(15)
<223> OTHER INFORMATION: triosephosphate isomerase 1 isoform 2

<400> SEQUENCE: 646

Val Val Leu Ala Tyr Glu Pro Val Trp Ala Ile Gly Thr Gly Lys
1               5                   10                  15

<210> SEQ ID NO 647
<211> LENGTH: 16
<212> TYPE: PRT
<213> ORGANISM: Homo Sapiens
<220> FEATURE:
<221> NAME/KEY: PEPTIDE
<222> LOCATION: (1)...(15)
<223> OTHER INFORMATION: triosephosphate isomerase 1 isoform 2

<400> SEQUENCE: 647

Val Thr Asn Gly Ala Phe Thr Gly Glu Ile Ser Pro Gly Met Ile Lys
1               5                   10                  15

<210> SEQ ID NO 648
<211> LENGTH: 20
<212> TYPE: PRT
<213> ORGANISM: Homo Sapiens
<220> FEATURE:
<221> NAME/KEY: PEPTIDE
<222> LOCATION: (1)...(20)
<223> OTHER INFORMATION: triosephosphate isomerase 1 isoform 2

<400> SEQUENCE: 648

Val Pro Ala Asp Thr Glu Val Val Cys Ala Pro Pro Thr Ala Tyr Ile
1               5                   10                  15

Asp Phe Ala Arg
            20

<210> SEQ ID NO 649
<211> LENGTH: 29
<212> TYPE: PRT
```

```
<213> ORGANISM: Homo Sapiens
<220> FEATURE:
<221> NAME/KEY: PEPTIDE
<222> LOCATION: (1)...(25)
<223> OTHER INFORMATION: triosephosphate isomerase 1 isoform 2

<400> SEQUENCE: 649

Glu Leu Ala Ser Gln Pro Asp Val Asp Gly Phe Leu Val Gly Gly Ala
 1               5                  10                  15

Ser Leu Lys Pro Glu Phe Val Asp Ile Ile Asn Ala Lys
            20                  25

<210> SEQ ID NO 650
<211> LENGTH: 19
<212> TYPE: PRT
<213> ORGANISM: Homo Sapiens
<220> FEATURE:
<221> NAME/KEY: PEPTIDE
<222> LOCATION: (1)...(15)
<223> OTHER INFORMATION: RecName: Full=Ig lambda-1 chain C regions

<400> SEQUENCE: 650

Ala Asn Pro Thr Val Thr Leu Phe Pro Pro Ser Ser Glu Glu Leu Gln
 1               5                  10                  15

Ala Asn Lys

<210> SEQ ID NO 651
<211> LENGTH: 10
<212> TYPE: PRT
<213> ORGANISM: Homo Sapiens
<220> FEATURE:
<221> NAME/KEY: PEPTIDE
<222> LOCATION: (1)...(10)
<223> OTHER INFORMATION: keratin 2

<400> SEQUENCE: 651

Tyr Glu Glu Leu Gln Val Thr Val Gly Arg
 1               5                  10

<210> SEQ ID NO 652
<211> LENGTH: 11
<212> TYPE: PRT
<213> ORGANISM: Homo Sapiens
<220> FEATURE:
<221> NAME/KEY: PEPTIDE
<222> LOCATION: (1)...(10)
<223> OTHER INFORMATION: keratin 2

<400> SEQUENCE: 652

Thr Ala Ala Glu Asn Asp Phe Val Thr Leu Lys
 1               5                  10

<210> SEQ ID NO 653
<211> LENGTH: 11
<212> TYPE: PRT
<213> ORGANISM: Homo Sapiens
<220> FEATURE:
<221> NAME/KEY: PEPTIDE
<222> LOCATION: (1)...(10)
<223> OTHER INFORMATION: keratin 2

<400> SEQUENCE: 653

Leu Ala Leu Asp Val Glu Ile Ala Thr Tyr Arg
 1               5                  10

<210> SEQ ID NO 654
<211> LENGTH: 12
```

```
<212> TYPE: PRT
<213> ORGANISM: Homo Sapiens
<220> FEATURE:
<221> NAME/KEY: PEPTIDE
<222> LOCATION: (1)...(10)
<223> OTHER INFORMATION: keratin 2

<400> SEQUENCE: 654

Asn Leu Asp Leu Asp Ser Ile Ile Ala Glu Val Lys
 1               5                  10

<210> SEQ ID NO 655
<211> LENGTH: 12
<212> TYPE: PRT
<213> ORGANISM: Homo Sapiens
<220> FEATURE:
<221> NAME/KEY: PEPTIDE
<222> LOCATION: (1)...(10)
<223> OTHER INFORMATION: keratin 2

<400> SEQUENCE: 655

Val Asp Leu Leu Asn Gln Glu Ile Glu Phe Leu Lys
 1               5                  10

<210> SEQ ID NO 656
<211> LENGTH: 11
<212> TYPE: PRT
<213> ORGANISM: Homo Sapiens
<220> FEATURE:
<221> NAME/KEY: PEPTIDE
<222> LOCATION: (1)...(10)
<223> OTHER INFORMATION: Human Fc gamma BP [AA 1-2843]

<400> SEQUENCE: 656

Leu Pro Val Val Leu Ala Asn Gly Gln Ile Arg
 1               5                  10

<210> SEQ ID NO 657
<211> LENGTH: 10
<212> TYPE: PRT
<213> ORGANISM: Homo Sapiens
<220> FEATURE:
<221> NAME/KEY: PEPTIDE
<222> LOCATION: (1)...(10)
<223> OTHER INFORMATION: Human Fc gamma BP [AA 1-2843]

<400> SEQUENCE: 657

Val Ala Tyr Asp Leu Val Tyr Tyr Val Arg
 1               5                  10

<210> SEQ ID NO 658
<211> LENGTH: 13
<212> TYPE: PRT
<213> ORGANISM: Homo Sapiens
<220> FEATURE:
<221> NAME/KEY: PEPTIDE
<222> LOCATION: (1)...(10)
<223> OTHER INFORMATION: Human Fc gamma BP [AA 1-2843]

<400> SEQUENCE: 658

Tyr Asp Leu Ala Phe Val Val Ala Ser Gln Ala Thr Lys
 1               5                  10

<210> SEQ ID NO 659
<211> LENGTH: 15
<212> TYPE: PRT
<213> ORGANISM: Homo Sapiens
<220> FEATURE:
<221> NAME/KEY: PEPTIDE
```

<222> LOCATION: (1)...(15)
<223> OTHER INFORMATION: Human Fc gamma BP [AA 1-2843]

<400> SEQUENCE: 659

Asn Val Ala Gln Leu Gln Ser Ser Val Asp Leu Ser Gly Ser Lys
1               5                   10                  15

<210> SEQ ID NO 660
<211> LENGTH: 9
<212> TYPE: PRT
<213> ORGANISM: Homo Sapiens
<220> FEATURE:
<221> NAME/KEY: PEPTIDE
<222> LOCATION: (1)...(5)
<223> OTHER INFORMATION: keratin 10

<400> SEQUENCE: 660

Asp Ala Glu Ala Trp Phe Asn Glu Lys
1               5

<210> SEQ ID NO 661
<211> LENGTH: 12
<212> TYPE: PRT
<213> ORGANISM: Homo Sapiens
<220> FEATURE:
<221> NAME/KEY: PEPTIDE
<222> LOCATION: (1)...(10)
<223> OTHER INFORMATION: keratin 10

<400> SEQUENCE: 661

Ala Leu Glu Glu Ser Asn Tyr Glu Leu Glu Gly Lys
1               5                   10

<210> SEQ ID NO 662
<211> LENGTH: 19
<212> TYPE: PRT
<213> ORGANISM: Homo Sapiens
<220> FEATURE:
<221> NAME/KEY: PEPTIDE
<222> LOCATION: (1)...(15)
<223> OTHER INFORMATION: keratin 10

<400> SEQUENCE: 662

Gly Ser Leu Gly Gly Gly Phe Ser Ser Gly Gly Phe Ser Gly Gly Ser
1               5                   10                  15

Phe Ser Arg

<210> SEQ ID NO 663
<211> LENGTH: 16
<212> TYPE: PRT
<213> ORGANISM: Homo Sapiens
<220> FEATURE:
<221> NAME/KEY: PEPTIDE
<222> LOCATION: (1)...(15)
<223> OTHER INFORMATION: keratin 10

<400> SEQUENCE: 663

Asn Val Gln Ala Leu Glu Ile Glu Leu Gln Ser Gln Leu Ala Leu Lys
1               5                   10                  15

<210> SEQ ID NO 664
<211> LENGTH: 19
<212> TYPE: PRT
<213> ORGANISM: Homo Sapiens
<220> FEATURE:
<221> NAME/KEY: PEPTIDE
<222> LOCATION: (1)...(15)
<223> OTHER INFORMATION: keratin 10

```
<400> SEQUENCE: 664

Ala Asp Leu Glu Met Gln Ile Glu Ser Leu Thr Glu Glu Leu Ala Tyr
1               5                   10                  15

Leu Lys Lys

<210> SEQ ID NO 665
<211> LENGTH: 10
<212> TYPE: PRT
<213> ORGANISM: Homo Sapiens
<220> FEATURE:
<221> NAME/KEY: PEPTIDE
<222> LOCATION: (1)...(10)
<223> OTHER INFORMATION: albumin preproprotein

<400> SEQUENCE: 665

Met Asp Asp Phe Ala Ala Phe Val Glu Lys
1               5                   10

<210> SEQ ID NO 666
<211> LENGTH: 12
<212> TYPE: PRT
<213> ORGANISM: Homo Sapiens
<220> FEATURE:
<221> NAME/KEY: PEPTIDE
<222> LOCATION: (1)...(10)
<223> OTHER INFORMATION: albumin preproprotein

<400> SEQUENCE: 666

Ala Val Met Asp Asp Phe Ala Ala Phe Val Glu Lys
1               5                   10

<210> SEQ ID NO 667
<211> LENGTH: 12
<212> TYPE: PRT
<213> ORGANISM: Homo Sapiens
<220> FEATURE:
<221> NAME/KEY: PEPTIDE
<222> LOCATION: (1)...(10)
<223> OTHER INFORMATION: albumin preproprotein

<400> SEQUENCE: 667

Arg His Pro Asp Tyr Ser Val Val Leu Leu Leu Arg
1               5                   10

<210> SEQ ID NO 668
<211> LENGTH: 15
<212> TYPE: PRT
<213> ORGANISM: Homo Sapiens
<220> FEATURE:
<221> NAME/KEY: PEPTIDE
<222> LOCATION: (1)...(15)
<223> OTHER INFORMATION: albumin preproprotein

<400> SEQUENCE: 668

Lys Val Pro Gln Val Ser Thr Pro Thr Leu Val Glu Val Ser Arg
1               5                   10                  15

<210> SEQ ID NO 669
<211> LENGTH: 21
<212> TYPE: PRT
<213> ORGANISM: Homo Sapiens
<220> FEATURE:
<221> NAME/KEY: PEPTIDE
<222> LOCATION: (1)...(20)
<223> OTHER INFORMATION: carcinoembryonic antigen-related cell adhesion
      molecule 6 (non-specific cross reacting antigen)
```

```
<400> SEQUENCE: 669

Ser Asp Pro Val Thr Leu Asn Val Leu Tyr Gly Pro Asp Gly Pro Thr
1               5                   10                  15

Ile Ser Pro Ser Lys
            20

<210> SEQ ID NO 670
<211> LENGTH: 22
<212> TYPE: PRT
<213> ORGANISM: Homo Sapiens
<220> FEATURE:
<221> NAME/KEY: PEPTIDE
<222> LOCATION: (1)...(20)
<223> OTHER INFORMATION: carcinoembryonic antigen-related cell adhesion
      molecule 6 (non-specific cross reacting antigen)

<400> SEQUENCE: 670

Ser Asp Leu Val Asn Glu Glu Ala Thr Gly Gln Phe His Val Tyr Pro
1               5                   10                  15

Glu Leu Pro Lys Pro Ser
            20

<210> SEQ ID NO 671
<211> LENGTH: 28
<212> TYPE: PRT
<213> ORGANISM: Homo Sapiens
<220> FEATURE:
<221> NAME/KEY: PEPTIDE
<222> LOCATION: (1)...(25)
<223> OTHER INFORMATION: carcinoembryonic antigen-related cell adhesion
      molecule 6 (non-specific cross reacting antigen)

<400> SEQUENCE: 671

Lys Leu Thr Ile Glu Ser Thr Pro Phe Asn Val Ala Glu Gly Lys Glu
1               5                   10                  15

Val Leu Leu Leu Ala His Asn Leu Pro Gln Asn Arg
            20                  25

<210> SEQ ID NO 672
<211> LENGTH: 9
<212> TYPE: PRT
<213> ORGANISM: Homo Sapiens
<220> FEATURE:
<221> NAME/KEY: PEPTIDE
<222> LOCATION: (1)...(5)
<223> OTHER INFORMATION: RecName: Full=Ig kappa chain V-III region HIC;
      Flags: Precursor

<400> SEQUENCE: 672

Leu Leu Ile Tyr Gly Ala Ser Ser Arg
1               5

<210> SEQ ID NO 673
<211> LENGTH: 15
<212> TYPE: PRT
<213> ORGANISM: Homo Sapiens
<220> FEATURE:
<221> NAME/KEY: PEPTIDE
<222> LOCATION: (1)...(15)
<223> OTHER INFORMATION: RecName: Full=Ig kappa chain V-III region HIC;
      Flags: Precursor

<400> SEQUENCE: 673

Ser Gly Ser Gly Ser Gly Thr Asp Phe Thr Leu Thr Ile Ser Arg
1               5                   10                  15
```

```
<210> SEQ ID NO 674
<211> LENGTH: 16
<212> TYPE: PRT
<213> ORGANISM: Homo Sapiens
<220> FEATURE:
<221> NAME/KEY: PEPTIDE
<222> LOCATION: (1)...(15)
<223> OTHER INFORMATION: RecName: Full=Ig kappa chain V-III region HIC;
      Flags: Precursor

<400> SEQUENCE: 674

Phe Ser Gly Ser Gly Ser Gly Thr Asp Phe Thr Leu Thr Ile Ser Arg
1               5                   10                  15

<210> SEQ ID NO 675
<211> LENGTH: 18
<212> TYPE: PRT
<213> ORGANISM: Homo Sapiens
<220> FEATURE:
<221> NAME/KEY: PEPTIDE
<222> LOCATION: (1)...(15)
<223> OTHER INFORMATION: RecName: Full=Ig kappa chain V-III region HIC;
      Flags: Precursor

<400> SEQUENCE: 675

Glu Ile Val Leu Thr Gln Ser Pro Gly Thr Leu Ser Leu Ser Pro Gly
1               5                   10                  15

Glu Arg

<210> SEQ ID NO 676
<211> LENGTH: 23
<212> TYPE: PRT
<213> ORGANISM: Homo Sapiens
<220> FEATURE:
<221> NAME/KEY: PEPTIDE
<222> LOCATION: (1)...(20)
<223> OTHER INFORMATION: RecName: Full=Ig kappa chain V-III region HIC;
      Flags: Precursor

<400> SEQUENCE: 676

Ala Thr Gly Ile Pro Asp Arg Phe Ser Gly Ser Gly Ser Gly Thr Asp
1               5                   10                  15

Phe Thr Leu Thr Ile Ser Arg
            20

<210> SEQ ID NO 677
<211> LENGTH: 22
<212> TYPE: PRT
<213> ORGANISM: Homo Sapiens
<220> FEATURE:
<221> NAME/KEY: PEPTIDE
<222> LOCATION: (1)...(20)
<223> OTHER INFORMATION: RecName: Full=Ig kappa chain V-III region HIC;
      Flags: Precursor

<400> SEQUENCE: 677

Ala Ser Gln Ser Val Ser Ser Ser Tyr Leu Ala Trp Tyr Gln Gln Lys
1               5                   10                  15

Pro Gly Gln Ala Pro Arg
            20

<210> SEQ ID NO 678
<211> LENGTH: 11
<212> TYPE: PRT
<213> ORGANISM: Homo Sapiens
<220> FEATURE:
<221> NAME/KEY: PEPTIDE
<222> LOCATION: (1)...(10)
```

<223> OTHER INFORMATION: intestinal alkaline phosphatase precursor

<400> SEQUENCE: 678

Gly Ser Ser Ile Phe Gly Leu Ala Pro Ser Lys
1               5                   10

<210> SEQ ID NO 679
<211> LENGTH: 10
<212> TYPE: PRT
<213> ORGANISM: Homo Sapiens
<220> FEATURE:
<221> NAME/KEY: PEPTIDE
<222> LOCATION: (1)...(10)
<223> OTHER INFORMATION: intestinal alkaline phosphatase precursor

<400> SEQUENCE: 679

Gly Phe Tyr Leu Phe Val Glu Gly Gly Arg
1               5                   10

<210> SEQ ID NO 680
<211> LENGTH: 13
<212> TYPE: PRT
<213> ORGANISM: Homo Sapiens
<220> FEATURE:
<221> NAME/KEY: PEPTIDE
<222> LOCATION: (1)...(10)
<223> OTHER INFORMATION: intestinal alkaline phosphatase precursor

<400> SEQUENCE: 680

Ala Asn Phe Gln Thr Ile Gly Leu Ser Ala Ala Ala Arg
1               5                   10

<210> SEQ ID NO 681
<211> LENGTH: 13
<212> TYPE: PRT
<213> ORGANISM: Homo Sapiens
<220> FEATURE:
<221> NAME/KEY: PEPTIDE
<222> LOCATION: (1)...(10)
<223> OTHER INFORMATION: intestinal alkaline phosphatase precursor

<400> SEQUENCE: 681

Asn Trp Tyr Ser Asp Ala Asp Met Pro Ala Ser Ala Arg
1               5                   10

<210> SEQ ID NO 682
<211> LENGTH: 14
<212> TYPE: PRT
<213> ORGANISM: Homo Sapiens
<220> FEATURE:
<221> NAME/KEY: PEPTIDE
<222> LOCATION: (1)...(10)
<223> OTHER INFORMATION: intestinal alkaline phosphatase precursor

<400> SEQUENCE: 682

Ala Leu Thr Glu Ala Val Met Phe Asp Asp Ala Ile Glu Arg
1               5                   10

<210> SEQ ID NO 683
<211> LENGTH: 14
<212> TYPE: PRT
<213> ORGANISM: Homo Sapiens
<220> FEATURE:
<221> NAME/KEY: PEPTIDE
<222> LOCATION: (1)...(10)
<223> OTHER INFORMATION: intestinal alkaline phosphatase precursor

<400> SEQUENCE: 683

Val Ile Pro Ala Glu Glu Glu Asn Pro Ala Phe Trp Asn Arg
1               5                   10

<210> SEQ ID NO 684
<211> LENGTH: 19
<212> TYPE: PRT
<213> ORGANISM: Homo Sapiens
<220> FEATURE:
<221> NAME/KEY: PEPTIDE
<222> LOCATION: (1)...(15)
<223> OTHER INFORMATION: intestinal alkaline phosphatase precursor

<400> SEQUENCE: 684

Asn Leu Ile Leu Phe Leu Gly Asp Gly Leu Gly Val Pro Thr Val Thr
1               5                   10                  15

Ala Thr Arg

<210> SEQ ID NO 685
<211> LENGTH: 11
<212> TYPE: PRT
<213> ORGANISM: Homo Sapiens
<220> FEATURE:
<221> NAME/KEY: PEPTIDE
<222> LOCATION: (1)...(10)
<223> OTHER INFORMATION: annexin A2 isoform 1

<400> SEQUENCE: 685

Ser Leu Tyr Tyr Tyr Ile Gln Gln Asp Thr Lys
1               5                   10

<210> SEQ ID NO 686
<211> LENGTH: 16
<212> TYPE: PRT
<213> ORGANISM: Homo Sapiens
<220> FEATURE:
<221> NAME/KEY: PEPTIDE
<222> LOCATION: (1)...(15)
<223> OTHER INFORMATION: annexin A2 isoform 1

<400> SEQUENCE: 686

Ser Ala Leu Ser Gly His Leu Glu Thr Val Ile Leu Gly Leu Leu Lys
1               5                   10                  15

<210> SEQ ID NO 687
<211> LENGTH: 16
<212> TYPE: PRT
<213> ORGANISM: Homo Sapiens
<220> FEATURE:
<221> NAME/KEY: PEPTIDE
<222> LOCATION: (1)...(15)
<223> OTHER INFORMATION: annexin A2 isoform 1

<400> SEQUENCE: 687

Gly Leu Gly Thr Asp Glu Asp Ser Leu Ile Glu Ile Ile Cys Ser Arg
1               5                   10                  15

<210> SEQ ID NO 688
<211> LENGTH: 17
<212> TYPE: PRT
<213> ORGANISM: Homo Sapiens
<220> FEATURE:
<221> NAME/KEY: PEPTIDE
<222> LOCATION: (1)...(15)
<223> OTHER INFORMATION: annexin A2 isoform 1

<400> SEQUENCE: 688

Thr Asp Leu Glu Lys Asp Ile Ile Ser Asp Thr Ser Gly Asp Phe Arg
1               5                   10                  15

Lys

<210> SEQ ID NO 689
<211> LENGTH: 18
<212> TYPE: PRT
<213> ORGANISM: Homo Sapiens
<220> FEATURE:
<221> NAME/KEY: PEPTIDE
<222> LOCATION: (1)...(15)
<223> OTHER INFORMATION: annexin A2 isoform 1

<400> SEQUENCE: 689

Arg Ala Glu Asp Gly Ser Val Ile Asp Tyr Glu Leu Ile Asp Gln Asp
1               5                   10                  15

Ala Arg

<210> SEQ ID NO 690
<211> LENGTH: 18
<212> TYPE: PRT
<213> ORGANISM: Homo Sapiens
<220> FEATURE:
<221> NAME/KEY: PEPTIDE
<222> LOCATION: (1)...(15)
<223> OTHER INFORMATION: serpin peptidase inhibitor, clade A, member 3
      precursor

<400> SEQUENCE: 690

Leu Tyr Gly Ser Glu Ala Phe Ala Thr Asp Phe Gln Asp Ser Ala Ala
1               5                   10                  15

Ala Lys

<210> SEQ ID NO 691
<211> LENGTH: 19
<212> TYPE: PRT
<213> ORGANISM: Homo Sapiens
<220> FEATURE:
<221> NAME/KEY: PEPTIDE
<222> LOCATION: (1)...(15)
<223> OTHER INFORMATION: serpin peptidase inhibitor, clade A, member 3
      precursor

<400> SEQUENCE: 691

Ala Val Leu Asp Val Phe Glu Glu Gly Thr Glu Ala Ser Ala Ala Thr
1               5                   10                  15

Ala Val Lys

<210> SEQ ID NO 692
<211> LENGTH: 17
<212> TYPE: PRT
<213> ORGANISM: Homo Sapiens
<220> FEATURE:
<221> NAME/KEY: PEPTIDE
<222> LOCATION: (1)...(15)
<223> OTHER INFORMATION: serpin peptidase inhibitor, clade A, member 3
      precursor

<400> SEQUENCE: 692

Leu Met Ile Ile Val Pro Thr Asp Thr Gln Asn Ile Phe Phe Met Ser
1               5                   10                  15

Lys

<210> SEQ ID NO 693
<211> LENGTH: 22
<212> TYPE: PRT
<213> ORGANISM: Homo Sapiens

```
<220> FEATURE:
<221> NAME/KEY: PEPTIDE
<222> LOCATION: (1)...(20)
<223> OTHER INFORMATION: serpin peptidase inhibitor, clade A, member 3
      precursor

<400> SEQUENCE: 693

Phe Asn Arg Pro Phe Leu Met Ile Ile Val Pro Thr Asp Thr Gln Asn
  1               5                  10                  15

Ile Phe Phe Met Ser Lys
              20

<210> SEQ ID NO 694
<211> LENGTH: 12
<212> TYPE: PRT
<213> ORGANISM: Homo Sapiens
<220> FEATURE:
<221> NAME/KEY: PEPTIDE
<222> LOCATION: (1)...(10)
<223> OTHER INFORMATION: mucin 13, epithelial transmembrane

<400> SEQUENCE: 694

Ser Asp Leu Gln Arg Pro Asn Pro Gln Ser Pro Phe
  1               5                  10

<210> SEQ ID NO 695
<211> LENGTH: 14
<212> TYPE: PRT
<213> ORGANISM: Homo Sapiens
<220> FEATURE:
<221> NAME/KEY: PEPTIDE
<222> LOCATION: (1)...(10)
<223> OTHER INFORMATION: mucin 13, epithelial transmembrane

<400> SEQUENCE: 695

Ile Ser Val Thr Val Ser Glu Thr Phe Asp Pro Glu Glu Lys
  1               5                  10

<210> SEQ ID NO 696
<211> LENGTH: 16
<212> TYPE: PRT
<213> ORGANISM: Homo Sapiens
<220> FEATURE:
<221> NAME/KEY: PEPTIDE
<222> LOCATION: (1)...(15)
<223> OTHER INFORMATION: mucin 13, epithelial transmembrane

<400> SEQUENCE: 696

Ser Thr Gly Phe Thr Asn Leu Gly Ala Glu Gly Ser Val Phe Pro Lys
  1               5                  10                  15

<210> SEQ ID NO 697
<211> LENGTH: 14
<212> TYPE: PRT
<213> ORGANISM: Homo Sapiens
<220> FEATURE:
<221> NAME/KEY: PEPTIDE
<222> LOCATION: (1)...(10)
<223> OTHER INFORMATION: mucin 13, epithelial transmembrane

<400> SEQUENCE: 697

Ser Ser Ser Ser Asn Phe Leu Asn Tyr Asp Leu Thr Leu Arg
  1               5                  10

<210> SEQ ID NO 698
<211> LENGTH: 16
<212> TYPE: PRT
<213> ORGANISM: Homo Sapiens
```

```
<220> FEATURE:
<221> NAME/KEY: PEPTIDE
<222> LOCATION: (1)...(15)
<223> OTHER INFORMATION: mucin 13, epithelial transmembrane

<400> SEQUENCE: 698

His Ile Glu Glu Glu Asn Leu Ile Asp Glu Asp Phe Gln Asn Leu Lys
 1               5                  10                  15

<210> SEQ ID NO 699
<211> LENGTH: 12
<212> TYPE: PRT
<213> ORGANISM: Homo Sapiens
<220> FEATURE:
<221> NAME/KEY: PEPTIDE
<222> LOCATION: (1)...(10)
<223> OTHER INFORMATION: zymogen granule membrane glycoprotein 2
      isoform 1

<400> SEQUENCE: 699

Val Gly Ala Ile Leu Glu Gln Gly Asp Thr Ser Arg
 1               5                  10

<210> SEQ ID NO 700
<211> LENGTH: 13
<212> TYPE: PRT
<213> ORGANISM: Homo Sapiens
<220> FEATURE:
<221> NAME/KEY: PEPTIDE
<222> LOCATION: (1)...(10)
<223> OTHER INFORMATION: zymogen granule membrane glycoprotein 2
      isoform 1

<400> SEQUENCE: 700

Val Gly Ala Ile Leu Glu Gln Gly Asp Thr Ser Arg Phe
 1               5                  10

<210> SEQ ID NO 701
<211> LENGTH: 12
<212> TYPE: PRT
<213> ORGANISM: Homo Sapiens
<220> FEATURE:
<221> NAME/KEY: PEPTIDE
<222> LOCATION: (1)...(10)
<223> OTHER INFORMATION: zymogen granule membrane glycoprotein 2
      isoform 1

<400> SEQUENCE: 701

Asn Thr Leu Ser Leu Val Asn Asp Phe Ile Ile Arg
 1               5                  10

<210> SEQ ID NO 702
<211> LENGTH: 15
<212> TYPE: PRT
<213> ORGANISM: Homo Sapiens
<220> FEATURE:
<221> NAME/KEY: PEPTIDE
<222> LOCATION: (1)...(15)
<223> OTHER INFORMATION: zymogen granule membrane glycoprotein 2
      isoform 1

<400> SEQUENCE: 702

Asn Trp Val Ser Val Thr Ser Pro Val Gln Ala Ser Ala Cys Arg
 1               5                  10                  15

<210> SEQ ID NO 703
<211> LENGTH: 10
<212> TYPE: PRT
<213> ORGANISM: Homo Sapiens
```

```
<220> FEATURE:
<221> NAME/KEY: PEPTIDE
<222> LOCATION: (1)...(10)
<223> OTHER INFORMATION: mucin 6, gastric

<400> SEQUENCE: 703

Asn Ile Ile Thr Gln Gln Val Asp Ala Arg
1               5                   10

<210> SEQ ID NO 704
<211> LENGTH: 12
<212> TYPE: PRT
<213> ORGANISM: Homo Sapiens
<220> FEATURE:
<221> NAME/KEY: PEPTIDE
<222> LOCATION: (1)...(10)
<223> OTHER INFORMATION: mucin 6, gastric

<400> SEQUENCE: 704

Ser Phe Asn Ile Ile Thr Gln Gln Val Asp Ala Arg
1               5                   10

<210> SEQ ID NO 705
<211> LENGTH: 15
<212> TYPE: PRT
<213> ORGANISM: Homo Sapiens
<220> FEATURE:
<221> NAME/KEY: PEPTIDE
<222> LOCATION: (1)...(15)
<223> OTHER INFORMATION: mucin 6, gastric

<400> SEQUENCE: 705

Ser Ala Ala Ser Phe Asn Ile Ile Thr Gln Gln Val Asp Ala Arg
1               5                   10                  15

<210> SEQ ID NO 706
<211> LENGTH: 10
<212> TYPE: PRT
<213> ORGANISM: Homo Sapiens
<220> FEATURE:
<221> NAME/KEY: PEPTIDE
<222> LOCATION: (1)...(10)
<223> OTHER INFORMATION: creatine kinase, mitochondrial 1B precursor

<400> SEQUENCE: 706

Val Val Val Asp Ala Leu Ser Gly Leu Lys
1               5                   10

<210> SEQ ID NO 707
<211> LENGTH: 13
<212> TYPE: PRT
<213> ORGANISM: Homo Sapiens
<220> FEATURE:
<221> NAME/KEY: PEPTIDE
<222> LOCATION: (1)...(10)
<223> OTHER INFORMATION: creatine kinase, mitochondrial 1B precursor

<400> SEQUENCE: 707

Ala Thr Gly Gly Val Phe Asp Ile Ser Asn Leu Asp Arg
1               5                   10

<210> SEQ ID NO 708
<211> LENGTH: 16
<212> TYPE: PRT
<213> ORGANISM: Homo Sapiens
<220> FEATURE:
<221> NAME/KEY: PEPTIDE
<222> LOCATION: (1)...(15)
<223> OTHER INFORMATION: creatine kinase, mitochondrial 1B precursor
```

```
<400> SEQUENCE: 708

Phe Asp Lys Pro Val Ser Pro Leu Leu Thr Ala Ala Gly Met Ala Arg
1               5                   10                  15

<210> SEQ ID NO 709
<211> LENGTH: 14
<212> TYPE: PRT
<213> ORGANISM: Homo Sapiens
<220> FEATURE:
<221> NAME/KEY: PEPTIDE
<222> LOCATION: (1)...(10)
<223> OTHER INFORMATION: creatine kinase, mitochondrial 1B precursor

<400> SEQUENCE: 709

Glu Val Phe Ala Asp Leu Phe Asp Pro Val Ile Gln Glu Arg
1               5                   10

<210> SEQ ID NO 710
<211> LENGTH: 21
<212> TYPE: PRT
<213> ORGANISM: Homo Sapiens
<220> FEATURE:
<221> NAME/KEY: PEPTIDE
<222> LOCATION: (1)...(20)
<223> OTHER INFORMATION: creatine kinase, mitochondrial 1B precursor

<400> SEQUENCE: 710

Ser Glu Val Glu Leu Val Gln Leu Val Ile Asp Gly Val Asn Tyr Leu
1               5                   10                  15

Ile Asp Cys Glu Arg
            20

<210> SEQ ID NO 711
<211> LENGTH: 26
<212> TYPE: PRT
<213> ORGANISM: Homo Sapiens
<220> FEATURE:
<221> NAME/KEY: PEPTIDE
<222> LOCATION: (1)...(25)
<223> OTHER INFORMATION: creatine kinase, mitochondrial 1B precursor

<400> SEQUENCE: 711

Thr Val Gly Met Val Ala Gly Asp Glu Glu Thr Tyr Glu Val Phe Ala
1               5                   10                  15

Asp Leu Phe Asp Pro Val Ile Gln Glu Arg
            20                  25

<210> SEQ ID NO 712
<211> LENGTH: 10
<212> TYPE: PRT
<213> ORGANISM: Homo Sapiens
<220> FEATURE:
<221> NAME/KEY: PEPTIDE
<222> LOCATION: (1)...(10)
<223> OTHER INFORMATION: keratin 8

<400> SEQUENCE: 712

Leu Ser Glu Leu Glu Ala Ala Leu Gln Arg
1               5                   10

<210> SEQ ID NO 713
<211> LENGTH: 11
<212> TYPE: PRT
<213> ORGANISM: Homo Sapiens
<220> FEATURE:
<221> NAME/KEY: PEPTIDE
```

```
<222> LOCATION: (1)...(10)
<223> OTHER INFORMATION: keratin 8

<400> SEQUENCE: 713

Leu Ala Leu Asp Ile Glu Ile Ala Thr Tyr Arg
1               5                  10

<210> SEQ ID NO 714
<211> LENGTH: 13
<212> TYPE: PRT
<213> ORGANISM: Homo Sapiens
<220> FEATURE:
<221> NAME/KEY: PEPTIDE
<222> LOCATION: (1)...(10)
<223> OTHER INFORMATION: keratin 8

<400> SEQUENCE: 714

Ala Ser Leu Glu Ala Ala Ile Ala Asp Ala Glu Gln Arg
1               5                  10

<210> SEQ ID NO 715
<211> LENGTH: 12
<212> TYPE: PRT
<213> ORGANISM: Homo Sapiens
<220> FEATURE:
<221> NAME/KEY: PEPTIDE
<222> LOCATION: (1)...(10)
<223> OTHER INFORMATION: keratin 8

<400> SEQUENCE: 715

Leu Glu Gly Leu Thr Asp Glu Ile Asn Phe Leu Arg
1               5                  10

<210> SEQ ID NO 716
<211> LENGTH: 15
<212> TYPE: PRT
<213> ORGANISM: Homo Sapiens
<220> FEATURE:
<221> NAME/KEY: PEPTIDE
<222> LOCATION: (1)...(15)
<223> OTHER INFORMATION: keratin 8

<400> SEQUENCE: 716

Asp Val Asp Glu Ala Tyr Met Asn Lys Val Glu Leu Glu Ser Arg
1               5                  10                  15

<210> SEQ ID NO 717
<211> LENGTH: 18
<212> TYPE: PRT
<213> ORGANISM: Homo Sapiens
<220> FEATURE:
<221> NAME/KEY: PEPTIDE
<222> LOCATION: (1)...(15)
<223> OTHER INFORMATION: keratin 8

<400> SEQUENCE: 717

Leu Lys Leu Glu Ala Glu Leu Gly Asn Met Gln Gly Leu Val Glu Asp
1               5                  10                  15

Phe Lys

<210> SEQ ID NO 718
<211> LENGTH: 12
<212> TYPE: PRT
<213> ORGANISM: Homo Sapiens
<220> FEATURE:
<221> NAME/KEY: PEPTIDE
<222> LOCATION: (1)...(10)
<223> OTHER INFORMATION: keratin 6B
```

```
<400> SEQUENCE: 718

Ala Asp Thr Leu Thr Asp Glu Ile Asn Phe Leu Arg
1               5                   10

<210> SEQ ID NO 719
<211> LENGTH: 12
<212> TYPE: PRT
<213> ORGANISM: Homo Sapiens
<220> FEATURE:
<221> NAME/KEY: PEPTIDE
<222> LOCATION: (1)...(10)
<223> OTHER INFORMATION: RecName: Full=Ig gamma-1 chain C region

<400> SEQUENCE: 719

Gly Pro Ser Val Phe Pro Leu Ala Pro Ser Ser Lys
1               5                   10

<210> SEQ ID NO 720
<211> LENGTH: 14
<212> TYPE: PRT
<213> ORGANISM: Homo Sapiens
<220> FEATURE:
<221> NAME/KEY: PEPTIDE
<222> LOCATION: (1)...(10)
<223> OTHER INFORMATION: RecName: Full=Ig gamma-1 chain C region

<400> SEQUENCE: 720

Ser Thr Ser Gly Gly Thr Ala Ala Leu Gly Cys Leu Val Lys
1               5                   10

<210> SEQ ID NO 721
<211> LENGTH: 17
<212> TYPE: PRT
<213> ORGANISM: Homo Sapiens
<220> FEATURE:
<221> NAME/KEY: PEPTIDE
<222> LOCATION: (1)...(15)
<223> OTHER INFORMATION: RecName: Full=Ig gamma-1 chain C region

<400> SEQUENCE: 721

Thr Thr Pro Pro Val Leu Asp Ser Asp Gly Ser Phe Phe Leu Tyr Ser
1               5                   10                  15

Lys

<210> SEQ ID NO 722
<211> LENGTH: 22
<212> TYPE: PRT
<213> ORGANISM: Homo Sapiens
<220> FEATURE:
<221> NAME/KEY: PEPTIDE
<222> LOCATION: (1)...(20)
<223> OTHER INFORMATION: RecName: Full=Ig gamma-1 chain C region

<400> SEQUENCE: 722

Gly Phe Tyr Pro Ser Asp Ile Ala Val Glu Trp Glu Ser Asn Gly Gln
1               5                   10                  15

Pro Glu Asn Asn Tyr Lys
            20

<210> SEQ ID NO 723
<211> LENGTH: 11
<212> TYPE: PRT
<213> ORGANISM: Homo Sapiens
<220> FEATURE:
<221> NAME/KEY: PEPTIDE
<222> LOCATION: (1)...(10)
```

<223> OTHER INFORMATION: superoxide dismutase 1, soluble

<400> SEQUENCE: 723

Gly Leu Thr Glu Gly Leu His Gly Phe His Val
1               5                   10

<210> SEQ ID NO 724
<211> LENGTH: 14
<212> TYPE: PRT
<213> ORGANISM: Homo Sapiens
<220> FEATURE:
<221> NAME/KEY: PEPTIDE
<222> LOCATION: (1)...(10)
<223> OTHER INFORMATION: superoxide dismutase 1, soluble

<400> SEQUENCE: 724

Gly Asp Gly Pro Val Gln Gly Ile Ile Asn Phe Glu Gln Lys
1               5                   10

<210> SEQ ID NO 725
<211> LENGTH: 16
<212> TYPE: PRT
<213> ORGANISM: Homo Sapiens
<220> FEATURE:
<221> NAME/KEY: PEPTIDE
<222> LOCATION: (1)...(15)
<223> OTHER INFORMATION: superoxide dismutase 1, soluble

<400> SEQUENCE: 725

Gly Asp Leu Gly Asn Val Thr Ala Asp Lys Asp Gly Val Ala Asp Val
1               5                   10                  15

<210> SEQ ID NO 726
<211> LENGTH: 17
<212> TYPE: PRT
<213> ORGANISM: Homo Sapiens
<220> FEATURE:
<221> NAME/KEY: PEPTIDE
<222> LOCATION: (1)...(15)
<223> OTHER INFORMATION: superoxide dismutase 1, soluble

<400> SEQUENCE: 726

Val Gly Asp Leu Gly Asn Val Thr Ala Asp Lys Asp Gly Val Ala Asp
1               5                   10                  15

Val

<210> SEQ ID NO 727
<211> LENGTH: 33
<212> TYPE: PRT
<213> ORGANISM: Homo Sapiens
<220> FEATURE:
<221> NAME/KEY: PEPTIDE
<222> LOCATION: (1)...(30)
<223> OTHER INFORMATION: superoxide dismutase 1, soluble

<400> SEQUENCE: 727

Gly Leu Thr Glu Gly Leu His Gly Phe His Val His Glu Phe Gly Asp
1               5                   10                  15

Asn Thr Ala Gly Cys Thr Ser Ala Gly Pro His Phe Asn Pro Leu Ser
                20                  25                  30

Arg

<210> SEQ ID NO 728
<211> LENGTH: 10
<212> TYPE: PRT
<213> ORGANISM: Homo Sapiens

```
<220> FEATURE:
<221> NAME/KEY: PEPTIDE
<222> LOCATION: (1)...(10)
<223> OTHER INFORMATION: enterokinase precursor

<400> SEQUENCE: 728

Phe Thr Glu Trp Ile Gln Ser Phe Leu His
 1               5                  10

<210> SEQ ID NO 729
<211> LENGTH: 12
<212> TYPE: PRT
<213> ORGANISM: Homo Sapiens
<220> FEATURE:
<221> NAME/KEY: PEPTIDE
<222> LOCATION: (1)...(10)
<223> OTHER INFORMATION: enterokinase precursor

<400> SEQUENCE: 729

Ala Ser Ile Trp Glu Thr Asn Pro Gly Thr Ile Arg
 1               5                  10

<210> SEQ ID NO 730
<211> LENGTH: 13
<212> TYPE: PRT
<213> ORGANISM: Homo Sapiens
<220> FEATURE:
<221> NAME/KEY: PEPTIDE
<222> LOCATION: (1)...(10)
<223> OTHER INFORMATION: enterokinase precursor

<400> SEQUENCE: 730

Met Thr Val Leu Leu Ile Thr Asn Asp Val Leu Ala Arg
 1               5                  10

<210> SEQ ID NO 731
<211> LENGTH: 24
<212> TYPE: PRT
<213> ORGANISM: Homo Sapiens
<220> FEATURE:
<221> NAME/KEY: PEPTIDE
<222> LOCATION: (1)...(20)
<223> OTHER INFORMATION: enterokinase precursor

<400> SEQUENCE: 731

Val Leu Ala Phe Asp Leu Gln Gln Met Ile Asp Glu Ile Phe Leu Ser
 1               5                  10                  15

Ser Asn Leu Lys Asn Glu Tyr Lys
            20

<210> SEQ ID NO 732
<211> LENGTH: 11
<212> TYPE: PRT
<213> ORGANISM: Homo Sapiens
<220> FEATURE:
<221> NAME/KEY: PEPTIDE
<222> LOCATION: (1)...(10)
<223> OTHER INFORMATION: meprin A alpha

<400> SEQUENCE: 732

Ile Leu Ala Asp Asn Leu Gly Leu Asn Ala Lys
 1               5                  10

<210> SEQ ID NO 733
<211> LENGTH: 10
<212> TYPE: PRT
<213> ORGANISM: Homo Sapiens
<220> FEATURE:
```

```
<221> NAME/KEY: PEPTIDE
<222> LOCATION: (1)...(10)
<223> OTHER INFORMATION: meprin A alpha

<400> SEQUENCE: 733

Leu Asp Phe Ser Ala Ile Asp Leu Glu Arg
 1               5                  10

<210> SEQ ID NO 734
<211> LENGTH: 11
<212> TYPE: PRT
<213> ORGANISM: Homo Sapiens
<220> FEATURE:
<221> NAME/KEY: PEPTIDE
<222> LOCATION: (1)...(10)
<223> OTHER INFORMATION: meprin A alpha

<400> SEQUENCE: 734

Ile Pro Glu Phe Asn Ser Ile Ile Gly Gln Arg
 1               5                  10

<210> SEQ ID NO 735
<211> LENGTH: 14
<212> TYPE: PRT
<213> ORGANISM: Homo Sapiens
<220> FEATURE:
<221> NAME/KEY: PEPTIDE
<222> LOCATION: (1)...(10)
<223> OTHER INFORMATION: meprin A alpha

<400> SEQUENCE: 735

Gln Val Ile Ile Thr Ile Leu Asp Gln Glu Pro Asp Val Arg
 1               5                  10

<210> SEQ ID NO 736
<211> LENGTH: 8
<212> TYPE: PRT
<213> ORGANISM: Homo Sapiens
<220> FEATURE:
<221> NAME/KEY: PEPTIDE
<222> LOCATION: (1)...(5)
<223> OTHER INFORMATION: sucrase-isomaltase

<400> SEQUENCE: 736

Ala Pro Glu Cys Tyr Phe Pro Arg
 1               5

<210> SEQ ID NO 737
<211> LENGTH: 12
<212> TYPE: PRT
<213> ORGANISM: Homo Sapiens
<220> FEATURE:
<221> NAME/KEY: PEPTIDE
<222> LOCATION: (1)...(10)
<223> OTHER INFORMATION: sucrase-isomaltase

<400> SEQUENCE: 737

Ile Lys Leu Pro Ser Asp Pro Ile Ser Thr Leu Arg
 1               5                  10

<210> SEQ ID NO 738
<211> LENGTH: 14
<212> TYPE: PRT
<213> ORGANISM: Homo Sapiens
<220> FEATURE:
<221> NAME/KEY: PEPTIDE
<222> LOCATION: (1)...(10)
<223> OTHER INFORMATION: sucrase-isomaltase
```

```
<400> SEQUENCE: 738

Phe Asn Cys Tyr Pro Asp Ala Asp Leu Ala Thr Glu Gln Lys
1               5                   10

<210> SEQ ID NO 739
<211> LENGTH: 22
<212> TYPE: PRT
<213> ORGANISM: Homo Sapiens
<220> FEATURE:
<221> NAME/KEY: PEPTIDE
<222> LOCATION: (1)...(20)
<223> OTHER INFORMATION: RecName: Full=Ig kappa chain V-III region SIE

<400> SEQUENCE: 739

Ala Ser Gln Ser Val Ser Asn Ser Tyr Leu Ala Trp Tyr Gln Gln Lys
1               5                   10                  15

Pro Gly Gln Ala Pro Arg
            20

<210> SEQ ID NO 740
<211> LENGTH: 13
<212> TYPE: PRT
<213> ORGANISM: Homo Sapiens
<220> FEATURE:
<221> NAME/KEY: PEPTIDE
<222> LOCATION: (1)...(10)
<223> OTHER INFORMATION: lipocalin 2

<400> SEQUENCE: 740

Trp Tyr Val Val Gly Leu Ala Gly Asn Ala Ile Leu Arg
1               5                   10

<210> SEQ ID NO 741
<211> LENGTH: 15
<212> TYPE: PRT
<213> ORGANISM: Homo Sapiens
<220> FEATURE:
<221> NAME/KEY: PEPTIDE
<222> LOCATION: (1)...(15)
<223> OTHER INFORMATION: lipocalin 2

<400> SEQUENCE: 741

Val Pro Leu Gln Gln Asn Phe Gln Asp Asn Gln Phe Gln Gly Lys
1               5                   10                  15

<210> SEQ ID NO 742
<211> LENGTH: 17
<212> TYPE: PRT
<213> ORGANISM: Homo Sapiens
<220> FEATURE:
<221> NAME/KEY: PEPTIDE
<222> LOCATION: (1)...(15)
<223> OTHER INFORMATION: lipocalin 2

<400> SEQUENCE: 742

Thr Phe Val Pro Gly Cys Gln Pro Gly Glu Phe Thr Leu Gly Asn Ile
1               5                   10                  15

Lys

<210> SEQ ID NO 743
<211> LENGTH: 21
<212> TYPE: PRT
<213> ORGANISM: Homo Sapiens
<220> FEATURE:
<221> NAME/KEY: PEPTIDE
<222> LOCATION: (1)...(20)
<223> OTHER INFORMATION: lipocalin 2
```

-continued

```
<400> SEQUENCE: 743

Ser Leu Gly Leu Pro Glu Asn His Ile Val Phe Pro Val Pro Ile Asp
1               5                   10                  15

Gln Cys Ile Asp Gly
            20

<210> SEQ ID NO 744
<211> LENGTH: 9
<212> TYPE: PRT
<213> ORGANISM: Homo Sapiens
<220> FEATURE:
<221> NAME/KEY: PEPTIDE
<222> LOCATION: (1)...(5)
<223> OTHER INFORMATION: orosomucoid 1 precursor

<400> SEQUENCE: 744

Ser Asp Val Val Tyr Thr Asp Trp Lys
1               5

<210> SEQ ID NO 745
<211> LENGTH: 11
<212> TYPE: PRT
<213> ORGANISM: Homo Sapiens
<220> FEATURE:
<221> NAME/KEY: PEPTIDE
<222> LOCATION: (1)...(10)
<223> OTHER INFORMATION: orosomucoid 1 precursor

<400> SEQUENCE: 745

Phe Asp Val Asn Asp Glu Lys Asn Trp Gly Leu
1               5                   10

<210> SEQ ID NO 746
<211> LENGTH: 12
<212> TYPE: PRT
<213> ORGANISM: Homo Sapiens
<220> FEATURE:
<221> NAME/KEY: PEPTIDE
<222> LOCATION: (1)...(10)
<223> OTHER INFORMATION: orosomucoid 1 precursor

<400> SEQUENCE: 746

Thr Tyr Met Leu Ala Phe Asp Val Asn Asp Glu Lys
1               5                   10

<210> SEQ ID NO 747
<211> LENGTH: 14
<212> TYPE: PRT
<213> ORGANISM: Homo Sapiens
<220> FEATURE:
<221> NAME/KEY: PEPTIDE
<222> LOCATION: (1)...(10)
<223> OTHER INFORMATION: orosomucoid 1 precursor

<400> SEQUENCE: 747

Phe Asp Val Asn Asp Glu Lys Asn Trp Gly Leu Ser Val Tyr
1               5                   10

<210> SEQ ID NO 748
<211> LENGTH: 14
<212> TYPE: PRT
<213> ORGANISM: Homo Sapiens
<220> FEATURE:
<221> NAME/KEY: PEPTIDE
<222> LOCATION: (1)...(10)
<223> OTHER INFORMATION: orosomucoid 1 precursor
```

```
<400> SEQUENCE: 748

Glu Gln Leu Gly Glu Phe Tyr Glu Ala Leu Asp Cys Leu Arg
 1               5                  10

<210> SEQ ID NO 749
<211> LENGTH: 15
<212> TYPE: PRT
<213> ORGANISM: Homo Sapiens
<220> FEATURE:
<221> NAME/KEY: PEPTIDE
<222> LOCATION: (1)...(15)
<223> OTHER INFORMATION: orosomucoid 1 precursor

<400> SEQUENCE: 749

Tyr Val Gly Gly Gln Glu His Phe Ala His Leu Leu Ile Leu Arg
 1               5                  10                  15

<210> SEQ ID NO 750
<211> LENGTH: 22
<212> TYPE: PRT
<213> ORGANISM: Homo Sapiens
<220> FEATURE:
<221> NAME/KEY: PEPTIDE
<222> LOCATION: (1)...(20)
<223> OTHER INFORMATION: orosomucoid 1 precursor

<400> SEQUENCE: 750

Phe Asp Val Asn Asp Glu Lys Asn Trp Gly Leu Ser Val Tyr Ala Asp
 1               5                  10                  15

Lys Pro Glu Thr Thr Lys
             20

<210> SEQ ID NO 751
<211> LENGTH: 11
<212> TYPE: PRT
<213> ORGANISM: Homo Sapiens
<220> FEATURE:
<221> NAME/KEY: PEPTIDE
<222> LOCATION: (1)...(10)
<223> OTHER INFORMATION: olfactomedin 4 precursor

<400> SEQUENCE: 751

Ser Tyr Thr Glu Leu Asp Phe Glu Leu Ile Lys
 1               5                  10

<210> SEQ ID NO 752
<211> LENGTH: 13
<212> TYPE: PRT
<213> ORGANISM: Homo Sapiens
<220> FEATURE:
<221> NAME/KEY: PEPTIDE
<222> LOCATION: (1)...(10)
<223> OTHER INFORMATION: olfactomedin 4 precursor

<400> SEQUENCE: 752

Ser Val Ser Leu Pro Asp Thr Thr Phe Pro Val Asp Arg
 1               5                  10

<210> SEQ ID NO 753
<211> LENGTH: 12
<212> TYPE: PRT
<213> ORGANISM: Homo Sapiens
<220> FEATURE:
<221> NAME/KEY: PEPTIDE
<222> LOCATION: (1)...(10)
<223> OTHER INFORMATION: olfactomedin 4 precursor

<400> SEQUENCE: 753
```

Val Gln Ser Ile Asn Tyr Asn Pro Phe Asp Gln Lys
1               5                   10

<210> SEQ ID NO 754
<211> LENGTH: 13
<212> TYPE: PRT
<213> ORGANISM: Homo Sapiens
<220> FEATURE:
<221> NAME/KEY: PEPTIDE
<222> LOCATION: (1)...(10)
<223> OTHER INFORMATION: olfactomedin 4 precursor

<400> SEQUENCE: 754

Leu Glu Thr Leu Asp Lys Asn Asn Val Leu Ala Ile Arg
1               5                   10

<210> SEQ ID NO 755
<211> LENGTH: 12
<212> TYPE: PRT
<213> ORGANISM: Homo Sapiens
<220> FEATURE:
<221> NAME/KEY: PEPTIDE
<222> LOCATION: (1)...(10)
<223> OTHER INFORMATION: nucleophosmin 1 isoform 1

<400> SEQUENCE: 755

Asp Met Asp Met Ser Pro Leu Arg Pro Gln Asn Tyr
1               5                   10

<210> SEQ ID NO 756
<211> LENGTH: 15
<212> TYPE: PRT
<213> ORGANISM: Homo Sapiens
<220> FEATURE:
<221> NAME/KEY: PEPTIDE
<222> LOCATION: (1)...(15)
<223> OTHER INFORMATION: nucleophosmin 1 isoform 1

<400> SEQUENCE: 756

Val Ser Leu Gly Gly Phe Glu Ile Thr Pro Pro Val Val Leu Arg
1               5                   10                  15

<210> SEQ ID NO 757
<211> LENGTH: 21
<212> TYPE: PRT
<213> ORGANISM: Homo Sapiens
<220> FEATURE:
<221> NAME/KEY: PEPTIDE
<222> LOCATION: (1)...(20)
<223> OTHER INFORMATION: nucleophosmin 1 isoform 1

<400> SEQUENCE: 757

Met Ser Val Gln Pro Thr Val Ser Leu Gly Gly Phe Glu Ile Thr Pro
1               5                   10                  15

Pro Val Val Leu Arg
            20

<210> SEQ ID NO 758
<211> LENGTH: 21
<212> TYPE: PRT
<213> ORGANISM: Homo Sapiens
<220> FEATURE:
<221> NAME/KEY: PEPTIDE
<222> LOCATION: (1)...(20)
<223> OTHER INFORMATION: nucleophosmin 1 isoform 1

<400> SEQUENCE: 758

Ala Asp Lys Asp Tyr His Phe Lys Val Asp Asn Asp Glu Asn Glu His
1               5                   10                  15

Gln Leu Ser Leu Arg
            20

<210> SEQ ID NO 759
<211> LENGTH: 28
<212> TYPE: PRT
<213> ORGANISM: Homo Sapiens
<220> FEATURE:
<221> NAME/KEY: PEPTIDE
<222> LOCATION: (1)...(25)
<223> OTHER INFORMATION: nucleophosmin 1 isoform 1

<400> SEQUENCE: 759

Thr Val Ser Leu Gly Ala Gly Ala Lys Asp Glu Leu His Ile Val Glu
1               5                   10                  15

Ala Glu Ala Met Asn Tyr Glu Gly Ser Pro Ile Lys
            20                  25

<210> SEQ ID NO 760
<211> LENGTH: 18
<212> TYPE: PRT
<213> ORGANISM: Homo Sapiens
<220> FEATURE:
<221> NAME/KEY: PEPTIDE
<222> LOCATION: (1)...(15)
<223> OTHER INFORMATION: immunoglobulin light chain variable region

<400> SEQUENCE: 760

Glu Ile Val Leu Thr Gln Ser Pro Ala Thr Leu Ser Leu Ser Pro Gly
1               5                   10                  15

Glu Arg

<210> SEQ ID NO 761
<211> LENGTH: 14
<212> TYPE: PRT
<213> ORGANISM: Homo Sapiens
<220> FEATURE:
<221> NAME/KEY: PEPTIDE
<222> LOCATION: (1)...(10)
<223> OTHER INFORMATION: galectin 3 binding protein

<400> SEQUENCE: 761

Glu Leu Ser Glu Ala Leu Gly Gln Ile Phe Asp Ser Gln Arg
1               5                   10

<210> SEQ ID NO 762
<211> LENGTH: 15
<212> TYPE: PRT
<213> ORGANISM: Homo Sapiens
<220> FEATURE:
<221> NAME/KEY: PEPTIDE
<222> LOCATION: (1)...(15)
<223> OTHER INFORMATION: galectin 3 binding protein

<400> SEQUENCE: 762

Trp Pro Ser Val Pro Thr Asp Leu Leu Gln Leu Leu Leu Pro Arg
1               5                   10                  15

<210> SEQ ID NO 763
<211> LENGTH: 11
<212> TYPE: PRT
<213> ORGANISM: Homo Sapiens
<220> FEATURE:
<221> NAME/KEY: PEPTIDE
<222> LOCATION: (1)...(10)

<223> OTHER INFORMATION: medium-chain acyl-CoA dehydrogenase isoform b
      precursor

<400> SEQUENCE: 763

Gly Ile Val Phe Glu Asp Val Lys Val Pro Lys
1               5                   10

<210> SEQ ID NO 764
<211> LENGTH: 13
<212> TYPE: PRT
<213> ORGANISM: Homo Sapiens
<220> FEATURE:
<221> NAME/KEY: PEPTIDE
<222> LOCATION: (1)...(10)
<223> OTHER INFORMATION: medium-chain acyl-CoA dehydrogenase isoform b
      precursor

<400> SEQUENCE: 764

Ile Tyr Gln Ile Tyr Glu Gly Thr Ser Gln Ile Gln Arg
1               5                   10

<210> SEQ ID NO 765
<211> LENGTH: 31
<212> TYPE: PRT
<213> ORGANISM: Homo Sapiens
<220> FEATURE:
<221> NAME/KEY: PEPTIDE
<222> LOCATION: (1)...(30)
<223> OTHER INFORMATION: medium-chain acyl-CoA dehydrogenase isoform b
      precursor

<400> SEQUENCE: 765

Ala Phe Ala Gly Asp Ile Ala Asn Gln Leu Ala Thr Asp Ala Val Gln
1               5                   10                  15

Ile Leu Gly Gly Asn Gly Phe Asn Thr Glu Tyr Pro Val Glu Lys
            20                  25                  30

<210> SEQ ID NO 766
<211> LENGTH: 11
<212> TYPE: PRT
<213> ORGANISM: Homo Sapiens
<220> FEATURE:
<221> NAME/KEY: PEPTIDE
<222> LOCATION: (1)...(10)
<223> OTHER INFORMATION: cathepsin D preproprotein

<400> SEQUENCE: 766

Phe Asp Gly Ile Leu Gly Met Ala Tyr Pro Arg
1               5                   10

<210> SEQ ID NO 767
<211> LENGTH: 18
<212> TYPE: PRT
<213> ORGANISM: Homo Sapiens
<220> FEATURE:
<221> NAME/KEY: PEPTIDE
<222> LOCATION: (1)...(15)
<223> OTHER INFORMATION: cathepsin D preproprotein

<400> SEQUENCE: 767

Ala Ile Gly Ala Val Pro Leu Ile Gln Gly Glu Tyr Met Ile Pro Cys
1               5                   10                  15

Glu Lys

<210> SEQ ID NO 768
<211> LENGTH: 17
<212> TYPE: PRT

```
<213> ORGANISM: Homo Sapiens
<220> FEATURE:
<221> NAME/KEY: PEPTIDE
<222> LOCATION: (1)...(15)
<223> OTHER INFORMATION: cathepsin D preproprotein

<400> SEQUENCE: 768

Ile Ser Val Asn Asn Val Leu Pro Val Phe Asp Asn Leu Met Gln Gln
1               5                   10                  15

Lys

<210> SEQ ID NO 769
<211> LENGTH: 21
<212> TYPE: PRT
<213> ORGANISM: Homo Sapiens
<220> FEATURE:
<221> NAME/KEY: PEPTIDE
<222> LOCATION: (1)...(20)
<223> OTHER INFORMATION: cathepsin D preproprotein

<400> SEQUENCE: 769

Leu Ser Arg Asp Pro Asp Ala Gln Pro Gly Gly Glu Leu Met Leu Gly
1               5                   10                  15

Gly Thr Asp Ser Lys
            20

<210> SEQ ID NO 770
<211> LENGTH: 12
<212> TYPE: PRT
<213> ORGANISM: Homo Sapiens
<220> FEATURE:
<221> NAME/KEY: PEPTIDE
<222> LOCATION: (1)...(10)
<223> OTHER INFORMATION: pancreatic lipase-related protein 2

<400> SEQUENCE: 770

Leu Leu Pro Trp Ser Pro Glu Asp Ile Asp Thr Arg
1               5                   10

<210> SEQ ID NO 771
<211> LENGTH: 9
<212> TYPE: PRT
<213> ORGANISM: Homo Sapiens
<220> FEATURE:
<221> NAME/KEY: PEPTIDE
<222> LOCATION: (1)...(5)
<223> OTHER INFORMATION: plastin 1

<400> SEQUENCE: 771

Leu Ser Pro Glu Glu Leu Leu Leu Arg
1               5

<210> SEQ ID NO 772
<211> LENGTH: 12
<212> TYPE: PRT
<213> ORGANISM: Homo Sapiens
<220> FEATURE:
<221> NAME/KEY: PEPTIDE
<222> LOCATION: (1)...(10)
<223> OTHER INFORMATION: plastin 1

<400> SEQUENCE: 772

Ala Tyr Phe His Leu Leu Asn Gln Ile Ala Pro Lys
1               5                   10

<210> SEQ ID NO 773
<211> LENGTH: 14
```

```
<212> TYPE: PRT
<213> ORGANISM: Homo Sapiens
<220> FEATURE:
<221> NAME/KEY: PEPTIDE
<222> LOCATION: (1)...(10)
<223> OTHER INFORMATION: plastin 1

<400> SEQUENCE: 773

Gln Phe Val Thr Pro Ala Asp Val Val Ser Gly Asn Pro Lys
 1               5                  10

<210> SEQ ID NO 774
<211> LENGTH: 23
<212> TYPE: PRT
<213> ORGANISM: Homo Sapiens
<220> FEATURE:
<221> NAME/KEY: PEPTIDE
<222> LOCATION: (1)...(20)
<223> OTHER INFORMATION: plastin 1

<400> SEQUENCE: 774

Gly Gly Glu Asp Gly Pro Ala Ile Ala Ile Asp Leu Ser Gly Ile Asn
 1               5                  10                  15

Glu Thr Asn Asp Leu Lys Arg
            20

<210> SEQ ID NO 775
<211> LENGTH: 12
<212> TYPE: PRT
<213> ORGANISM: Homo Sapiens
<220> FEATURE:
<221> NAME/KEY: PEPTIDE
<222> LOCATION: (1)...(10)
<223> OTHER INFORMATION: cystatin A

<400> SEQUENCE: 775

Pro Ala Thr Pro Glu Ile Gln Glu Ile Val Asp Lys
 1               5                  10

<210> SEQ ID NO 776
<211> LENGTH: 12
<212> TYPE: PRT
<213> ORGANISM: Homo Sapiens
<220> FEATURE:
<221> NAME/KEY: PEPTIDE
<222> LOCATION: (1)...(10)
<223> OTHER INFORMATION: cystatin A

<400> SEQUENCE: 776

Thr Gln Val Val Ala Gly Thr Asn Tyr Tyr Ile Lys
 1               5                  10

<210> SEQ ID NO 777
<211> LENGTH: 14
<212> TYPE: PRT
<213> ORGANISM: Homo Sapiens
<220> FEATURE:
<221> NAME/KEY: PEPTIDE
<222> LOCATION: (1)...(10)
<223> OTHER INFORMATION: cystatin A

<400> SEQUENCE: 777

Thr Asn Glu Thr Tyr Gly Lys Leu Glu Ala Val Gln Tyr Lys
 1               5                  10

<210> SEQ ID NO 778
<211> LENGTH: 18
<212> TYPE: PRT
```

```
<213> ORGANISM: Homo Sapiens
<220> FEATURE:
<221> NAME/KEY: PEPTIDE
<222> LOCATION: (1)...(15)
<223> OTHER INFORMATION: cystatin A

<400> SEQUENCE: 778

Ser Leu Pro Gly Gln Asn Glu Asp Leu Val Leu Thr Gly Tyr Gln Val
 1               5                  10                  15

Asp Lys

<210> SEQ ID NO 779
<211> LENGTH: 18
<212> TYPE: PRT
<213> ORGANISM: Homo Sapiens
<220> FEATURE:
<221> NAME/KEY: PEPTIDE
<222> LOCATION: (1)...(15)
<223> OTHER INFORMATION: intestinal mucin 3

<400> SEQUENCE: 779

Ala Ala Pro Thr Gly Tyr Glu Glu Phe Tyr Phe Pro Leu Val Glu Ala
 1               5                  10                  15

Thr Arg

<210> SEQ ID NO 780
<211> LENGTH: 7
<212> TYPE: PRT
<213> ORGANISM: Homo Sapiens
<220> FEATURE:
<221> NAME/KEY: PEPTIDE
<222> LOCATION: (1)...(5)
<223> OTHER INFORMATION: galectin 3

<400> SEQUENCE: 780

Ile Ala Leu Asp Phe Gln Arg
 1               5

<210> SEQ ID NO 781
<211> LENGTH: 15
<212> TYPE: PRT
<213> ORGANISM: Homo Sapiens
<220> FEATURE:
<221> NAME/KEY: PEPTIDE
<222> LOCATION: (1)...(15)
<223> OTHER INFORMATION: galectin 3

<400> SEQUENCE: 781

Met Leu Ile Thr Ile Leu Gly Thr Val Lys Pro Asn Ala Asn Arg
 1               5                  10                  15

<210> SEQ ID NO 782
<211> LENGTH: 21
<212> TYPE: PRT
<213> ORGANISM: Homo Sapiens
<220> FEATURE:
<221> NAME/KEY: PEPTIDE
<222> LOCATION: (1)...(20)
<223> OTHER INFORMATION: carcinoembryonic antigen-related cell adhesion
      molecule 1 isoform 1 precursor

<400> SEQUENCE: 782

Gln Ile Val Gly Tyr Ala Ile Gly Thr Gln Gln Ala Thr Pro Gly Pro
 1               5                  10                  15

Ala Asn Ser Gly Arg
                20
```

<210> SEQ ID NO 783
<211> LENGTH: 26
<212> TYPE: PRT
<213> ORGANISM: Homo Sapiens
<220> FEATURE:
<221> NAME/KEY: PEPTIDE
<222> LOCATION: (1)...(25)
<223> OTHER INFORMATION: carcinoembryonic antigen-related cell adhesion
      molecule 1 isoform 1 precursor

<400> SEQUENCE: 783

Val Asp Gly Asn Arg Gln Ile Val Gly Tyr Ala Ile Gly Thr Gln Gln
1               5                   10                  15

Ala Thr Pro Gly Pro Ala Asn Ser Gly Arg
            20                  25

<210> SEQ ID NO 784
<211> LENGTH: 11
<212> TYPE: PRT
<213> ORGANISM: Homo Sapiens
<220> FEATURE:
<221> NAME/KEY: PEPTIDE
<222> LOCATION: (1)...(10)
<223> OTHER INFORMATION: dihydrolipoamide S-succinyltransferase (E2
      component of 2-oxo-glutarate complex)

<400> SEQUENCE: 784

Val Glu Gly Gly Thr Pro Leu Phe Thr Leu Arg
1               5                   10

<210> SEQ ID NO 785
<211> LENGTH: 14
<212> TYPE: PRT
<213> ORGANISM: Homo Sapiens
<220> FEATURE:
<221> NAME/KEY: PEPTIDE
<222> LOCATION: (1)...(10)
<223> OTHER INFORMATION: dihydrolipoamide S-succinyltransferase (E2
      component of 2-oxo-glutarate complex)

<400> SEQUENCE: 785

Thr Pro Ala Phe Ala Glu Ser Val Thr Glu Gly Asp Val Arg
1               5                   10

<210> SEQ ID NO 786
<211> LENGTH: 17
<212> TYPE: PRT
<213> ORGANISM: Homo Sapiens
<220> FEATURE:
<221> NAME/KEY: PEPTIDE
<222> LOCATION: (1)...(15)
<223> OTHER INFORMATION: dihydrolipoamide S-succinyltransferase (E2
      component of 2-oxo-glutarate complex)

<400> SEQUENCE: 786

Thr Pro Ala Phe Ala Glu Ser Val Thr Glu Gly Asp Val Arg Trp Glu
1               5                   10                  15

Lys

<210> SEQ ID NO 787
<211> LENGTH: 11
<212> TYPE: PRT
<213> ORGANISM: Homo Sapiens
<220> FEATURE:
<221> NAME/KEY: PEPTIDE
<222> LOCATION: (1)...(10)
<223> OTHER INFORMATION: RecName: Full=Ig mu chain C region

```
<400> SEQUENCE: 787

Asp Val Met Gln Gly Thr Asp Glu His Val Val
1               5                   10

<210> SEQ ID NO 788
<211> LENGTH: 12
<212> TYPE: PRT
<213> ORGANISM: Homo Sapiens
<220> FEATURE:
<221> NAME/KEY: PEPTIDE
<222> LOCATION: (1)...(10)
<223> OTHER INFORMATION: RecName: Full=Ig mu chain C region

<400> SEQUENCE: 788

Tyr Ala Ala Thr Ser Gln Val Leu Leu Pro Ser Lys
1               5                   10

<210> SEQ ID NO 789
<211> LENGTH: 15
<212> TYPE: PRT
<213> ORGANISM: Homo Sapiens
<220> FEATURE:
<221> NAME/KEY: PEPTIDE
<222> LOCATION: (1)...(15)
<223> OTHER INFORMATION: RecName: Full=Ig mu chain C region

<400> SEQUENCE: 789

Tyr Val Thr Ser Ala Pro Met Pro Glu Pro Gln Ala Pro Gly Arg
1               5                   10                  15

<210> SEQ ID NO 790
<211> LENGTH: 25
<212> TYPE: PRT
<213> ORGANISM: Homo Sapiens
<220> FEATURE:
<221> NAME/KEY: PEPTIDE
<222> LOCATION: (1)...(25)
<223> OTHER INFORMATION: RecName: Full=Ig mu chain C region

<400> SEQUENCE: 790

Tyr Ala Ala Thr Ser Gln Val Leu Leu Pro Ser Lys Asp Val Met Gln
1               5                   10                  15

Gly Thr Asp Glu His Val Val Cys Lys
            20                  25

<210> SEQ ID NO 791
<211> LENGTH: 11
<212> TYPE: PRT
<213> ORGANISM: Homo Sapiens
<220> FEATURE:
<221> NAME/KEY: PEPTIDE
<222> LOCATION: (1)...(10)
<223> OTHER INFORMATION: selenium binding protein 1

<400> SEQUENCE: 791

Ile Tyr Val Val Asp Val Gly Ser Glu Pro Arg
1               5                   10

<210> SEQ ID NO 792
<211> LENGTH: 13
<212> TYPE: PRT
<213> ORGANISM: Homo Sapiens
<220> FEATURE:
<221> NAME/KEY: PEPTIDE
<222> LOCATION: (1)...(10)
<223> OTHER INFORMATION: selenium binding protein 1

<400> SEQUENCE: 792
```

Leu Thr Gly Gln Leu Phe Leu Gly Gly Ser Ile Val Lys
1               5                   10

<210> SEQ ID NO 793
<211> LENGTH: 18
<212> TYPE: PRT
<213> ORGANISM: Homo Sapiens
<220> FEATURE:
<221> NAME/KEY: PEPTIDE
<222> LOCATION: (1)...(15)
<223> OTHER INFORMATION: selenium binding protein 1

<400> SEQUENCE: 793

Asn Thr Gly Thr Glu Ala Pro Asp Tyr Leu Ala Thr Val Asp Val Asp
1               5                   10                  15

Pro Lys

<210> SEQ ID NO 794
<211> LENGTH: 19
<212> TYPE: PRT
<213> ORGANISM: Homo Sapiens
<220> FEATURE:
<221> NAME/KEY: PEPTIDE
<222> LOCATION: (1)...(15)
<223> OTHER INFORMATION: immunoglobulin M chain

<400> SEQUENCE: 794

Glu Val Gln Leu Val Glu Ser Gly Gly Gly Leu Val Gln Pro Gly Gly
1               5                   10                  15

Ser Leu Arg

<210> SEQ ID NO 795
<211> LENGTH: 15
<212> TYPE: PRT
<213> ORGANISM: Homo Sapiens
<220> FEATURE:
<221> NAME/KEY: PEPTIDE
<222> LOCATION: (1)...(15)
<223> OTHER INFORMATION: immunoglobulin M chain

<400> SEQUENCE: 795

Val Glu Ser Gly Gly Gly Leu Val Gln Pro Gly Gly Ser Leu Arg
1               5                   10                  15

<210> SEQ ID NO 796
<211> LENGTH: 14
<212> TYPE: PRT
<213> ORGANISM: Homo Sapiens
<220> FEATURE:
<221> NAME/KEY: PEPTIDE
<222> LOCATION: (1)...(10)
<223> OTHER INFORMATION: immunoglobulin M chain

<400> SEQUENCE: 796

Glu Ser Gly Gly Gly Leu Val Gln Pro Gly Gly Ser Leu Arg
1               5                   10

<210> SEQ ID NO 797
<211> LENGTH: 11
<212> TYPE: PRT
<213> ORGANISM: Homo Sapiens
<220> FEATURE:
<221> NAME/KEY: PEPTIDE
<222> LOCATION: (1)...(10)
<223> OTHER INFORMATION: immunoglobulin M chain

<400> SEQUENCE: 797

Asn Ser Leu Tyr Leu Gln Met Asn Ser Leu Arg
1               5                  10

<210> SEQ ID NO 798
<211> LENGTH: 21
<212> TYPE: PRT
<213> ORGANISM: Homo Sapiens
<220> FEATURE:
<221> NAME/KEY: PEPTIDE
<222> LOCATION: (1)...(20)
<223> OTHER INFORMATION: Ig kappa chain V-III region VG

<400> SEQUENCE: 798

Ala Ser Gln Ser Val Ser Ser Tyr Leu Ala Trp Tyr Gln Gln Lys Pro
1               5                   10                  15

Gly Gln Ala Pro Arg
            20

<210> SEQ ID NO 799
<211> LENGTH: 9
<212> TYPE: PRT
<213> ORGANISM: Homo Sapiens
<220> FEATURE:
<221> NAME/KEY: PEPTIDE
<222> LOCATION: (1)...(5)
<223> OTHER INFORMATION: Ig kappa chain V-III region VG

<400> SEQUENCE: 799

Leu Leu Ile Tyr Asp Ala Ser Asn Arg
1               5

<210> SEQ ID NO 800
<211> LENGTH: 19
<212> TYPE: PRT
<213> ORGANISM: Homo Sapiens
<220> FEATURE:
<221> NAME/KEY: PEPTIDE
<222> LOCATION: (1)...(15)
<223> OTHER INFORMATION: Ig heavy chain V-III region VH26

<400> SEQUENCE: 800

Glu Val Gln Leu Leu Glu Ser Gly Gly Gly Leu Val Gln Pro Gly Gly
1               5                   10                  15

Ser Leu Arg

<210> SEQ ID NO 801
<211> LENGTH: 11
<212> TYPE: PRT
<213> ORGANISM: Homo Sapiens
<220> FEATURE:
<221> NAME/KEY: PEPTIDE
<222> LOCATION: (1)...(10)
<223> OTHER INFORMATION: Ig heavy chain V-III region VH26

<400> SEQUENCE: 801

Asn Thr Leu Tyr Leu Gln Met Asn Ser Leu Arg
1               5                   10

<210> SEQ ID NO 802
<211> LENGTH: 16
<212> TYPE: PRT
<213> ORGANISM: Homo Sapiens
<220> FEATURE:
<221> NAME/KEY: PEPTIDE
<222> LOCATION: (1)...(15)
<223> OTHER INFORMATION: Ig heavy chain (VH4) V region

```
<400> SEQUENCE: 802

Leu Ser Ser Val Thr Ala Ala Asp Thr Ala Val Tyr Tyr Cys Ala Arg
1               5                   10                  15

<210> SEQ ID NO 803
<211> LENGTH: 14
<212> TYPE: PRT
<213> ORGANISM: Homo Sapiens
<220> FEATURE:
<221> NAME/KEY: PEPTIDE
<222> LOCATION: (1)...(10)
<223> OTHER INFORMATION: Ig heavy chain (VH4) V region

<400> SEQUENCE: 803

Ser Val Thr Ala Ala Asp Thr Ala Val Tyr Tyr Cys Ala Arg
1               5                   10

<210> SEQ ID NO 804
<211> LENGTH: 12
<212> TYPE: PRT
<213> ORGANISM: Homo Sapiens
<220> FEATURE:
<221> NAME/KEY: PEPTIDE
<222> LOCATION: (1)...(10)
<223> OTHER INFORMATION: Ig heavy chain (VH4) V region

<400> SEQUENCE: 804

Thr Ala Ala Asp Thr Ala Val Tyr Tyr Cys Ala Arg
1               5                   10
```